US012364724B2

(12) United States Patent
Fong et al.

(10) Patent No.: US 12,364,724 B2
(45) Date of Patent: *Jul. 22, 2025

(54) ONCOLYTIC VIRUS EXPRESSING A CAR T CELL TARGET AND USES THEREOF

(71) Applicant: City of Hope, Duarte, CA (US)

(72) Inventors: Yuman Fong, Duarte, CA (US); Saul J. Priceman, Duarte, CA (US); Stephen J. Forman, Duarte, CA (US); Nanhai Chen, Duarte, CA (US); Anthony K. Park, Duarte, CA (US)

(73) Assignee: City of Hope, Duarte, CA (US)

( * ) Notice: Subject to any disclaimer, the term of this patent is extended or adjusted under 35 U.S.C. 154(b) by 110 days.

This patent is subject to a terminal disclaimer.

(21) Appl. No.: 16/637,909

(22) PCT Filed: Aug. 10, 2018

(86) PCT No.: PCT/US2018/046313

§ 371 (c)(1),
(2) Date: Feb. 10, 2020

(87) PCT Pub. No.: WO2019/033030

PCT Pub. Date: Feb. 14, 2019

(65) Prior Publication Data

US 2020/0215132 A1 Jul. 9, 2020

Related U.S. Application Data

(60) Provisional application No. 62/544,707, filed on Aug. 11, 2017.

(51) Int. Cl.

| | |
|---|---|
| ***A61K 35/768*** | (2015.01) |
| ***A61K 38/17*** | (2006.01) |
| ***A61K 39/00*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C12N 7/00*** | (2006.01) |

(52) U.S. Cl.

CPC .......... *A61K 35/768* (2013.01); *A61K 38/177* (2013.01); *A61K 40/11* (2025.01); *A61K 40/31* (2025.01); *A61K 40/4211* (2025.01); *A61P 35/00* (2018.01); *C12N 7/00* (2013.01); *C12N 2710/24021* (2013.01); *C12N 2710/24032* (2013.01); *C12N 2770/32021* (2013.01); *C12N 2770/32022* (2013.01); *C12N 2770/32032* (2013.01)

(58) Field of Classification Search

CPC .................................................... A61K 35/768

See application file for complete search history.

(56) References Cited

U.S. PATENT DOCUMENTS

| | | | |
|---|---|---|---|
| 7,446,179 B2 | 11/2008 | Jensen et al. | |
| 9,180,150 B2 | 11/2015 | Erbs et al. | |
| 12,084,687 B2 * | 9/2024 | Fong | C12N 7/00 |
| 2021/0077554 A1 | 3/2021 | Aalipour et al. | |

FOREIGN PATENT DOCUMENTS

| | | | |
|---|---|---|---|
| WO | WO 2016/009017 | 1/2016 | |
| WO | WO-2016044811 A1 * | 3/2016 | A61K 35/17 |
| WO | WO-2017046747 A1 * | 3/2017 | A61K 31/454 |
| WO | WO 2017/075440 | 5/2017 | |
| WO | WO 2018/031694 | 2/2018 | |
| WO | WO 2019/118918 | 6/2019 | |

OTHER PUBLICATIONS

Parato et. al. Molecular Therapy 20(4):749-758. (2012) (Year: 2012).*

Schutsky et. al. Oncotarget 6(30): 28911-28928 (2015) (Year: 2015).*

Sánchez-Sampedro et. al. Viruses. 7:1726-1803. (2015) (Year: 2015).*

Goldufsky et. al. (Oncolytic Virotherapy. 2:31-46 (2013)) (Year: 2013).*

Andtbacka et al., "Talimogene Laherparepvec Improves Durable Response Rate in Patients With Advanced Melanoma, " J Clin Oneal., 2015, 33(25):2780-2788.

Bejcek et al., "Development and Characterization of Three Recombinant Single Chain Antibody Fragments (scFvs) Directed against the CD19 Antigen," Cancer Research, 1995, 55:2346-2351.

Chan & McFadden, "Oncolytic Poxviruses," Annu Rev Viral., 2014, 1(1):119-141.

Chen & Szalay, "Oncolytic virotherapy of cancer," Cancer Management in Men: Chemotherapy, Biological Therapy, Hyperthermia and Supporting Measures, Cancer Growth and Progression, Nov. 3, 2010, 16:295-316.

Chen et al., "Oncolytic vaccinia virus: a theranostic agent for cancer," Future Viral., 2010, 5(6):763-784.

Edelman et al., "The Covalent Structure of an Entire yG Immunoglobulin Molecule," Proc Natl Acad Sci USA., 1969, 63:78-85.

Evgin et al., "Potent Oncolytic Activity of Raccoonpox Virus in the Absence of Natural Pathogenicity," Mol Ther., May 2010, 18(5):896-902.

Gubser et al., "Poxvirus genomes: a phylogenetic analysis," J Gen Virol., Jan. 2004, 85(Pt 1):105-117.

International Preliminary Report on Patentability in International Application No. PCT/US2018/046313, dated Feb. 11, 2020, 8 pages.

International Search Report in International Application No. PCT/US2018/046313, dated Nov. 20, 2018, 15 pages.

(Continued)

*Primary Examiner* — Meera Natarajan
*Assistant Examiner* — Francesca Edgingtongiordano
(74) *Attorney, Agent, or Firm* — Fish & Richardson P.C.

(57) ABSTRACT

An oncolytic poxvirus encoding a truncated human CD19 is used in conjunction with a chimeric antigen receptor to treat solid tumors.

11 Claims, 24 Drawing Sheets

Specification includes a Sequence Listing.

(56) References Cited

OTHER PUBLICATIONS

Park et al., "CD19-targeted CAR T-cell therapeutics for hematologic malignancies: interpreting clinical outcomes to date," Blood, 2016, 127(26):3312-3320.
Park, "Delivering Chimeric Antigen Receptor (CAR) Targets by Oncolytic Virus to Treat Solid Tumors," 2016, Poster, 20 pages.
Poh, "First Oncolytic Viral Therapy for Melanoma," Cancer discovery, Nov. 8, 2015, 6(1):6.
Rintoul et al., "ORFV: a novel oncolytic and immune stimulating parapoxvirus therapeutic," Mol Ther., 2012, 20(6):1148-1157.
Russell et al., "Oncolytic virotherapy," Nat Biotechnol., Jul. 10, 2012, 30(7):658-670.
Thome et al., "Rational strain selection and engineering creates a broad-spectrum, systemically effective oncolytic poxvirus, JX-963," J Clin Invest., 2007, 7(11):3350-3358.
Yu et al., "Clinical trials with oncolytic adenovirus in China," Curr Cancer Drug Targets., 2007, 7(2):141-148.
Zola et al., "Preparation and characterization of a chimeric CD 19 monoclonal antibody," Immunol Cell Biol., 1991, 69:411-422.
CN Office Action in Chinese Appln. No. 201880064280.9, dated Jan. 9, 2023, 16 pages (with English translation).
CN Office Action in Chinese Appln. No. 201880064280.9, dated Sep. 21, 2023, 10 pages (with English translation).
JP Office Action in Japanese Appln. No. 2020-507619, mailed on Oct. 24, 2023, 5 pages (with English translation).
Yong et al., "Research progress on improving the anti-cancer activity and safety of CAR-T cells therapy," Journal of Pharmaceutical Practice, Jul. 25, 2016, 34(4):372-376 (English Abstract).
Zhang et al., "Risks and Solutions to Chimeric Antigen Receptor-Engineered T Cell-based Cancer Immunotherapy," Acta Pharmaceutica Sinica, Jul. 1, 2016, 51(7):1032-1038 (Abstract Only).
Qin et al., "Genome scale patterns of recombination between coinfecting vaccinia viruses," Journal of Virology, May 2014, 88(10):5277-5286.
Gardner et al., "CD19CAR T Cell Products of Defined CD4:CD8 Composition and Transgene Expression Show Prolonged Persistence and Durable MRD-Negative Remission in Pediatric and Young Adult B-Cell ALL," Blood, Dec. 2016, 128(22):219, 3 pages.
Gardner et al., "Decreased Rates of Severe CRS Seen with Early Intervention Strategies for CD19 CAR-T Cell Toxicity Management," Blood, Dec. 2016, 128(22):586, 3 pages.

* cited by examiner

Multiplicity of Infection

SEQUENCE LISTING

<160> NUMBER OF SEQ ID NOS: 38

<210> SEQ ID NO 1
<211> LENGTH: 189415
<212> TYPE: DNA
<213> ORGANISM: Artificial Sequence
<220> FEATURE:
<223> OTHER INFORMATION: Synthetic Polynucleotide

<400> SEQUENCE: 1
gagaaagaga taaaactttt ttacgactcc atcagaaaga ggtttaatat ttttgtgaga 60
ccatcgaaga gagaaagaga aagagatagt tagtctagat atttttctta gtacaaaagt 120
caatgtttta aaatatatgg acaagaattt gtctgtataa aaacttgtgt gaaattttgt 180
accaaagaaa aaatgtgagc agtatcccct acatggattt tactagatca tttatatacc 240
aaaaaatatt atacgatcta cgttttatta tatgatttta acgtgtaaat tataaacatt 300
attttatgat atacaattgt ctggtaacct agatgggcat aggggatgtt gataagctcg 360
acgagtatat gttgttggac gttattgttt aagaaatagt tgatgcatca gaaagagaat 420
aaaaaatatt ttagtgagac catcgaagag agaaagagat aaaacttttt tacgactcca 480
tcagaaagag gtttaatatt tttgtgagac catcgaagag agaaagagaa taaaaatatt 540
ttatgactcc attgaagaga gaaagagaaa atgagaatga gaataaaaat attttagtga 600
caccatcaga aagaggttta atatttttgt gagaccatcg aagagagaaa gagaataaaa 660
atattttatg actccattga agagagaaag agaaaatgag aatgagaata aaaatatttt 720
agtgacacca tcagaaagag gtttaatatt ttttatgaga ccatcaaaga gagaaagaga 780
ataaaaatat ttttgtaaaa cttttttat gagaccatca aagagagaaa gagaataaaa 840
atatttttgt aaaacttttt ttatgagacc atcaaagaga gaaagagaat aaaaatattt 900
ttgtaaaact ttttttatga gaccatcaaa gagagaaaga gaataaaaat atttttgtaa 960
aacttttttt atgagaccat caaagagaga aagagaataa aaatattttt gtaaaacttt 1020
ttttatgaga ccatcaaaga gagaaagaga ataaaaaaat atttttgtaa aacttttttt 1080
atgagaccat cagaaagagg tttaatattt ttgtgatacc ctgaaaggaa ataggaatag 1140
gaatagtgtc ataatcgtat cacactattg agacagaaaa agaagaagtc gcgagaggta 1200
actttttgtt ttgcaaaccg gaatatagtg tccggtacac ttttttaatt cgtggtgtgc 1260
ctgaatcgtt cgattaaccc tactcatcca atttcagatg aatagagtta tcgattcaga 1320
cacacgcttt gagttttgtt gaatcgatga gtgaagtatc atcggttgca ccttcagatg 1380
ccgatccgtc gacatacttg acctcaagtt cagatgattc cttgcacatg tctccgatac 1440
gaacgctaaa ctctagattc ttgacacatt ttgtatcgac gatcgttgaa ccgatgatat 1500

-continued

```
cttcgtaact cactttctta tgagagatgt tagacccgag tactggatgg gtcttgatgt   1560
cgctgtcttt ctcttcttcg ctacatctga tgtcgataga cacctcacag tctttccatc   1620
agcggattct gagatggatt taatctgagg acatttggtg aatccaaagt tcattctcag   1680
acctccaccg atgatggagt aataagtggt aggaggatct acatcctcga ctgattccac   1740
ctcgggatct ggatctgact cggactctgt aatttccgtt acggattggc aaatcttatc   1800
atcggtcggt gtttggtctt gctttgtgac tttgataata acatcgattc ccatatgatg   1860
tttgttttct tcttccgtac acgatgagga tgattgctga agactggcag gcacatgcat   1920
gccagtacga tatattgttt catgattgct attgattgag tactgttctt tatgattcta   1980
cttccttacc gtgcaataaa ttagaatata ttttctactt ttacgagaaa ttaattattg   2040
tatttatggg tgaaaaactt actataaaaa gcgggtgggt ttggaattag tgatcagttt   2100
atgtatatcg caactaccgg gcatatggct acattaccca catgataaga gattgtatca   2160
gtttcgtagt cttgagtatt ggtattacta tatagtatat agatgtcgac gctagagtta   2220
ctgtctccga atgcggcatg atagtatcat tctttgcttt cgttaactgt ttggaggaag   2280
aatctttgtt attgcattta atctcgaaat tcagagtgca caccttttctc ctgtaaagaa   2340
tcctgaagtt gctaccttat taagaacgga gaagtatcca tcacgaaaga cgggattaca   2400
gtctttatga ttcatagtaa tagttagttc cgacgttgag atggattcgc tgagaccggt   2460
agtggtcgtc cgagtacacg atgtgtcgtt gacgggatac agattaattt ccacatcgat   2520
atagttaaag gtatttctgg gtacgggttt gagatcgtcg tacatgggaa atgaaatgtg   2580
actgtctgaa tgtatggctt taagatagct gtgataccgt atacaggtcg gtgtcggaga   2640
ttcgaatctc tttaaggcga cttatgtcac gatgatggaa tctatcttat cgaatgatat   2700
atttttcata aatacacttt tatagtcctc gtttaaacag aatttactat gtagttccgc   2760
gaatgactcg tcccttaata ggcagtaggc tagtatcttt tttacgtagt aatcgtcgta   2820
gggagagaca tcttgtagaa caacgattta atcataggta gagatacttt cagtctgtgg   2880
tggatgatgt cattcacaac atccgccttg tatatgatgt ttctgttttc aaacaccaag   2940
tcgaataccg tctttagtcg gaaggttgat gtcgtatccg atgtatgagg caacattgtt   3000
gttacaattt tgaaaggcgg tattatagta ttcgtctttc tgaatgtcga acctatctag   3060
tagataccgt agtatattga gagtgtatcc ttgattatgt tttatgaata gataaagtag   3120
atgttgtcct tcttcctttt gttcgtgcca attgagtaac attatgagaa tatgacctgt   3180
tgcacaatcg ttccatgatg ggtgtacaat caagattatt acgtatcctc gtatcggctc   3240
ctcgagataa aagagcatac accacacgag gactatgttt ggtatactgt tgaaggtaag   3300
tgtgtaaccg cgttaatgtt tgctccataa tctattatcg cgtagatgaa tcgcttctcg   3360
gctcgcatct tagtgtgact taacttgtaa taattgcttt tgtagaacgt ggatatgtgt   3420
ttacagtagt aatgaagaga agtgagtcca tcctcgtcga cgcaattagg gtcggatcct   3480
ttgtacagaa cgtaatagtt taagctccca ttgaatttat atctaagata acacagcaat   3540
agatcggatg atttactaaa gtcatcaatg gtgtccgtta gtatatcaaa gatcttgtta   3600
tcgattgata gtgaatgaat cagatagtgg tgtagaggaa tatgtccttt ttcatccttg   3660
ctatcaaagt tacgcatgcc gtggtgtaac aatatcttta atacagatgg attaaatcgt   3720
gtattcatcg tatagcaatg taatggagag ttacctcgtt tattcagatc gcagtgttta   3780
ataactagct taaacagatg agacgatgta tccacatcaa agaacgtaaa atacatatga   3840
```

-continued

```
caaacattgt tgacagaaac gtgaccttca ttcttaccgt cgtccataaa tacgttaggt   3900
atgtaccaca tactgtcgcg aacgatgcgt acaatctcgt ccatctcata atgatttact   3960
ttttcataat taaagatgtg aaagaaaaac agaacaatat attttttag taatgtttat    4020
gcgagacata taaaataaac tccgtgttta tgatcatttt taacagcaac acattcaata   4080
ttgtattgtt atttttatat tatttacaca attaacaata tattattagt ttatattact   4140
gaattaataa tataaaattc ccaatcttgt cataaacaca cactgagaaa cagcataaac   4200
acaaaatcca tcaaaaatgt cgatgaaata tctgatgttg ttgttcgctg ctatgataat   4260
cagatcattc gccgatagtg gtaacgctat cgaaacgaca tcgccagaaa ttacaaacgc   4320
tacaacagat attccagcta tcagattatg cggtccagag ggagatggat attgtttaca   4380
cggtgactgt atccacgcta gagatattga cggtatgtat tgtagatgct ctcatggtta   4440
tacaggcatt agatgtcagc atgtagtatt agtagactat caacgttcag aaaacccaaa   4500
cactacaacg tcatatatcc catctcccgg tattatgctt gtattagtag gcattattat   4560
tattacgtgt tgtctattat ctgtttatag gttcactcga cgaactaaac tacctataca   4620
agatatggtt gtgccataat tttataaat tttttatga gtatttttac aaaaaaaatg     4680
tataaagtgt atgtcttatg tatatttata aaaatgctaa gtatgcgatg tatctatgtt   4740
atttgtattt atctaaacaa tacctctacc tctagatatt atacaaaaat tttttatttc   4800
ggcatattaa agtaaaatct agttaccttg aaaatgaata cagtgggtgg ttccgtatca   4860
ccagtaagaa cataatagtc gaatacagta tccgattgag attttgcata caatactagt   4920
ctagaaagaa atttgtaatc atcttctgtg acgggagtcc atatatctgt atcatcgtct   4980
agtttatcag tgtcccatgc tatattcctg ttatcatcat tagttaatga aaataactct   5040
cgtgcttcag aaaagtcaaa tattgtatcc atacatacat ctccaaaact atcgcttata   5100
cgtttatctt taacgatacc tatacctaga tggttattta ctaacagaca ttttccagat   5160
ctattgacta taactcctat agtttccaca tcaaccaagt aatgatcatc tattgttata   5220
taacaataac ataactcttt tccattttta tcagtatgta tatctatatc aacgtcgtcg   5280
ttgtagtgaa tagtagtcat tgatctatta tatgaaacgg atatgtctag aacggcaatt   5340
gttttacgtc cagttaacac tttctttgat ttaaagtcta gagtctttgc aaacataata   5400
tccttatccg actttatatt tcctgtaggg tggtataatt ttattttgcc tccacatatc   5460
ggtgtttcca aatatattac tagacaatat tccatatagt tattagttaa gggtacccaa   5520
ttagaacacg tacgcttatt atcatcattt ggatcgtatt tcataaaagt tattgtacta   5580
tcgatgtcaa cacattctac attttttaat cgtctatata gtatttttct gatattttct   5640
ataaatatcag aattgtcttc catcggaagt tgtatactat cggaatcagt tacatgttta  5700
aataattctc tgatgtcatt ccttatacaa tcaaattcat tattaaacag tttaatagtc   5760
tgtagacctt tatcgtcgta aatatccatt gtcttattag ttacgcttat ttttatgtgt   5820
tttacgttgc tttattatat tttataagaa tgattgtttg acgaatcacg agaactatta   5880
agacacatta ttaggtatat attataaaaa agtttttgat tacgatgtta taagaggaaa   5940
gaggacacat taacatcata catcaattaa ctacattctt ataacatcgt aatcaaaaga   6000
attgcaattt tgatgtataa caactgtcaa tgggttatgg aattgtatat tacatattat   6060
acggtatgtt ggtaacgaca aataccgatc ggtaattgtc tgccggtgta atagaattat   6120
atatatctat ctattacacc ggctgagtat gcataataat aagttgtggt agtatgatct   6180
ccatatttat aatttaggac tttgtattca gtatttttgg aatcataaaa aataaaaaaa   6240
```

```
agttttacta atttaaaatt taaaaagtat ttacattttt ttcactgttt agtcgcggat   6300
atggaattcg atcctgccaa aatcaataca tcatctatag atcatgtaac aatattacaa   6360
tacatagatg aaccaaatga tataagacta acagtatgca ttatccgaaa tattaataac   6420
attacatatt atatcaatat cacaaaaata aatacacatt tggctaatca atttcgggct   6480
tggaaaaaac gtatcgccgg aagggactat atgactaact tatctagaga tacaggaata   6540
caacaatcaa aacttactga aactatacgt aactgtcaaa aaaatagaaa catatatggt   6600
ctatatatac actacaattt agttattaat gtggttattg attggataac cgatgtgatt   6660
gttcaatcaa tattaagagg gttggtaaat tggtacatag ctaataatac ctatactcca   6720
aatacaccca ataatacaac aaccatttct gagttggata tcatcaaaat actggataaa   6780
tacgaggacg tgtatagagt aagtaaagaa aaagaatgtg gaatttgcta tgaagttgtt   6840
tactcaaaac gatagatact ttggtttatt ggattcgtgt actcatatat tttgcataac   6900
atgcatcaat atatggcata aaacacgaag agaaaccggt gcgtcggata attgtcctat   6960
atgtcgtacc cgttttagaa acataacaat gagcaagttc tataagctag ttaactaata   7020
aataaaaagt ttaatttgtt gacgacgtat gtcgttattt ttctcgtatg aaagattaaa   7080
ttcaattcaa ttcgttgttt ctaatataat ctgccgtatt ggatggattc tcaagacaat   7140
tgcatttaga ttatattatc atgaataaaa atagtagcac gcactacttc agccaaatat   7200
tctttttgga aacgccatct atcgtagtga ggacacaagt gaacctataa ttatcaaatt   7260
tattagtatc agtcacatga aggactttct gtagagtgac gattctacca tctatggtac   7320
taacggtttc atcctccttg ataccctcac ccaaatgttc tataaattta gcatcctcgt   7380
ccgatctcat atcctttgcc aaccaataca tgtagctaaa attaggcata aatttcacac   7440
atccagtgca acgaaattct ccagaagatg ttacgatgtt taggttagga catttgattt   7500
cgtcggcatt aacatatggg tgaacacacc catacatgaa agcgatgaga aataggattc   7560
tcatcttgcc aaaatatcac tagaaaaaat ttatttatca attttaaagg tataaaaaat   7620
acttattgtt gctcgaatat tttgtatttg atggtatacg gaagattaga aatgtaggta   7680
ttatcatcaa ctgattctat ggttttatgt attctatcat gtttcactat tgcgtcggaa   7740
ataaatatcat atgcttccac atatatttta ttttgtttta actcataata ctcacgtaat   7800
tctggattat tggcatatct atgaataatt ttagctccat gatcagtaaa tattaatgag   7860
aacatagtat taccacctac cattattttt ttcatttcgt tcaattcttg attgcaaaga   7920
tctatataat cattatagcg ttgacttatg gactctggaa tcttagacga tgtacagtca   7980
tctataatca tggcatattt aatacattgt tttatagcat agtagttatc tacgatgtta   8040
gatatttctc tcaatgaatc aatcacacaa tctaatgtag gtttatgaca taatagcatt   8100
ttcagcagtt caatgtttct agattcgttg atggcaatgg ctatacatgt atatccgtta   8160
tttgatctaa tgttgacatc tgaaccggat tctagcagta aagatactag agattgttta   8220
ttatatctaa cagccttgtg aagaagtgtt tctcctcgtt tgtcaatcat gttaatgtct   8280
ttaagataag gtaggcaaat gtttatagta ctaagaattg ggcaagcata agacatgtca   8340
caaagaccct ttttgtatgt ataagtgtaa aaattataac attcatagtt ggatttacat   8400
aggtgtccaa tcgggatctc tccatcatcg agataattga tggcatctcc cttccttttt   8460
tagtagatat ttcatcgtgt aagaatcaat attaatattt ctaaagtatt cgtgtatagc   8520
ctctttattt accacagttc catattccac tagagggata tcgccgaatg tcatatactc   8580
```

```
aattagtata tgttggagga catccgagtt cattgttttc aatatcaaaa agatggtttc   8640
cttatcattt ctccatagtg gtacaatact acacattatt ccgtgcggct ttccattttc   8700
caaaaacaat ttgaccaaat ctaaatctac atctttattg tatctataat cactatttag   8760
ataatcagcc ataattactc gagtgcaaca tgttagatcg tctatatatg aataagcagt   8820
gttatctatt cctttcatta acaatttaac gatgtctata tctatatgag atgacttaat   8880
ataatattga agagctgtac aatagttttt atctatagaa gacggcttga ttccgtgatt   8940
aattagacat ttaacaactt ccggacgcac atatgctctc gtatccgact ttgaatacag   9000
atgagagatg atatacagat gcaatacggt accgcaattt cgtagttgat aatcatcata   9060
cgcgtatcag tactcgtcct cataaagaac actgcagcca ttttctatga acaaatcaat   9120
aattttagga acaggatcat tgtcattaca taattttcta taactgaacg atggttttca   9180
catttaacac tcaagtcaaa tccatgttct accaacacct ttatcaagtc aacgtctaca   9240
tttttggatt tcatatagct gaatatatta aagtcattta tgttgctaaa tccagtggct   9300
tctagtagag ccatcgctat atcctttaac tttaacatgt ctactatttg tgtattcttc   9360
taatggggta gctgtctcca atttttgcgt aatggattag tgccactgtc tagtagtagt   9420
ttgacgacct cgacattatt acaatgctca ttaaaaaggt atgcgtgtaa agcattattc   9480
ttgaattggt tcctggtatc attaggatct ctgtctctca acatctgttt aagttcatcg   9540
agagccacct cctcattttc cagatagtca aacattttga ctgaatgagc tactgtgaac   9600
tctatacacc cacacaacta atgtcattaa atattatttt tttgaatgta tttataccat   9660
gtcaaaaact tgtacaatta ttaataaaaa taatttagtg tttaaatttt accagttcca   9720
gattttacac ctccgttaac cccacttttt acaccactgg acgatcctcc tccccacatt   9780
ccaccgccac cagatgtata agttttagat cctttattac taccatcatg tccatggata   9840
aagacactcc acatgccgcc actactaccc cctttagaag acatattaat aagacttaag   9900
gacaagttta acaataaaat taatcacgag taccctacta ccaacctaca ctattatatg   9960
attatagttt ctatttttac agtaccttaa ctaaagtctc tagtcacaag agcaatacta  10020
ccaacctaca ctattatatg attatagttt ctatttttat aggaacgcgt acgagaaaat  10080
caaatgtcta atttctaacg gtagtgttga taaacgatta tcgtcaatgg atacctcctc  10140
tatcatgtcg tctattttct tactttgttc tattaactta ttagcattat atattatttg  10200
attataaaac ttatattgct tattagccca atctgtaaat atcggattat taacatatcg  10260
tttctttgta ggtttattta acatgtacat cactgtaagc atgtccgtac catttatttt  10320
aatttgacgc atatccgcaa tttctttttc gcagtcggtt ataaattcta tatatgatgg  10380
atacatgcta catgtgtact tataatcgac taatatgaag tacttgatac atattttcag  10440
taacgattta ttattaccac ctatgaataa gtacctgtga tcgtctaggt aatcaactgt  10500
tttcttaata cattcgatgg ttggtaattt actcagaata atttccaata tcttaatata  10560
taattctgct atttctggga tatatttatc tgccagtata acacaaatag taatacatgt  10620
aaacccatat tttgttatta tattaatgtc tgcgccatta tctattaacc attctactag  10680
gctgacacta tgcgacttaa tacaatgata aagtatacta catccatgtt tatctatttt  10740
gtttatatca tcaatatacg gcttacaaag ttttagtatc gataacacat ccaactcacg  10800
catagagaag gtagggaata atggcataat atttattagg ttatcatcat tgtcattatc  10860
tacaactaag tttccatttt ttaaaatata ctcgacaact ttaggatctc tattgccaaa  10920
tttttgaaaa tatttattta tatgcttaaa tctatataat gtagctcctt catcaatcat  10980
```

```
acatttaata acattgatgt atactgtatg ataagataca tattctaaca atagatcttg  11040
tatagaatct gtatatcttt taagaattgt ggatattagg atattattac gtaaactatt  11100
acacaattct aaaatataaa acgtatcacg gtcgaataat agttgatcaa ctatataatt  11160
atcgattttg tgatttttct tcctaaactg tttacgtaaa tagttagata gaatattcat  11220
tagttcatga ccactatagt tactatcgaa taacgcgtca aatatttccc gtttaatatc  11280
gcatttgtca agataataat agagtgtggt atgttcacga taagtataat aacgcatctc  11340
tttttgtgt gaaattaaat agtttatcac gtccaaagat gtagcataac catcttgtga  11400
cctagtaata atataataat agagaactgt tttacccatt ctatcatcat aatcagtggt  11460
gtagtcgtaa tcgtaatcgt ctaattcatc atcccaatta taatattcac cagcacgtct  11520
aatctgttct attttgatct tgtatccata ctgtatgttg ctacatgtag gtattccttt  11580
atccaataat agtttaaaca catctacatt gggatttgat gttgtagcgt atttctctac  11640
aatattaata ccatttttga tactatttat ttctatacct ttcgaaatta gtaatttcaa  11700
taagtctata tcgatgttat cagaacatag atattcgaat atatcaaaat cattgatatt  11760
tttatagtcg actgacgaca ataacaaaat cacaacatcg tttttgatat tattattttt  11820
cttggtaacg tatgccttta atggagtttc accatcatac tcatataatg gatttgcacc  11880
actttctatc aatgattgtg cactgctggc atcgatgtta aatgttttac aactatcata  11940
gagtatctta tcgttaacca tgattggttg ttgatgctat cgcatttttt ggtttctttc  12000
atttcagtta tgtatggatt tagcacgttt gggaagcatg agctcatatg atttcagtac  12060
tgtagtgtca gtactattag tttcgatcag atcaatgtct agatctatag aatcaaaaca  12120
cgataggtca gaagataatg aatatctgta cgcttctttt tgtactgtaa cttctggttt  12180
tgttagatgg ttgcatcgtg ctttaacatc aatggtacaa attttatcct cgctttgtgt  12240
atcatattcg tctctagtat aaaattctat attcagatta tcatgcgatg tgtatacgct  12300
aacggtatca ataaacggag cacaccattt agtcataaca gtaatccaaa attttttaaa  12360
gtatatctta acgaaagaag ttgtgtcatt gtctacggtg tatggtacta gatcctcata  12420
agtgtatata tctagagtaa tgtttaattt attaaatggt tgataatatg gatcctcatg  12480
acaatttccg aagatggaaa tgagatatag acatgcaata aatctaatcg aagacatggt  12540
tactccttaa aaaaatacga ataatcacct tggctattta gtaagtgtca tttaacacta  12600
tactcatatt aatccatgga ctcataatct ctatacggga ttaacggatg ttctatatac  12660
ggggatgagt agttttcttc tttaacttta tactttttac taatcatatt tagactgatg  12720
tatgggtaat agtgtttaaa gagttcgttc tcatcatcag aataaatcaa tatctctgtt  12780
tttttgttat acagatgtat tacagcctca tatattacgt aatagaacgt gtcatctacc  12840
ttattaactt tcaccgcata gttgtttgca aatacggtta atcctttgac ctcgtcgatt  12900
tccgaccaat ctgggcgtat aatgaatcta aactttaatt tcttgtaatc attcgaaata  12960
atttttagtt tgcatccgta gttatcccct ttatgtaact gtaaatttct caacgcgata  13020
tctccattaa taatgatgtc gaattcgtgc tgtataccca tactgaatgg atgaactaac  13080
gaatatcaac ggcgttaata gtaatttact ttttcatctt tacatattgg gtactagttt  13140
tactatcata agtttataaa ttccacaagc tactatggaa taagccaacc atcttagtat  13200
accacacatg tcttaaagtt tattaattaa ttacatgttg ttttatatat atcgctacga  13260
atttaaagag aaatcagttt aggaagaaaa aaattatcta tctacatcat cacgtctctg  13320
```

```
tattctacga tagagtgcta ctttaagatg agacatatcc gtgtcatcaa aaatatactc  13380
cattaaaatg attattccgg cagcgaactt gatattggat atatcacaac ctttgttaat  13440
atctacgaca atagacagca gtcccatggt tccataaaca gtgagtttat ctttctttga  13500
agcgatagtt tgtagagatc ttataaaacc gtcaaacgac atcgcattta tatctttagc  13560
taattcatat atgttaccat cgtaatatct aaccgcgtct atcttaaacg tttccatcgc  13620
tttaaagacg tttccgatag atggtctcat ttcatcagtc atactgagcc aacaaatata  13680
atcgtgtata acatctttga tagaatcaga ctctaaagaa aacgaatcgg ctttattata  13740
cgcattcatg ataaacttaa tgaaaaatgt ttttcgttgt ttaagttgga tgaatagtat  13800
gtcttaataa ttgttattat ttcattaatt aatatttagt aacgagtaca ctctataaaa  13860
acgagaatga cataactagt tatcaaagtg tctaggacgc gtaattttca tatggtatag  13920
atcctgtaag cattgtctgt attctggagc tattttcttt atcgcattag taagttcaga  13980
atatgttata aatttaaatc gaataacgaa catgacttta gtaaagtcgt ctatattaac  14040
tcttttattt tctagccatc gtaataccat gtttaagata gtatattctc tagttactac  14100
gatctcatcg ttgtctagaa tatcacatac tgaatctaca tccaatttta gaaattggtc  14160
tgtgttacat atctcttcta tattattgtt gatgtattgt cgtagaaaac tattacgtag  14220
accattttct ttataaaacg aatatatagt actccaatta tctttaccga tatatttgca  14280
cacataatcc attctctcaa tcactacatc tttaagattt tcgttgttaa gatatttggc  14340
taaactatat aattctatta gatcatcaac agaatcagta tatatttttc tagatccaaa  14400
gacgaactct ttggcgtcct ctataatatt cccagaaaag atattttcgt gttttagttt  14460
atcgagatct gatctgttca tatacgccat gattgtacgg tacgttatga taaccgcata  14520
aaataaaaat ccattttcat ttttaaccaa tactattcat aattgagatt gatgtaatac  14580
tttgttactt tgaacgtaaa gacagtacac ggatccgtat ctccaacaag cacgtagtaa  14640
tcaaatttgg tgttgttaaa cttcgcaata ttcatcaatt tagatagaaa cttatactca  14700
tcatctgttt taggaatcca tgtattatta ccactttcca acttatcatt atcccaggct  14760
atgtttcgtc catcatcgtt gcgcagagtg aataattctt ttgtattcgg tagttcaaat  14820
atatgatcca tgcatagatc ggcaaagcta ttgtagatgt gatttttcct aaatctaata  14880
taaaactcgt ttactagcaa acactttcct gatttatcga ccaagacaca tatggtttct  14940
aaatctatca agtggtgggg atccatagtt atgacgcagt aacatagatt attacattct  15000
tgactgtcgc taatatctaa atatttattg ttatcgtatt ggattctgca tatagatggc  15060
ttgtatgtca aagatataga acacataacc aatttatagt cgcgctttac attctcgaat  15120
ctaaagttaa gagatttaga aaacattata tcctcggatg atgttatcac tgtttctgga  15180
gtaggatata ttaaagtctt tacagatttc gtccgattca aataaatcac taaataatat  15240
cccacattat catctgttag agtagtatca ttaaatctat tatattttat gaaagatata  15300
tcactgctca cctctatatt tcgtacattt ttaaactgtt tgtataatat ctctctgata  15360
caatcagata tatctattgt gtcggtagac gataccgtta catttgaatt aatggtgttc  15420
cattttacaa cttttaacaa gttgaccaat tcatttctaa tagtatcaaa ctctccatga  15480
ttaaatattt taatagtatc cattttatat cactacggac acaaagtagc tgacataaac  15540
cattgtataa tttttatgtt ttatgtttat tagcgtacac attttggaag ttccggcttc  15600
catgtatttc ctggagagca agtagatgat gaggaaccag atagtttata tccgtacttg  15660
cacttaaagt ctacattgtc gttgtatgag tatgatcttt taaacccgct agacaagtat  15720
```

```
ccgtttgata ttgtaggatg tggacattta acaatctgac acgtgggtgg atcggaccat  15780
tctcctcctg aacacaggac accagagtta ccaatcaacg aatatccact attgcaacta  15840
taagttacaa cgctcccatc ggtataaaaa tcctcgtatc cgttatgtct tccgttggat  15900
atagatggag gggattggca tttaacagat tcacaaatag gtgcctcggg attccatacc  15960
atagatccag tagatcctaa ttcacaatac gatttagatt caccgatcaa ctgatatccg  16020
ctattacaag agtacgttat actagagcca aagtctactc cgccaatatc aagttggcca  16080
ttatcgatat ctcgaggcga tgggcatctc cgtttaatac attgattaaa gagtgtccat  16140
ccagtacctg tacatttagc atatataggt cccatttttt gctttctgta tccaggtaga  16200
catagatatt ctatagtgtc tcctatgttg taattagcat tagtttccac actattctta  16260
aattttatat taatgggacg tgaaggaata ggacagtatg atagaacgca tcctattccc  16320
aacaatgtca ggaacgtcac gctctccacc ttcatattta tttatccgta aaaatgttat  16380
cctggacatc gtacaaataa taaaaaagcc catatatgtt tgctattgta gaaattgttt  16440
ttcacagttg ctcaaaaacg atggcagtga cttatgagtt tcatctttag taaacatatc  16500
ataatattcg atattacgag ttgacatatc gaacaaattc caagtatttg attttggata  16560
atattcgtat tttgcatctg ctataattaa gatataatca ccgcaagaac acacgaacat  16620
ctttcctaca tggttaaagt acatgtataa ttctatccat ttgtcttcct taactatata  16680
tttgtataga taattacgag tctcataagt aattccagta attgcataga tgtcaccatc  16740
gtactctaca gcataaacta tactatgatg tctaggcatg ggagactttt ttatccaacg  16800
atttttagtg aaacattcta catcgtttaa tactacatat ttctcatacg tggtataaac  16860
tccacccatt acatatatat catcgtttac gaataccgac gcgcctgaat atctaggagt  16920
aattaagttt ggaagtctta tccatttcga agtgccgtgt ttcaaatatt ctgccacacc  16980
cgttgaaata gaaaattcta atcctcctat tacatataac tttccatcgt taacacaagt  17040
actaacttct gattttaacg acgacatatt agtaaccgtt ttccattttt tcgttttaag  17100
atctacccgc gatacggaat aaacatgtct attgttaatc atgccgccaa taatgtatag  17160
acaattatgt aaaacatttg cattatagaa ttgtctatct gtattaccga ctatcgtcca  17220
atattctgtt ctaggagagt aatgggttat tgtggatata taatcagagt ttttaatgac  17280
tactatatta tgttttatac catttcgtgt cactggcttt gtagatttgg atatagttaa  17340
tcccaacaat gatatagcat tgcgcatagt attagtcata aacttgggat gtaaaatgtt  17400
gatgatatct acatcgtttg gatttttatg tatccacttt aataatatca tagctgtaac  17460
atcctcatga tttacgttaa cgtcttcgtg ggataagata gttgtcagtt catcctttga  17520
taattttcca aattctggat cggatgtcac cgcagtaata ttgttgatta tttctaacat  17580
cgacgcatta tatagttttt taattccata ttgtttagaa aagttaaaca tccttataca  17640
atttgtggaa ttaatattat gaatcatagt ttttacacat agatctacta caggcgtaac  17700
atcaattatt acggcagcaa ctagtatcat ttctacattg tttatggtga tgtttatctt  17760
cttccagcgc atatagtcta atagcgattc aaacgcgtga tagtttatac cattcaatat  17820
aatcacttca tcatttatat ggtgctcctg aatgcgttta aaaaaattat acggagacgc  17880
cgtaataatt tccttattca cttgtataat ttccccattg atagaaaata tcacgctttc  17940
cattcttgaa gtactataag taattatagt ataatgtaaa cgtttatata ttcaatattt  18000
ttataaaaat cattttgaca ttaattcctt tttaaatttc cgtctatcat ctatagaaac  18060
```

```
gtattctatg aatttataaa atgcttttac gtgtcctatc gtaggcgata gaaccgctaa  18120
aaagcctatc gaatttctac aaaagaatct attatatggt atagggagag tataaaacat  18180
taaatgcccg tacttattaa agtattcagt agccaatcct aactctttcg aatacttatt  18240
aatggctctt gttctgtacg aatctatttt tttgaacaac ggacctagtg gtatatcttg  18300
ttctatgtat ctaaaataat gtctgactag atccgttagt ttaatatcct cagtcatctt  18360
gtctagaatg gcaaatctaa ctgcgggttt aggctttagt ttagttttta tatctacatc  18420
tatgtcttta tctaacacca aaaatataat agctaatatt ttattacaat catccggata  18480
ttcttctacg atctcactaa ctaatgtttc tttggttata ctagtatagt cacgatcaga  18540
caaataaaga aaatcagatg atcgatgaat aatacattta aattcatcat ctgtaagatt  18600
tttgagatgt ctcattaaaa tattattagg gttagtactc attatcattc ggcagctatt  18660
acttatttta ttatttttca ccatatagat caatcattag atcatcaaaa tatgtttcaa  18720
tcatcctaaa gagtatggtg aatgactctt cccatctaat ttctgaacgt tcaccaatgt  18780
ctctagccac tttggcacta atagcgatca ttcgcttagc gtcttctata ttattaactg  18840
gttgattcaa tctatctagc aatggaccgt cggacagcgt cattctcatg ttcttaatca  18900
atgtacatac atcgccgtca tctaccaatt catccaacaa cataagcttt ttaaaatcat  18960
cattataata ggtttgatcg ttgtcatttc tccaaagaat atatctaata agtagagtcc  19020
tcatgattag ttaacaacta ttttttatgt taaatcaatt agtacaccgc tatgtttaat  19080
acttattcat attttagttt ttaggattga gaatcaatac aaaaaattaa tgcatcatta  19140
attttagaaa tacttagttt ccacgtagtc aatgaaacat ttgaactcat cgtacaggac  19200
gttctcgtac aggacgtaac tataaaccgg tttatatttg ttcaagatag atacaaatcc  19260
gataactttt tttacgaatt ctacgggatc cactttaaaa gtgtcatacc gggttctttt  19320
tattctttta aacagatcaa tggtgtgatg ttgattaggt cttttacgaa tttgatatag  19380
aatagcgttc acatatcctc cataatggtc aatcgccatt tgttcgtatg tcataaattc  19440
tttaattata tgacactgtg tattatttag ttcatccttg ttcatcatta ggaatctatc  19500
caaaatggca attatactag aactataggt gcgttgtata cacatattga tgtgtctgtt  19560
tatacaatcc atgatatttg gatccatgct actaccttcg ggtaaaattg tagcatcata  19620
taccatttct agtactttag gttcattatt atccattgca gaggacgtca tgatcgaatc  19680
ataaaaaaat atattatttt tatgttattt tgttaaaaat aatcatcgaa tacttcgtaa  19740
gatactcctt catgaacata atcagttaca aaacgtttat atgaagtaaa gtatctacga  19800
tttttacaaa agtccggatg cataagtaca aagtacgcga taaacggaat aataatagat  19860
ttatctagtc tatctttttc tatagctttc atagttagat acatggtctc agaagtagga  19920
ttatgtaaca tcagcttcga taaaatgact gggttattta gtcttacaca ttcgctcata  19980
catgtatgac cgttaactac agagtctaca ctaaaatgat tgaacaatag atagtctacc  20040
attgtttcgt attcagatag tacagcgtag tacatggcat cttcacaaat tatatcattg  20100
tctaatagat atttgacgca tcttatggat cccacttcaa cagccatctt aaaatcggta  20160
aaatcatatt gctttccttt atcattaata atttctaaaa catcatctct atcataaaag  20220
atacaaatat taactgtttg atccgtaata acattgctag tcgatagcaa tttgttaata  20280
agatgcgctg ggctcaatgt cttaataaga agtgtaagag gactatctcc gaatttgttt  20340
tgtttattaa catccgttga tggaagtaaa agatctataa tgtctacatt cttgactgtt  20400
ttagagcata caatatggag aggtgtattt ccatcatgat ctggttttga gggactaatt  20460
```

```
cctagtttca tcatccatga gattgtagaa gcttttggat tgtctgacat aagatgtcta  20520
tgaatatgat ttttgccaaa tttatccact atcctggctt cgaatccgat ggacattatt  20580
tttttaaaca ctctttctga aggatctgta cacgccaaca acggaccaca tccttcttca  20640
tcaaccgagt tgttaatctt ggctccatac tgtaccaata aatttattct ctctatgact  20700
tcatcatctg ttcccgagag ataatataga ggtgttttat tatgtttatc acacgcgttt  20760
ggatctgcgc cgtgcgtcag cagcatcgcg actattctat tattattaat tttagaagct  20820
atatgcaatg gataatttcc atcatcatcc gtctcatttg gagagtatcc tctatgaaga  20880
agttcttcga caaatcgttc atctagtcct ttaattccac aatacgcatg tagaatgtga  20940
taattatttc cagaaggttc gatagcttgt agcatattcc taaatacatc taaattttta  21000
ctattatatt tggcataaag agatagataa tactcggccg acataatgtt gtccattgta  21060
gtataaaaat taatatttct atttctattt ctgtatattt gcaacaattt actctctata  21120
acaaatatca taacttagtt cttttatgtc aagaaggcac tggtttagtt catctataaa  21180
tgtcacgcca taactaccac gcatgccata ctcagaatta tgataaagat atttatcctt  21240
ggggtgtagg taatggggat taatctttgt tggatcagtc tctaagttaa cacatgtcac  21300
acatgatcca tttatagtta tatcacacga tgatgattta tgaattgatt ccggaagatc  21360
gctatcgtat tttgtggttc cacaattcat ttccatacat gttattgtca cactaatatt  21420
atgatgaact ttatctagcc gctgagtggt aaacaacaga acagatagtt tattatcttt  21480
accaacaccc tcagccgctg ccacaaatct ctgatccgta tccatgatgg tcatgtttat  21540
ttctagtccg tatccagtca acactatgtt agcatttctg tcgatatagc tttcactcat  21600
atgacactca ccaataatag tagaattaat gtcgtaattt acaccaatag tgagttcggc  21660
ggcaaagtac caataccggt aatcttgtcg aggaggacat atagtattct tgtattctac  21720
tgaatacccg agagatgcga tacaaaagag taagactaat ttgtaaacca tcttactcaa  21780
aatatgtaac aatagtacga tgcaatgagt aagacaatag gaaatctatc ttatatacac  21840
ataattattc tatcaatttt accaattagt tagtgtaatg ttaacaaaaa tgtgggagaa  21900
tctaattagt ttttctttac acaattgacg tacatgagtc tgagttcctt gtttttgcta  21960
attatttcat ccaatttatt attcttgact atatcgagat cttttgtata ggagtcagac  22020
ttgtattcaa catgcttttc tataatcatt ttagctattt cggcatcatc caatagtaca  22080
ttttccagat tagcagaata gatattaatg tcgtatttga acagagcctg taacatctca  22140
atgtctttat tatctatagc caatttaatg tccggaatga agagaaggga attattggtg  22200
tttgtcgacg tcatatagtc gagcaagaga atcatcatat ccacgtgtcc atttttttata  22260
gtggtgtgaa tacaactaag gagaatagcc agatcaaaag tagatggtat ctctgaaaga  22320
aagtaggaaa caatacttac atcattaagc atgacggcat gataaaatga agttttccat  22380
ccagttttcc catagaacat cagtctccaa tttttcttaa caaacagttt taccgtttgc  22440
atgttaccac tatcaaccgc ataatacaat gcggtgtttc ccttgtcatc aaattgtgaa  22500
tcatccagtc cactgaatag caaaatcttt actattttgg tatcttccaa tgtggctgcc  22560
tgatgtaatg gaaattcatt ctctagaaga tttttcaatg ctccagcgtt caacaacgta  22620
catactagac gcacgttatt atcagctatt gcataataca aggcactatg tccatggaca  22680
tccgccttaa atgcatcttt gctagagaga aagcttttca gctgcttaga cttccaagta  22740
ttaattcgtg acagatccat gtctgaaacg agacgctaat tagtgtatat tttttcattt  22800
```

-continued

```
tttataattt tgtcatattg caccagaatt aataatatct ctaatagatc tgattagtag  22860
atacatggct atcgcaaaac aacatataca catttaataa aaataatatt tattaagaaa  22920
attcagattt cacgtaccca tcaatataaa taaaataatg attccttaca ccgtacccat  22980
attaaggaga ttccacctta cccataaaca atataaatcc agtaatatca tgtctgatga  23040
tgaacacaaa tggtgtatta aattccagtt tttcaggaga tgatctcgcc gtagctacca  23100
tgatagtaga tgcctctgct acagttcctt gttcgtcgac atctatcttt gcattctgaa  23160
acattttata aatatataat gggtccctag tcatatgttt aaacaacgca ttatctggat  23220
taaacatact aggagccatc atttcggcta tcgacttaat atccctctta ttttcgatag  23280
aaaatttagg gagtttaaga ttgtacactt tattccctaa ttgaaacgac caatagtcta  23340
attttgcagc cgtaatagaa tctgtgaaat gggtcatatt atcacctatt gccaggtaca  23400
tactaatatt agcatcctta tacggaaggc gtaccatatc atattcttcg tcatcgattg  23460
tgattgtatt tccttgcaat ttagtaacta cgttcatcat gggaaccgtt ttcgtaccgt  23520
acttattagt aaaactagca ttgcgtgttt tagtgatatc aaacggatat tgccatatac  23580
ctttaaaata tatagtatta atgattgccc atagagtatt attgtcgagc atattagaat  23640
ctactacatt agacataccg gatctacgtt ctactataga attaatttta ttaaccgcat  23700
ctcgtctaaa gtttaatcta tataggccga atctatgata ttgttgataa tacgacggtt  23760
taatgcacac agtattatct acgaaacttt gataagttag atcagtgtac gtatatttag  23820
atgttttcag cttagctaat cctgatatta attctgtaaa tgctggaccc agatctcttt  23880
ttctcaaatc catagtcttc aataattcta ttctagtatt acctgatgca ggcaatagcg  23940
acataaacat agaaaacgaa taaccaaacg gtgagaagac aatattatca tcttgaatat  24000
ttttatacgc tactataccg gcattggtaa atccttgcag acgataggta gacactgaac  24060
acgttaacga tagtatcaat aacgcaatca tgattttatg gtattaataa ttaaccttat  24120
ttttatgttc ggtataaaaa ttattgatgt ctacacatcc ttttgtaatt gacatctata  24180
tatccttttg tataatcaac tctaatcact ttaactttta cagttttccc taccagttta  24240
tccctatatt caacatatct atccatatgc atcttaacac tctctgccaa gatagcttca  24300
aagtgaggat agtcaaaaag ataaatatat agagcataat cattctcgta tactctgccc  24360
tttattacat cacccgcatt gggcaacgaa taacaaaatg caagcatctt gttaacgggc  24420
tcgtaaattg ggataaaaat tatgttttta tatctatttt attcaagaga atattcagga  24480
atttcttttt ccggttgtat ctcatcgcag tatatatcat ttgtacattg tttcatattt  24540
tttaatagtc tacacctttt agtaggacta gtatcgtaca attcatagct gtattttgaa  24600
ttccaatcac gcataaaaat atcttccaat tgttgacgaa gacctaatcc atcatccggt  24660
gtaatattaa tagatgctcc acatgtatcc gtaaagtaat ttcctgtcca atttgaggta  24720
cctatatacg ccgttttatc ggttaccata tatttggcat ggtttaccct agaatacgga  24780
atgggaggat cagcatctgg tacaataaat agctttactt ctatatttat gtttttagat  24840
tttagcatag cgatagatct taaaaagttt ctcatgataa acgaagatcg ttgccagcaa  24900
ctaatcaata gcttaacgga tacttgtctg tctatagcgg ctcttcttaa ttcatcttct  24960
atataaggcc aaaacaaaat attgcctgcc ttcgaataaa taatagggat aaagttcata  25020
acagatacat aaacgaattt actcgcattt ctaatacatg acaataaagc ggttaaatca  25080
ttggttcttt ccatagtaca tagttgttgc ggtgcagaag caataaatac agagtgtgga  25140
acaccactta cgttaatact aagaggatga tctgtattat aatacgacgg ataaaagttt  25200
```

```
ttccaattat atggtagatt gttaactcca agataccagt atacctcaaa aatttgagtg  25260
agatccgctg ccaagttcct attattgaag atcgcaatac ccaattcttt gacctgagtt  25320
agtgatctcc aatccatgtt agcgcttcct aaataaatat gtgtattatc agatatccaa  25380
aattttgtat gaagaactcc tcctaggata tttgtaatat ctatgtatcg tacttcaact  25440
ccggccattt gtagtctttc aacatccttt aatggtttgt tagatttatt gacggctact  25500
ctaactctta ctcctctttt gggtaattgt acaatctcgt ttaatattat cgtgccgaaa  25560
ttcgtaccca cttcatccga taaactccaa taaaaagatg atatatctag tgtttttgtg  25620
gtattggata gaatttccct ccacatgtta aatgtagaca aatatacttt atcaaattgc  25680
atacctatag gaatagtctc tgtaatcact gcgattgtat tatccggatt cattttattt  25740
gttaaaaaat aatcctatat cacttcactc tattaaaaat ccaagtttct atttctttca  25800
tgactgattt tttaacttca tccgtttcct tatgaagatg atgtttggca ccttcataaa  25860
tttttatttc tctattacaa tttgcatgtt gcatgaaata atatgcacct aaaacatcgc  25920
taatctcatt gtttgttccc tggagtatga gagtcggggg gtgttaatct tgggaattat  25980
ttttctaacc ttgttggtag ccttcaagac ctgactagca aatccagcct taattttttc  26040
atgattgatt aatgggtcgt attggtattt ataaacttta tccatatctc tagatactga  26100
ttctggacat agctttccga ctggcgcatt tggtgtgatg gttcccataa gtttggcagc  26160
tagcagattc agttttgaaa cagcatctgc attaactaga ggagacatta gaatcattgc  26220
tgtaaacaag tttggattat cgtaagaggc tagtatagaa attgttgctc ccatggaatg  26280
cccaataaga agactggaac tcctaaataa gtagatttaa tagttaccac gtgctgtacc  26340
acatctctaa catacgtacc aaagtcatca atcatcattt tttcaccatt acttcttcca  26400
tgtccaatat gatcatgtga gaatactaaa attcctaacg atgatatgtt ttcagctagt  26460
tcgtcataac gtccagaatg tttaccagct ccatgactta tgaatactaa tgccttagga  26520
tatgtaatag gtttccaata tatgtaatca ttgtccagat tgaacataca gtttgcactc  26580
atgattcacg ttatataact atcaatatta acagttcgtt tgatgatcat attattttta  26640
tgttttattg ataattgtaa aaacatacaa ttaaatcaat atagaggaag gagacggcta  26700
ctgtcttttg tgagatagtc atggcgacta aattagatta tgaggatgct gtttttttact  26760
ttgtggatga tgataaaata tgtagtcgcg actccatcat cgatctaata gatgaatata  26820
ttacgtggag aaatcatgtt atagtgttta acaaagatat taccagttgt ggaagactgt  26880
acaaggaatt gatgaagttc gatgatgtcg ctatacggta ctatggtatt gataaaatta  26940
atgagattgt cgaagctatg agcgaaggag accactacat caattttaca aaagtccatg  27000
atcaggaaag tctattcgct accataggaa tatgtgctaa aatcactgaa cattggggat  27060
acaaaaaagat ttcagaatct agattccaat cattgggaaa cattacagat ctgatgaccg  27120
acgataatat aaacatcttg atactttttc tagaaaaaaa attgaattga tgatataggg  27180
gtcttcataa cgcataatta ttacgttagc attctatatc cgtgttaaaa aaaattatcc  27240
tatcatgtat ttgagagttt tatatgtagc aaacatgata gctgtgatgc caataagctt  27300
tagatattca cgcgtgctag tgttagggat ggtattatct ggtggtgaaa tgtccgttat  27360
ataatctaca aaacaatcat cgcatatagt atgcgatagt agagtaaaca tttttatagt  27420
ttttactgga ttcatacatc gtctacccaa tttggttata aatgaaattg tcgccaatct  27480
tacacccaac cccttgttat ccattagtat agtattaact tcgttattta tgtcataaac  27540
```

```
tgtaaatgat tttgtagatg ccatatcata catgatattc atgtccctat tataatcatt  27600
actaacttta tcacaatata tgttgataat atctatatat gatctagtct ttgtgggcaa  27660
ctgtctatac aagtcgtcta aacgttgttt actcatatag tatcgaacag ccatcattac  27720
atggtcccgt tccgttgata gataatcgag tatgttagtg gacttgtcaa atctatatac  27780
catattttct ggaagtggat atacatagtc gtgatcaaca ttattgctag cctcatcttc  27840
tatatcatgt actataccat tatctatatc atctacataa tctacgatat tattacacat  27900
aaacatcgac aacatactat tgtttattat ctaagtcctg ttgatccaaa cccttgatct  27960
cctctatttg tactatctag agattgtact tcttccagtt ctggataata tatacgttga  28020
tagattagct gagctattct atctccagta tttacattaa acgtacattt tccattatta  28080
ataagaatga ctcctatgtt tcccctataa tcttcgtcta ttacaccacc tcctatatca  28140
atgcctttta gtgacagacc agacctagga gctattctac catagcaaat cttaggcatg  28200
gacatactaa tatctgtctt aattaactgt ctttctcctg gagggatagt ataatcgtaa  28260
gcgctataca aatcatatcc ggcagcaccc ggcgattgcc tagtaggaga tttagctctg  28320
ttagtttcct taacaaatct aactggtgag ttaatattca tgttgaacat aaaactaata  28380
ttttatttca aaattattta ccatcccata tattccatga ataagtgtga tgattgtaca  28440
cttctatagt atctatatac gattcacgat aaaatcctcc tatcaatagc agtttattat  28500
ccactatgat caattctgga ttatccctcg gataaatagg atcatctatc agagtccatg  28560
tattgctgga ttcacaataa aattccgcat ttctaccaac caagaataac cttctaccga  28620
acactaacgc gcatgattta taatgaggat aataagtgga tggtccaaac tgccactgat  28680
catgattggg tagcaaatat tctgtagttg tatcagtttc agaatgtcct cccattacgt  28740
atataacatt gtttatagat gccactgctg gattacatct aggtttcaga agactcggca  28800
tattaaccca agcagcatcc ccgtggaacc aacgctcaac agatgtggga tttggtagac  28860
ctcctactac gtataattta ttgttagcgg gtatcccgct agcatacagt ctggggctat  28920
tcatcggagg aattggaatc caattgtttg atatataatt tacagctata gcattgttat  28980
gtatttcatt gttcatccat ccaccgatga gatatactac ttctccaaca tgagtacttg  29040
tacacatatg gaatatatct ataatttgat ccatgttcat aggatactct atgaatggat  29100
acttgtatga tttgcgtggt tgtttatcac aatgaaatat tttggtacag tctagtatcc  29160
attttacatt atttatacct ctgggagaaa gataatttga cctgattaca tttttgataa  29220
ggagtagcag atttcctaat ttatttcttc gctttatata ccacttaatg acaaaatcaa  29280
ctacataatc ctcatctgga acatttagtt catcgctttc tagaataagt ttcatagata  29340
gataatcaaa attgtctatg atgtcatctt ccagttccaa aaagtgtttg gcaataaagt  29400
ttttagtatg acataagaga ttggatagtc cgtattctat acccatcatg taacactcga  29460
cacaatattc ctttctaaaa tctcgtaaga taaagtttat acaagtgtag atgataaatt  29520
ctacagaggt taatatagaa gcacgtaata aattgacgac gttatgacta tctatatata  29580
cctttccagt atacgagtaa ataactatag aagttaaact gtgaatgtca aggtctagac  29640
aaaccctcgt aactggatct ttatttttcg tgtatttttg acgtaaatgt gtgcgaaagt  29700
aaggagataa ctttttcaat atcgtagaat tgactattat attgccacct atagcatcaa  29760
taattgtttt gaatttctta gtcatagaca atgctaatat attcttacag tacacagtat  29820
taacaaatat cggcatttat gtttctttaa aagtcaacat ctagagaaaa atgattatct  29880
ttttgagaca taactcccat tttttggtat tcacccacac gtttttcgaa aaaattagtt  29940
```

```
tttccttcca atgatatatt ttccatgaaa tcaaacggat tggtaacatt ataaattttt  30000
ttaaatccca attcagaaat caatctatcc gcgacgaatt ctatatatgt tttcatcatt  30060
tcacaattca ttcctataag tttaactgga agagccgcag taagaaattc ttgttcaatg  30120
gatactgcat ctgttataat agatctaacg gtttcttcac tcggtggata caataaatgt  30180
ttaaacatca aacatgcgaa gtcgcagtgt agaccctcgt ctctactaat tagttcgttg  30240
gaaaacgtga gtccgggcat taggccacgc tttttaagcc aaaatatgga agcgaatgat  30300
ccggaaaaga agattccttc tactgcagca aaggcaataa gtctctctcc ataaccggcg  30360
ctgtcatgta tccacttttg agcccaatcg gccttctttt ttacacaagg catcgtttct  30420
atggcattaa agagatagtt tttttcatta ctatctttaa cataagtatc gatcaaaaga  30480
ctatacattt ccgaatgaat gttttcaatg gccatctgaa atccgtagaa acatctagcc  30540
tcggtaatct gtacttctgt acaaaatcgt tccgccaaat tttcattcac tattccgtca  30600
ctggctgcaa aaaacgccaa tacatgtttt ataaaatatt tttcgtctgg tgttagttta  30660
ttccaatcat tgatatcttt agatatatct acttcttcca ctgtccaaaa tgatgcctct  30720
gcctttttat acatgttcca gatgtcataa tattggattg ggaaaataac aaatctattt  30780
ggatttggtg caaggatggg ttccataact aaattaacaa tatcaataaa ttttttttca  30840
gttatctata tgcctgtact tggatttttt gtacatcgat atcgccgcaa tcactacaat  30900
aattacaagt attattgata gcattgttat tagtactatc ataattaaat tatcgacatt  30960
catgggtgct gaataatcgt tattatcatc attatcattt tgtaattgtg acatcatact  31020
aaataaatcg tttgcgagat tgttgtggga agcgggcatg gaggatgcat tatcattatt  31080
atttaacgcc ttccatttgg attcacaaat gttacgcaca ttcaacattt tatggaaact  31140
ataattttgt gaaaacagat aacaagaaaa ctcgttatcg ttcaaatttt taacgatagt  31200
aaaccgatta aacgtcgagc taatttctaa cgctagcgac tctgttggat atgggtttcc  31260
agatatatat cttttcagtt cccctacgta tctataatca tctgtaggaa atggaagata  31320
tttccattta tctactgttc ctaatatcat atgtggtggt gtagtagaac cattaagcgc  31380
gaaagatgtt atttcgcatc gtattttaac ttcgcaataa tttctggtta gataacgcac  31440
tctaccagtc aagtcaatga tattagcctt tacagatata ttcatagtag tcgtaacgat  31500
gactccatct tttagatgcg atactccttt gtatgtacca gaatcttcgt acctcaaact  31560
cgatatattt aaacaagtta atgagatatt aacgcgtttt atgaatgatg atatataacc  31620
agaagtttta tcctcggtgg ctagcgctat aaccttatca ttataatacc aactagtgtg  31680
attaatatgt gacacgttag tgtgggtaca aatatgtaca ttatcgtcta cgtcgtattc  31740
gatacatccg catacagcca acaaatataa aatgacaaat actctaacgc cgttcgtacc  31800
catcttgatg cggtttaata aatgttttga tttcaattta ttgtaaaaaa agattcggtt  31860
ttatactgtt cgatattctc attgcttata ttttcatcta tcatctccac acagtcaaat  31920
ccgtggttag catgcacctc atcaaccggt aaaagactat cggactcttc tatcattata  31980
actctagaat atttaatttg gtcattatta atcaagtcaa ttatcttatt tttaacaaac  32040
gtgagtattt tactcatttt ttataaaaac ttttagaaat atacagactc tatcgtgtgt  32100
ctatatcttc tttttatatc caatgtattt atgtctgatt tttcttcatt tatcatatat  32160
aatggtccaa attctacacg tgcttcggat tcatccagat cattaaggtt cttataattg  32220
taacatcctt ctcttccctc ttctacatct tccttcttat tcttattctt agcgtcacag  32280
```

```
aatctaccac agcaggatcc catgacgagc gtcatattaa actaattcat tttcaattat  32340
aatatactgg taatgaccat taaaataaaa atattcttca taaccggtaa gaaagtgaaa  32400
agttcacatt gaaactatgt cagtagtata catcatgaaa tgagatgaaa tgatgatata  32460
tatactctat tttggtggag gattatatga tataattcgt ggataatcat ttttaagaca  32520
catttcttta ttcgtaaatc ttttcacgtt aaatgagtgt ccatattttg caatttcttc  32580
atatgatggc ggtgtacgtg gacgaggctg ctcctgttct tgttgtagtc gccgactgtc  32640
gtgtttgcgt ttagatccct ccattatcgc gattgcgtag atggagtact attatatacc  32700
ttgtaattaa atttttttat taattaaacg tataaaaacg ttccgtatct gtatttaaga  32760
gccagatttc gtctaataga acaaatagct acagtaaaaa taactagaat aattgctaca  32820
cccactagaa accacggatc gtaatacggc aatcggtttt cgataatagg tggaacgtat  32880
attttattta aggacttaac aattgtctgt aaaccacaat ttgcttccgc ggatcctgta  32940
ttaactatct gtaaaagcat atgttgaccg ggcggagccg aacattctcc gatatctaat  33000
ttctgtatat ctataatatt attaacctcc gcatacgcat tacagttctt ttctagcttg  33060
gataccgcac taggtacatc gtctagatct attcctattt cttcagcgat agctcttcta  33120
tccttttccg gaagcaatga aatcacttca ataaatgatt caaccatgag tgtgaaacta  33180
agtcgagaat tactcatgca tttgttagtt attcggagcg cgcaattttt aaactgtcct  33240
ataacctctc ctatatgaat agcacaagtg acattagtag ggatagaatg ttgagctaat  33300
ttttgtaaat aactatctat aaaaagatta tacaaagttt taaactcttt agtttccgcc  33360
atttatccag tctgagaaaa tgtctctcat aataaatttt tccaagaaac taattgggtg  33420
aagaatggaa acctttaatc tatatttatc acagtctgtc ttggtacaca tgatgaattc  33480
ttctaatgct gtactaaatt cgatatcttt ttcgatttct ggatatgttt ttaataaagt  33540
atgaacaaag aaatggaaat cgtaatacca gttatgttta actttgaaat tgttttttat  33600
tttcttgtta atgattccag ccacttggga aaagtcaaag tcgtttaatg ccgatttaat  33660
acgttcatta aaaacaaact ttttatcctt tagatgaatt attattggtt cattggaatc  33720
aaaaagtaag atattatcgg gtttaagatc tgcgtgtaaa aagttgtcgc agcatggtag  33780
ttcgtaaatt ttaatgtata acagagccat ctgtaaaaag ataaacttta tgtattgtac  33840
caaagattta aatcctaatt tgatagctaa ctcggtatct actttatctg cagaatacag  33900
tgctagggga aaaattataa tatttcctct ttcgtattcg tagttagttc tcttttcatg  33960
ttcgaaaaag tgaaacatgc ggttaaaata gtttataaca ttaatattac tgttaataac  34020
tgccgggtaa aagtgggata gtaatttcac gaatttgata ctgtcctttc tctcgttaaa  34080
cgcctttaaa aaaactttag aagaatatct caatgagagt tcctgaccat ccatagtttg  34140
tatcaataat agcaacatat gaagaacccg tttatacaga gtatgtaaaa atgttaattt  34200
atagtttaat cccatggccc acgcacacac gattaatttt ttttcatctc cctttagatt  34260
gttgtataga aatttgggta ctgtgaactc cgccgtagtt tccatgggac tatataattt  34320
tgtggcctcg aatacaaatt ttactacata gttatctatc ttaaagacta taccatatcc  34380
tcctgtagat atgtgataaa aatcgtcgtt tataggataa aatcgtttat ccttttgttg  34440
gaaaaaggat gaattaatgt aatcattctc ttctatcttt agtagtgttt ccctattaaa  34500
attcttaaaa taatttaaca atctaactga cggagcccaa ttttggtgta aatctaattg  34560
ggacattata ttgttaaaat acaaacagtc tcctaatata acagtatctg ataatctatg  34620
gggagacatc cattgatatt caggggatga atcattggca acacccattt attgtacaaa  34680
```

```
aagccccaat ttacaaacga aagtccaggt ttgatagaga caaactatta actattttgt  34740
ctctgttttt aatttcttta gtaatgaaat tattcacaat atcagtatct tctttatcta  34800
ccagagattt tactaacttg ataaccttgg ctgtctcatt caatagggta gtaatatttg  34860
tatgtgtgat attgatatct ttttgaattg tttcttttag aagtgattct ttgatggtgc  34920
cagcatacga attacaataa tgcagaaact cggttaacat gcaggaatta tagtaagcca  34980
attccaattg ttgcctgtat tgtattagag tattaatatg cgcaatggtg tccttgcgtt  35040
tctctgatag aatgcgagca gcgattttgg cgttatcatt tgacgatatt tctggaatga  35100
cgaatcctgt ttctactaac tttttggtag gacaaagtga aacaatcaag aagatagctt  35160
ctcctcctat ttgtggaaga aattgaactc ctctagatga tctactgacg atagtatctc  35220
cttgacagat attggaccga attacagaag tacctggaat gtaaagccct gaaacccccct  35280
catttttttaa gcagattgtt gccgtaaatc ctgcactgtg accaagatag agagctcctt  35340
tggtgaatcc atctctatgt ttcagtttaa ccaagaaaca gtcagctggt ctaaaatttc  35400
catctctatc taatacagca tctaacttga tgtcaggaac tatgaccggt ttaatgttat  35460
atgtaacatt gagtaaatcc ttaagttcat aatcatcact gtcatcagtt atgtacgatc  35520
caaacaatgt ttctaccggc atagtggata cgaagatgct atccatcaga atgtttccct  35580
gattagtatt ttctatatag ctattcttct ttaaacgatt ttccaaatca gtaactatgt  35640
tcattttttt aggagtagga cgcctagcca gtatggaaga ggattttcta gatcctctct  35700
tcaacatctt tgatctcaat ggaatgcaaa accccatagt gaaacaacca acgataaaaa  35760
taatattgtt tttcactttt tataatttta ccatctgact catggattca ttaatatctt  35820
tataagagct actaacgtat aattctttat aactgaactg agatatatac accggatcta  35880
tggtttccat aattgagtaa atgaatgctc ggcaataact aatggcaaat gtatagaaca  35940
acgaaattat actagagttg ttaaagttaa tattttctat gagctgttcc aataaattat  36000
ttgttgtgac tgcgttcaag tcataaatca tcttgatact atccagtaaa cagtctttaa  36060
gttctggaat attatcatcc cattgtaaag cccctaattc gactatcgaa tatcctgctc  36120
tgatagcagt ttcaatatcg acggacgtca atactgtaat aaaggtggta gtattgtcat  36180
catcgtgata aactactgga atatggtcgt tagtaggtac ggtaacttta cacaacgcga  36240
tatataactt tccttttgta ccatttttaa cgtagttggg acgtcctgca gggtattgtt  36300
ttgaagaaat gatatcgaga acagatttga tacgatattt gttggattcc tgattattta  36360
ctataatata atctagacag atagatgatt cgataaatag aaaaggtata tcgttggtag  36420
gataatacat ccccattcca gtattctcgg atactctatt aatgacacta gttaagaaca  36480
tgtcttctat tctagaaaac gaaaacatcc tacatggact cattaaaact tctaacgctc  36540
ctgattgtgt ctcgaatgcc tcgtacaagg atttcaagga tgccatagat tctttgacca  36600
acgatttaga attgcgttta gcatctgatt tttttattaa atcgaatggt cggctctctg  36660
gtttgctacc ccaatgataa caatagtctt gtaaagataa accgcaagaa aatttatacg  36720
catccatcca aataacccta gcaccatcgg atgatattaa tgtattatta tagattttcc  36780
atccacagtt attgggccag tatactgtta gcaacggtat atcgaataga ttactcatgt  36840
aacctactag aatgatagtt cgtgtactag tcataaatatc tttaatccaa tctaagaaat  36900
ataaaattag atcttttaca ctgttaaagt taacaaaggt attacccgga tacgtggata  36960
tcatatatgg cattggtcca ttatcagtaa tagctccata aactgatacg gcgatggttt  37020
```

```
ttatatgtgt ttgatctaac gaggaagaaa ttcgcgccca caattcatct ctagatatgt  37080
atttaatatc aaacggtaac acatcaattt cgggacgcgt atatgtttct aaatttttaa  37140
tccaaatata atgatgacct atatgcccta ttatcatact gtcaactata gtacacctag  37200
agaacttacg atacatctgt ttcctgtaat cgttaaattt tacaaatcta taacatgcta  37260
aacctttttga cgacaaccat tcattaattt ctgatatgga atctgtattc tcgataccgt  37320
attgttctaa agccagtgct atatctccct gttcgtggga acgctttcgt ataatatcga  37380
tcaacggata atctgaagtt tttggagaat aatatgactc atgatctatt tcgtccataa  37440
acaatctaga catagggaatt ggaggcgatg atcttaattt tgtgcaatga gtcgtcaatc  37500
ctataacttc taatcttgta atattcatca tcgacataat actatctatg ttatcatcgt  37560
atattagtat accatgacct tcttcatttc gtgccaaaat gatatacagt cttaaatagt  37620
tacgcaatat ctcaatagtt tcataattgt tagctgtttt catcaagatt tgtaccctgt  37680
ttaacatgat ggcgttctat acgtttctat tttctatttt ttaaattttt aacgatttac  37740
tgtggctaga tacccaatct ctctcaaata ttttttttagc ctcgcttaca agctgtttat  37800
ctatactatt aaaactgacg aatccgtgat tttggtaatg ggttccgtcg aaatttgccg  37860
aagtgatatg aacatattcg tcgtcgacta tcaacaattt tgtattattc tgaatagtga  37920
aaaccttcac agatagatca ttttgaacac acaacgcgtc tagacttctg gcggttgcca  37980
tagaatatac gtcgttctta tcccaattac caactagaag tctgatctta actcctctat  38040
taatggctgc ttctataatg gagttgtaaa tgtcgggcca atagtagcta ttaccgtcga  38100
cacgtgtagt gggaactatg gccaaatgtt caatatctat actagtctta gctgacctga  38160
gtttatcaat aactacatcg gtatctagat ctctagaata tcccaatagg tgttccggag  38220
aatcagtaaa gaacactcca cctataggat tcttaatatg atacgcagtg ctaactggca  38280
gacaacaagc cgcagagcat aaattcaacc atgaattttt tgcgctatta aaggctttaa  38340
aagtatcaaa tcttctacga agatctgtgg ccagcggggg ataatcagaa tatacaccta  38400
acgttttaat cgtatgtata gatcctccag taaatgacgc gtttcctaca taacatcttt  38460
catcatctga cacccaaaaa caaccgagta gtagtcccac attatttttt ttatctatat  38520
taacggttat aaaatttata tccgggcagt gactttgtag ctctcccaga tttcttttcc  38580
ctcgttcatc tagcaaaact attattttaa tcccttttttc agatgcctct tttagtttat  38640
caaaaataag cgctccccta gtcgtactca gaggattaca acaaaaagat gctatgtata  38700
tatatttctt agctagagtg ataatttcgt taaaacattc aaatgttgtt aaatgatcgg  38760
atctaaaatc catattttct ggtagtgttt ctaccagcct acattttgct cccgcaggta  38820
ccgatgcaaa tggccacatt tagttaacat aaaaacttat acatcctgtt ctatcaacga  38880
ttctagaata tcatcggcta tatcgctaaa attttcatca aagtcgacat cacaacctaa  38940
ctcagtcaat atattaagaa gttccatgat gtcatcttcg tttatttcta tatccgtatc  39000
cattgtagat tgttgaccga ttatcgagtt taaatcatta ctaatactca atccttcaga  39060
atacaatctg tgtttcattg taaatttata ggcggtgtat ttaagttggt agattttcaa  39120
ttatgtatca atatagcaac agtagttctt gctcctcctt gattctagca tcctcttcat  39180
tattttcttc tacgtacata aacatgtcca atacgttaga caacacaccg acgatggcgg  39240
ccgccacaga cacgaatatg actaaaccga tgaccattta aaaacccctc tctagctttc  39300
acttaaactg tatcgattat tcttttagaa catgtataat ataaaaacat tattctattt  39360
cgaatttagg cttccaaaaa tttttcatcc gtaaaccgat aataatatat atagacttgt  39420
```

```
taatagtcgg aataaataga ttaatgctta aactatcatc atctccacga ttagagatac  39480
aatatttaca ttctttttgc tgtttcgaaa ctttatcaat acacgttaat acaaacccag  39540
gaaggagata ttgaaactga ggctgttgaa aatgaaacgg tgaatacaat aattcagata  39600
atgtaaaatc atgattccgt attctgatga tattagaact gctaatggat gtcgatggta  39660
tgtatctagg agtatctatt ttaacaaagc atcgatttgc taatatacaa ttatcctttt  39720
gattaattgt tattttattc atattcttaa aaggtttcat atttatcaat tcttctacat  39780
taaaaatttc catttttaat ttatgtagcc ccgcaatact cctcattacg tttcattttt  39840
tgtctataat atccatttttg ttcatctcgg tacatagatt atccaattga gaagcgcatt  39900
tagtagtttt gtacatttta agtttattga caaatcgtcg aaaactagtt atagttaaca  39960
ttttattatt tgataccctg atattaatac ccctgccgtt actattattt ataactgatg  40020
taatccacgt aacattagaa ttaattatcg atagtaatgc atcgacgctt ccaaaattgt  40080
ctattataaa ctcaccgata attttttat tgcatgtttt catattcatt aggattatca  40140
aatctttaat cttattacga ttgtatgcgt tgatattgca agacgtcatt ctaaaagacg  40200
gaggatctcc atcaaatgcc aaacaatcac gtacaaagta catggaaata ggttttgttc  40260
tattgcgcat catagattta tatagaacac ccgtagaaat actaatttgt tttactctat  40320
aaaatactaa tgcatctatt tcatcgtttt gtataacgtc tttccaagtg tcaaattcca  40380
aatttttttc attgatagta ccaaattctt ctatctcttt aactacttgc atagataggt  40440
aattacagtg atgcctacat gccgtttttt gaaactgaat agatgcgtct agaagcgatg  40500
ctacgctagt cacaatcacc actttcatat ttagaatata tgtatgtaaa aatatagtag  40560
aatttcattt tgtttttttc tatgctataa atgaattctc attttgcatc tgctcatact  40620
ccgttttata tcaataccaa agaaggaaga tatttggttc taaaagccgt taaagtatgc  40680
gatgttagaa ctgtagaatg tgaaggaagt aaagcttcct gcgtactcaa agtagataaa  40740
ccctcatcac ccgcgtgtga gagaagacct tcgtcccctt ccagatgcga gagaatgaat  40800
aacccaggaa aacaagttcc gtttatgagg acggacatgc tacaaaatat gttcgcggct  40860
aatcgcgata atgtagcttc tagacttttg tcctaaaata ctattatatc cttttcgata  40920
ttaataaatc cgtgtcgtcc aggtttttta tctctttcag tatgtgaata gataggtatt  40980
ttatctctat tcatcatcga atttaagaga tccgataaac attgtttgta ttctccagat  41040
gtcagcatct gatacaacaa tatatgtgca cataaacctc tggcacttat ttcatgtacc  41100
ttccccttat cactaaggag aatagtattt gagaaatatg tatacatgat attatcatga  41160
attagatata cagaatttgt aacactctcg aaatcacacg atgtgtcggc gttaagatct  41220
aatatatcac tcgataacac attttcatct agatacacta gacatttttt aaagctaaaa  41280
tagtctttag tagtgacagt aactatgcga ttattttcat cgatgataca tttcatcggc  41340
atattattac gcttaccatc aaagactata ccatgtgtat atctaacgta ttctagcatg  41400
gttgccatac gcgcattaaa cttttcagga tctttggata gatcttccaa tctatctatt  41460
tgagaaaaca tttttatcat gttcaatagt tgaaacgtcg gatccactat atagatatta  41520
tctataaaga ttttaggaac tacgttcatg gtatcctggc gaatattaaa actatcaatg  41580
atatgattat cgttttcatc ttttatcacc atatagtttc taagatatgg gatttttactt  41640
aatataatat tatttcccgt gataaatttt attagaaagg ccaaatctat aagaaaagtc  41700
ctagaattag tctgaagaat atctatatcg ccgtatagta tatttggatt aattagatat  41760
```

-continued

```
agagaatatg atccgtaaca tatacaactt ttattatggc gtctaagata ttcttccatc  41820
aacttattaa catttttgac tagggaagat acattatgac gtcccattac ttttgccttg  41880
tctattactg cgacgttcat agaatttagc atatctcttg ccaattcttc cattgatgtt  41940
acattataag aaattttaga tgaaattaca tttggagctt taatagtaag aactcctaat  42000
atgtccgtgt atgtggtcac taatacagat tgtagttcta taatcgtaaa taatttacct  42060
atattatatg tttgagtctg tttagaaaag tagctaagta tacgatcttt tatttctgat  42120
gcagatgtat taacatcgga aaaaaatctt tttttattct tttttactaa agatacaaat  42180
atgtctttgt taaaaacagt tattttttga atatttctag cttgtaattt taacatatga  42240
tattcgttca cactaggtac tctgcctaaa taggtttcta taatctttaa tgtaatatta  42300
ggaaaagtat tctgatcagg attcctattc attttgagga tttaaaactc tgattattgt  42360
ctaatatggt ctctacgcaa actttttcac agagcgatag agtttttgat aactcgtttt  42420
tcttaagaaa tataaaacta ctgtctccag agctcgctct atcttttatt ttatctaatt  42480
cgatacaaac tcctgatact ggttcagaaa gtaattcatt aattttcagt cctttataga  42540
agatatttaa tatagataat acaaaatctt cagtttttga tatcgatctg attgatccta  42600
gaactagata tattaataac gtgctcatta ggcagtttat ggcagcttga taattagata  42660
tagtatattc cagttcatat ttattagata ccgcattgcc cagattttga tattctatga  42720
attcctctga aaataaatcc aaaataacta gacattctat tttttgtgga ttagtgtact  42780
ctcttccctc tatcatgttc actactggtg tccacgatga taaatatcta gagggaatat  42840
aatatagtcc ataggatgcc aatctagcaa tgtcgaataa ctgtaatttt attcttcgct  42900
cttcattatg aattgattct tgaggtataa acctaacaca aattatatta ttagactttt  42960
cgtatgtaat gtctttcatg ttataagttt ttaatcctgg aatagaatct attttaatga  43020
ggcttttaaa cgcagagttc tccaacgagt caaagcataa tactctgttg tttttcttat  43080
atacgatgtt acgattttct tctttgaatg gaataggttt ttgaattagt ttataattac  43140
aacataatag ataaggaagt gtgcaaatag tacgcggaaa aaacataata gctcccctgt  43200
tttcatccat ggttttaagt aaatgatcac tggcttcttt agtcaatgga tattcgaaca  43260
ttaaccgttt catcatcatt ggacagaatc catatttttt aatgtaaaga gtgatcaaat  43320
cattgtgttt attgtaccat cttgttgtaa atgtgtattc ggttatcgga tctgctcctt  43380
tttctattaa agtatcgatg tcgatctcgt ctaagaattc aactatatcg acatatttca  43440
tttgtataca cataaccatt actaacgtag aatgtatagg aagagatgta acgggaacag  43500
ggtttgttga ttcgcaaact attctaatac ataattcttc tgttaatacg tcttgcacgt  43560
aatctattat agatgccaag atatctatat aattattttg taagatgatg ttaactatgt  43620
gatctatata agtagtgtaa taattcatgt attttgatat atgttccaac tctgtctttg  43680
tgatgtctag tttcgtaata tctatagcat cctcaaaaaa tatattcgca tatattccca  43740
agtcttcagt tctatcttct aaaaaatctt caacgtatgg aatataataa tctattttac  43800
ctcttctgat atcattaatg atatagtttt tgacactatc ttctgtcaat tgattcttat  43860
tcactatatc taagaaacgg atagcgtccc taggacgaac tactgccatt aatatctcta  43920
ttatagcttc tggacataat tcatctatta taccagaatt aatgggaact attccgtatc  43980
tatctaacat agttttaaga aagtcagaat ctaagacttg atgttcatat attggttcat  44040
acatgaaatg atctctattg atgatagtga ctatttcatt ctctgaaaat tggtaactca  44100
ttctatatat gctttccttg ttgatgaagg atagaatata ctcaatagaa tttgtaccaa  44160
```

```
caaactgttc tcttatgaat cgtatatcat catctgaaat aatcatgtaa ggcatacatt  44220
taacaattag agacttgtct cctgttatca atatactatt cttgtgataa tttatgtgtg  44280
aggcaaattt gtccacgttc tttaattttg ttatagtaga tatcaaatcc aatggagcta  44340
cagttcttgg cttaaacaga tatagttttt ctggaacgaa ttctacaaca ttattataaa  44400
ggactttggg tagataagtg ggatgaaatc ctattttaat taatgcgata gccttgtcct  44460
cgtgcagata tccaaacgct tttgtgatag tatggcattc attgtctaga aacgctctac  44520
gaatatctgt gacagatatc atctttagag aatatactag tcgcgttaat agtactacaa  44580
tttgtatttt ttaatctatc tcaataaaaa aattaatatg tatgattcaa tgtataacta  44640
aactactaac tgttattgat aactagaatc agaatctaat gatgacgtaa ccaagaagtt  44700
tatctactgc caatttagct gcattatttt tagcatctcg tttagatttt ccatctgcct  44760
tatcgaatac tcttccgtcg atatctacac aggcataaaa tgtaggagag ttactaggcc  44820
ccactgattc aatacgaaaa gaccaatctc tcttagttat ttggcagtac tcattaataa  44880
tggtgacagg gttagcatct ttccaatcaa taattttttt agccggaata acatcatcaa  44940
aagacttatg atcctctctc attgattttt cgcgggatac atcatctatt atggcgtcag  45000
ccataacatc agcatccggc ttatccgcct ccgttgtcat aaaccaacga ggaggaatat  45060
cgtcggagct gtacaccata gcactacgtt gaagatcgta cagagcttta ttaacttctc  45120
gcttctccat attaagttgt ctagttagtt gtgcagcagt agctccttcg attccaatgt  45180
ttttaatagc cgcacacaca atctctgcgt cagaacgctc gtcaatatag atcttagaca  45240
tttttagaga gaactaacac aaccagcaat aaaactaatt tattttatca ttttttttatt  45300
catcatcctc tggtggttcg tcgtttctat cgaatgtgga tctgattaac ccgtcatcta  45360
taggtgatgc tggttctgga gattctggag gagatggatt attatctgga agaatctctg  45420
ttatttcctt gttttcatgt atcgattgcg ttgtaacatt aagattgcga aatgctctaa  45480
atttgggagg cttaaagtgt tgtttgcaat ctctacacgc atgtctaact agtggaggtt  45540
cgtcagcggc tctagtttga atcatcatcg gcgtagtatt cctactttta cagttaggac  45600
acggtgtatt gtatttctcg tcgagaacgt taaaataatc gttgtaactc acatccttta  45660
ttttatctat attgtattct actcctttct taatgcattt tataccgaat aagagatagc  45720
gaaggaattc tttttcggtg ccgctagtac ccttaatcat atcacatagt gttttatatt  45780
ccaaatttgt ggcaatagac ggtttatttc tatacgatag tttgtttctg gaatcctttg  45840
agtattctat accaatatta ttctttgatt cgaatttagt ttcttcgata ttagattttg  45900
tattacctat attcttgatg tagtactttg atgatttttc catggcccat tctattaagt  45960
cttccaagtt ggcatcatcc acatattgtg atagtaattc tcggatatca gtagcggcta  46020
ccgccattga tgtttgttca ttggatgagt aactactaat gtatacattt tccatttata  46080
acacttatgt attaactttg ttcatttata ttttttcatt attatgttga tattaacaaa  46140
agtgaatata tatatatgtt aataattgta ttgtggttat acggctacaa ttttataatg  46200
agtgaaagtc agtgtccgat gatcaatgac gatagcttta ctctgaaaag aaagtatcaa  46260
atcgatagtg cggagtcaac aataaaaatg gataagaaga ggataaagtt tcagaataga  46320
gccaaaatgg taaaagaaat aaatcagaca ataagagcag cacaaactca ttacgagaca  46380
ttgaaactag gatacataaa atttaagaga atgattagga ctactactct agaagatata  46440
gcaccatcta ttccaaataa tcagaaaact tataaactat tctcggacat ttcagccatc  46500
```

-continued

```
ggcaaagcat cacagaatcc gagtaagatg gtatatgctc tgctgcttta catgtttccc  46560
aatttgtttg gagatgatca tagattcatt cgttatagaa tgcatccaat gagtaaaatc  46620
aaacacaaga tcttctctcc tttcaaactt aatcttatta gaatattagt ggaagaaaga  46680
ttctataata atgaatgcag atctaataaa tggaaaataa ttggaacaca agttgataaa  46740
atgttgatag ctgaatctga taaatataca atagatgcaa ggtataacct aaaacccatg  46800
tatagaatca agggagaatc tgaagaagat accctcttta tcaaacagat ggtagaacaa  46860
tgtgtgacat cccaggaatt ggtggaaaaa gtgttgaaga tactgtttag agatttgttc  46920
aagagtggag aatacaaagc gtacagatac gatgatgatg tagaaaatgg atttattgga  46980
ttggatacac taaaattaaa cattgttcat gatatagttg aaccatgtat gcctgttcgt  47040
aggccagtgg ctaagatact gtgtaaagaa atggtaaata aatactttga gaatccgcta  47100
catattattg gtaaaaatct tcaagagtgc attgactttg ttagtgaata ggcatttcat  47160
ctttctccaa tactaattca aattgttaaa ttaataatgg atagtataaa tagttattag  47220
tgataaaata gtaaaaataa ttattagaat aagagtgtag tatcatagat aactctcttc  47280
tataaaaatg gattttattc gtagaaagta tcttatatac acagtagaaa ataatataga  47340
ttttttaaag gatgatacat taagtaaagt aaacaatttt accctcaatc atgtactagc  47400
tctcaagtat ctagttagca attttcctca acacgttatt actaaggatg tattagctaa  47460
taccaatttt tttgttttca tacatatggt acgatgttgt aaagtgtacg aagcggtttt  47520
acgacacgca tttgatgcac ccacgttgta cgttaaagca ttgactaaga attatttatc  47580
gtttagtaac gcaatacaat cgtacaagga aaccgtgcat aaactaacac aagatgaaaa  47640
atttttagag gttgccgaat acatggacga attaggagaa cttataggcg taaattatga  47700
cttagttctt aatccattat ttcacggagg ggaacccatc aaagatatgg aaatcatttt  47760
tttaaaactg tttaagaaaa cagacttcaa agttgttaaa aaattaagtg ttataagatt  47820
acttatttgg gcatacctaa gcaagaaaga tacaggcata gagtttgcgg ataatgatag  47880
acaagatata tatactctat ttcaacaaac tggtagaatc gtccatagca atctaacaga  47940
aacgtttaga gattatatct ttcccggaga taagactagc tattgggtgt ggttaaacga  48000
aagtatagct aatgatgcgg atatcgttct taatagacac gccattacca tgtatgataa  48060
aattcttagt tatatatact ctgagataaa acagggacgc gttaataaaa acatgcttaa  48120
gttagtttat atctttgagc ctgaaaaaga tatcagagaa cttctgctag aaatcatata  48180
tgatattcct ggagatatcc tatctattat tgatgcaaaa aacgacgatt ggaaaaaata  48240
ttttattagt ttttataaag ctaattttat taacggtaat acatttatta gtgatagaac  48300
gtttaacgag gacttattca gagttgttgt tcaaatagat cccgaatatt tcgataatga  48360
acgaattatg tctttattct ctacgagtgc tgcggacatt aaacgatttg atgagttaga  48420
tattaataac agttatatat ctaatataat ttatgaggtg aacgatatca cattagatac  48480
aatggatgat atgaagaagt gtcaaatctt taacgaggat acgtcgtatt atgttaagga  48540
atacaataca tacctgtttt tgcacgagtc ggatcccatg gtcatagaga acggaatact  48600
aaagaaactg tcatctataa aatccaagag tagacggctg aacttgttta gcaaaaacat  48660
tttaaaatat tatttagacg gacaattggc tcgtctaggt cttgtgttag atgattataa  48720
aggagacttg ttagttaaaa tgataaacca tcttaagtct gtggaggatg tatccgcatt  48780
cgttcgattt tctacagata aaaaccctag tattcttcca tcgctaatca aaactatttt  48840
agctagttat aatatttcca tcatcgtctt atttcaaagg tttttaagag ataatctata  48900
```

```
tcatgtagaa gaattcttgg ataaaagcat ccatctaacc aagacggata agaaatatat  48960
acttcaattg ataagacacg gtagatcata gaacagacca aatatattat taataatttg  49020
tatatacata gatataatta tcacatatta aaaattcaca catttttgat aaatgggaac  49080
tgctgcaaca attcagactc ccaccaaatt aatgaataaa gaaaatgcag aaatgatttt  49140
ggaaaaaatt gttgatcata tagttatgta tattagtgac gaatcaagtg attcagaaaa  49200
taatcctgaa tatattgatt ttcgtaacag atacgaagac tatagatctc tcattataaa  49260
aagtgatcac gagtttgtaa agctatgtaa aaatcatgca gagaaaagtt ctccagaaac  49320
gcaacaaatg attatcaaac acatatacga acaatatctt attccagtat ctgaagtact  49380
attaaaacct ataatgtcca tgggtgacat aattacatat aacggatgta aagacaatga  49440
atggatgcta gaacaactct ctaccctaaa ctttaacaat ctccgcacat ggaactcatg  49500
tagcataggc aatgtaacgc gtctgtttta tacatttttt agttatctga tgaaagataa  49560
actaaatata taagtataat cccattctaa tactttaacc tgatgtatta gcatcttatt  49620
agaatattaa cctaactaaa agacataaca taaaaactca ttacatagtt gataaaaagc  49680
ggtaggatat aaatattatg gctgccaccg ttccgcgttt tgacgacgtg tacaaaaatg  49740
cacaaagaag aattctagat caagaaacat tttttagtag aggtctaagt agaccgttaa  49800
tgaaaaacac atatctattt gataattacg cgtatggatg gataccagaa actgcaattt  49860
ggagtagtag atacgcaaac ttagatgcaa gtgactatta tcccatttcg ttgggattac  49920
ttaaaaagtt cgagtttctc atgtctctat ataaaggtcc tattccagta tacgaagaaa  49980
aagtaaatac tgaattcatt gctaatggat cgttctctgg tagatacgta tcatatcttc  50040
gaaagttttc tgctcttcca acaaacgagt ttattagttt tttgttactg acttccattc  50100
caatctataa tatcttgttc tggtttaaaa atactcagtt tgatattact aaacacacat  50160
tattcagata cgtctataca gataatgcca aacacctggc gttggctagg tatatgcatc  50220
aaacaggaga ctataagcct ttgtttagtc gtctcaaaga gaattatata tttaccggtc  50280
ccgttccaat aggtatcaaa gatataaatc accctaatct tagtagagca agaagtccat  50340
ccgattatga gacattagct aatattagta ctatattgta ctttaccaag tatgatccgg  50400
tattaatgtt tttattgttt tacgtacctg ggtattcaat tactacaaaa attactccag  50460
ccgtagaata tctaatggat aaactgaatc taacaaagag cgacgtacaa ctgttgtaaa  50520
ttattttatg cttcgtaaaa tgtaggtttt gaaccaaaca ttctttcaaa gaatgagatg  50580
cataaaactt tattatccaa tagattgact atttcggacg tcaatcgttt aaagtaaact  50640
tcgtaaaata ttctttgatc actgccgagt ttaaaacttc tatcgataat tgtttcatat  50700
gttttaatat ttacaagttt tttggtccat ggtacattag ccggacaaat atatgcaaaa  50760
taatatcgtt ctccaagttc tatagtttct ggattatttt tattatattc agtaaccaaa  50820
tacatattag ggttatctgc ggatttataa tttgagtgat gcattcgact caacataaat  50880
aattctagag gagacgatct actatcaaat tcggatcgta aatctgtttc taaagaacgg  50940
agaatatcta tacatacctg attagaattc atccgtcctt cagacaacat ctcagacagt  51000
ctggtcttgt atgtcttaat catattctta tgaaacttgg aaacatctct tctagtttca  51060
ctagtacctt tattaattct ctcaggtaca gattttgaat tcgacgatgc cgagtatttc  51120
atcgttgtat atttcttctt cgattgcata atcagattct tatataccgc ctcaaactct  51180
attttaaaat tattaaacaa tactctatta ttaatcagtc gttctaactc ctttgctatt  51240
```

-continued

```
tctatggact tatctacatc ttgactgtct atctctgtaa acacggagtc ggtatctcca  51300
tacacgctac gaaaacgaaa tctgtaatct ataggcaacg atgttttcac aatcggatta  51360
atatctctat cgtccatata aaatggatta cttaatggat tggcaaaccg taacataccg  51420
ttagataact ctgctccatt tagtaccgat tctagataca agatcattct acgtcctatg  51480
gatgtgcaac tcttagccga agcgtatgag tatagagcac tatttctaaa tcccatcaga  51540
ccatatactg agttggctac tatcttgtac gtatattgca tggaatcata gatggccttt  51600
tcagttgaac tggtagcctg ttttaacatc tttttatatc tggctctctc tgccaaaaat  51660
gttcttaata gtctaggaat ggttccttct atcgatctat cgaaaattgc tatttcagag  51720
atgaggttcg gtagtctagg ttcacaatga accgtaatat atctaggagg tggatatttc  51780
tgaagcaaga gctgattatt tatttcttct tccaatctat tggtactaac aacgacaccg  51840
actaatgttt ccggagatag atttccaaag atacacacat taggatacag actgttataa  51900
tcaaagatta atacattatt actaaacatt ttttgttttg gagcaaatac cttaccgcct  51960
tcataaggaa acttttgttt tgtttctgat ctaactaaga tagttttagt ttccaacaat  52020
agctttaaca gtggaccctt gatgactgta ctcgctctat attcgaatac catggattga  52080
ggaagcacat atgttgacgc acccgcgtct gtttttgttt ctactccata atactcccac  52140
aaatactgac acaaacaagc atcatgaata cagtatctag ccatatctaa agctatgttt  52200
agattataat ccttatacat ctgagctaaa tcaacgtcat cctttccgaa agataattta  52260
tatgtatcat taggtaaagt aggacataat agtacgactt taaatccatt ttcccaaata  52320
tctttacgaa ttactttaca tataatatcc tcatcaacag tcacataatt acctgtggtt  52380
aaaacctttg caaatgcagc ggctttgcct ttcgcgtccg tagtatcgtc accgatgaac  52440
gtcatttctc taactcctct atttaatact ttacccatgc aactgaacgc gttcttggat  52500
atagaatcca atttgtacga atccaatttt tcagattttt gaatgaatga atatagatcg  52560
aaaaatatag ttccattatt gttattaacg tgaaacgtag tattggccat gccgcctact  52620
cccttatgac tagactgatt tctctcataa atacagagat gtacagcttc ctttttgtcc  52680
ggagatctaa agataatctt ctctcctgtt aataactcta gacgattagt aatatatctc  52740
agatcaaagt tatgtccgtt aaaggtaacg acatagtcga acgttagttc caacaattgt  52800
ttagctattc gtaacaaaac tatttcagaa cataaaacta gttctcgttc gtaatccatt  52860
tccattagtg actgtatcct caaacatcct ctatcgacgg cttcttgtat ttcctgttcc  52920
gttaacatct cttcattaat gagcgtaaac aataatcgtt taccacttaa atcgatataa  52980
cagtaacttg tatgcgagat tgggttaata aatacagaag gaaacttctt atcgaagtga  53040
cactctatat ctagaaataa gtacgatctt gggatatcga atctaggtat ttttttagcg  53100
aaacagttac gtggatcgtc acaatgataa catccattgt taatctttgt caaatattgc  53160
tcgtccaacg agtaacatcc gtctggagat atcccgttag aaatataaaa ccaactaata  53220
ttgagaaatt catccatggt ggcattttgt atgctgcgtt tctttggctc ttctatcaac  53280
cacatatctg cgacggagca ttttctatct ttaatatcta gattataact tattgtctcg  53340
tcaatgtcta tagttctcat ctttcccaac ggcctcgcat taaatggagg aggagacaat  53400
gactgatata tttcgtccgt cactacgtaa taaaagtaat gaggaaatcg tataaatacg  53460
gtctcaccat ttcgacatct ggatttcaga tataaaaatc tgttttcacc gtgactttca  53520
aaccaattaa tgcaccgaac atccatttat agaatttaga aatatatttt catttaaatg  53580
aatcccaaac attggggaag agccgtatgg accattattt ttatagtact ttcgcaagcg  53640
```

```
ggtttagacg gcaacataga agcgtgtaaa cgaaaactat atactatagt tagcactctt  53700
ccatgtcctg catgtagacg gcacgcgact atcgctatag aggacaataa tgtcatgtct  53760
agcgatgatc tgaattatat ttattatttt ttcatcagat tatttaacaa tttggcatct  53820
gatcccaaat acgcgatcga tgtgacaaag gttaaccctt tataaactta acccattata  53880
aaacttatga ttagtcacga ctgaaataac cgcgtgatta ttttttggta taattctaca  53940
cggcatggtt tctgtgacta tgaattcaac ccccgttaca ttagtgaaat ctttaacaaa  54000
cagcaagggt tcgtcaaaga cataaaactc attgtttaca atcgaaatag accccctatc  54060
acacttaaaa taaaaaatat ccttatcctt taccaccaaa taaaattctg attggtcaat  54120
gtgaatgtat tcacttaaca gttccacaaa tttatttatt aactccgagg cacatacatc  54180
gtcggtattt tttatggcaa actttactct tccagcatcc gtttctaaaa aaatattaac  54240
gagttccatt tatatcatcc aatattattg aaatgacgtt gatggacaaa tgatacaaat  54300
aagaaggtac ggtacctttg tccaccatct cctccaattc atgctctatt ttgtcattaa  54360
ctttaatgta tgaaaacagt acgccacatg cttccatgac agtgtgtaac actttggata  54420
caaaatgttt gacattagta taattgttca agactgtcaa tctataatag atagtagcta  54480
taatatattc tatgatggta ttgaagaaga tgacaacctt ggcatattga tcatttaaca  54540
cagacatggt atcaacagat agcttgaatg aaagagaatc agtaattgga ataagcgtct  54600
tctcgatgga gtgtccgtat accaacatgt ctgatatttt gatgtattcc attaaattat  54660
ttagtttttt ctttttattc tcgttaaaca gcatttctgt caacggaccc caacatcgtt  54720
gaccgattaa gttttgattg atttttccgt gtaaggcgta tctagtcaga tcgtatagcc  54780
tatccaataa tccatcgtct gtgcgtagat cacatcgtac actttttaat tctctataga  54840
agagcgacag acatctggag caattacaga cagcaatttc tttattctct acagatgtaa  54900
gatacttgaa gacattccta tgatgatgca gaattttgga taacacggta ttgatggtat  54960
ctgttaccat aattcctttg atggctgata gtgtcagagc acaagatttc caatctttga  55020
caatttttag caccattatc tttgttttga tatctatatc agacagcatg gtgcgtctga  55080
caacacaagg attaagacgg aaagatgaaa tgattctctc aacatcttca atggatacct  55140
tgctattttt tctggcatta tctatatgtg cgagaatatc ctctagagaa tcagtatcct  55200
ttttgatgat agtggatctc aatgacatgg gacgtctaaa ccttcttatt ctatcaccag  55260
attgcatggt gatttgtctt ctttctttta tcataatgta atctctaaat tcatcggcaa  55320
attgtctata tctaaaatca taatatgaga tgtttacctc tacaaatatc tgttcgtcca  55380
atgttagagt atttacatca gttttgtatt ccaaattaaa catggcaacg gatttaattt  55440
tatattcctc tattaagtcc tcgtcgataa taacagaatg tagataatca tttaatccat  55500
cgtacatggt tggaagatgc tcgttgacaa aatctttaat tgtcttgatg aaggtgggac  55560
tatatctaac atcttgatta ataaaattta taacattgtc cataggatac tttgtaacta  55620
gttttataca catctcttca tcggtaagtt tagacagaat atcgtgaaca ggtggtatat  55680
tatattcatc agatatacga agaacaatgt ccaaatctat attgtttaat atattatata  55740
gatgtagtgt agctcctaca ggaatatctt taactaagtc aatgatttca tcaaccgtta  55800
gatctatttt aaagttaatc atataggcat tgatttttaa aaggtatgta gccttgacta  55860
cattctcatt aattaaccat tccaagtcac tgtgtgtaag aagattatat tctatcataa  55920
gcttgactac atttggtccc gataccatta aagaattctt atgatataag gaaacagatt  55980
```

-continued

```
ttaggtactc atctactcta caagaatttt ggagagcctt aacgatatca gtgacgttta  56040
ttatttcagg aggaaaaaac ctaacattga gaatatcgga attaatagct tccagataca  56100
gtgattttgg caatagtccg tgtaatccat aatccagtaa cacgagctgg tgcttgctag  56160
acacctttc aatgtttaat ttttttgaaa taagctttga taaagccttc ctcgcaaatt  56220
ccggatacat gaacatgtcg gcgacatgat taagtattgt tttttcatta tttttatatt  56280
ttctcaacaa gttctcaata ccccaataga tgatagaata tcacccaatg cgtccatgtt  56340
gtctatttcc aacaggtcgc tatatccacc aatagaagtt ttcccaaaaa agattctagg  56400
aacagttcta ccaccagtaa tttgttcaaa atagtcacgc aattcatttt cgggtttaaa  56460
ttctttaata tcgacaattt catacgctcc tcttttgaaa ctaaacttat ttagaatatc  56520
cagtgcattt ctacaaaaag gacatgtata cttgacaaaa attgtcactt tgttattggc  56580
caacctttgt tgtacaaatt cctcggccat tttaatattt aagtgatata aaactatctc  56640
gacttattta actctttagt cgagatatat ggacgcagat agctatatga tagccaacta  56700
cagaaggcaa acgctataaa aaacataatt acgacgagca tatttataaa tatttttatt  56760
cagcattact tgatatagta atattaggca cagtcaaaca ttcaaccact ctcgatacat  56820
taactctctc attttcttta acaaattctg caatatcttc gtaaaaagat tcttgaaact  56880
ttttagaata tctatcgact ctagatgaaa tagcgttcgt caacatacta tgttttgtat  56940
acataaaggc gcccatttta acagtttcta gtgacaaaat gctagcgatc ctaggatcct  57000
ttagaatcac atagattgac gattcgtctc tcttagtaac tctagtaaaa taatcataca  57060
atctagtacg cgaaataata ttatccttga cttgaggaga tctaaacaat ctagttttga  57120
gaacatcgat aagttcatcg ggaatgacat acatactatc tttaatagaa ctcttttcat  57180
ccagttgaat ggattcgtcc ttaaccaact gattaatgag atcttctatt ttatcatttt  57240
ccagatgata tgtatgtcca ttaaagttaa attgtgtagc gcttcttttt agtctagcag  57300
ccaatacttt aacatcacta atatcgatat acaaaggaga tgatttatct atggtattaa  57360
gaattcgttt ttcgacatct gtcaaaacca attccttttt gcctgtatca tccagttttc  57420
catcctttgt aaagaaatta ttttctacta gactattaat aagactgata aggattcctc  57480
cataattgca caatccaaac tttttcacaa aactagactt tacaagatct acaggaatgc  57540
gtacttcagg tttcttagct tgtgattttt tcttttgtgg acattttctt gtgaccaact  57600
catctaccat ttcattgatt ttagcagtga aataagcttt caatgcacgg gcactgatac  57660
tattgaaaac gagttgatct tcaaattccg ccatttaagt tcaccaaaca acttttaaat  57720
acaaatatat caatagtagt agaataagaa ctataaaaaa aataataatt aaccaatacc  57780
aaccccaaca accggtatta ttagttgatg tgactgtttt ctcatcactt agaacagatt  57840
taacaatttc tataaagtct gtcaaatcat cttccggaga ccccataaat acaccaaata  57900
tagcggcgta caacttatcc atttatacat tgaatattgg cttttcttta tcgctatctt  57960
catcatattc atcatcaata tcaacaagtc ccagattacg agccagatct tcttctacat  58020
tttcagtcat tgatacacgt tcactatctc cagagagtcc gataacgtta gccaccactt  58080
ctctatcaat gattagtttc ttgagtgcga atgtaatttt tgtttccgtt ccggatctat  58140
agaaaactac aggtgtgata attgccttgg ccaattgtct ttctctttta ctgagtgatt  58200
ctagttcacc ttctatagat ctgagaatgg atgattctcc agtcgaaaca tattctacca  58260
tggctccgtt taatttgttg atgaagatgg attcatcctt aaatgttttc tctgtaatag  58320
tttccaccga aagactatgc aaagaatttg gaatgcgttc cttgtgctta atgtttccat  58380
```

```
agacggcttc tagaagttga tacaacatag gactagccgc ggtaactttt atttttagaa  58440
agtatccatc gcttctatct tgtttagatt tatttttata aagtttagtc tctccttcca  58500
acataataaa agtggaagtc atttgactag ataaactatc agtaagtttt atagagatag  58560
acgaacaatt agcgtattga gaagcattta gtgtaacgta ttcgatacat tttgcattag  58620
atttactaat cgattttgca tactctataa cacccgcaca agtctgtaga gaatcgctag  58680
atgcagtagg tcttggtgaa gtttcaactc tcttcttgat taccttactc atgattaaac  58740
ctaaataatt gtactttgta atataatgat atatattttc actttatctc atttgagaat  58800
aaaaatgttt ttgtttaacc actgcatgat gtacagattt cggaatcaca aaccaccggt  58860
ggttttattt tatccttgtc caatgtgaat tgaatgggag cggatgcggg tttcgtacgt  58920
agatagtaca ttcccgtttt tagaccgaga ctccatccgt aaaaatgcat actcgttagt  58980
ttggaataac tcggatctgc tatatggata ttcatagatt gactttgatc gatgaaggct  59040
cccctgtctg cagccatttt tatgatcgtc ttttgtggaa tttcccaaat agttttataa  59100
actcgcttaa tatcttctgg aaggtttgta ttctgaatgg atccaccatc tgccataatc  59160
ctattcttga tctcatcatt ccataatttt ctctcggtta aaactctaag gagatgcgga  59220
ttaactactt gaaattctcc agacaatact ctccgagtgt aaatattact ggtatacggt  59280
tccaccgact cattatttcc caaaatttga gcagttgatg cagtcggcat aggtgccacc  59340
aataaactat ttctaagacc gtatgttctg attttatctt ttagaggttc ccaattccaa  59400
agatccgacg gtacaacatt ccaaagatca tattgtagaa taccgttact ggcgtacgat  59460
cctacatatg tatcgtatgg tccttccttc tcagctagtt cacaactcgc ctctaatgca  59520
ccgtaataaa tggtttcgaa gatcttctta tttagatctt gtgcttccag gctatcaaat  59580
ggataattta agagaataaa cgcgtccgct aatccttgaa caccaatacc gataggtcta  59640
tgtctcttat tagagatttc agcttctgga ataggataat aattaatatc tataatttta  59700
ttgagatttc tgacaattac tttgaccaca tccttcagtt tgagaaaatc aaatcgccca  59760
tctattacaa acatgttcaa ggcaacagat gccagattac aaacggctac ctcattagca  59820
tccgcatatt gtattatctc agtgcaaaga ttactacact tgatagttcc taaattttgt  59880
tgattactct ttttgttaca cgcatcctta taaagaatga atggagtacc agtttcaatc  59940
tgagattcta taatcgcttt ccagacgact cgagccttta ttatagattt gtatctcctt  60000
tctctttcgt atagtgtata caatcgttcg aactcgtctc cccaaacatt gtccaatcca  60060
ggacattcat ccggacacat caacgaccac tctccgtcat ccttcactcg tttcataaag  60120
agatcaggaa tccaaagagc tataaataga tctctggttc tatgttcctc gtttcctgta  60180
ttctttttaa gatcgaggaa cgccataata tcagaatgcc acggttccaa gtatatggcc  60240
ataactccag gccgtttgtt tcctccctga tctatgtatc tagcggtgtt attataaact  60300
ctcaacattg gaataatacc gtttgatata ccattggtac cggagatata gcttccactg  60360
gcacgaatat tactaattga tagacctatt ccccctgcca ttttagagat taatgcgcat  60420
cgttttaacg tgtcatagat accctctatg ctatcatcga tcatgttaag tagaaaacag  60480
ctagacattt ggtgacgact agttcccgca ttaaataagg taggagaagc gtgcgtaaac  60540
catttttcag aaagtagatt gtacgtctca atagctgagt ctatatccca ttgatgaatt  60600
cctactgcga cacgcattaa catgtgctga ggtctttcaa cgatcttgtt gtttattttc  60660
aacaagtagg atttttccaa agttttaaaa ccaaaatagt tgtatgaaaa gtctcgttcg  60720
```

```
taaataataa ccgagttgag tttatcctta tatttgttaa ctatatccat ggtgatactt  60780
gaaataatcg gagaatgttt cccattttta ggattaacat agttgaataa atcctccatc  60840
acttcactaa atagtttttt tgtttccttg tgtagatttg atacggctat tctggcggct  60900
agaatggcat aatccggatg ttgtgtagta caagtggctg ctatttcggc tgccagagtg  60960
tccaattcta ccgttgttac tccattatat attccttgaa taaccttcat agctatttta  61020
ataggatcta tatgatccgt gtttaagcca taacataatt ttctaatacg agacgtgatt  61080
ttatcaaaca tgacattttc cttgtatcca tttcgtttaa tgacaaacat ttttgttggt  61140
gtaataaaaa aattatttaa cttttcatta atagggattt gacgtacgta gcgtacaaaa  61200
tgattgttcc tggtatatag ataaagagtc ctatatattt gaaaatcgtt acggctcgat  61260
taaactttaa tgattgcata gtgaatatat cattaggatt taactccttg actatcaggg  61320
cggcaccaga aattaccatc aaaagcatta atacagttat gcctatcgca gttagaacgg  61380
ttatagcatc caccatttat atctaaaaat tagatcaaag aatatgtgac aaagtcctag  61440
ttgtatattg agaattgaca aaacaatgtt tcttacatat ttttttttta ttagtaaccg  61500
acttaatagt aggaactgga aaactagact tgattattct ataagtatag atacccttcc  61560
aaataatatt ctctttgata aaagttccag aaaatgtaga attttttaaa aagttatctt  61620
ttgctattac caagattgtg tttagacgct tattattaat atgagtgatg aaatccacac  61680
cgcctctaga tatcgccttt atttccacat tagatggtaa atccaatagt gaaactatct  61740
ttttaggaat gtatggactc gcgtttagag gagtgaacgt cttgggcgtc ggaaaggatg  61800
attcgtcaaa cgaataaaca atttcacaaa tggatgttaa tgtattagta ggaaattttt  61860
tgacgctagt ggaattgaag attctaatgg atgatgttct acctatttca tccgataaca  61920
tgttaatttc cgacaccaac ggttttaata tttcgatgat atacggtagt ctctctttcg  61980
gacttatata gcttattcca caatacgagt cattatatac tccaaaaaac aaaataacta  62040
gtataaaatc tgtatcgaat gggaaaaacg aaattatcga cataggtata gaatccggaa  62100
cattgaacgt attaatactt aattcttttt ctgtggtaag taccgatagg ttattgacat  62160
tgtatggttt taaatattct ataacttgag acttgataga tattagtgat gaattgaaaa  62220
ttatttttat caccacgtgt gtttcaggat catcgtcgac gcccgtcaac caaccgaatg  62280
gagtaaaata aatatcatta atatatgctc taaatattag tatttttatt aatcctttga  62340
ttatcatctt ctcgtacgcg aatgattcca tgatcaagag tgatttgaga acatcctccg  62400
gagtattaat gggcttagta aacagtacat cgttgcaata ataaaagtta tccaagttaa  62460
aggatattat gcattcgttt aaagatatca cctcatctga cggagacaat tttttggtag  62520
gttttagaga ctttgaagct acttgtttaa caaagttatt catcgtcgtt tactattcta  62580
tttaattttg tagttaattt atcacatatc acattaattg actttttggt ccacttttcc  62640
atacgtttat attcttttaa tcctgcgtta tccgtttccg ttatatccag tgatagatcg  62700
tgcaggttaa atagaatgct cttaaataat gtcattttct tatccgctaa aaatttaaag  62760
aatgtataaa ccttttttcag agatttgaaa ctcttaggtg gtgtcctagt acacaatatc  62820
ataaacaaac taataaacat tccacattca gattccaaca gctgattaac ttctacatta  62880
atacagccta ttttcgctcc aaatgtacat tcgaaaaatc tgaataaaac atcgatgtca  62940
caatttgtat tatccaatac agaatgtctg tgattcgtgt taaaaccatc ggagaaggaa  63000
tagaaataaa aattattata gtggtggaat tcagttggaa tattgcctcc ggagtcataa  63060
aaggatacta aacattgttt tttatcataa attacacatt tccaatgaga caaataacaa  63120
```

```
aatccaaaca ttacaaatct agaggtagaa cttttaattt tgtctttaag tatatacgat  63180
aagatatgtt tattcataaa cgcgtcaaat ttttcatgaa tcgctaagga gtttaagaat  63240
ctcatgtcaa attgtcctat ataatccact tcggatccat aagcaaactg agagactaag  63300
ttcttaatac ttcgattgct catccaggct cctctctcag gctctatttt catcttgacg  63360
acctttggat tttcaccagt atgtattcct ttacgtgata aatcatcgat tttcaaatcc  63420
atttgtgaga agtctatcgc cttagatact ttttcccgta gtcgaggttt aaagaaatac  63480
gctaacggta tactagtagg taactcaaag acatcatata tagaatggta acgcgtcttt  63540
aactcgtcgg ttaactcttt cttttgatcg agttcgtcgc tactattggg tctgctcagg  63600
tgccccaact ctactagttc caacatcata ccgataggaa tacaagacac tttgccagcg  63660
gttgtagatt tatcatattt ctccactaca tatccgttac aatttgttaa aaatttagat  63720
acatctatat tgctacataa tccagctagt gaatatatat gacataataa attggtaaat  63780
cctagttctg gtattttact aattactaaa tctgtatatc tttccattta tcatggaaaa  63840
gaatttacca gatatcttct tttttccaaa ctgcgttaat gtattctctt acaaatattc  63900
acaagatgaa ttcagtaata tgagtaaaac ggaacgtgat agtttctcat tggccgtgtt  63960
tccagttata aaacatagat ggcataacgc acacgttgta aaacataaag gaatatacaa  64020
agttagtaca gaagcacgtg gaaaaaaagt atctcctcca tcactaggaa aacccgcaca  64080
cataaaccta accgcgaagc aatatatata cagtgaacac acaataagct ttgaatgtta  64140
tagttttcta aaatgtataa caaatacaga aatcaattcg ttcgatgagt atatattaag  64200
aggactatta gaagctggta atagtttaca gatattttcc aattccgtag gtaaacgaac  64260
agatactata ggtgtactag ggaataagta tccatttagc aaaattccat tggcctcatt  64320
aactcctaaa gcacaacgag agatattttc agcgtggatt tctcatagac ctgtagtttt  64380
aactggagga actggagtgg gtaagacgtc acaggtaccc aagttattgc tttggtttaa  64440
ttatttattt ggtggattct ctactctaga taaaatcact aactttcacg aaagaccagt  64500
cattctatct cttcctagga tagctttagt tagattgcat agcaatacca ttttaaaatc  64560
attgggattt aaggtactag atggatctcc tatttcttta cggtacggat ctataccgga  64620
agaattaata aacaaacaac caaaaaaata tggaattgta ttttctaccc ataagttatc  64680
tctaacaaaa ctatttagtt atggcactct tattatagac gaagttcatg agcatgatca  64740
aataggagat attattatag cagtagcgag aaagcatcat acgaaaatag attctatgtt  64800
tttaatgact gccacgttag aggatgaccg agaacggcta aaagtatttt tacctaatcc  64860
cgcatttata catattcctg gagatacact gtttaaaatt agcgaggtat ttattcataa  64920
taagataaat ccatcttcca gaatggcata catagaagaa gaaaagagaa atttagttac  64980
tgctatacag atgtatactc ctcctgatgg atcatccggt atagtctttg tggcatccgt  65040
tgcacagtgt cacgaatata aatcatattt agaaaaaaga ttaccgtatg atatgtatat  65100
tattcatggt aaggtcttag atatagacga aatattagaa aaagtgtatt catcacctaa  65160
tgtatcgata attatttcta ctccttattt ggaatccagc gttactatac gcaatgttac  65220
acacatttat gatatgggta aagtttttgt ccccgctcct tttggaggat cgcaagaatt  65280
tatttctaaa tctatgagag atcaacgaaa aggaagagta ggaagagtta atcctggtac  65340
atacgtctat ttctatgatc tgtcttatat gaagtctata cagcgaatag attcagaatt  65400
tctacataat tatatattgt acgctaataa gtttaatcta acactccccg aagatttgtt  65460
```

```
tataatccct acaaatttgg atattctatg gcgtacaaag gaatatatag actcgttcga  65520
tattagtaca gaaacatgga ataaattatt atccaattat tatatgaaga tgatagagta  65580
tgctaaactt tatgtactaa gtcctattct cgctgaggag ttggataact ttgagaggac  65640
gggagaatta actagtattg tacgagaagc cattttatct ctaaatttac gaattaagat  65700
tttaaatttt aaacataaag atgatgatac gtatatacac ttttgtaaaa tattattcgg  65760
tgtctataac ggaacaaacg ctactatata ttatcataga cctctaacgg gatatatgaa  65820
tatgatttca gatactatat ttgttcctgt agataataac taaaaatcaa actctaatga  65880
ccacatcttt ttttagagat gaaaaatttt ccacatctcc ttttgtagac acgactaaac  65940
attttgcaga aaaaagttta ttagtgttta gataatcgta tacttcatca gtgtagatag  66000
taaatgtgaa cagataaaag gtattcttgc tcaatagatt ggtaaattcc atagaatata  66060
ttaatccttt cttcttgaga tcccacatca tttcaaccag agacgtttta tccaatgatt  66120
tacctcgtac tataccacat acaaaactag attttgcagt gacgtcgtac ctggtattcc  66180
taccaaacaa aattttactt ttagttcttt tagaaaattc taaggtagaa tctctatttg  66240
ccaatatgtc atctatggaa ttaccactag caaaaaatga tagaaatata tattgataca  66300
tcgcagctgg ttttgatcta ctatacttta aaaacgaatc agattccata attgcctgta  66360
tatcatcagc tgaaaaacta tgttttacac gtattccttc ggcatttctt tttaatgata  66420
tatcttgttt agacaatgat aaagttatca tgtccatgag agacgcgtct ccgtatcgta  66480
taaatatttc attagatgtt agacgcttca ttaggggtat acttctataa ggtttcttaa  66540
ttagtccatc atttgttgcg tcaagaacta ctatcggatg ttgttgggta tctctagtgt  66600
tacacatggc cttactaaag tttgggtaaa taactatgat atctctatta attatagatg  66660
catatatttc atttgtcaag gatattagta tcgacttgct atcgtcatta atacgtgtaa  66720
tgtaatcata taaatcatgc gatagccaag gaaaattcaa atagatgttc atcatataat  66780
cgtcgctata attcatatta atactttgac attgactaat ttgtaatata gcctcgccac  66840
gaagaaagct ctcgtattca gtttcatcga taaaggatac cgttaaatat aactggttgc  66900
cgatagtctc atagtctatt aagtggtaag tttcgtacaa atacagaatc cctaaaatat  66960
tatctaatgt tggattaatc tttaccataa ctgtataaaa tggagacgga gtcataacta  67020
ttttaccgtt tgtacttact ggaatagacg aaggaataat ctccggacat gctggtaaag  67080
acccaaatgt ctgtttgaag aaatccaatg ttccaggtcc taatctctta acaaaaaatta  67140
cgatattcga tcccgatatc ctttgcattc tatttaccag catatcacga actatattaa  67200
gattatctat catgtctatt ctcccaccgt tatataaatc gcctccgcta agaaacgtta  67260
gtatatccat acaatggaat acttcatttc taaaatagta ttcgttttct aattctttaa  67320
tgtgaaatcg tatactagaa agggaaaaat tatctttgag ttttccgtta gaaaagaacc  67380
acgaaactaa tgttctgatt gcgtccgatt ccgttgctga attaatggat ttacaccaaa  67440
aactcatata acttctagat gtagaagcat tcgctaaaaa attagtagaa tcaaaggata  67500
taagtagatg ttccaacaag tgagcaattc ccaagatttc atctatatca ttctcgaatc  67560
cgaaattaga aattcccaag tagatatcct ttttcatccg atcgttgatg aaaatacgaa  67620
ctttattcgg taagacaatc atttactaag gagtaaaata ggaagtaatg ttcgtatgtc  67680
gttatcatcg tataaattaa aggtgtgttt tttaccatta agtgacatta taattttacc  67740
aatattggaa ttataatata ggtgtatttg cgcactcgcg acggttgatg catcggtaaa  67800
tatagctgta tctaatgttc tagtcggtat ttcatcattt cgctgtctaa taatagcgtt  67860
```

```
ttctctatct gtttccatta cagctgcctg aagtttattg gtcggataat atgtaaaata  67920
ataagaaata catacgaata acaaaaataa aataagatat aataaagatg ccatttagag  67980
atctaatttt gtttaacttg tccaaattcc tacttacaga agatgaggaa tcgttggaga  68040
tagtgtcttc cttatgtaga ggatttgaaa tatcttatga tgacttgata acttactttc  68100
cagataggaa ataccataaa tatatttcta aagtatttga acatgtagat ttatcggagg  68160
aattaagtat ggaattccat gatacaactc tgagagattt agtctatctt agattgtaca  68220
agtattccaa gtgtatacgg ccgtgttata aattaggaga taatctaaaa ggcatagttg  68280
ttataaagga caggaatatt tatattagag aagcaaatga tgacttgata gaatatctcc  68340
tcaaggaata cactcctcag atttatacat attctaatga gcgcgtcccc ataactggtt  68400
caaaattaat tctttgtgga ttttctcaag ttacatttat ggcgtataca acgtcgcata  68460
taacaacaaa taaaaaggta gatgttctcg tttccaaaaa atgtatagat gaactagtcg  68520
atccaataaa ttatcaaata cttcaaaatt tatttgataa aggaagcgga acaataaaca  68580
aaatactcag gaagatattt tattcggtaa ccggtggcca aactccataa tttgcttttt  68640
ctatttcgga ttttagaatt tccaaattca ccagcgattt atcggttttg gtgaaatcca  68700
aggatttatt aatgtccaca aatgccattt gttttgtctg tggattgtat ttgaaaatgg  68760
aaacgatgta gttagataga tgcgctgcaa agtttcctat tagggttccg cgctttacgt  68820
cacccagcat acttgaatca ccatccttta aaaaaaatga taagatatca acatggagta  68880
tatcatactc ggattttaat tcttctactg catcactgac attttcacaa atactacaat  68940
acggtttacc gaaaataatc agtacgttct tcatttatgg gtatcaaaaa cttaaaatcg  69000
ttactgctgg aaaataaatc actgacgata ttagatgata atttatacaa agtatacaat  69060
ggaatatttg tggatacaat gagtatttat atagccgtcg ccaattgtgt cagaaactta  69120
gaagagttaa ctacggtatt cataaaatac gtaaacggat gggtaaaaaa gggagggcat  69180
gtaacccttt ttatcgatag aggaagtata aaaattaaac aagacgttag agacaagaga  69240
cgtaaatatt ctaaattaac caaggacaga aaaatgctag aattagaaaa gtgtacatcc  69300
gaaatacaaa atgttaccgg atttatggaa gaagaaataa aggcagaaat gcaattaaaa  69360
atcgataaac tcacatttca aatatattta tctgattctg ataacataaa aatatcattg  69420
aatgagatac taacacattt caacaataat gagaatgtta cattatttta ttgtgatgaa  69480
cgagacgcag aattcgttat gtgtctcgag gctaaaacac atttctctac cacaggagaa  69540
tggccgttga taataagtac cgatcaggat actatgctat ttgcatctac tgataatcat  69600
cctaagatga taaaaaactt aactcaactg tttaaatttg ttccctcggc agaggataac  69660
tatttagcaa aattaacggc gttagtgaat ggatgtgatt tctttcctgg actctatggg  69720
gcatctataa cacccaccaa cttaaacaaa atacaattgt ttagtgattt tacaatcgat  69780
aatatagtca ctagtttggc aattaaaaat tattatagaa agactaactc taccgtagac  69840
gtgcgtaata ttgttacgtt tataaacgat tacgctaatt tagacgatgt ctactcgtat  69900
gttcctcctt gtcaatgcac tgttcaagaa tttatatttt ccgcattaga tgaaaaatgg  69960
aacaatttta aatcatctta tttagagacc gttccgttac cctgccaatt aatgtatgca  70020
ttagaaccac gcaaggagat tgatgtttca gaagttaaaa ctttatcatc ttatatagat  70080
ttcgaaaata ctaaatcaga tatcgatgtt ataaaatcta tatcttcgat cttcggatat  70140
tctaacgaaa actgtaacac tatagtgttc ggcatctata aggataattt actactgagt  70200
```

```
ataaatagtt cattttactt taacgatagt ctgttaataa ccaatactaa aagtgataat  70260
ataataaata taggttacta gattaaaaat ggtgttccaa ctcgtgtgct ctacatgcgg  70320
caaagatatt tctcacgaac gatataaatt gattatacga aaaaaatcat taaaggatgt  70380
actcgtcagt gtaaagaacg aatgttgtag gttaaaatta tctacacaaa tagaacctca  70440
acgtaactta acagtgcaac ctctattgga tataaactaa tatggatccg gttaatttta  70500
tcaagacata tgcgcctaga ggttctatta tttttattaa ttataccatg tcattaacaa  70560
gtcatttgaa tccatcgata gaaaaacatg tgggtattta ttatggtacg ttattatcgg  70620
aacacttggt agttgaatct acctatagaa aaggagttcg aatagtccca ttggatagtt  70680
tttttgaagg atatcttagt gcaaaagtat acatgttaga gaatattcaa gttatgaaaa  70740
tagcagctga tacgtcatta actttattgg gtattccgta tggatttggt catgatagaa  70800
tgtattgttt taaattggta gctgaatgtt ataaaaatgc cggtattgat acatcgtcta  70860
aacgaatatt aggtaaagat atttttctga gccaaaactt cacagatgat aatagatgga  70920
taaagatata tgattctaat aatttaacat tttggcaaat tgattacctt aaagggtgag  70980
ttaatatgca taactactcc tccgttgttt tttccctcgt tctttttctt aacgttgttt  71040
gccatcactc tcataatgta aagatattct aaaatggtaa acttttgcat atcggacgca  71100
gaaattggta taaatgttgt aattgtatta tttcccgtca atggactagt cacagctcca  71160
tcagttttat atcctttaga gtatttctca ctcgtgtcta acattctaga gcattccatg  71220
atctgtttat cgttgatatt ggccggaaag atagattttt tattttttat tatattacta  71280
ttggcaattg tagatataac ttctggtaaa tatttttcta ccttttcaat ctcttctatt  71340
ttcaagccgg ctatatattc tgctatattg ttgctagtat caatacettt tctggctaag  71400
aagtcatatg tggtattcac tatatcagtt ttaactggta gttccattag cctttccact  71460
tctgcagaat aatcagaaat tggttcttta ccagaaaatc cagctactat aataggctca  71520
ccgatgatca ttggcaaaat cctatattgt accagattaa tgagagcata tttcatttcc  71580
aataattctg ctagttcttg agacattgat ttatttgatg aatctagttg gttctctaga  71640
tactctacca tttctgccgc atacaataac ttgttagata aaatcagggt tatcaaagtg  71700
tttagcgtgg ctagaatagt gggcttgcat gtattaaaga atgcggtagt atgagtaaac  71760
cgttttaacg aattatatag tctccagaaa tctgtggcgt tacatacatg agccgaatga  71820
catcgaagat tgtccaatat ttttaatagc tgctctttgt ccattatttc tatatttgac  71880
tcgcaacaat tgtagatacc attaatcacc gattcctttt tcgatgccgg acaatagcac  71940
aattgtttag ctttggactc tatgtattca gaattaatag atatatctct taatacagat  72000
tgcactatac attttgaaac tatgtcaaaa attgtagaac gacgctgttc tgcagccatt  72060
taactttaaa taatttacaa aaatttaaaa tgagcatccg tataaaaatc gataaactgc  72120
gccaaattgt ggcatatttt tcagagttca gtgaagaagt atctataaat gtagactcga  72180
cggatgagtt aatgtatatt tttgccgcct tgggcggatc tgtaaacatt tgggccatta  72240
tacctctcag tgcatcagtg ttctaccgcg gagccgaaaa cattgtgttt aatcttcctg  72300
tgtccaaggt aaaatcgtgt ttgtgtagtt ttcacaatga tgccatcata gatatagaac  72360
ctgatctgga aaataatcta gtaaaacttt ctagttatca tgtagtaagt gtcgattgta  72420
acaaggaact gatgcctatt aggacagata ctactatttg tctaagtata gatcaaaaga  72480
aatcttacgt gtttaatttt cacaagtatg aagaaaaatg ttgtggtaga accgtcattc  72540
atttagaatg gttgttgggc tttatcaagt gtattagtca gcatcagcat ttggctatta  72600
```

```
tgtttaaaga tgacaatatt attatgaaga ctcctggtaa tactgatgcg ttttccaggg  72660
aatattctat gactgaatgt tctcaagaac tacaaaagtt ttctttcaaa atagctatct  72720
cgtctctcaa caaactacga ggattcaaaa agagagtcaa tgtttttgaa actagaatcg  72780
taatggataa tgacgataac attctaggaa tgttgttttc ggatagagtt caatccttta  72840
agatcaacat ctttatgacg tttttagatt aatactttca atgagataaa tatgggtggc  72900
ggagtaagtg ttgagctccc taaacgggat ccgcctccgg gagtacccac tgatgagatg  72960
ttattaaacg tggataaaat gcatgacgtg atagctcccg ctaagctttt agaatatgtg  73020
catataggac cactagcaaa agataaagag gataaagtaa agaaaagata tccagagttt  73080
agattagtca acacaggacc cggtggtctt tcggcattgt taagacaatc gtataatgga  73140
accgcaccca attgctgtcg cacttttaat cgtactcatt attggaagaa ggatggaaag  73200
atatcagata agtatgaaga gggtgcagta ttagaatcgt gttggccaga cgttcacgac  73260
accggaaaat gcgatgttga tttattcgac tggtgtcagg gggatacgtt cgatagaaac  73320
atatgccatc agtggatcgg ttcagccttt aataggagta atagaactgt agagggtcaa  73380
caatcgttaa taaatctgta taataagatg caaacattat gtagtaaaga tgctagtgta  73440
ccaatatgtg aatcattttt gcatcattta cgcgcacaca atacagaaga tagcaaagag  73500
atgatcgatt atattctaag acaacagtct gcggacttta aacagaaata tatgagatgt  73560
agttatccca ctagagataa gttagaagag tcattaaaat atgcggaacc tcgagaatgt  73620
tgggatccag agtgttcgaa tgccaatgtt aatttcttgc taacacgtaa ttataataat  73680
ttaggacttt gcaatattgt acgatgtaat actagcgtga acaacttaca gatggataaa  73740
acttcctcat taagattgtc atgtggatta agcaatagtg atagattttc tactgttccc  73800
gtcaatagag caaaagtagt tcaacataat attaaacact cgttcgacct aaaattgcat  73860
ttgatcagtt tattatctct cttggtaata tggatactaa ttgtagctat ttaaatgggt  73920
gccgcggcaa gcatacagac gacggtgaat acactcagcg aacgtatctc gtctaaatta  73980
gaacaagaag cgaatgctag tgctcaaaca aaatgtgata tagaaatcgg aaatttttat  74040
atccgacaaa accatggatg taacctcact gttaaaaata tgtgctctgc ggacgcggat  74100
gctcagttgg atgctgtgtt atcagccgct acagaaacat atagtggatt aacaccggaa  74160
caaaaagcat acgtgccagc tatgtttact gctgcgttaa acattcagac gagtgtaaac  74220
actgttgtta gagattttga aaattatgtg aaacagactt gtaattctag cgcggtcgtc  74280
gataacaaat taaagataca aaacgtaatc atagatgaat gttacggagc cccaggatct  74340
ccaacaaatt tggaatttat taatacagga tctagcaaag gaaattgtgc cattaaggcg  74400
ttgatgcaat tgacgactaa ggccactact caaatagcac ctaaacaagt tgctggtaca  74460
ggagttcagt tttatatgat tgttatcggt gttataatat tggcagcgtt gtttatgtac  74520
tatgccaagc gtatgttgtt cacatccacc aatgataaaa tcaaacttat tttagccaat  74580
aaggaaaacg tccattggac tacttacatg gacacattct ttagaacttc tccgatggtt  74640
attgctacca cggatatgca aaactgaaaa tatattgata atattttaat agattaacat  74700
ggaagttatc actgatcgtc tagacgatat agtgaaacaa aatatagcgg atgaaaaatt  74760
tgtagatttt gttatacacg gtctagagca tcaatgtcct gctatacttc gaccattaat  74820
taggttgttt attgatatac tattatttgt tatagtaatt tatattttta cggtacgtct  74880
agtaagtaga aattatcaaa tgttgttggc gttggtggcg ctagtcatca cattaactat  74940
```

```
tttttattac tttatactat aatagtacta gactgacttc taacaaacat ctcacctgcc  75000
ataaataaat gcttgatatt aaagtcttct atttctaaca ctattccatc tgtggaaaat  75060
aatactctga cattatcgct aattgacaca tcggtgagtg atatgcctat aaagtaataa  75120
tcttctttgg gcacatatac cagtgtacca ggttctaaca acctatttac tggtgctcct  75180
atagcatact ttttctttac cttgagaata tccatcgttt gcttggtcaa tagcgatatg  75240
tgattttttta tcaaccactc gaaaaagtaa ttggagtgtt catatcctct acgggctatt  75300
gtctcatggc cgtgtatgaa atttaagtaa cacgactgtg gtagatttgt tctatagagc  75360
cggttgccgc aaatagatag aactaccaat atgtctgtac aaatgttaaa cattaattga  75420
ttaacagaaa aaacaatgtt cgttctggga atagaaacca gatcaaaaca aaattcgtta  75480
gaatatatgc cacgtttata cattgaatat aaaataacta cagtttgaaa aataacagta  75540
tcatttaaac atttaacttg cggggttaat ctcacaactt tactgttttt gaactgttca  75600
aaatatagca tagatccgtg agaaatacgt ttagccgcct ttaatagagg aaatcccacc  75660
gcctttctgg atctcaccaa cgacgatagt tctgaccagc aactcatttc ttcatcatcc  75720
acctgtttta acatataata ggcaggagat agatatccgt cattgcaata ttccttctcg  75780
taggcacaca atctaatatt gataaaatct ccattctctt ctctgcattt attatcttgt  75840
ttcggtggct gattaggctg tagtcttggt ttaggctttg gtatatcgtt gttgaatcta  75900
ttttggtcat taaatctttc atttcttcct ggtatatttt tatcacctcg tttggttgga  75960
tttttgtcta tattatcgtt tgtaacatcg gtacgggtat tcatttatca caaaaaaaac  76020
ttctctaaat gagtctactg ctagaaaacc tcatcgaaga agataccata ttttttgcag  76080
gaagtatatc tgagtatgat gatttacaaa tggttattgc cggcgcaaaa tccaaatttc  76140
caagatctat gctttctatt tttaatatag tacctagaac gatgtcaaaa tatgagttgg  76200
agttgattca taacgaaaat atcacaggag caatgtttac cacaatgtat aatataagaa  76260
acaatttggg tctaggagat gataaactaa ctattgaagc cattgaaaac tatttcttgg  76320
atcctaacaa tgaagttatg cctcttatta ttaataatac ggatatgact gccgtcattc  76380
ctaaaaaaag tggtaggaga aagaataaga acatggttat cttccgtcaa ggatcatcac  76440
ctatcttgtg tattttcgaa actcgtaaaa agattaatat ttataaagaa aatatggaat  76500
ccgcgtcgac tgagtataca cctatcggag acaacaaggc tttgatatct aaatatgcgg  76560
gaattaatgt cctgaatgtg tattctcctt ccacatccat gagattgaat gccatttacg  76620
gattcaccaa taaaaataaa ctagagaaac ttagtactaa taaggaacta gaatcgtata  76680
gttctagccc tcttcaagaa cccattaggt taaatgattt tctgggacta ttggaatgtg  76740
ttaaaaagaa tattcctcta acagatattc cgacaaagga ttgattacta taaatggaga  76800
atgttcctaa tgtatacttt aatcctgtgt ttatagagcc cacgtttaaa cattctttat  76860
taagtgttta taaacacaga ttaatagttt tatttgaagt attcgttgta ttcattctaa  76920
tatatgtatt ttttagatct gaattaaata tgttctttat gcctaaacga aaaatacccg  76980
atcctattga tagattacga cgtgctaatc tagcgtgtga agacgataaa ttaatgatct  77040
atggattacc atggatgaca actcaaacat ctgcgttatc aataaatagt aaaccgatag  77100
tgtataaaga ttgtgcaaag cttttgcgat caataaatgg atcacaacca gtatctctta  77160
acgatgttct tcgcagatga tgattcattt tttaagtatt tggctagtca agatgatgaa  77220
tcttcattat ctgatatatt gcaaatcact caatatctag actttctgtt attattattg  77280
atccaatcaa aaaataaatt agaagccgtg ggtcattgtt atgaatctct ttcagaggaa  77340
```

```
tacagacaat tgacaaaatt cacagacttt caagatttta aaaaactgtt taacaaggtc  77400
cctattgtta cagatggaag ggtcaaactt aataaaggat atttgttcga ctttgtgatt  77460
agtttgatgc gattcaaaaa agaatcctct ctagctacca ccgcaataga tcctattaga  77520
tacatagatc ctcgtcgtga tatcgcattt tctaacgtga tggatatatt aaagtcgaat  77580
aaagtgaaca ataattaatt ctttattgtc atcatgaacg gcggacatat tcagttgata  77640
atcggcccca tgttttcagg taaaagtaca gaattaatta gacgagttaa acgttatcaa  77700
atagctcaat ataaatgcgt gactataaaa tattctaacg ataatagata cggaacggga  77760
ctatggacgc atgataagaa taattttgaa gcattggaag caactaaact atgcgatgtt  77820
ttggaattaa ttacagattt ctccgtgata ggtatcgatg aaggacagtt ctttccagac  77880
attgttgaat tctgtgagcg tatggcaaac gaaggaaaaa tagttatagt agccgcactc  77940
gatgggacat ttcaacgtaa accgtttaat aatattttga atcttattcc attatctgaa  78000
atggtggtaa aactaactgc tgtgtgtatg aaatgcttta aggaggcttc cttttctaaa  78060
cgattgggtg aggaaaccga gataaaaata ataggaggta atgatatgta tcaatcggtg  78120
tgtagaaagt gttacatcga ctcataatat tatatttttt atctaaaaaa ctaaaaataa  78180
acattgatta aattttaata taatacttaa aaatggatgt tgtgtcgtta gataaaccgt  78240
ttatgtattt tgaggaaatt gataatgagt tagattacga accagaaagt gcaaatgagg  78300
tcgcaaaaaa actgccgtat caaggacagt taaaactatt actaggagaa ttatttttc  78360
ttagtaagtt acagcgacac ggtatattag atggtgccac cgtagtgtat ataggatctg  78420
ctcccggtac acatatacgt tatttgagag atcatttcta taatttagga gtgatcatca  78480
aatggatgct aattgacggc cgccatcatg atcctatttt aaatggattg cgtgatgtga  78540
ctctagtgac tcggttcgtt gatgaggaat atctacgatc catcaaaaaa caactgcatc  78600
cttctaagat tattttaatt tctgatgtga gatccaaacg aggaggaaat gaacctagta  78660
cggcggattt actaagtaat tacgctctac aaaatgtcat gattagtatt ttaaaccccg  78720
tggcgtctag tcttaaatgg agatgcccgt ttccagatca atggatcaag gacttttata  78780
tcccacacgg taataaaatg ttacaacctt ttgctccttc atattcagct gaaatgagat  78840
tattaagtat ttataccggt gagaacatga gactgactcg agttaccaaa ttagacgctg  78900
taaattatga aaaaaagatg tactacctta ataagatcgt ccgtaacaaa gtagttgtta  78960
actttgatta tcctaatcag gaatatgact attttcacat gtactttatg ctgaggaccg  79020
tgtactgcaa taaaacattt cctactacta aagcaaaggt actatttcta caacaatcta  79080
tatttcgttt cttaaatatt ccaacaacat caactgaaaa agttagtcat gaaccaatac  79140
aacgtaaaat atctagcaaa aattctatgt ctaaaaacag aaatagcaag agatccgtac  79200
gcggtaataa atagaaacgt gctactgaga tatactaccg atatagagta taatgattta  79260
gttactttaa taaccgttag acataaaatt gattctatga aaactgtgtt tcaggtattt  79320
aacgaatcat ccataaatta tactccggtt gatgatgatt atggagaacc aatcattata  79380
acatcgtatc ttcaaaaagg tcataacaag tttcctgtaa attttctata catagatgtg  79440
gtaatatctg acttatttcc tagctttgtt agactagata ctacagaaac taatatagtt  79500
aatagtgtac tacaaacagg tgatggtaaa aagactcttc gtcttcccaa aatgttagag  79560
acggaaatag ttgtcaagat tctctatcgc cctaatatac cattaaaaat tgttagattt  79620
ttccgcaata acatggtaac tggagtagag atagccgata gatctgttat ttcagtcgct  79680
```

```
gattaatcaa ttagtagaga tgagataaga acattataat aatcaataat atatcttata  79740
tcttatatct tatatcttat atcttgttta gaaaaatgct aatattaaaa tagctaacgc  79800
tagtaatcca atcggaagcc atttgatatc tataataggg tatctaattt cctgatttaa  79860
atagcggaca gctatattct cggtagctac tcgtttggaa tcacaaacat tatttacatc  79920
taatttacta tctgtaatgg aaacgtttcc caatgaaatg gtacaatccg atacattgca  79980
ttttgttata ttttttttta aagaggctgg taacaacgca tcgcttcgtt tacatggctc  80040
gtaccaacaa taatagggta atcttgtatc tattcctatc cgtactatgc ttttatcagg  80100
ataaatacat ttacatcgta tatcgtcttt gttagcatca cagaatgcat aaatttgttc  80160
gtccgtcatg ataaaaattt aaagtgtaaa tataactatt atttttatag ttgtaataaa  80220
aagggaaatt tgattgtata ctttcggttc tttaaaagaa actgacttga taaaaatggc  80280
tgtaatctct aaggttacgt atagtctata tgatcaaaaa gagattaatg ctacagatat  80340
tatcattagt catgttaaaa atgacgacga tatcggtacc gttaaagatg gtagactagg  80400
tgctatggat ggggcattat gtaaaacttg tgggaaaacg gaattggaat gtttcggtca  80460
ctggggtaaa gtaagtattt ataaaactca tatagttaag cctgaattta tttcagaaat  80520
tattcgttta ctgaatcata tatgtattca ctgcggatta ttgcgttcac gagaaccgta  80580
ttccgacgat attaacctaa aagagttatc gggacacgct cttaggagat taaaggataa  80640
aatattatcc aagaaaaagt catgttggaa cagcgaatgt atgcaaccgt atcaaaaaat  80700
tactttttca aagaaaaagg tttgtttcgt caacaagttg gatgatatta acgttcctaa  80760
ttctctcatc tatcaaaagt taatttctat tcatgaaaag ttttggccat tattagaaat  80820
tcatcaatat ccagctaact tattttatac agactacttt cccatccctc cgctgattat  80880
tagaccggct attagttttt ggatagatag tatacccaaa gaaaccaatg aattaactta  80940
cttattaggt atgatcgtta agaattgtaa cttgaatgct gatgaacagg ttatccagaa  81000
ggcggtaata gaatacgatg atattaaaat tatttctaat aacactacca gtatcaattt  81060
atcatatatc acatccggca aaaataatat gattagaagt tatatcgtcg cccggcgaaa  81120
agatcagacc gctagatctg taattggtcc cagtacatct atcaccgtta atgaggtagg  81180
aatgcccgca tatattagaa atacacttac agaaaagata tttgttaatg cctttacagt  81240
ggataaagtt aaacaactat tagcgtcaaa ccaagttaaa ttttacttta ataaacgatt  81300
aaaccaatta acaagaatac gccaaggaaa gtttatcaaa aataaaatac atttattgcc  81360
tggtgattgg gtagaagtag ctgttcaaga atatacaagt attatttttg gaagacagcc  81420
gtctctacat agatacaacg tcatcgcttc atctatcaga gctaccgaag gagatactat  81480
caaaatatct cccggaattg ccaactctca aaatgctgat ttcgacgggg atgaggaatg  81540
gatgatatta gaacaaaatc ctaaagctgt aattgaacaa agtattctta tgtatccgac  81600
gacgttactc aaacacgata ttcatggagc cccccgtttat ggatctattc aagatgaaat  81660
cgtagcagcg tattcattgt ttaggataca agatctttgt ttagatgaag tattgaacat  81720
cttggggaaa tatggaagag agttcgatcc taaaggtaaa tgtaaattca gcggtaaaga  81780
tatctatact tacttgatag gtgaaaagat taattatccg ggtctcttaa aggatggtga  81840
aattattgca aacgacgtag atagtaattt tgttgtggct atgaggcatc tgtcattggc  81900
tggactctta tccgatcata agtcgaacgt ggaaggtatc aactttatta tcaagtcatc  81960
ttatgttttt aagagatatc tatctattta cggttttggg gtgacattca aagatctgag  82020
accaaattcg acgttcacta ataaattgga ggccatcaac gtagaaaaaa tagaacttat  82080
```

```
caaagaagca tacgccaaat atctcaacga tgtaagagac gggaaaatag ttccattatc  82140
taaagcttta gaggcggact atgtggaatc catgttatcc aacttgacaa atcttaatat  82200
ccgagagata gaagaacata tgagacaaac gctgatagat gatccagata ataacctcct  82260
gaaaatggcc aaagcgggtt ataaagtaaa tcctacagaa ctaatgtata ttctaggtac  82320
gtatggacaa caaaggattg atggtgaacc agcagagact cgagtattgg gtagagtctt  82380
accttactat cttccagact ctaaggatcc agaaggaaga ggttacattc ttaattcttt  82440
aacaaaagga ttaacgggtt ctcaatatta cttttcgatg ctggttgcaa gatctcaatc  82500
tactgatatc gtctgtgaaa catcacgtac cggaacactg gctagaaaaa tcattaaaaa  82560
gatggaggat atggtggtcg acggatacgg acaagtagtt ataggtaata cgctcatcaa  82620
gtacgccgcc aattatacca aaattctagg ctcagtatgt aaacctgtag atcttatcta  82680
tccagatgag tccatgactt ggtatttgga aattagtgct ctgtggaata aaataaaaca  82740
gggattcgtt tactctcaga aacagaaact tgcaaagaag acattggcgc cgtttaattt  82800
cctagtattc gtcaaaccca ccactgagga taatgctatt aaggttaagg atctgtacga  82860
tatgattcat aacgtcattg atgatgtgag agagaaatac ttctttacgg tatctaatat  82920
agattttatg gagtatatat tcttgacgca tcttaatcct tctagaatta gaattacaaa  82980
agaaacggct atcactatct ttgaaaagtt ctatgaaaaa ctcaattata ctctaggtgg  83040
tggaactcct attggaatta tttctgcaca ggtattgtct gagaagttta cacaacaagc  83100
cctgtccagt tttcacacta ctgaaaaaag tggtgccgtc aaacaaaaac ttggtttcaa  83160
cgagtttaat aacttgacta atttgagtaa gaataagacc gaaattatca ctctggtatc  83220
cgatgatatc tctaaacttc aatctgttaa gattaatttc gaatttgtat gtttgggaga  83280
attaaatcca gacatcactc ttcgaaaaga aacagatagg tatgtagtag atataatagt  83340
caatagatta tacatcaaga gagcagaaat taccgaatta gtcgtcgaat atatgattga  83400
acgatttatc tcctttagcg tcattgtaaa ggaatggggt atggaaacat tcattgagga  83460
tgaggataat attagattta ctgtctacct aaatttcgtt gaaccggaag aattgaatct  83520
tagtaagttt atgatggttc ttccgggtgc cgccaacaag ggcaagatta gtaaattcaa  83580
gattcctatc tctgactata cgggatatga cgacttcaat caaacaaaaa agctcaataa  83640
gatgactgta gaactcatga atctaaaaga attgggttct ttcgatttgg aaaacgtcaa  83700
cgtgtatcct ggagtatgga atacatacga tatcttcggt atcgaggccg ctcgtgaata  83760
cttgtgcgaa gccatgttaa acacctatgg agaagggttc gattatctgt atcagccttg  83820
tgatcttctc gctagtttac tatgtgctag ttacgaacca gaatcagtga ataaattcaa  83880
gttcggcgca gctagtactc ttaagagagc tacgttcgga gacaataaag cattgttaaa  83940
cgcggctctt cataaaaagt cagaacctat taacgataat agtagctgcc actttttag   84000
caaggtccct aatataggaa ctggatatta caaatacttt atcgacttgg gtcttctcat  84060
gagaatggaa aggaaactat ctgataagat atcttctcaa aagatcaagg aaatggaaga  84120
aacagaagac ttttaattct tatcaataac atatttttct atgatctgtc ttttaaacga  84180
tggattttcc acaaatgcgc ctctcaagtc cctcatagaa tgatacacgt ataaaaaata  84240
tagcataggc aatgactcct tatttttaga cattagatat gccaaaatca tagccccgct  84300
tctatttact cccgcagcac aatgaaccaa cacgggctcg tttcgttgat cacatttaga  84360
taaaaaggcg gttacgtcgt caaaatattt actaatatcg gtagttgtat catctaccaa  84420
```

```
cggtatatga ataatattaa tattagagtt aggtaatgta tatttatcca tcgtcaaatt  84480
taaaacatat ttgaacttaa cttcagatga tggtgcatcc atagcatttt tataatttcc  84540
caaatacaca ttattggtta cccttgtcat tatagtggga gatttggctc tgtgcatatc  84600
tccagttgaa cgtagtagta agtatttata caaacttttc ttatccattt ataacgtaca  84660
aatggataaa actactttat cggtaaacgc gtgtaattta gaatacgtta gagaaaaggc  84720
tatagtaggc gtacaagcag ccaaaacatc aacacttata ttctttgtta ttatattggc  84780
aattagtgcg ctattactct ggtttcagac gtctgataat ccagtcttta atgaattaac  84840
gagatatatg cgaattaaaa atacggttaa cgattggaaa tcattaacgg atagcaaaac  84900
aaaattagaa agtgatagag gtagacttct agccgctggt aaggatgata tattcgaatt  84960
caaatgtgtg gatttcggcg cctattttat agctatgcga ttggataaga aaacatatct  85020
gccgcaagct attaggcgag gtactggaga cgcgtggatg gttaaaaagg cggcaaaggt  85080
cgatccatct gctcaacaat tttgtcagta tttgataaaa cacaagtcta ataatgttat  85140
tacttgtggt aatgagatgt taaatgaatt aggttatagc ggttatttta tgtcaccgca  85200
ttggtgttcc gattttagta atatggaata gtgttagata aatgcggtaa cgaatgttcc  85260
tgtaaggaac cataacagtt tagatttaac gttaaagatg agcataaaca taataaacaa  85320
aattacaatc aaacctataa cattaatatc aaacaatcca aaaaatgaaa tcagtggagt  85380
agtaaacgcg tacataactc ctggataacg tttagtagct gccgttccta ttctagacca  85440
aaaattcggt ttcatgtttt cgaaacggtg ttctgcaaca agtcggggat cgtgttctac  85500
atatttggcg gcattatcca gtatctgcct attgatcttc atttcgtttt caattctggc  85560
tatttcaaaa taaaatcccg atgatagacc tccagacttt ataatttcat ctacgatgtt  85620
cagcgccgta gtaactctaa taatataggc tgataagcta acatcatacc ctcctgtata  85680
tgtgaatatg gcatgatttt tgtccattac aagctcggtt ttaactttat tgcctgtaat  85740
aatttctctc atctgtagga tatctatttt tttgtcatgc attgccttca agacgggacg  85800
aagaaacgta atatcctcaa taacgttatc gttttctaca ataactacat attctacctt  85860
tttattttct aactcggtaa aaaaattaga atcccatagg gctaaatgtc tagcgatatt  85920
tcttttcgtt tcctctgtac acatagtgtt acaaaaccct gaaaagaagt gagtatactt  85980
gtcatcattt ctaatgtttc ctccagtcca ctgtataaac gcataatcct tgtaatgatc  86040
tggatcatcc ttgactacca caacatttct tttttctggc ataacttcgt tgtcctttac  86100
atcatcgaac ttctgatcat taatatgctc atgaacatta ggaaatgttt ctgatggaag  86160
tctatcaata actggcacaa caataacagg agttttcgcc gccgccattt agttattgaa  86220
attaatcata tacaactctt taatacgagt tatattttcg tctatccatt gtttcacatt  86280
tacatatttc gacaaaaaga tataaaatgc gtattccaat gcttctctgt ttaatgaatt  86340
actaaaatat acaaacacgt cactgtctgg caataaatga tatcttagaa tattgtaaca  86400
atttattttg tattgcacat gttcgtgatc tatgagttct tcttcgaatg gcataggatc  86460
tccgaatctg aaaacgtata aataggagtt agaataataa tatttgagag tattggtaat  86520
atataaactc tttagcggta taattagttt ttttctctca atttctattt ttagatgtga  86580
tggaaaaatg actaattttg tagcattagt atcatgaact ctaatcaaaa tcttaatatc  86640
ttcgtcacac gttagctctt tgaagttttt aagagatgca tcagttggtt cgaccgatgg  86700
agtaggtgca acaatttttt gttcgatgta tgtatgtact ggagccattg ttttaactat  86760
aatggtgctt gtatcgaaaa actttaatgc agatagcgga agctcttcgc cgcgactttc  86820
```

```
tacatcgtaa ttgggttcta acgccgatct ctgaatggat actagttttc taagttctaa  86880
tgtgattctc tgaaaatgta aatccaattc ctccggcatt atagatgtgt atacatcggt  86940
aaataaaact atagtatcca acgatccctt ctcgcaaatt ctagtcttaa ccaaaaaatc  87000
gtatataacc acggagatgg cgtatttaag agtggattct tctaccgttt tgttcttgga  87060
tgtcatatag gaaactataa agtccgcact actgttaaga atgattacta acgcaactat  87120
atagttcaaa ttaagcattt tggaaacata aaataactct gtagacgata cttgactttc  87180
gaataagttt gcagacaaac gaagaaagaa cagacctctc ttaatttcag aagaaaactt  87240
tttttcgtat tcctgacgtc tagagtttat atcaataaga aagttaagaa ttagtcggtt  87300
aatgttgtat ttcattaccc aagtttgaga tttcataata ttatcaaaag acatgataat  87360
attaaagata aagcgctgac tatgaacgaa atagctatat ggttcgctca aaaatatagt  87420
cttgttaaac gtggaaacga taactgtatt tttaatcacg tcagcggcat ctaaattaaa  87480
tataggtata tttattccac acactctaca atatgccaca ccatcttcat aataaataaa  87540
ttcgttagca aaattattaa ttttagtgaa atagttagcg tcaactttca tagcttcctt  87600
caatctaatt tgatgctcac acggtgcgaa ttccactcta acatcccttt tccatgcctc  87660
aggttcatcg atctctataa tatctagttt tttgcgtttc acaaacacag gctcgtctct  87720
cgcgatgaga tctgtatagt aactatgtaa atgataacta gatagaaaga tgtagctata  87780
tagatgacga tcctttaaga gaggtataat aactttaccc caatcagata gactgttgtt  87840
atggtcttcg gaaaaagaat ttttataaat ttttccagta ttttccaaat atacgtactt  87900
aacatctaaa aaatccttaa tgataatagg aatggataat ccgtctattt tataaagaaa  87960
tacatatcgc acattatact tttttttgga aatgggaata ccgatgtgtc tacataaata  88020
tgcaaagtct aaatattttt tagagaatct taattggtcc aaattctttt ccaagtacgg  88080
taatagattt ttcatattga acggtatctt cttaatctct ggttctagtt ccgcattaaa  88140
tgatgaaact aagtcactat ttttataact aacgattaca tcacctctaa catcatcatt  88200
taccagaata ctgatcttct tttgtcgtaa atacatgtct aatgtgttaa aaaaaagatc  88260
atacaagtta tacgtcattt catctgtggt attcttgtca ttgaaggata aactcgtact  88320
aatctcttct ttaacagcct gttcaaattt atatcctata tacgaaaaaa tagcaaccag  88380
tgtttgatca tccgcgtcaa tattctgttc tatcgtagtg tataacaatc gtatatcttc  88440
ttctgtgata gtcgatacgt tataaaggtt gataacgaaa atatttttat ttcgtgaaat  88500
aaagtcatcg taggattttg gacttatatt cgcgtctagt agatatgctt ttatttttgg  88560
aatgatctca attagaatag tctctttaga gtccatttaa agttacaaac aactaggaaa  88620
ttggtttatg atgtataatt tttttagttt ttatagattc tttattctat acttaaaaaa  88680
tgaaaataaa tacaaaggtt cttgagggtt gtgttaaatt gaaagcgaga aataatcata  88740
aattatttca ttatcgcgat atccgttaag tttgtatcgt aatggcgtgg tcaattacga  88800
ataaagcgga tactagtagc ttcacaaaga tggctgaaat cagagctcat ctaaaaaata  88860
gcgctgaaaa taaagataaa aacgaggata ttttcccgga agatgtaata attccatcta  88920
ctaagcccaa aaccaaacga gccactactc ctcgtaaacc agcggctact aaaagatcaa  88980
ccaaaaagga ggaagtggaa gaagaagtag ttatagagga atatcatcaa acaactgaaa  89040
aaaattctcc atctcctgga gtcagcgaca ttgtagaaag cgtggccgct gtagagctcg  89100
atgatagcga cggggatgat gaacctatgg tacaagttga agctggtaaa gtaaatcata  89160
```

```
gtgctagaag cgatctttct gacctaaagg tggctaccga caatatcgtt aaagatctta  89220
agaaaattat tactagaatc tctgcagtat cgacggttct agaggatgtt caagcagctg  89280
gtatctctag acaatttact tctatgacta aagctattac aacactatct gatctagtca  89340
ccgagggaaa atctaaagtt gttcgtaaaa aagttaaaac ttgtaagaag taaatgcgtg  89400
cacttttta taaagatggt aaactcttta ccgataataa ttttttaaat cctgtatcag  89460
acgataatcc agcgtatgag gttttgcaac atgttaaaat tcctactcat ttaacagatg  89520
tagtagtata tgaacaaacg tgggaggagg cgttaactag attaattttt gtgggaagcg  89580
attcaaaagg acgtagacaa tacttttacg gaaaaatgca tgtacagaat cgcaacgcta  89640
aaagagatcg tatttttgtt agagtatata acgttatgaa acgaattaat tgttttataa  89700
acaaaaatat aaagaaatcg tccacagatt ccaattatca gttggcggtt tttatgttaa  89760
tggaaactat gtttttttatt agatttggta aaatgaaata tcttaaggag aatgaaacag  89820
tagggttatt aacactaaaa aataaacaca tagaaataag tcccgatgaa atagttatca  89880
agtttgtagg aaaggacaaa gtttcacatg aatttgttgt tcataagtct aatagactat  89940
ataaaccgct attgaaactg acggatgatt ctagtcccga agaatttctg ttcaacaaac  90000
taagtgaacg aaaggtatac gaatgtatca aacagtttgg tattagaatc aaggatctcc  90060
gaacgtatgg agtcaattat acgtttttat ataattttg gacaaatgta aagtccatat  90120
ctcctcttcc atcaccaaaa aagttaatag cgttaactat caaacaaact gctgaagtgg  90180
taggtcatac tccatcaatt tcaaaaagag cttacatggc aacgactatt ttagaaatgg  90240
taaaggataa aaatttttta gatgtagtat ctaaaactac gttcgatgaa ttcctatcta  90300
tagtcgtaga tcacgttaaa tcatctacgg atggatgata tagatcttta cacaaataat  90360
tacaagaccg ataaatggaa atggataagc gtatgaaatc tctcgcaatg accgctttct  90420
ttggggagct aagcacatta gatattatgg cattgataat gtctatattt aaacgccatc  90480
caaacaatac cattttttca gtggataagg atggtcagtt tatgattgat ttcgaatacg  90540
ataattataa ggcttctcaa tatttggatc tgaccctcac tccgatattt ggagatgaat  90600
gcaagactca cgcatcgagt atagccgaac aattggcgtg tgcggatatt attaaagagg  90660
atattagcga atacatcaaa actactcccc gtcttaaacg atttataaaa aaataccgca  90720
atagatcaga tactcgcatc agtcgagata cagaaaagct taaaatagct ctagctaaag  90780
gcatagatta cgaatatata aaagacgctt gttaataagt aaatgaaaaa aaactagtcg  90840
tttataataa aacacaatat ggatgccaac atagtatcat cttctactat tgcaacgtat  90900
atagacgctt tagcgaagaa tgcttcagaa ttagaacaga ggtctaccgc atacgaaata  90960
aataatgaat tggaactagt atttattaag ccgccattaa ttactttgac aaatgtagtg  91020
aatatctcta cgattcagga atcgtttatt cgatttaccg ttactaataa ggaaggtgtt  91080
aaaattagaa ctaagattcc attatctaag gtacatggtc tagatgtaaa aaatgtacag  91140
ttagtagatg ctatagataa catagtttgg gaaaagaaat cattagtgac ggaaaatcgt  91200
cttcacaaag aatgcttgtt gagactatcg acagaggaac gtcatatatt tttggattac  91260
aagaaatatg gatcctctat ccgactagaa ttagtcaatc ttattcaagc aaaaacaaaa  91320
aactttacga tagactttaa gctaaaatat tttctaggat ccggtgccca atctaaaagt  91380
tctttgttgc acgctattaa tcatccaaag tcaaggccta atacatctct ggaaatagaa  91440
ttcacaccta gagacaatga aaaagttcca tatgatgaac taataaagga attgacgact  91500
ctatcacgtc atatatttat ggcttctcca gagaatgtaa ttctttctcc gcctattaac  91560
```

```
gcacctataa agacttttat gttgcctaaa caagatatag taggtctgga tctggaaaat  91620
ctatatgccg taactaagac tgacggcatt cctataacta tcagagttac atcaaacggg  91680
ttgtattgtt attttacaca tcttggttat attattagat atcctgttaa gagaataata  91740
gattccgaag tagtagtctt tggtgaggca gttaaggata agaactggac cgtatatctc  91800
attaagctaa tagagcctgt gaatgcaatc aatgatagac tagaagaaag taagtatgtt  91860
gaatctaaac tagtggatat ttgtgatcgg atagtattca agtcaaagaa atatgaaggt  91920
ccgtttacta caactagtga agtcgtcgat atgttatcta catatttacc aaagcaacca  91980
gaaggtgtta ttctgttcta ttcaaaggga cctaaatcta acattgattt taaaattaaa  92040
aaggaaaata ctatagacca aactgcaaat gtagtattta ggtacatgtc cagtgaacca  92100
attatctttg gagaatcgtc tatctttgta gagtataaga aatttagcaa cgataaaggc  92160
tttcctaaag aatatggttc tggtaagatt gtgttatata acggcgttaa ttatctaaat  92220
aatatctatt gtttggaata tattaataca cataatgaag tgggtattaa gtccgtggtt  92280
gtacctatta agtttatagc agaattctta gttaatggag aaatacttaa acctagaatt  92340
gataaaacca tgaaatatat taactcagaa gattattatg gaaatcaaca taatatcata  92400
gttgaacatt taagagatca aagcatcaaa ataggagata tctttaacga ggataaacta  92460
tcggatgtgg gacatcaata cgccaataat gataaattta gattaaatcc agaagttagt  92520
tattttacga ataaacgaac tagaggaccg ttgggaattt tatcaaacta cgtcaagact  92580
cttcttattt ctatgtattg ttccaaaaca tttttagacg attccaacaa acgaaaggta  92640
ttggcgattg attttggaaa cggtgctgac ctggaaaaat acttttatgg agagattgcg  92700
ttattggtag cgacggatcc ggatgctgat gctatagcta gaggaaatga aagatacaac  92760
aaattaaact ctggaattaa aaccaagtac tacaaatttg actacattca ggaaactatt  92820
cgatccgata catttgtctc tagtgtcaga gaagtattct attttggaaa gtttaatatc  92880
atcgactggc agtttgctat ccattattct tttcatccga gacattatgc taccgtcatg  92940
aataacttat ccgaactaac tgcttctgga ggcaaggtat taatcactac catggacgga  93000
gacaaattat caaaattaac agataaaaag acttttataa ttcataagaa tttacctagt  93060
agcgaaaact atatgtctgt agaaaaaata gctgatgata gaatagtggt atataatcca  93120
tcaacaatgt ctactccaat gactgaatac attatcaaaa agaacgatat agtcagagtg  93180
tttaacgaat acggatttgt tcttgtagat aacgttgatt tcgctacaat tatagaacga  93240
agtaaaaagt ttattaatgg cgcatctaca atggaagata gaccgtctac aaaaaacttt  93300
ttcgaactaa atagaggagc cattaaatgt gaaggtttag atgtcgaaga cttacttagt  93360
tactatgttg tttatgtctt ttctaagcgg taaataataa tatggtatgg gttctgatat  93420
ccccgttcta aatgcattaa ataattccaa tagagcgatt tttgttccta taggaccttc  93480
caactgtgga tactctgtat tgttaataga tatattaata cttttgtcgg gtaacagagg  93540
ttctacgtct tctaaaaata aaagtttgat aacatctggc ctgttcataa ataaaaactt  93600
ggcgattcta tatatactct tattatcaaa tctagccatt gtcttataga tgtgagctac  93660
tgtaggtgta ccatttgatt ttctttctaa tactatatat ttctctcgaa gaagttcttg  93720
cacatcatct gggaataaaa tactactgtt gagtaaatca gttatttttt ttatatcgat  93780
attgatggac atttttatag ttaaggataa taagtatccc aaagtagata acgacgataa  93840
cgaagtattt atacttttag gaaatcacaa tgactttatc agatcaaaat taacaaaatt  93900
```

```
aaaggagcat gtatttttt ctgaatatat tgtgactcca gataaatatg gatctttatg  93960
cgtcgaatta aatgggtcta gttttcagca cggcggtaga tatatagagg tggaggaatt  94020
tatagatgct ggaagacaag ttagatggtg ttctacatcc aatcatatat ctgaagatat  94080
acccgaagat atacacactg ataaatttgt catttatgat atatacactt ttgacgcttt  94140
caagaataaa cgattggtat tcgtacaggt acctccgtcg ttaggagatg atagctattt  94200
gactaatccg ttattgtctc cgtattatcg taattcagta gccagacaaa tggtcaatga  94260
tatgattttt aatcaagatt catttttaaa atatttatta gaacatctga ttagaagcca  94320
ctatagagtt tctaaacata taacaatagt tagatacaag gataccgaag aattaaatct  94380
aacgagaata tgttataata gagataagtt taaggcgttt gtattcgctt ggtttaacgg  94440
cgtttcggaa aatgaaaagg tactagatac gtataaaaag gtatctaatt tgatataatg  94500
aattcagtga ctgtatcaca cgcgccatat actattactt atcacgatga ttgggaacca  94560
gtaatgagtc aattggtaga gttttataac gaagtagcca gttggctgct acgagacgag  94620
acgtcgccta ttcctgataa gttctttata cagttgaaac aaccgcttag aaataaacga  94680
gtatgtgtgt gcggtataga tccgtatccg aaagatggaa ctggtgtacc gttcgaatca  94740
ccaaatttta caaaaaaatc aattaaggag atagcttcat ctatatctag attaaccgga  94800
gtaattgatt ataaaggtta taaccttaat ataatagacg ggttatacc ctggaattat  94860
tacttaagtt gtaaattagg agaaacaaaa agtcacgcga tctactggga taagatttcc  94920
aagttactgc tgcagcatat aactaaacac gttagtgttc tttattgttt gggtaaaaca  94980
gatttctcga atatacgggc caagttagaa tccccggtaa ctaccatagt cggatatcat  95040
ccagcggcta gagaccgcca attcgagaaa gatagatcat ttgaaattat caacgtttta  95100
ctggaattag acaacaaggc acctataaat tgggctcaag ggtttattta ttaatgcttt  95160
agtgaaattt taacttgtgt tctaaatgga tgcggctatt agaggtaatg atgttatctt  95220
tgttcttaag actataggtg tcccgtcagc gtgcagacaa aatgaagatc caagatttgt  95280
agaagcattt aaatgcgacg agttagaaag atatattgag aataatccag aatgtacact  95340
attcgaaagt cttagggatg aggaagcata ctctatagtc agaattttca tggatgtaga  95400
tttagacgcg tgtctagacg aaatagatta tttaacggct attcaagatt ttattatcga  95460
ggtgtcaaac tgtgtagcta gattcgcgtt tacagaatgc ggcgccattc atgaaaatgt  95520
aataaaatcc atgagatcta atttttcatt gactaagtct acaaatagag ataaaacaag  95580
ttttcatatt atctttttag acacgtatac cactatggat acattgatag ctatgaaacg  95640
aacactatta gaattaagta gatcatctga aaatccacta acaagatcga tagacactgc  95700
cgtatatagg agaaaaacaa ctcttcgggt tgtaggtact aggaaaaatc caaattgcga  95760
cactattcat gtaatgcaac caccgcatga taatatagaa gattacctat tcacttacgt  95820
ggatatgaac aacaatagtt attacttttc tctacaacaa cgattggagg atttagttcc  95880
tgataagtta tgggaaccag ggtttatttc attcgaagac gctataaaaa gagtttcaaa  95940
aatattcatt aattctataa taaactttaa tgatctcgat gaaaataatt ttacaacggt  96000
accactggtc atagattacg taacaccttg tgcattatgt aaaaaacgat cgcataaaca  96060
tccgcatcaa ctatcgttgg aaaatggtgc tattagaatt tacaaaactg gtaatccaca  96120
tagttgtaaa gttaaaattg ttccgttaga tggtaataaa ctgtttaata ttgcacaaag  96180
aattttagac actaactctg ttttattaac cgaacgagga gaccatatag tttggattaa  96240
taattcatgg aaatttaaca gcgaagaacc cttgataaca aaactaattt tgtcaataag  96300
```

```
acatcaacta cctaaggaat attcaagcga attactctgt ccaagaaaac gaaagactgt  96360
agaagctaac atacgagaca tgttagtaga ttcagtagag accgatacct atccggataa  96420
acttccgttt aaaaatggtg tattggacct ggtagacgga atgttttact ctggagatga  96480
tgctaaaaaa tatacgtgta ctgtatcaac cggatttaaa tttgacgata caaagttcgt  96540
cgaagacagt ccagaaatgg aagagttaat gaatatcatt aacgatatcc aaccattaac  96600
ggatgaaaat aagaaaaata gagagctata tgaaaaaaca ttatctagtt gtttatgtgg  96660
tgctaccaaa ggatgtttaa cattcttttt tggagaaact gcaactggaa agtcgacaac  96720
caaacgtttg ttaaagtctg ctatcggtga cctgtttgtt gagacgggtc aaacaatttt  96780
aacagatgta ttggataaag gacctaatcc atttatcgct aacatgcatt tgaaaagatc  96840
tgtattctgt agcgaactac ctgattttgc ctgtagtgga tcaaagaaaa ttagatctga  96900
caatattaaa aagttgacag aaccttgtgt cattggaaga ccgtgtttct ccaataaaat  96960
taataataga aaccatgcga caatcattat cgatactaat tacaaacctg tttttgatag  97020
gatagataac gcattaatga gaagaattgc cgtcgtgcga ttcagaacac acttttctca  97080
accttctggt agagaggctg ctgaaaataa tgacgcgtac gataaagtca aactattaga  97140
cgaggggtta gatggtaaaa tacaaaataa tagatataga ttcgcatttc tatacttgtt  97200
ggtgaaatgg tacagaaaat atcatgttcc tattatgaaa ctatatccta caccggaaga  97260
gattccggac tttgcattct atctcaaaat aggtactctg ttagtatcta gctctgtaaa  97320
gcatattcca ttaatgacgg acctctccaa aaagggatat atattgtacg ataatgtggt  97380
cactcttccg ttgactactt tccaacagaa aatatccaag tattttaatt ctagactatt  97440
tggacacgat atagagagct tcatcaatag acataagaaa tttgccaatg ttagtgatga  97500
atatctgcaa tatatattca tagaggatat ttcatctccg taaatatatg ctcatatatt  97560
tatagaagat atcacatatc taaatgaata ccggaatcat agatttattt gataatcatg  97620
ttgatagtat accaactata ttacctcatc agttagctac tctagattat ctagttagaa  97680
ctatcataga tgagaacaga agcgtgttat tgttccatat tatgggatca ggtaaaacaa  97740
taatcgcttt gttgttcgcc ttggtagctt ccagatttaa aaaggtttac attctagtgc  97800
ctaatatcaa cattttgaaa atttttaatt ataatatggg tgtagctatg aacttgttta  97860
atgacgaatt catagctgag aatatcttta ttcattccac aacaagtttt tattctctta  97920
attataacga taacgtcatt aattataacg gattatctcg ctacaataac tctattttta  97980
tcgttgatga ggcacataat atctttggga ataatactgg agaacttatg accgtgataa  98040
aaaataaaaa caagattcct tttctactat tgtctggatc tcccattact aacacaccta  98100
atactctggg tcatattata gatttaatgt ccgaagagac gatagatttt ggtgagatta  98160
ttagtcgtgg taagaaagta attcagacac ttcttaacga acgcggtgtg aatgtactta  98220
aggatttgct taaaggaaga atatcatatt acgaaatgcc tgataaagat ctaccaacga  98280
taagatatca cggacgtaag tttctagata ctagagtagt atattgtcac atgtctaaac  98340
ttcaagagag agattatatg attactagac gacagctatg ttatcatgaa atgtttgata  98400
aaaatatgta taacgtgtca atggcagtat tgggacaact taatctgatg aataatttag  98460
atactttatt tcaggaacag gataaggaat tgtacccaaa tctgaaaata aataatggcg  98520
tgttatacgg agaagaattg gtaacgttaa acattagttc caaatttaaa tactttatta  98580
atcggataca gacactcaac ggaaaacatt ttatatactt ttctaattct acatatggtg  98640
```

```
gattggtaat taaatatatc atgctcagta atggatattc tgaatataat ggttctcagg  98700
gaactaatcc acatatgata aacggcaaac caaaaacatt tgctatcgtt actagtaaaa  98760
tgaaatcgtc tttagaggat ctattagatg tgtataattc tcctgaaaac gatgatggca  98820
gtcaattgat gtttttgttt tcatcaaaca ttatgtccga atcctatact ctaaaagagg  98880
taaggcatat ttggtttatg actatcccag atactttttc tcaatacaac caaattcttg  98940
gacgatctat tagaaaattc tcttacgccg atatttctga accagttaat gtatatcttt  99000
tagccgccgt atattccgat ttcaatgacg aagtaacgtc attaaacgat tacacacagg  99060
atgaattgat taatgtttta ccatttgaca tcaaaaagct gttgtatcta aaatttaaga  99120
cgaaagaaac gaatagaata tactctattc ttcaagagat gtctgaaacg tattctcttc  99180
caccacatcc atcaattgta aaagttttat tgggagaatt ggtcagacaa tttttttata  99240
ataattctcg tattaagtat aacgactcca agttacttaa aatggttaca tcagttataa  99300
aaaataaaga agacgctagg aattacatag atgatattgt aaacggtcac ttctttgtat  99360
cgaataaagt atttgataaa tctcttttat acaaatacga aaacgatatt attacagtac  99420
cgtttagact ttcctacgaa ccatttgttt ggggagttaa ctttcgtaaa gaatataacg  99480
tggtatcttc tccataaaac tgatgaaata tataaagaaa taaatgtcga gctttgttac  99540
caatggatac cttccagtta cattggaacc acacgagctg acgttagaca taaaaactaa  99600
tattaggaat gccgtatata agacgtatct ccatagagaa attagtggta aaatggccaa  99660
gaaaatagaa attcgtgaag acgtggaatt acctctcggc gaaatagtta ataattctgt  99720
agttataaac gttccgtgtg taataaccta cgcgtattat cacgttgggg atatagtcag  99780
aggaacatta aacatcgaag atgaatcaaa tgtaactatt caatgtggag atttaatctg  99840
taaactaagt agagattcgg gtactgtatc atttagcgat tcaaagtact gctttttttcg  99900
aaatggtaat gcgtatgaca atggcagcga agtcactgcc gttctaatgg aggctcaaca  99960
aggtatcgaa tctagttttg tttttctcgc gaatatcgtc gactcataaa aaagagaata 100020
gcggtaagta taaacacgaa tactatggca ataattgcga atgttttatt ctcttcgata 100080
tatttttgat aatatgaaaa acatgtctct ctcaaatcgg acaaccatct cataaaatag 100140
ttctcgcgcg ctggagaggt agttgctgct cgtataatct ccccagaata atatacttgc 100200
gtgtcgtcgt tcaatttata cggatttcta tagttctctg ttatataatg cggttttcca 100260
tcatgattag acgacgacaa tagtgttctg aatttagata gttgatcaga atgaatgttt 100320
attggcgttg gaaaaattat ccatacagcg tctgcagagt ggttgatagt tgttcctaga 100380
tatgtaaaat aatccaactt actaggcagc aaattgtcta gataaaatac tgaatcaaac 100440
ggtgcagacg tattggcgga tctaatggaa tccaattgat taactatctt ttgaaaatat 100500
acatttttat gatccaatac ttgtaagaat atagaaataa tgataagtcc atcatcgtgt 100560
tttttttgcct cttcataaga actatatttt tttttattcc aatgaacaag attaatctct 100620
ccagagtatt tgtacacatc tatcaagtga ttggatccat aatcgtcttc ctttccccaa 100680
tatatatgta gtgatgataa cacatattca ttggggagaa accctccact tatatatcct 100740
cctttaaaat taatccttac tagttttcca gtgttctgga tagtggttgg tttcgactca 100800
ttataatgta tgtctaacgg cttcaatcgc gcgttagaaa ttgctttttt agtttctata 100860
ttaataggag atagttgttg cggcatagta aaaatgaaat gataactgtt taaaaatagc 100920
tcttagtatg ggaattacaa tggatgagga agtgatattt gaaactccta gagaattaat 100980
atctattaaa cgaataaaag atattccaag atcaaaagac acgcatgtgt ttgctgcgtg 101040
```

tataacaagt gacggatatc cgttaatagg agctagaaga acttcattcg cgttccaggc 101100
gatattatct caacaaaatt cagattctat ctttagagta tccactaaac tattacggtt 101160
tatgtactac aatgaactaa gagaaatctt tagacggttg agaaaaggtt ctatcaacaa 101220
tatcgatcct cactttgaag agttaatatt attgggtggt aaactagata aaaaggaatc 101280
tattaaagat tgtttaagaa gagaattaaa agaggaaagt gatgaacgta taacagtaaa 101340
agaatttgga aatgtaattc taaaacttac aacacgggat aaattattta ataaagtata 101400
tataagttat tgcatggcgt gttttattaa tcaatcgttg gaggatttat cgcatactag 101460
tatttacaat gtagaaatta gaaagattaa atcattaaat gattgtatta acgacgataa 101520
atacgaatat ctgtcttata tttataatat gctagttaat agtaaatgaa cttttacaga 101580
tctagtataa ttagtcagat tattaagtat aatagacgac tagctaagtc tattatttgc 101640
gaggatgact ctcaaattat tacactcacg gcattcgtta accaatgcct atggtgtcat 101700
aaacgagtat ccgtgtccgc tattttatta actactgata acaaaatatt agtatgtaac 101760
agacgagata gttttctcta ttctgaaata attagaacta gaaacatgtc tagaaagaaa 101820
cgattatttc tgaattattc caattatttg tccaaacagg aaagaagtat actatcgtca 101880
ttttttctc tagatccagc tactactgat aatgatagaa tagatgctat ttatccgggt 101940
ggcataccca aaaggggtga gaatgttcca gagtgtttat ccagggaaat taaagaagaa 102000
gttaatatag acaattcttt tgtattcata gacactcggt tttttattca tggcatcata 102060
gaagatacca ttattaataa attttttgag gtaatcttct ttgtcggaag aatatcttta 102120
acgagtgatc aaatcattga tacatttaaa agtaatcatg aaatcaagga tctaatattt 102180
ttagatccga attcaggtaa tggactccaa tacgaaattg caaaatatgc tctagatact 102240
gcaaaactca aatgttatgg ccatagagga tgttattacg aatcattaaa aaaattaact 102300
gaggatgatt gattagaaaa tataaattaa tttaccatcg tgtattttta taacgggatt 102360
gtccggcata tcatgtagat agttaccgtc tacatcgtat actcgaccat ctacgccttt 102420
aaatcctcta tttattgaca ttaatctatt agaattggaa taccaaatat tagtaccctc 102480
aattagttta ttggtaatat ttttttaga cgatagatcg atggctcttg aaaccaaggt 102540
tttccaaccg gactcattgt cgatcggtga gaagtctttt tcattagcat gaatccattc 102600
taatgatgta tgtttaaaca ctctaaacaa ttggacaaat tcttttgatt tgctttgaat 102660
gatttcaaat aggtcttcgt ctacagtagg cataccatta gataatctag ccattataaa 102720
gtgcacgttt acatatctac gttctggagg agtaagaacg tgactattga gacgaatggc 102780
tcttcctact atctgacgaa gagacgcctc gttccatgtc atatctaaaa tgaagatatc 102840
attaattgag aaaaaactaa taccctcgcc tccactagaa gagaatacgc atgttttaat 102900
gcattctccg ttagtgtttg attcttggtt aaactcagcc accgccttga ttctagtatc 102960
ttttgttcta gatgagaact ctatattaga gataccaaag actttgaaat atagtaataa 103020
gatttctatt cctgactgat taacaaatgg ttcaaagact agacatttac catgggatgc 103080
taatattccc aaacatacat ctataaattt gacgcttttc tcttttaatt cagtaaatag 103140
agagatatca gccgcactag catccccttt caatagttct ccctttttaa aggtatctaa 103200
tgcggattta gaaaactctc tatctcttaa tgaattttta aaatcattat atagtgttgc 103260
tatctcttgc gcgtattcgc ccggatcacg attttgtctt tcaggaaagc tatcgaacgt 103320
aaacgtagta gccatacgtc tcagaattct aaatgatgat atacctgttt ttatttcagc 103380

```
gagtttagcc ttttgataaa tttcttcttg ctttttcgac atattaacgt atcgcattaa 103440
tactgttttc ttagcgaatg atgcagaccc ttctacgtca tcaaaaatag aaaactcgtt 103500
attaactatg tacgaacata ggcctcctag tttggagact aattctttct catcaactag 103560
acgtttattc tcaaatagcg attggtgttg taaggatcct ggtcgtagta agttaaccaa 103620
catggtgaat tcttgcacac tattaacgat aggtgtagcc gataaacaaa tcatcttatg 103680
gtttttttaat gcgatggtct tagataaaaa attatatact gaacgagtag gacggatctt 103740
accatcttct ttgattaatg atttagaaat gaagttatga cattcatcaa taatgacgca 103800
tattctactc ttggaattaa tagttttgat attagtaaaa aatttatttc taaaattttg 103860
atcatcgtaa ttaataaaaa tacaatcctt cgttatctct ggagcgtatc tgagtatagt 103920
gttcatccaa ggatcttcta tcaaagcctt tttcaccaat aagataatag cccaattcgt 103980
ataaatatcc ttaagatgtt tgagaatata tacagtagtc attgttttac cgacacccgt 104040
ttcatggaac aataaaagag aatgcatact gtctaatcct aagaaaactc ttgctacaaa 104100
atgttgataa tccttgaggc gtactacgtc cgaccccatc atttcaacgg gcatattagt 104160
agttctgcgc aatgcataat cgatataggc cgcgtgtgat ttactcattt atgagtgata 104220
agtaataact atgttttaaa aatcacagca gtagtttaac tagtcttctc tgatgtttgt 104280
tttcgatact ttttgaatca gaagtcatac tagaataaag caacgagtga acgtaataga 104340
gagcttcgta tactctattc gaaaactcta agaacttatt aatgaattcc gtatccactg 104400
gattgtttaa aatactaaat tgaacactgt tcacatcctt ccaagaagaa gacttagtga 104460
cggacttaac atgagacata aataaatcca aatttttttt acaaacatca ctagccacca 104520
taatggcgct atctttcaac cagctatcgc ttacgcattt tagcagtcta acatttttaa 104580
agagactaca atatattctc atagtatcga ttacacctct accgaataaa gttggaagtt 104640
taataataca atatttttcg tttacaaaat caaataatgg tcgaaacacg tcgaaggtta 104700
acatcttata atcgctaatg tatagattgt tttcagtgag atgattatta gatttaatag 104760
catctcgttc acgtttgaac agtttattgc gtgcgctgag gtcggcaact acggcgtccg 104820
ctttagtact cctcccataa tactttacgc tattaatctt taaaatttca tagactttat 104880
ctagatcgct ttctggtaac atgatatcat gtgtaaaaag ttttaacatg tcggtcggca 104940
ttctatttag atcattaact ctagaaatct gaagaaagta attagctccg tattccagac 105000
taggtaatgg gcttttacct agagacagat taagttctgg caatgtttca taaaatggaa 105060
gaaggacatg cgttccctcc cggatatttt ttacaatttc atccatttac aactctatag 105120
tttgttttca ttattattag ttattatctc ccataatctt ggtaatactt accccttgat 105180
cgtaagatac cttatacagg tcattacata caactaccaa ttgtttttgt acataataga 105240
ttggatggtt gacatccatg gtggaataaa ctactcgaac agatagttta tctttccccc 105300
tagatacatt agccgtaata gttgtcggcc taaagaatat ctttggtgta aagttaaaag 105360
ttagggttct tgttccatta ttgctttttg tcagtagttc attataaatt ctcgagatgg 105420
gtccgttctc tgaatataga acatcatttc caaatctaac ttctagtcta gaaataatat 105480
cggtcttatt cttaaaatct attcccttga tgaagggatc gttaatgaac aaatccttgg 105540
cctttgattc ggctgatcta ttatctccgt tatagacgtt acgttgacta gtccaaagac 105600
ttacaggaat agatgtatcg atgatgttga tactatgtga tatgtgagca aagattgttc 105660
tcttagtggc atcactatat gttccagtaa tggcggaaaa ctttttagaa atgttatata 105720
taaaagaatt ttttcgtgtt ccaaacatta gcagattagt atgaagataa acactcatat 105780
```

tatcaggaac attatcaatt tttacataca catcagcatc ttgaatagaa acgataccat 105840
cttctggaac ctcaacaatc tcggcagact ccggataacc agtcggtggg ccatcactaa 105900
caataactag atcatccaac aatctactca catatgcatc tatataatct ttttcatctt 105960
gtgagtaccc tggatacgaa ataaatttat tatccgtatt tccataataa ggtttagtat 106020
aaacagagag cgatgttgcc gcatgaactt cagttacagt cgccgttggt tggtttattt 106080
gacctattac tctcctaggt ttctctataa acgatggttt aatttgtaca ttcttaacca 106140
tatatccaat aaagctcaat tcaggaacat aaacaaattc tttgttgaac gtttcaaagt 106200
cgaacgaaga gtcacgaata acgatatcgg atactggatt gaaggttacc gttacggtaa 106260
tttttgaatc ggatagttta agactgctga atgtatcttc cacatcaaac ggagttttaa 106320
tataaacgta tactgtagat ggttctttaa tagtgtcatt aggagttagg ccaatagaaa 106380
tatcattaag ttcactagaa tatccagagt gtttcaaagc aattgtatta ttgatacaat 106440
tattatataa ttcttcgccc tcaatttccc aaataacacc gttacacgaa gagatagata 106500
cgtgattaat acatttatat ccaacatatg gtacgtaacc gaatcttccc ataccttaa 106560 cttctggaag ttccaaactc agaaccaaat gattaagcgc agtaatatac tgatccctaa 106620
tttcgaagct agcgatagcc tgattgtctg gaccatcgtt tgtcataact ccggatagag 106680
aaatatattg cggcatatat aaagttggaa tttgactatc gactgcgaag acattagacc 106740
gtttaataga gtcatcccca ccgatcaaag aattaatgat agtattattc attttctatt 106800
taaaatggaa aaagcttaca ataaactccg tagagaaata tctataattt gtgagttttc 106860
cttaaagtaa cagcttccgt aaacgccgtc tttatctctt agtaagttta ttgtatttat 106920 aacctttcc ttatcttcat agaatactaa aggcaacaaa gaaatttttg gttcttctct 106980
aagagctacg tgagacttaa ccatagacgc caacgaatcc ctacatattt tagaacagaa 107040
atacccaact tcaccaccct tgaatgtctc aatactaata ggtttaaaaa ccaaatcttg 107100
attacaaaac caacacttat caattacact atttgtctta atagacacat ctgccataga 107160
tttataatac tttggtagta tacaagcgag tgcttcttct ttagcgggct taaagactgc 107220
tttaggtgct gaaataacca catctggaag gcttactcgc ttagccattt aattacggaa 107280
ctattttttt atacttctaa tgagcaagta gaaaacctct catctacaaa aacatactcg 107340
tgtccataat cctctaccat agttacacgt tttttagatc tcatatgtgc taaaaagttt 107400
tcccatacta attggttact attattttc gtataatttt taacagtttg aggttttaga 107460
tttttagtta cagaagtgat atcgaatatt ttatccaaaa agaatgaata attaattgtc 107520
ttagaaggag tgttttcttg gcaaaagaat accaagtgct taaatatttc tactacttca 107580
ttaatctttt ctgtactcag attcagtttc tcatctttta cttgattgat tatttcaaag 107640
actaacttat aatccttttt atttattctc tcgttagcct taagaaaact agatacaaaa 107700
tttgcatcta catcatccgt ggatatttga tttttttcca tgatatccaa gagttccgag 107760
ataatttctc cagaacattg atgagacaat aatctccgca atacatttct caaatgaata 107820
agtttattag acacatggaa gtttgacttt ttttgtacct ttgtacattt ttgaaatacc 107880
gactcgcaaa aaatacaata ttcatatcct tgttcagata ctataccgtt gtgtctacaa 107940
ccgctacata atcgtagatt catgttaaca ctctacgtat ctcgtcgtcc aatattttat 108000
ataaaaacat tttatttcta gacgttgcca gaaaatcctg taatattttt agtttttttgg 108060 gctgtgaata aagtatcgcc ctaatattgt taccgtcttc cgccaatata gtagttaaat 108120

```
tatccgcaca tgcaaaagaa caccgcttag gcggattcag tacaatgtta tatttttcgt 108180
accaactcat ttaaatatca taatctaaaa tagttctgta atatgtctag cgctaatata 108240
ttgatcataa tcctgtgcat aaattaagat acaacaatgt ctcgaaatca tcgacatggc 108300
ttcttccata gttagaagat cgtcgtcaaa gttagcaacg tgattcatca acatttgctg 108360
ttttgaggca gcaaatactg aaccgtcgcc attcaaccat tcataaaaac catcgtctga 108420
atccattgat aatttcttgt actggttttt gagagctcgc atcaatctag catttctagc 108480
tcccggattg aaaacagaaa gaggatcgta catccagggt ccattttctg taaatagaat 108540
cgtataatgt cccttcaaga agatatcaga cgatccacaa tcaaagaatt ggtctccgag 108600
tttgtaacaa actgcggact ttaacctata catgataccg tttagcatga tttctggtga 108660
tacgtcaatc ggagtatcat ctattagaga tctaaagccg gtgtaacatt ctccaccaaa 108720
catattctta ttctgacgtc gttctacata aaacatcatt gctccattaa cgataacagg 108780
ggaatgaaca gcactaccca tcacattagt tcccaatgga tcaatgtgtg taactccaga 108840
acatcttcca tatcctatgt taggaggagc gaacaccact cttccactat tgccatcgaa 108900
tgccatagaa taaatatcct tggaattgat agaaatcgga ctgtcggatg ttgtgatcat 108960
cttcatagga ttaacaacta tgtatggtgc cgcctgaagt ttcatatcgt aactgatgcc 109020
gtttataggt ctagccacag aaaccaacgt aggtctaaat ccaactatag acaaaataga 109080
agccaatatc tgttcctcat ctgtcataac ttgagagcat ccagtatgaa taatcttcat 109140
tagatgggga tctaccgcat catcatcgtt acaataaaaa attcccattc taatgttcat 109200
aattgctttt ctaatcatgg tatgcatgtt tgctctctga atctctgtgg aaattagatc 109260
tgatacacct gtaatcacta tcggattatc ctccgtaaga cgattaacca acaacatata 109320
attataagac tttacttttc taaattcata aagttgctgg attaggctat aggtgtctcc 109380
atgtacatac gcgttctcga gcgcaggaag tttaataccg aatagtgcca tcagaatagg 109440
atgaatatag taattagttt ctggttttct ataaataaaa gacaaatctt gtgaactaga 109500
catatcggta aaatgcatgg attggaatcg tgtagtcgac agaagaatat gatgattaga 109560
tggagagtat attttatcta actctttgag ttggtcaccg attctaggac tagctcgaga 109620
atgaataagt actaaaggat gagtacattt cacagaaaca ctagcattgt tcaatgtgct 109680
ctttacatgg gtaaggagtt gaaatagctc gtttctattt gttctgacaa tatttagttt 109740
attcataatg ttaagcatat cctgaatagt aaagttagat gtgtcatact tgttagtagt 109800
tagatattta gcaattgcat tcccatcatt tctcaatctc gtactccaat catgtgtaga 109860
tgctacttcg tcgatggaaa ccatacaatc ctttttgata ggctgttgag attgattatt 109920
tcctgcacgt ttaggtttgg tacgttgatt tctagcccct gcagatataa agtcatcgtc 109980
tacaattttg gataatgaat tgcatacact acaagacaaa gatttatcag aagtgtgaat 110040
atgatcttca tctaccaaag aaagagtttg attagtataa ctagatttta gtcctgcgtt 110100
agatgttaaa aaaacatcgc tattgaccac ggcttccatt atttatattc gtagttttta 110160
ctcgaaagcg tgattttaat atccaatctt attacttttg gaatcgttca aaacctttga 110220
ctagttgtag aatttgatct attgccctac gcgtatactc ccttgcatca tatacgttcg 110280
tcaccagatc gtttgtttcg gcctgaagtt ggtgcatatc tttttcaaca ctcgacatga 110340
gatccttaag ggccatatcg tctagatttt gttgagatgc tgctcctgga tttggatttt 110400
gttgtgctgt tgtacatact gtaccaccag taggtgtagg agtacataca gtggccacaa 110460
taggaggttg aggaggtgta accgttggag tagtacaaga aatacttcca tccgattgtt 110520
```

```
gtgtacatgt agttgttggt aacgtctgag aaggttgggt agatggcggt gtcgtcgtct 110580
tttgatcttt attaaattta gagataatat cctgaacagc attgctcggc gtcaacgctg 110640
gaaggagtga actcgccggc gcatcagtat ctgcagacag ccaatcaaaa agattagaca 110700
tatcagatga tgtattagtt tgttgtcgtg gttttggtgt aggagcagta ctactaggta 110760
gaagaatagg agccgatgta ggtgtcggaa ccggaaccgg ctgtggagtt atatgaatag 110820
ttggttgtag cggttggata ggctgtctgc tggcggccat catattatct ctagctagtt 110880
gttctcgcaa ctgtctttga taatacgact cttgagactt tagtcctatt tcaatcgctt 110940
catccttttt cgtatccgga tccttttttt cagaataata gattgacgac tttggtgtag 111000
aggattctgc cagcccctgt gagaacttgt taaagaagtc catttaaggc tttaaaattg 111060
aattgcgatt ataagattaa atggcagaca cagacgatat tatcgactat gaatccgatg 111120
atctcactga atacgaggat gatgaagaag aggaagaaga tggagagtca ctagaaacta 111180
gtgatataga tcccaaatct tcttataaga ttgtagaatc agcatccact catatagaag 111240
atgcgcattc caatcttaaa catataggga atcatatatc tgctcttaaa cgacgctata 111300
ctagacgtat aagtctattt gaaatagcgg gtataatagc agaaagctat aacttgcttc 111360
aacgaggaag attacctcta gtttcagaat tttctgacga aacgatgaag caaaatatgc 111420
tacatgtaat tatacaagag atagaggagg gttcttgtcc tatagtcatc gaaaagaacg 111480
gagaattgtt gtcggtaaac gattttgaca aagatggtct aaaattccat ctagactata 111540
ttatcaaaat ttggaaactt caaaaacgat attagaattt atacgaatat cgttctctaa 111600
atgtcacaat caagtctcgc atgttcagca atttattgtc gtactttata tcgtgttcat 111660
taacgatatc ttgcaaaata gtaatgattc tatcttcctt cgatagatat tcttcagaga 111720
ttattgtctt atattctttc ttgttatccg atatgaattt gataagactt tgaacattat 111780
taatacccgt ctgtttaatt ttttctacag atattttagt tttggcagat tctatcgtat 111840
ctgtcaatag acatccaaca tcgacattcg acgtcaattg tctataaatc aacgtataaa 111900
ttttagaaat aacattagcg aattgttgtg cattgatgtc gttattctga aacagtatga 111960
ttttaggtag cattttctta acaaagagaa cgtatttatt gttactcagt tgaacagatg 112020
atatatccag attactaacg catctgattc cgtataccaa actttcagaa gaaatggtgt 112080
acaattgttt gtattcattc aatgtctcct tttcagaaat tagtttagag tcgaatactg 112140
caataatttt caagagatag ttttcatcag ataagatttt atttagtgta gatatgataa 112200
aactattgtt ttgttggaga acttgatacg ccgcgttctc tgtagtcgac gctctcaaat 112260
gggaaacgat ctccattatt tttttggaat cggatactat atcttcggta tcttgacgca 112320
gtctagtata catagagtta agagagatta gagtttgtac attaagcaac atgtctctaa 112380
atgtggctac aaacttttcc tttttcacat catctagttt attatatacc gatttcacaa 112440
cggcaccaga tttaaggaac cagaatgaaa aactctgata actacaatat ttcatcatag 112500
ttacgatttt atcatcttct atagttggtg taatagcgca taccttttc tccaagactg 112560
gaaccaacgt cataaaaatg tttaaatcaa aatccatatc aacatctgat gcgctaagac 112620
cagtctcgcg ttcaagatta tctttactaa tggtgacgaa ctcatcgtat agaactctaa 112680
gtttgtccat tatttattta cagatttagt tgtttaattt atttgtgctc ttccagagtt 112740
gggatagtat ttttctaacg tcggtattat attattagga tctacgttca tatgtatcat 112800
aatattaatc atccacgttt tgataaatct atctttagct tctgaaataa cgtatttaaa 112860
```

```
caaaggagaa aaatatttag ctacggcatc agacgcaata acattttttg taaatgtaac 112920
gtatttagac gacagatctt cgttaaaaag ttttccatct atgtagaatc catcggttgt 112980
taacaccatt cccgcgtcag attgaatagg agtttgaata gtttgttttg gaaatagatc 113040
cttcaataac ttatagttgg gtgggaaaaa atcgatttta tcactagact ctttcttttt 113100
tactatcatt acctcatgaa ctatttcttg aatgagtata tgtattttct ttcctatatc 113160
ggacgcgttc attggaaaat ataccatgtc gttaactata agaatatttt tatcctcgtt 113220
tacaaactga ataatatcag atgtagttcg taaacgaact atatcatcac cagcacaaca 113280
tctaactata tgatatccac tagtttcctt tagccgttta ttatcttgtt ccatattagc 113340
agtcattcca tcatttaaga aggcgtcaaa aataataggg agaaatgaca ttttggattc 113400
tgttacgact ttaccaaaat taaggatata cggacttact atctttttct caacgtcaat 113460
ttgatgaaca cacgatgaaa atgtgcttct atgagattga tcatgtagaa aacaacaagg 113520
gatacaatat ttccgcatat catgaaatat attaagaaat cccaccttat tatatttccc 113580
caaaggatcc atgcacgtaa acattatgcc gttatcatta ataaagactt ctttctcatc 113640
ggatctgtaa aagttgttac tgattttttt cattccagga tctagataat taataatgat 113700
gggttttcta ttcttattct ttgtattttg gcatatccta gaccagtaaa cagtttccac 113760
tttggtaaaa tcagcagact tttgaacgct attaaacatg gcattaatgg caataactaa 113820
aaatgtaaaa tatttttcta tgttaggaat atggttttc actttaatag atatatggtt 113880
tttggccaaa atgatagata ttttttatc cgaggatagt aaaatattat tagtcgccgt 113940
ctctataaaa atgaagctag tctcgatatc caattttatt ctagaattga taggagtcgc 114000
caaatgtacc ttatacgtta tatctccctt gatgcgttcc atttgtgtat ctatatcgga 114060
cacaagatct gtaaatagtt ttacgttatt aatcatcacg gtatcgccgt cgctagataa 114120
cgctaatgta ccatccaagt cccaaatgga gagatttaac tgttcatcgt ttagaataaa 114180
atgattaccg gtcatattaa taaagtgttc atcgtatcta gataacaacg acttataatt 114240
aatgtccaag tcttgaactc gctgaatgat ctttttttaac ccagttagtt ttagattggt 114300
acgaaatata ttgttaaact ttgattctat agtaatgtcc aaatctagtt gtggaaatac 114360
ttccatcaac attgtttcaa acttgataat attattatct acatcttcgt acgatccaaa 114420
ttccggaata gatgtatcgc acgctctggc cacccagata accaaaaagt cacacgctcc 114480
aggatataca ttgtataaaa agctatcgtt ttttagtagg gtttttttct gcgtgtatac 114540
gaagggatta aaaatagtat tatcaacgta actatattcc aaattattct tatgagaata 114600
gataataata tcgtccttaa tatctaacaa atttcctaaa tatcccttta attgagtcat 114660
tcgaagcgtc aatagaatat gtctcttaac tatttccggc tgttgtatat ttaaatgact 114720
tcgtaaaaaa taatatatgg gcgacttctc atctatgtaa tcatatggag tgagatatag 114780
ggctcgttct acctcctgcc ccttacccac ctgtaatacc aattgcggac ttactatata 114840
tcgcatattt atatcgtggg gtaaagtgaa aatctactac cgatgatgta agtcttacaa 114900
tgttcgaacc agtaccagat cttaatttgg aggcctccgt agaactaggg gaggtaaata 114960
tagatcaaac aacacctatg ataaaggaga atagcggttt tatatcccgc agtagacgtc 115020
tattcgccca tagatctaag gatgatgaga gaaaactagc actacgattc tttttacaaa 115080
gactttattt tttagatcat agagagattc attatttgtt cagatgcgtt gacgctgtaa 115140
aagacgtcac tattaccaaa aaaaataaca ttatcgtggc gccttatata gcacttttaa 115200
ctatcgcatc aaaaggatgc aaacttacag aaacaatgat tgaagcattc tttccagaac 115260
```

```
tatataatga acatagtaag aaatttaaat tcaactctca agtatccatc atccaagaaa 115320
aactcggata ccagtttgga aactatcacg tttatgattt tgaaccgtat tactctacag 115380
tagctctggc tattcgagat gaacattcat ctggcatttt taatatccgt caagagagtt 115440
atctggtaag ttcattatct gaaataacat atagatttta tctaattaat ctaaaatctg 115500
atcttgttca atggagtgct agtacgggcg ctgtaattaa tcaaatggta aatactgtat 115560
tgattacagt gtatgaaaag ttacaactgg tcatagaaaa tgattcacaa tttacatgtt 115620
cattggctgt ggaatcaaaa cttccaataa aattacttaa agatagaaat gaattattta 115680
caaaattcat taacgagtta aaaaagacca gttcattcaa gataagcaaa cgcgataagg 115740
atacgctact aaaatatttt acttaggact ggagttagaa tttatagacg actcatttcg 115800
tttatcatta ttactaccat cattattagt attcttcttg ttatcttgtt cagaaatata 115860
cagcaatgct atgcctaata ctaaatacat tatcatgctt gcaatggctc taacaacgac 115920
gaaccaaaat gaatttggtc gtagcttttg ttcacaaaaa tacataaaga aatgtctaca 115980
taaatctatg gcgccattgg ctacttgaaa tagcgccagt cctcctacag attttaatat 116040
agctgtataa catgacattt attcatcatc aaaagagaca gagtcaccat ctgtcatatt 116100
tagatttttt ttcatgtgtt caaagtatcc tctactcatt tcattataat agtttatcat 116160
acttagaatt ttaggacgga tcaatgagta agacttgact agatcgtcag tagtaatttg 116220
tgcatcgtct attctgcatc cgcttcgtcg aataatgtat agcatcgctt tgagattctc 116280
catagctatc aagtctttat acaatgacat ggaaatatct gtgaatactt tatacttctc 116340
caacatcgat gccttaacat catcgcctac tttagcattg aaaatacgtt ctattgtgta 116400
gatggatgta acaagatttt taaacaacaa tgccatctta cacgatgatt gcctcaagtc 116460
tccaatcgtt tgtttagaac gattagctac agagtccaat gcttggctga ctagcatatt 116520
attatcttta gaaattgtat tcttcaatga ggcgtttatc atatctgtga tttcgttagt 116580
catattacag tctgactggg ttgtaatgtt atccaacata tcacctatgg atacggtaca 116640
cgtaccagca tttgtaataa tcctatctaa gatgttgtat ggcattgcgc agaaaatatc 116700
ttctcctgta atatctccac tctcgataaa tctactcaga ttattcttaa atgccttatt 116760
ctctggagaa aagatatcag tgtccatcat ttcattaata gtatacgcag aaaagatacc 116820
acgagtatca attctatcca agatacttat cggttccgag tcacagataa tggtttcctc 116880
tccttcggga gatcctgcat agaaatatct aggacaatag tttctatact gtctgtaact 116940
ctgataatct ctaaagtcac taactgatac catgaaattg agaagatcaa acgctgaagt 117000
aattaatttt tctgcctcgt ttttactaca actagttttc atcaatgtag tgacgatgta 117060
ttgtttagtt actttggtc taatactgat gatagagata ttattgcttc ccataatgga 117120
tcttctagta gtcaccttaa agcccattga tgcgaatagc agatagataa agtcttggta 117180
tgactccttt ctaatatagt acggactacc tttgtcaccc aactttatac ccacataagc 117240
cataacaacc tctttaatag ccgtttcatg aggtttatca gccatgagcc tgagtagttg 117300
gaagaatctc atgaatcccg tctcagaaag tcctatatgc atgatagatt tatctttcct 117360
gggaaactct cgtatagtca tagatgaaat actcttcaaa gtttctgaaa taagattagt 117420
aacagtctta cctccgacta ctctgggtaa caaacaaact ctaataggtg ttttctctgc 117480
ggagataata tcagaaagga tagagcaata agtagtatta ttgtgattat aaagaccgaa 117540
tacataacag gtagaattta taaacatcat gtcctgaagg tttttagact tgtattcctc 117600
```

```
gtaatccata ccgtcccaaa acatggattt ggtaactttg atagccgtag atctttgttc 117660
cttcgccaac aggttaaaga aattaataaa gaatttgttg tttctattta tgtccacaaa 117720
ttgcacgttt ggaagcgcca cggttacatt cactgcagca ttttgaggat cgcgagtatg 117780
aagtacgatg ttattgttta ctggtatatc tggaaagaaa tctaccagtc taggaataag 117840
agattgatat cgcatagaaa tagtaaagtt tataatctca tcatcgaaga gcattttgtt 117900
accattgtaa taaatatcca ctctgtcata tgtataaatg aagtactgtt caaacatgat 117960
gagatgttta tatgttggca tagtagtgag atcgacgttt ggtaatggca atgtattaag 118020
attaactcca taatgtctag cagcatctgc gatgttataa gcgtcgtcaa agcggggtcg 118080
atcttgtatt gttatatatt gtctaacacc tataagatta tcaaaatctt gtctgcttaa 118140
tacaccgtta acaatttttg ccttgaattc ttttattggt gcattaataa catccttata 118200
gaggatgtta aacaaataag tgttatcaaa gttaagatct ggatatttct tttctgctag 118260
aacatccatt gagtcggagc catctggttt aatataacca ccgataaatc tagctctgta 118320
ttctgtatcc gtcaatctaa tattaagaag gtgttgagtg aaaggtggaa gatcgtaaaa 118380
gctgtgagta ttaatgatag gattagtttc cgaactaatg ttaattgggg tattaataat 118440
atctatattt ccagcgttaa gtgtaacatt aaacagtttt aattcacgtg aagtagtatc 118500
aattaaataa ttaatgccca atttggatat agcagcctga agctcatctt gtttagttac 118560
ggatcctaat gagttattaa gcaatatatc gaacggatga acgaaggttg ttttgagttt 118620
gtcgcatact ttgtaatcta gacatagatg cggaagaacg gtagaaacta tacgaaataa 118680
atattcagag tcctctaatt gatcaagagt aactattgac ttaataggca tcatttattt 118740
agtattaaat gacgaccgta ccagtgacgg atatacaaaa cgatttaatt acagagtttt 118800
cagaagataa ttatccatct aacaaaaatt atgaaataac tcttcgtcaa atgtctattc 118860
taactcacgt taacaacgtg gtagatagag aacataatgc cgccgtagtg tcatctccag 118920
aggaaatatc ctcacaactt aatgaagatc tatttccaga tgatgattca ccggccacta 118980
ttatcgaacg agtacaacct catactacta ttattgacga tactccacct cctacgtttc 119040
gtagagagtt attaatatcg gaacaacgtc aacaacgaga aaaaagattt aatattacag 119100
tatcgaaaaa tgctgaagca ataatggaat ctagatctat gataacttct atgccaacac 119160
aaacaccatc cttgggagta gtttatgata aagataaaag aattcagatg ttagaggatg 119220
aagtggttaa tcttagaaat caacgatcta atacaaaatc atctgataat ttagataatt 119280
ttaccaaaat actatttggt aagactccgt ataaatcaac agaagttaat aagcgtatag 119340
ccatcgttaa ttatgcaaat ttgaacgggt ctcccttatc agtcgaggac ttggatgttt 119400
gttcagagga tgaaatagat agaatctata aaacgattaa acaatatcac gaaagtagaa 119460
aacgaaaaat tatcgtcact aacgtgatta ttattgtcat aaatattatc gagcaagcat 119520
tgctaaaact cggatttgaa gaaatcaaag gactgagtac cgatatcact tcagaaatta 119580
tcgatgtgga gatcggagat gactgcgatg ctgtagcatc aaaactagga atcggtaaca 119640
gtccggttct taatattgta ttgtttatac tcaagatatt cgttaaacga attaaaatta 119700
tttaatttaa tacattccca tatccagaca acaatcgtct ggattaatct gttcctgtcg 119760
tctcataccg gacgacatat taatcttttt attagtgggc atctttttag atggtttctt 119820
tttcccagca ttaactgagt cgatacctag aagatcgtga ttgatctctc cgaccattcc 119880
acgaacttct aattggccgt ctctgacggt accataaact attttaccag cattagtaac 119940
agcttggaca atctgaccat ccatcgcatt gtacgatgta gtagtaactg ttgttctacg 120000
```

```
tttaggagca ccagaagtat ttttggagcc cttggaggct gatgtagaag aagacgagga 120060
ttttgatttt ggtttacatg taatacattt tgaactcttt gattttgtat cacatgcgcc 120120
ggcagtcaca tctgtttgag aattaagatt attgttgcct cctttgacgg ctgcatctcc 120180
accgatttgc gctagtagat ttttaagctg tggtgtaatc ttattaactg tttcgatata 120240
atcatcgtaa ctgcttctaa cggctaaatt ttttttatcc gccatttaga agctaaaaat 120300
atttttattt atgcagaaga tttaactaga ttatacaatg aactaatatg atccttttcc 120360
agattattta caaacttggt attttttggt tctggaggag gcgaatttaa attcggactt 120420
ggattcagat tttgtaagtt cttgatctta ttatacatcg agtataggat ggcgacagta 120480
actgctacac aaataccgat caaaagaaga ataccaatca tttattgaca ataacttcac 120540
tattgatcaa gtatgcaata tatcatcttt tcactaaata agtagtaata atgattcaac 120600
aatgtcgaga tatatggacg ataataattt agttcatgga aatatcgcta tgattggtgt 120660
gaatgactcc gctaactctg tggggtgcgc agtgctttcc ccacatagaa taaattagca 120720
ttccgactgt gataataata ccaagtataa acgccataat actcaatact ttccatgtac 120780
gagtgggact ggtagactta ctaaagtcaa taaaggcgaa gatacacgaa agaatcaaaa 120840
gaatgattcc agcgattagc acgccggaaa aataatttcc aatcataagc atcatgtcca 120900
tttaactaat aaaaatttta aatcgccgaa tgaacaaagt ggaatataaa ccatataaaa 120960
acaatagttt gtactgcaaa aataatatct atttttgttt tcgaagatat ggtaaaatta 121020
aatagtagta cacagcatgt tataactaac agcagcaacg gctcgtaatt acttatcatt 121080
tactagacga aaaggtggtg ggatattttc ttgctcaaat aatacgaata tatcacccat 121140
ccattttatg cgatgtttat atactctaat ctttaataga tctatagacg acgggtttac 121200
caacaatata gattttatcg attcatctaa tttaaaccct tccttaaacg tgaatgatct 121260
attatctggc ataacgatga ctctacctga tgaatcggac aatgtactgg gccatgtaga 121320
ataaattatc aacgaattat cgtctacgaa catttatatc atttgtttta attttaggac 121380
gcgaataaat ggatataaaa tagaaaataa cagatattac aaccagtgtt atggccgcgc 121440
ccaaccaggt aggcagtttt attttatctt ttactacagg ttctcctgga tgtacgtcac 121500
caacggcgga cgtagttcta gtacaattag acgtaagttc cgcttgggaa ttttttaacg 121560
ctaaagagtt aacgttaatc gtgcacccaa cgtatttaca tctagttctt tgaacatctt 121620
gattataata taaccatttt ctatctctag attcgtcggt gcactcatgt aaccaacata 121680
ccctaggtcc taaatattta tctccggaat tagattttgg ataattcgcg caccaacaat 121740
ttctatttcc tttatgatcg ttacaaaaga cgtataatgc cgtatcccca aaagtaaaat 121800
aatcaggacg aataattcta ataaactcag aacaatatct cgcatccata tgtttggagc 121860
aaatatcgga ataagtagac atagccggtt tccgttttgc acgtaaccat tctaaacaat 121920
tggggtttcc aggatcgttt ctacaaaatc cagtcatgaa atcgtcacaa tgttctgtct 121980
tgtaattatt attaaatatt tttggacagt gtttggtatt tgtcttagaa caacattttg 122040
ctacgctatc actatcgccc aggagataat cctttttat aaaatgacat cgttgcccgg 122100
atgctatata atcagtagcg tgttttaaat ccttaatata ttcaggagtt acctcgttct 122160
gataatagat taatgatcca ggacgaaatt tgaaagaact acatggttct ccatgaatta 122220
atacatattg tttagcaaat tcaggaacta taaaactact acaatgatct atcgacatac 122280
catctatcaa acaaaacttg ggtttaattt ctcccggaga tgtttcataa tagtacgtat 122340
```

-continued

```
aactttcttc tgcaaactta acagctctat tatattcagg ataattaaaa cctaattcca 122400
tatatttgtc tcgtatatct gctattcctg gtgctatttt gattctatta agagtaacag 122460
ctgcccccat tcttaataat cgtcagtatt taaactgtta aatgttggta tatcaacatc 122520
taccttattt cccgcagtat aaggtttgtt gcaggtatac tgttcaggaa tggttacatt 122580
tatacttctt ctatagtcct gtctttcgat gttcatcaca tatgcaaaga acagaataaa 122640
caaaataatg taagaaataa tattaaatat ctgtgaattc gtaaatacat tgattgccat 122700
aataattaca gcagctacaa tacacacaat agacattccc acagtgttgc cattacctcc 122760
acgatacatt tgagttacta agcaataggt aataactaag ctagtaagag gcaatagaaa 122820
agatgagata aatatcatca atatagagat tagaggaggg ctatatagag ccaagacgaa 122880
caaaatcaaa ccgagtaacg ttctaacatc attatttttg aagattccca aataatcatt 122940
cattcctcca taatcgtttt gcatcatacc tccatcttta ggcataaacg attgctgctg 123000
ttcctctgta aataaatctt tatcaagcac tccagcaccc gcagagaagt cgtcaagcat 123060
attgtaatat cttaaataac tcatttatat attaaaaaat gtcactatta aagatggagt 123120
ataatcttta tgccgaacta aaaaaaatga cttgtggtca acccctaagt ctttttaacg 123180
aagacgggga tttcgtagaa gttgaaccgg gatcatcctt taagtttctg atacctaagg 123240
gattttacgc ctctccttcc gtaaagacga gtctagtatt cgagacatta acaacgaccg 123300
ataataaaat cactagtatc aatccaacaa atgcgccaaa gttatatcct cttcaacgca 123360
aagtcgtatc tgaagtagtt tctaatatga ggaaaatgat cgaatcaaaa cgtcctctat 123420
acattactct tcacttggcg tgtggatttg gtaagactat taccacgtgt tatcttatgg 123480
ctacacacgg tagaaaaacc gtcatttgcg tacccaataa aatgttaata catcaatgga 123540
agacacaggt agaggcagtc ggattggaac ataagatatc catagatgga gtaagtagtc 123600
tattaaagga actaaagact caaagtccgg atgtattaat agtagtcagt agacatctga 123660
caaacgatgc cttttgtaaa tatatcaata agcattatga tttgttcatc ttggatgaat 123720
cacatacgta taatctgatg aacaatacag cagttacaag atttttagcg tattatcctc 123780
cgatgatgtg ttattttta actgctacac ctagaccatc taacagaatt tattgtaaca 123840
gtattattaa tattgccaag ttatccgatc taaaaaaaac tatctatgcg gtagatagtt 123900
tttttgagcc atattccaca gacaatatta gacatatgat aaaacgatta gatggaccat 123960
ctaataaata tcatatatat actgagaagt tattatctgt agacgagcct agaaatcaac 124020
ttattcttga taccctggta gaagaattca agtcaggaac tattaatcgc attttagtta 124080
ttactaaact acgtgaacat atggtattct tctacaaacg attattagat cttttcggac 124140
cagaggttgt atttatagga gacgcccaaa atagacgtac tccagatatg gtcaaatcaa 124200
tcaaggaact aaatagattt atattcgtat ccaccttatt ttattccggt actggtttag 124260
atattcctag tttggattcg ttgttcattt gctcggcagt aatcaacaat atgcaaatag 124320
agcaattact agggagggta tgtcgagaaa cagaactatt agataggacg gtatatgtat 124380
ttcctaacac atccatcaaa gaaataaagt acatgatagg aaatttcatg caacgaatta 124440
ttagtctgtc tgtagataaa ctaggattta aacaaaaaag ttatcggaaa catcaagaat 124500
ccgatcccac ttctgtatgt acaacatcct ccagagaaga acgtgtatta aatagaatat 124560
ttaactcgca aaatcgttaa gaagtttaag cgacgatccg catgctgcgc aggccagtgt 124620
attacccctc atagtattaa tataatccaa tgatactttt gtgatgtcgg aaatcttaac 124680
caatttagac tgacaggcag aacacgtcat gcaatcatca tcgtcatcga taactgtagt 124740
```

```
cttgggcttc tttttgcggc tcttcattcc ggaacgcaca ttggtgctat ccatttaggt 124800
agtaaaaaat aagtcagaat atgccctata gcacgatcgt gcaaaacctg gtatatcgtc 124860
tctatcttta tcacaatata gtgtatcgac atctttatta ttattgacct cgtttatctt 124920
ggaacatgga atgggaacat ttttgttatc aacggccatc tttgccttaa ttccagatgt 124980
tgtaaaatta taactaaaca gtctatcatc gacacaaatg aaattcttgt ttagacgttt 125040
gtagtttacg tatgcggctc gttcgcgtct catttttttca gatattgcag gtactataat 125100
attaaaaata agaatgaaat aacataggat taaaaataaa gttatcatga cttctagcgc 125160
tgatttaact aacttaaaag aattacttag tctgtacaaa agtttgagat tttcagattc 125220
tgcggctata gaaaagtata attctttggt agaatgggga acatctactt actggaaaat 125280
aggcgtgcaa aaggtagcta atgtcgagac gtcaatatct gattattatg atgaggtaaa 125340
aaataaaccg tttaatattg atccgggcta ttacattttc ttaccggtat attttgggag 125400
cgtctttatt tattcgaagg gtaaaaatat ggtagaactt ggatctggaa actcttttca 125460
aataccagat gatatgcgaa gtgcgtgtaa caaagtatta gacagcgata acggaataga 125520
ctttctgaga tttgttttgt taaacaatag atggataatg gaagatgcta tatcaaaata 125580
tcagtctcca gttaatatat ttaaactagc tagtgagtac ggattaaaca tacccaaata 125640
tttagaaatt gaaatagagg aagacacatt atttgacgac gagttatact ctattataga 125700
acgctctttc gatgataaat ttccaaaaat atccatatcg tatattaagt tgggagaact 125760
taggcggcaa gttgtagact tttcaaatt ctcgttcatg tatattgagt ccatcaaggt 125820
agatcgtata ggagataata tttttattcc tagcgttata acaaaatcag gaaaaaagat 125880
attagtaaaa gatgtagacc atttaatacg atccaaggtt agagaacata catttgtaaa 125940
agtaaaaaag aaaaacacat tttccatttt atacgactat gatggaaacg gaacagaaac 126000
tagaggagaa gtaataaaac gaattataga cactatagga cgagactatt atgttaacgg 126060
aaagtatttc tctaaggttg gtagtgcagg cttaaagcaa ttgactaata aattagatat 126120
taatgagtgc gcaactgtcg atgagttagt tgatgagatt aataaatccg gaactgtaaa 126180
acgaaaaata aaaaaccaat cagcatttga tttaagcaga gaatgtttgg gatatccaga 126240
agcggatttt ataacgttag ttaataacat gcggttcaaa atagaaaatt gtaaggttgt 126300
aaatttcaat attgaaaata ctaattgttt aaataacccg agtattgaaa ctatatatgg 126360
aaactttaac cagttcgtct caatctttaa tatcgtcacc gatgtcaaaa aaagattatt 126420
cgagtgaaat aatatgcgcc tttgatatag gtgcaaaaaa tcctgccaga actgttttag 126480
aagtcaagga taactccgtt agggtattgg atatatcaaa attagactgg agttctgatt 126540
gggaaaggcg catagctaaa gatttgtcac aatatgaata cactacagtt cttctagaac 126600
gtcagcctag aaggtcgccg tatgttaaat ttatctattt tattaaaggc tttttatatc 126660
atacatcggc tgccaaagtt atttgcgtct cgcctgtcat gtctggtaat tcatatagag 126720
atcgaaaaaa gagatcggtc gaagcatttc ttgattggat ggacacattc ggattgcgag 126780
actccgttcc ggatagacgc aaattagacg atgtagcgga tagtttcaat ttggctatga 126840
gatacgtatt agataaatgg aatactaatt atacacctta taataggtgt aaatctagaa 126900
attacataaa aaaaatgtaa taacgttagt aacgccatta tggataatct atttaccttt 126960
ctacatgaaa tagaagatag atatgccaga actattttta actttcatct aataagttgc 127020
gatgaaatag gagatatata tggtcttatg aaagaacgca tttcctcaga ggatatgttt 127080
```

```
gataatatag tgtataataa agatatacat cctgccatta agaaactagt gtattgcgac 127140
atccaactta ctaaacacat tattaatcag aatacgtatc cggtatttaa cgattcttca 127200
caagtgaaat gttgtcatta tttcgacata aactcagata atagcaatat tagctctcgt 127260
acagtagaga tatttgagag ggaaaagtca tctcttgtat catatattaa aactaccaat 127320
aagaagagaa aggtcaatta cggcgaaata aagaaaactg ttcatggagg cactaatgca 127380
aattactttt ccggtaaaaa gtctgacgag tatctgagta ctacagttag atccaacatt 127440
aatcaacctt ggatcaaaac catctctaag aggatgagag ttgatatcat taatcactct 127500
atagtaacgc gtggaaaaag ctctatatta caaactatag aaattatttt tactaataga 127560
acatgtgtga aaatattcaa ggattctact atgcacatta ttctatccaa ggacaaggat 127620
gaaaaggggt gtatacacat gattgacaaa ttattctatg tctattataa tttatttctg 127680
ttgttcgagg atatcatcca aaacgagtac tttaaagaag tagctaatgt tgtaaaccac 127740
gtactcacgg ctacggcatt agatgagaaa ttattcctaa ttaagaaaat ggctgaacac 127800
gatgtttatg gagttagcaa tttcaaaata gggatgttta acctgacatt tattaagtcg 127860
ttggatcata ccgttttccc ctctctgtta gatgaggata gcaaaataaa gttttttaag 127920
gggaaaaagc tcaatattgt agcattacga tctctggagg attgtataaa ttacgtgact 127980
aaatccgaga atatgataga aatgatgaag gaaagatcga ctattttaaa tagcatagat 128040
atagaaacgg aatcggtaga tcgtctaaaa gaattgcttc taaaatgaaa aaaaacactg 128100
attcagaaat ggatcaacga ctcggatata agtttttggt gcctgatcct aaagccggag 128160
ttttttatag accgttacat ttccaatatg tatcgtattc taattttata ttgcatcgat 128220
tgcatgaaat cttgaccgtc aagcggccac tcttatcgtt taagaataat acagaacgaa 128280
ttatgataga aattagcaat gttaaagtga ctcctccaga ttactcacct ataatcgcga 128340
gtattaaagg taagagttat gacgcattag ccacgttcac tgtaaatatc tttaaagagg 128400
taatgaccaa agagggtata tccatcacta aaataagtag ttatgaggga aaagattctc 128460
atttgataaa aattccgcta ctaataggat acgggaataa aaatccactt gatacagcca 128520
agtatcttgt tcctaatgtc ataggtggag tctttatcaa taaacaatct gtcgaaaaag 128580
taggaattaa tctagtagaa aagattacaa catggccaaa atttagggtt gttaagccaa 128640
actcattcac tttctcgttt tcctccgtat cccctcctaa tgtattaccg acaagatatc 128700
gccattacaa gatatctctg gatatatcac aattggaagc gttgaatata tcatcgacaa 128760
agacatttat aacggtcaat attgttttgc tgtctcaata tttatctaga gtgagtctag 128820
aattcattag acgtagttta tcatacgata tgcctccaga agttgtctat ctagtaaacg 128880
cgataataga tagtgctaaa cgaattactg aatctattac tgactttaat attgatacat 128940
acattaatga cctggtggaa gctgaacaca ttaaacaaaa atctcagtta acgattaacg 129000
agttcaaata tgaaatgctg cataactttt tacctcatat gaactataca cccgatcaac 129060
taaagggatt ttatatgata tctttactaa gaaagtttct ctactgtatc ttccacactt 129120
ctagatatcc agatagagat tcgatggttt gtcatcgcat cctaacgtac ggcaaatatt 129180
ttgagacgtt ggcacatgat gaattagaga attacatagg caacatccga aacgatatca 129240
tgaacaatca caagaacaga ggcacttacg cggtaaacat tcatgtacta acaactcccg 129300
gacttaatca cgcgttttct agcttattga gtggaaagtt caaaaagtca gacggtagtt 129360
atcgaacaca tcctcactat tcatggatgc agaatatttc tattcctagg agtgttggat 129420
tttatccgga tcaagtaaag atttcaaaga tgttttctgt cagaaaatac catccaagtc 129480
```

```
aatatcttta cttttgttca tcagacgttc cggaaagagg tcctcaggta ggtttagtat 129540
ctcaattgtc tgtcttgagt tccattacaa atatactaac gtctgagtat ttggatttgg 129600
aaaagaaaat ttgtgagtat atcagatcat attataaaga tgatataagt tactttgaaa 129660
caggatttcc aatcactata gaaaatgctc tagtcgcatc tcttaatcca aatatgatat 129720
gtgattttgt aactgacttt agacgtagaa aacggatggg attcttcggt aacttggagg 129780
taggtattac tttagttagg gatcacatga atgaaattcg cattaatatt ggagcgggaa 129840
gattagtcag accattcttg gttgtggata acggagagct catgatggat gtgtgtccgg 129900
agttagaaag cagattagac gacatgacat tctctgacat tcagaaagag tttccgcatg 129960
tcatcgaaat ggtagatata gaacaattta cttttagtaa cgtatgtgaa tcggttcaaa 130020
aatttagaat gatgtcaaag gatgaaagaa agcaatacga tttatgtgac tttcctgccg 130080
aatttagaga tggatatgtg gcatcttcat tagtgggaat caatcacaat tctggaccca 130140
gagctattct tggatgtgct caagctaaac aagctatctc ttgtctgagt tcggatatac 130200
gaaataaaat agacaatgga attcatttga tgtatccaga gaggccaatc gtgattagta 130260
aggctttaga aacttcaaag attgcggcta attgcttcgg ccaacatgtt actatagcat 130320
taatgtcgta caaaggtatc aatcaagagg atggaattat catcaaaaaa caatttattc 130380
agagaggcgg tctcgatata gttaccgcaa agaaacatca agtagaaatt ccattggaaa 130440
actttaataa caaagaaaga gataggtcta acgcctattc aaaattagaa agtaatggat 130500
tagttagact gaatgctttc ttggaatccg gagacgctat ggcacgaaat atctcatcaa 130560
gaactcttga agatgatttt gctagagata atcagattag cttcgatgtt tccgagaaat 130620
ataccgatat gtacaaatct cgcgttgaac gagtacaagt agaacttact gacaaagtta 130680
aggtacgagt attaaccatg aaagaaagaa gacccattct aggagacaaa tttaccacta 130740
gaacgagtca aaagggaaca gtcgcgtatg tcgcggatga aacggaactt ccatacgacg 130800
aaaatggtat cacgccagat gtcattatta attctacatc catcttctct agaaaaacta 130860
tatctatgtt gatagaagtt attttaacag ccgcatattc tgctaagccg tacaacaata 130920
agggagaaaa ccgacctgtc tgttttccta gtagtaacga aacatccatc gatacatata 130980
tgcaattcgc taaacaatgt tatgagcatt caaatccgaa attgtctgat gaagaattat 131040
cggataaaat cttttgtgaa aagattctct atgatcctga aacggataag ccttatgcat 131100
ccaaagtatt ttttggacca atttattact tgcgtctgag acatttaact caggacaagg 131160
caaccgttag atgtagaggt aaaaagacga agctcattag acaggcgaat gagggacgaa 131220
aacgtggagg aggtatcaag ttcggagaaa tggagagaga ctgtttaata gcgcatggcg 131280
cagccaatac tattacagaa gttttgaaag attcggaaga agattatcaa gatgtgtatg 131340
tttgtgaaaa ttgtggagac atagcagcac aaatcaaggg tattaataca tgtcttagat 131400
gttcaaaact taatctctct cctctcttaa caaaaattga taccacgcac gtatctaaag 131460
tatttcttac tcaaatgaac gccagaggcg taaaagtcaa attagatttc gaacgaagac 131520
ctccttcgtt ttataaacca ttagataaag ttgatctcaa gccgtctttt ctggtgtaat 131580
attctagttt ggtagtagat acatatcaat atcatcaaat tcgagatccg aattataaaa 131640
tgggcgtgga ttgttaacta tagaatcgga cgtctgatat tcgaaaatct gtggagtttc 131700
aggttttggt ggaggtgtaa ctgctacttg ggatactgaa gtctgatatt cagaaagctg 131760
tggatgttct ggttcggcat ccaccgatgg tgtcacatca ctaatcggtt cggtaacgtc 131820
```

```
tgtggatgga ggtgctactt ctacagaacc tgtagcctca gttgtcaacg gagatacatt 131880

tttaatgcga gaaaatgtat aatttggtaa tggtttctca tgtggatctg aagaagaggt 131940

aagatatcta ctagaaagat accgatcacg ttctagttct cttttgtaga acttaacttt 132000

ttctttctcc gcatctagtt gatattccaa cctcttcacg ttactacgtt cagattccaa 132060

ttcacgttcg catgggttac ctccgcagtt tttacgagcg atttcacgtt cagccttcat 132120

gcgtctctcc ctctctctat cgagtttatc agagcagtct ttctgaaggc gatcgaactc 132180

cataaatttc tccaacgctt tgattgtttc catagatttc cgaacttcag cttctaggac 132240

ggcgattctt tttctttcga attcacagct ggatgtacaa ccgtttccat taccgccatc 132300

tctaagtttc ttttctagat cggcaacatt tcatccccat gccttttaca ttcctcgagt 132360

ctactgtcgt cgaaatatcg ttccagctcc ttttcgacat caataacttt agcacgttgt 132420

ctctcaagct ctcttttgta gttatctgat tccctggcac gtttaagatc ttcatgcaat 132480

tgagtcagct cttaacttcc tctcttgctt cttcgtcata gtacgcgcaa tcactgtgag 132540

atccattgtt accacgtcta cactcggcga gctcgcgttt aagagattca atttcccgtt 132600

tgtattggtc catgtttcca ttgctaccac cattagattt acaggctgct agttgtcgtt 132660

cgagatcaga aatacgggtt ttcttggaat tgatttcgtc gatgtacttg gcatcgaaac 132720

acttattaag ttctttttcc aattctacga ttttatttct ttcgcgagtc aattccctcc 132780

tgtagtaact atctgttttg tcagattcac gctctctacg tagactttct tgcaagttac 132840

taatttgttc cctagcacgt ccgagtttag ttttatatgc tgaatagagt tctgattcat 132900

cctttgagca gatctctagc gatcgtttaa gattcctgat tctagtcttt agcctattta 132960

cctcctcaga agatgttccg ttaccgttgc gtttacactc gttaagctgt ctatcaagat 133020

ccatgattct atctctaaga cgttgcatct ctctttccat atcagcattg ctttcattat 133080

tacgtctgca gtcactcaac tgtctttcaa tatctgagat tctatctcta agacgtcgca 133140

tctctctctg tttcagcatt ggtttcatta ttacgtctac agtcgttcaa ctgtctttca 133200

agatctgata ttctagattg gagtctgcta atctctgtag cattttcacg gcattcactc 133260

agttgtcttt caagatctga aattttagat tggagtctgc taatctctgt aagatttcct 133320

cctccgctct cgatgcagtt ggtcaactta ttctctagtt ctctaatacg cgaacgcagt 133380

gcatcaactt cttgcgtgtc ttcctggttg cgtgtacatt catcgagtct agattcgaga 133440

tctctaacgc gtcgtcgttc ttcctcaagt tctctgcgta ctacagaaag cgtgtcccta 133500

tcttgttgat atttagcaat ttctgattct agagtactga ttttgcttac gtagttacta 133560

atagttgtct tggccttatc aagatcctcc ttgtatttgt cgcattcctt gatatcccta 133620

cgaagtctgg acagttccca ttcgacatta cgacgtttat cgatttcagc tcggagatcg 133680

tcatcgcgtt gttttagcca catacgactg agttcaagtt ctcgttgaca agatccatct 133740

acttttccat tcctaatagt atccagttcc ttttctagtt ctgaacgcat ttctcgttcc 133800

ctatcaagcg attctctcaa ttctcggata gtcttcttat caatttctaa taaatctgaa 133860

ccatcatctg tcccattttg aatatccctg tgttctttga tctcttttgt aagtcggtcg 133920

attctttcgg ttttataaac agaatccctt tccaaagtcc taatcttact gagtttatca 133980

ctaagttctg cattcaattc ggtgagtttt ctcttggctt cttccaactc tgttttaaac 134040

tctccactat ttccgcattc ttcctcgcat ttatctaacc attcaattag tttattaata 134100

actagttggt aatcagcgat tcctatagcc gttcttgtaa ttgtgggaac ataattagga 134160

tcttctaatg gattgtatgg cttgatagca tcatctttat cattattagg gggatggaca 134220
```

accttaattg gttggtcctc atctcctcca gtagcgtgtg gttcttcaat accagtgtta 134280
gtaataggct taggcaaatg cttgtcgtac gcgggcactt cctcatccat caagtattta 134340
taatcgggtt ctacttcaga atattctttt ctaagagacg cgacttcggg agttagtaga 134400
agaactctgt ttctgtatct atcaacgctg gaatcaatac tcaagttaag gatagcgaat 134460
acctcatcgt catcatccgt atcttctgaa acaccatcat atgacatttc atgaagtcta 134520
acgtattgat aaatagaatc agatttagta ttaaacagat ccttaacctt tttagtaaac 134580
gcatatgtat attttagatc tccagatttc ataatatgat cacatgcctt aaatgtcagt 134640
gcttccatga tataatctgg aacactaatg ggtgacgaaa aagatacagc accatatgct 134700
acgttgataa ataaatctga accactaagt agataatgat taatgttaag gaaaagaaaa 134760
tattcagtgt ataggtatgt cttggcgtca tatcttgtac taaacacgct aaacagtttg 134820
ttaatgtgat caatttccaa tagattaatt agagcagcgg gaataccaac aaacatatta 134880
ccacatccgt attttctatg aatatcacat atcatgttaa aaaatcttaa tagaagagcg 134940
aatatctcgt ctgacttaat gagacgtagt tcagcagcaa cataagtcat aactgtaaat 135000
agaacatact ttcctgtagt gttgattcta gactccacat caacaccatt attaaaaata 135060
gttttatata catctttaat ctgctctccg ttaatcgtcg aacgttctag tatacggaaa 135120
cactttgatt tcttatctgt agttaatgac ttagtgatat cacgaagaat attacgaatt 135180
acatttcttg tttttcttga gagacctgat tcagaactca actcatcgtt ccatagtttt 135240
tctacctcag tggcgaaatc tttggagtgc ttggtacatt tttcaataag gttcgtgacc 135300
tccatttatt ataaaaaatt tattcaaaac ttaactacaa tcgggtaatt ataagatcgt 135360
aaatctccca tgtggcggaa tactaccatc tatcgcatgt ggatggacag taggtaatgg 135420
ccatgggaac agtaatgatt gcatatttat ctttcttgct agtattactg catattgtcc 135480
caatgtttcg atgtgatgtt ctaacctatc aactgccgct gtatcacaac aatagtgtcc 135540
gatgaaatta agattatgat ccaatgtgtt taatatatga ttatcaagtc ttatacgatc 135600
cgcgtctttt ttgacaggat caggttcttc tacaggaaga agtttcggcc tcttatgata 135660
ttcatgtctg ggaaacggtg gtctagggtg aggctccggt atcggagtgg gttttggatt 135720
ataatcatca tcgtctatga catcatcatc atcttcgact tcgatattta ttttgctatc 135780
ttgatgatgt cctgtatcag ttgcattttc agcactcgac tgaatattag cgcattcatt 135840
gtctattatt accatatttc taaacccaaa atgtatgtgt tgaacatcag tactatcgtt 135900
gatgagtctt atagcatgaa ttcgcttatc gttatcgggt ttatcttctg tcaccttagc 135960
aattcctttt ttattaaact ctacataatc atatccattt ctattgtttg ttctaatata 136020
aacgagtata gcatcattgc taaatttttc aatagtatcg aaaacagaat atcctaaacc 136080
atataatata tattcaggga cactcaaact aaatgtccag gattctccta aatacgtaaa 136140
ctttaatagt gcgaaatcat tcaaaaatct accacttata gatagatagt acataaatgc 136200
gtatagtagt ctacctatct ctttattatg aaaaccggca ttacgatcat atatgtcgtg 136260
atatacctgt gatccgttta cgttaaacca taaatacatg ggtgatccta taaacatgaa 136320
tttatttcta attctcagag ctatagttaa ttgaccgtgt aatatttgct tacatgcata 136380
cttgatacgc tcattaataa aatttttatc attgctcgtt atctcagaat cgtatatata 136440
aggagtacca tcgtgattct taccagatat tatacaaaat actatatata aaatatattg 136500
accaacgtta gtaatcatat aaatgtttaa cgttttaaat tttgtattca atgatccatt 136560
atcatacgct agcatggtct tatgatattc attctttaaa atataatatt gtgttagcca 136620
ttgcattggg gctcctaatg gagatttttt attctcatcc attttaggat aggctttcat 136680
aaagtcccta ataacttcgt gaataatgtt tctatgtttt ctactgatgc atgtatttgc 136740
ttcgattttt ttatcccatg tttcatctat catagattta aacgcagtaa tgctcgcaac 136800
attaacatct tgaaccgttg gtacaattcc gttccataaa tttataatgt tcgccattta 136860
tataactcat tttttgaata tacttttaat taacaaaaga gttaagttac tcatatgggc 136920
gccgtccagt ctgaacatca atctttttag ccagagatat catagccgct cttagagttt 136980
cagcgtgatt ttccaaccta aatagaactt catcgttgcg tttacaacac ttttctattt 137040
gttcaaactt tgttgttaca ttagtaatct ttttttccaa attagttagc cgttgtttga 137100
gagtttcctc attgtcgtct tcatcggctt taacaattgc ttcgcgttta gcctctggct 137160
ttttagcagc ctttgtagaa aaaaattcag ttgctggaat tgcaagatcg tcatctccgg 137220
ggaaaagagt tccgtccatt taaagtacag attttagaaa ctgacactct gcgttattta 137280
tatttggtac aacacatgga ttataaatat cgatgttaat aacatcagaa aatgtaaagt 137340
ctatacattg ttgcatcgtg ttaaattttc taatggatct agtattattg ggtccaactt 137400
ctgcctgaaa tccaaatatg gaagcggata caaaaccgtt tcctggataa accacacatc 137460
tccacttttg ctttacatca gaaattgtgt cgttgacatc ttgaactctc ctatctaatg 137520
ccggtgttcc acctatagat tttgaatatt cgaatgctgc atgagtagca ttaaattcct 137580
taatattgcc ataattttca tatattgagt aaccctggat aaaaagtaaa cacaccgcag 137640
ccgtcgctac cacaataaaa aaaattgata gagagttcat ttataatcta ttagaagctg 137700
acaaaatttt tttacacgca tcagacaatg ctttaataaa tagttcaaca tctacttttg 137760
tcatatcgaa ccgatggtat gattctaacc tagaattaca tccgaaaaag ttgactatgt 137820
tcatagtcat taagtcatta acaaacaaca ttccagactc tggattataa gacgatactg 137880
tttcgtcaca attacctacc ttaatcatgt gattatgaat attggctatt agagcacctt 137940
ctaagaaatc tataatatct ttgaaacacg atttaaaatc aaaccacgaa tatacttcta 138000
cgaagaaagt tagtttaccc ataggagaaa taactataaa tggagatcta aatacaaaat 138060
ccggatctat gatagtttta acattattat attctctatt aaatacctcc acatctaaaa 138120
atgttaattt tgaaactatg tcttcgttta ttaccgtacc tgaactaaac gctataagct 138180
ctattgtttg agaactcttt aaacgatatt cttgaaatac atgtaacaaa gtttccttta 138240
actcggtcgg tttatctacc atagttacag aatttgtatc cttatctata atataataat 138300
caaaatcgta taaagttata taattatcgc gttcagattg ggatcttttc aaatagacta 138360
aaaaccccat ttctctagta agtatcttat gtatatgttt gtaaaatatc ttcatggtgg 138420
gaatatgctc taccgcagtt agccattcct cattgacagc ggtagatgta ttagacaaaa 138480
ctattccaat gtttaacaag ggccatttta cgagattatt aaatccttgt ttgataaatg 138540
tagccaatga gggttcgagt tcaacgacga ttgaattctc ttcccgcgga tgctgcatga 138600
tgaacgacgg gatgttgttc gattgatttg gaattctttt tcgacttttt gtttatatta 138660
aatattttaa aatttatagc ggatagcaat tcatgtacca cggataatgt agacgcgtat 138720
tgcgcatcga tatctttatt attagataaa tttatcaata aatgtgagaa gtttgcctcg 138780
ttaaggtctt ccatttaaat attatataaa catttgtgtt tgtatcttat tcgtctttta 138840
tggaatagtt ttttactagt aaagctgcaa ttacacactt tgtccgtaaa acataaatat 138900
aaacaccagc ttttatcaat cgttccaaaa agtcgacggc ggacattttt aacatggcat 138960

```
ctattttaaa tacacttagg tttttggaaa aaacatcatt ttataattgt aacgattcaa 139020
taactaaaga aaagattaag attaaacata agggaatgtc atttgtattt tataagccaa 139080
agcattctac cgttgttaaa tacttgtctg gaggaggtat atatcatgat gatttggttg 139140
tattggggaa ggtaacaatt aatgatctaa agatgatgct attttacatg gatttatcat 139200
atcatggagt gacaagtagt ggagcaattt acaaattggg atcgtctatc gatagacttt 139260
ctctaaatag gactattgtt acaaaagtta ataattatga tgatacattt tttgacgacg 139320
atgattgatc gctattgcac aattttgttt ttttactttc taatatagcg tttagattct 139380
ttttcatgtg cgaatattga tttactaaaa tatcgatgtt taacttttgt tctatgacgt 139440
ccttatcagc ggtatcggta catatacgta attcaccttc acaaaatacg gagtcttcga 139500
taataatagc caatcgatta ttggatctag cggtctgtat catattcaac atgtttaata 139560
tatcctttcg tttccccttt acaggcatcg atcgtagcat attttccgcg tctgagatgg 139620
aaatgttaaa actacaaaaa tgcgtaatgt tagcccgtcc taatattggt acgtgtctat 139680
aagtttggca tagtagaata atagacgtgt ttaaatgcct tccaaagttt aagaattcta 139740
ttagagtatt gcattttgat agtttatcgc ctacatcatc aaaaataagt aaaaagtgtg 139800
ctgatttttt atgattttgt gcgacagcaa tacatttttc tatgttactt ttagttcgta 139860
tcagattata ttctagagat tcctgactac taacgaaatt aatatgattt ggccaaatgt 139920
atccatcata atctggatta taaacgggtg taaacaagaa tatatgttta tattttttaa 139980
ctagtgtaga aaacagagat agtaaataga tagtttttcc agatccagat cctcccgtta 140040
aaaccattct aaacggcatt tttaataaat tttctcttga aaattgtttt tcttggaaac 140100
aattcataat tatatttaca gttactaaat taatttgata ataaatcaaa atatggaaaa 140160
ctaaggtcgt tagtagggag gagaacaaag aaggcacatc gtgacataaa taacatttat 140220
tatcatgatg acaccagaaa acgacgaaga gcagacatct gtgttctccg ctactgttta 140280
cagagacaaa attcagggaa agaataaacg caaacgcgtg attggtctat gtattagaat 140340
atctatggtt atttcactac tatctatgat taccatgtcc gcgtttctca tagtgcgcct 140400
aaatcaatgc atgtctgcta acgaggctgc tattactgac gccgctgttg ccgttgctgc 140460
tgcatcatct actcatagaa aggttgcgtc tagcactacg caatatgatc acaaagaaag 140520
ctgtaatggt ttatattacc agggttcttg ttatatatta cattcagact accagttatt 140580
ctcggatgct aaagcaaatt gcactgcgga atcatcaaca ctacccaata aatccgatgt 140640
cttgactacc tggctcattg attatgttaa ggatacatgg ggatctgatg gtaatccaat 140700
tacaaaaact acatccgatt atcaagattc tgatgtatca caagaagtta gaaagtattt 140760
ttgtgttaaa acaatgaact aatatttatt tttgtacatt aataaatgaa atcgcttaat 140820
agacaaactg taagtaggtt taagaagttg tcggtgccgg ccgctataat gatgatactc 140880
tcaaccatta ttagtggcat aggaacattt ctgcattaca aagaagaact gatgcctagt 140940
gcttgcgcca atggatggat acaatacgat aaacattgtt atttagatac taacattaaa 141000
atgtctacag ataatgcggt ttatcagtgt cgtaaattac gagccagatt gcctagaccg 141060
gatactagac atctgagagt attgtttagt attttttata aagattattg ggtaagttta 141120
aaaaagacca atgataaatg gttagatatt aataatgata aagatataga tattagtaaa 141180
ttaacaaatt ttaaacaact aaacagtacg acggatgctg aagcgtgtta tatatacaag 141240
tctggaaaac tggttaaaac agtatgtaaa agtactcaat ctgtactatg tgttaaaaaa 141300
```

ttctacaagt gacaacaaaa aatgaattaa taataagtcg ttaacgtacg ccgccatgga 141360
cgccgcgttt gttattactc caatgggtgt gttgactata acagatacat tgtatgatga 141420
tctcgatatc tcaatcatgg actttatagg accatacatt ataggtaaca taaaaactgt 141480
ccaaatagat gtacgggata taaaatattc cgacatgcaa aaatgctact ttagctataa 141540
gggtaaaata gttcctcagg attctaatga tttggctaga ttcaacattt atagcatttg 141600
tgccgcatac agatcaaaaa ataccatcat catagcatgc gactatgata tcatgttaga 141660
tatagaagat aaacatcagc cattttatct attcccatct attgatgttt ttaacgctac 141720
aatcatagaa gcgtataacc tgtatacagc tggagattat catctaatca tcaatccttc 141780
agataatctg aaaatgaaat tgtcgtttaa ttcttcattc tgcatatcag acggcaatgg 141840
atggatcata attgatggga aatgcaatag taattttta tcataaaagt tgtaaagtaa 141900
ataataaaac aataaatatt gaactagtag tacgtatatt gagcaatcag aaatgatgct 141960
ggtacctctt atcacggtga ccgtagttgc gggaacaata ttagtatgtt atatattata 142020
tatttgtagg aaaaagatac gtactgtcta taatgacaat aaaattatca tgacaaaatt 142080
aaaaaagata aagagttcta attccagcaa atctagtaaa tcaactgata gcgaatcaga 142140
ctgggaggat cactgtagtg ctatggaaca aaacaatgac gtagataata tttctaggaa 142200
tgagatattg gacgatgata gcttcgctgg tagtttaata tgggataacg aatccaatgt 142260
tatggcgcct agcacagaac acatttacga tagtgttgct ggaagcacgc tgctaataaa 142320
taatgatcgt aatgaacaga ctatttatca gaacactaca gtagtactta atgaagatac 142380
caaacagaat cctaactatt catccaatcc tttcgtaaat tataataaaa ccagtatttg 142440
tagcaagtca aatccgttca ttacagaact caacaataaa tttagtgaga ataatccgtt 142500
tagacgagca catagcgatg attatcttaa taagcaagaa caagatcatg aacacgatga 142560
tatagaatca ttggtgtgat tagtttcctt tttataaaat tgaagtaata tttagtatta 142620
ttgctgccgt cacgttgtac aaatggagat attccctgta ttcggcattt ctaaaattag 142680
caattttatt gctaataatg actgtagata ttatatagat acagaacatc aaaaaattat 142740
atctgatgag atcaatagac agatggatga aacggtactt cttaccaaca tcttaagcgt 142800
agaagttgta aatgacaatg agatgtacca tcttattcct catagattat cgacgattat 142860
actctgtatt agttctgtcg gaggatgtgt tatctctata gataatgacg tcaatggcaa 142920
aaatattcta acctttccca ttgatcatgc tgtaatcata tccccactga gtaaatgtgt 142980
cgtagttagc aagggtccta caaccatatt ggttgttaaa gcggatatac ctagcaaacg 143040
attggtaaca tcgtttacaa acgacatact gtatgtaaac aatctatcac tgattaatta 143100
tttgccgttg tctgtattca ttattagacg agttaccgac tatttggata gacacatatg 143160
cgatcagata tttgcgaata ataagtggta ttccattata accatcgaca ataagcagtt 143220
tcctattcca tcaaactgta taggtatgtc ctctgccaag tacataaatt ctagcatcga 143280
gcaagatact ttaatacatg tttgtaacct cgagcatcca ttcgacttag tatacaaaaa 143340
aatgcagtcg tacaattctg tacctatcaa ggaacaaata ttgtacggta gaattgataa 143400
tataaatatg agcattagta tttctgtgga ttaatagatt tctagtatgg ggatcattaa 143460
tcatctctaa tctctaaata cctcataaaa cgaaaaaaaa gctattatca aatactgtac 143520
ggaatggatt cattctcttc tctttttatg aaactctgtt gtatatctac tgataaaact 143580
ggaagcaaaa aatctgataa aaagaataag aataagatca aggattatta taaaataaca 143640
atagttcctg gttcctcttc cacgtctact agctcgtggt attatacaca tgcctagtaa 143700

```
tagtctcttt gcgttgacgg aaagcagact agaaataaca ggctaaaatg ttcagacacc 143760
ataatagttc ccaacccaga taataacaga gtaccatcaa cacattcctt taaactcaat 143820
cccaaaccca aaaccgttaa aatgtatccg gccaattgat agtagataat gaggtgtaca 143880
gcgcatgata atttacacag taaccaaaat gaaaatactt tagtaattat aagaaatata 143940
gatggtaacg tcatcatcaa caatccaata atatgccgga gagtaaacat tgacggataa 144000
aacaaaaatg ctccgcataa ctctatcatg gcaataacac aaccaaatac ttgtaagatt 144060
cctaaattag tagaaaatac aacggatatc gatgtataag tgatctcgag aaataataag 144120
aataaagtaa tgcccgtaaa gataaacatc aacattgttt ggtaatcatt aaaccaatta 144180
gtatgaagtt gaactaattt cacagtagat tttattccag tattatcccc gcatgtataa 144240
gtacctggta agatatcttt atattccata atcaatgaga catcactatc tgataacgaa 144300
tgaagtctag cactagtatg ccatttactt aatattgtcg tcttggaagt tttattataa 144360
gttaaaatat catggttatc caatttccat ctaatatact ttgtcggatt atctatagta 144420
cacggaataa tgatggtatc attacatgct gtatactcta tggtctttgt agttgttata 144480
acaaccaacg tatagaggta tatcaacgat attctaactc ttgacatttt ttatttattt 144540
aaaatgatac ctttgttatt tattttattc tattttgcta acggtattga atggcataag 144600
tttgaaacga gtgaagaaat aatttctact tacttattag acgacgtatt atacacgggt 144660
gttaatgggg cggtatacac attttcaaat aataaactaa acaaaactgg tttaactaat 144720
aataattata taacaacatc tataaaagta gaggatgcgg aaccaataac ggaaatccca 144780
aatgttggaa aatagacggt tcagacgacc caaaacatag aggtagagga tacgctcctt 144840
atcaaaatag caaagtaacg ataatcagtc acaacggatg tgtactatct gacataaaca 144900
tatcaaaaga aggaattaaa cgatggagaa gatttgacgg accatgtggt tatgatttat 144960
acacggcgga taacgtaatt ccaaaagatg gtttacgagg agcattcgtc gataaagatg 145020
gtacttatga caaagtttac attcttttca ctgatactat cggctcaaag agaattgtca 145080
aaattccgta tatagcacaa atgtgcctaa acgacgaagg tggtccatca tcattgtcta 145140
gtcatagatg gtcgacgttt ctcaaagtcg aattagaatg tgatatcgac ggaagaagtt 145200
atagacaaat tattcattct agaactataa aaacagataa tgatacgata ctatatgtat 145260
tcttcgatag tccttattcc aagtccgcat tatgtaccta ttctatgaat accattaaac 145320
aatctttttc tacgtcaaaa ttggaaggat atacaaagca attgccgtct ccagctcctg 145380
gtatatgttt accagctgga aaagttgttc cacataccac gtttgaagtc atagaaaaat 145440
ataatgtact agatgatatt ataaagcctt tatctaacca acctatcttc gaaggaccgt 145500
ctggtgttaa atggttcgat ataaaggaga aggaaaatga acatcgggaa tatagaatat 145560
acttcataaa agaaaattct atatattcgt tcgatacaaa atctaaacaa actcgtagct 145620
cgcaagtcga tgcgcgacta ttttcagtaa tggtaacttc gaaaccgtta tttatagcag 145680
atatagggat aggagtagga atgccacaaa tgaaaaaaat acttaaaatg taatcttaat 145740
cgagtacacc gcacgacaat gaacaaacat aagacagatt atgctggtta tgcttgctgc 145800
gtaatatgcg gtctaattgt tggaattatt tttacagcga cactattaaa agttgtagaa 145860
cgtaaattag ttcatacacc atcaatagat aaaacgataa aagatgcata tattagagaa 145920
gattgtccta ctgactggat aagctataat aataaatgta tccatttatc tactgatcga 145980
aaaaacctgg gaggaaggac gtaatgcatg caaagctcta aatccaaatt cggatctaat 146040
```

```
taagatagag actccaaacg agttaagttt tttaagaagc cttagacgag gctattgggt 146100
aggagaatcc gaaatattaa accagacaac cccatataat tttatagcta aaaatgccac 146160
gaagaatgga actaaaaaac ggaaatatat ttgtagtaca acgaatactc ccaaactgca 146220
ttcgtgttac actatataac aattacacta catttttatc ataacactac ttcggttaga 146280
tgttttagaa aaaaataaat atcgccgtac cgttcttgtt tttataaaaa taacaattaa 146340
caattatcaa attttttctt taatatttta cgtggttgac cattcttggt ggtaaaataa 146400
tctcttagtg ttggaatgga atgctgttta atgtttccgc actcatcgta tattttgacg 146460
tatgcagtca catcgtttac gcaatagtca gactgtagtt ctatcatgct tcctacatca 146520
gaaggaggaa cagttttaaa gtctcttggt tttaatctat tgccattagt tttcatgaaa 146580
tcctttgttt tatccacttc acattttaaa taaatgtcca ctatacattc ttctgttaat 146640
tttactagat cgtcatgggt catagaattt ataggttccg tagtccatgg atccaaacta 146700
gcaaacttcg cgtatacggt atcgcgatta gtgtatacac caactgtatg aaaattaaga 146760
aaacagttta ataaatcaac agaaatattt aatcctccgt ttgatacaga tgcgccatat 146820
ttatggattt cggattcaca cgttgtttgt ctgaggtgtt cgtctagtgt tgcttctacg 146880
taaacttcga ttcccatata ttctttattg tcagaatcgc ataccgattt atcatcatac 146940
actgtttgaa aactaaatgg tatacacatc aaaataataa ataataacga gtacattctg 147000
caatattgtt atcgtaattg gaaaattagt gttcgagtga gtcggattat gtgagtactg 147060
gattgtatat tttattttat attttgtaat aagaataaaa tgctaatgtc aagtttattc 147120
caatagatgt cttattaaaa aacatatata ataaataaca atggctgaat ggcataaaat 147180
tatcgaggat atctcaaaaa ataataagtt cgaggatgcc gccatcgttg attacaagac 147240
tacaaagaat gttctagctg ctattcctaa cagaacattt gccaagatta atccgggtga 147300
aattattcct ctcatcacta atcgtaatat tctaaaacct cttattggtc agaaatattg 147360
tattgtatat actaactctc taatggatga gaacacgtat gctatggagt tgcttactgg 147420
gtacgcccct gtatctccga tcgttatagc gagaactcat accgcactta tatttttgat 147480
gggtaagcca acaacatcca gacgtgatgt gtatagaacg tgtagagatc acgctacccg 147540
tgtacgcgca actggtaatt aaaataaaaa gtaatattca tatgtagtgt caattttaaa 147600
tgatgatgat gaaatggata atatccatat tgacgatgtc aataatgccg gtattggcat 147660
acagctcatc gatttttaga tttcattcag aggatgtgga attatgttat gggcatttgt 147720
attttgatag gatctataat gtagtaaata taaaatataa tccgcatatt ccatatagat 147780
ataattttat taatcgcacg ttaaccgtag atgaactaga cgataatgtc tttttttacac 147840
atggttattt tttaaaacac aaatatggtt cacttaatcc tagtttgatt gtctcattat 147900
caggaaactt aaaatataat gatatacaat gctcagtaaa tgtatcgtgt ctcattaaaa 147960
atttggcaac gagtacatct actatattaa catctaaaca taagacttat tctctacatc 148020
ggtccacgtg tattactata ataggatacg attctattat atggtataaa gatataaatg 148080
acaagtataa tgacatctat gattttactg caatatgtat gctaatagcg tctacattga 148140
tagtgaccat atacgtgttt aaaaaaataa aaatgaactc ttaattatgc tatgctatta 148200
gaaatggata aaatcaaaat tacggttgat tcaaaaattg gtaatgttgt taccatatcg 148260
tataacttgg aaaagataac tattgatgtt acacctaaaa agaaaaaaga aaaggatgta 148320
ttattagcgc aatcagttgc tgtcgaagag gcaaaagatg tcaaggtaga agaaaaaaat 148380
attatcgata ttgaagatga cgatgatatg gatgtagaaa gcgcataata cgatctataa 148440
```

aaataagtat ataataaata ctttttattt acggtactct tgtagtggtg ataccctact 148500
caattatttt tttaaaaaaa tacttattct gattcttcta gccatttccg tgttcgttcg 148560
aatgccacat cgacgttaaa gataggggag tagttgaaat ctagttctgc attgttggta 148620
cgcacctcaa atgtagtgtt ggatatcttc aacgtatagt tgttgagtag tgatggtttt 148680
ctaaatagaa ttctcttcat atcattcttg cacgcgtaca tttttagcat ccatcttgga 148740
attctagatc cttgttctat tcccaatggt ttcatcaata gaagattaaa catatcgtac 148800
gaacacgatg gagagtaatc gtagcaaaag taagcatttc ctttaatctt agatcccgga 148860
tactggatat attttgcagc caacacgtgc atccatgcag catttcctac atatacccgg 148920
ctatgcaccg cgtcatcatc gactgtacga tacataatgt taccgtgttg cttacattgc 148980
tcgtaaaaga ctttcgtcaa tttgtctcct tctccgtaaa ttccagtggg tcttaggcaa 149040
caagtataca attttgctcc attcatgatt acggaattat tggctttcat aaccagttgc 149100
tcggccatac gtttactttt tgcgtataca tgtcctggtg atatatcata aagggtatgc 149160
tcatggccga tgaatggatc accgtgttta ttgggtccta ttgcttccat gctactagta 149220
tagatcaaat acttgattcc taggtccaca caagctgcca atatagtctg tgttccataa 149280
tagtttactt tcatgatttc attatcggtg tattttccaa atacatccac tagagcagcc 149340
gtatgaataa tcagatttac cccatctagc gcttctctca ccttatcaaa gtcgtttata 149400
tcacattgta tatagtttat aaccttaact ttcgaggtta ttggttgtgg atcttctaca 149460
atatctatga ctctgatttc ttgaacatca tctgcactaa ttaacagttt tactatatac 149520
ctgcctagaa atccggcacc accagtaacc gcgtacacgg ccattgctgc cactcataat 149580
atcagactac ttattctatt ttactaaata atggctgttt gtataataga ccacgataat 149640
atcagaggag ttatttactt tgaaccagtc catggaaaag ataaagtttt aggatcagtt 149700
attggattaa aatccggaac gtatagtttg ataattcatc gttacggaga tattagtcaa 149760
ggatgtgatt ccataggcag tccagaaata tttatcggta acatctttgt aaacagatat 149820
ggtgtagcat atgtttattt agatacagat gtaaatatat ttacaattat tggaaaggcg 149880
ttatctattt caaaaaatga tcagagatta gcgtgtggag ttattggtat ttcttacata 149940
aatgaaaaga taatacattt tcttacaatt aacgagaatg gcgtttgata tatcagttaa 150000
tgcgtctaaa acaataaatg cattagttta cttttctact cagcaaaata aattagtcat 150060
acgtaatgaa gttaatgata cacactacac tgtcgaattt gatagggaca aagtagttga 150120
cacgtttatt tcatataata gacataatga caccatagag ataagagggg tgcttccaga 150180
ggaaactaat attggttgcg cggttaatac gccggttagt atgacttact tgtataataa 150240
gtatagtttt aaactgattt tagcagaata tataagacac agaaatacta tatccggcaa 150300
tatttattcg gcattgatga cactagatga tttggctatt aaacagtatg gagacattga 150360
tctattattt aatgagaaac ttaaagtaga ctccgattcg ggactatttg actttgtcaa 150420
ctttgtaaag gatatgatat gttgtgattc tagaatagta gtagctctat ctagtctagt 150480
atctaaacat tgggaattga caaataaaaa gtataggtgt atggcattag ccgaacatat 150540
atctgatagt attccaatat ctgagctatc tagactacga tacaatctat gtaagtatct 150600
acgcggacac actgagagca tagaggatga atttgattat tttgaagacg atgattcgtc 150660
tacatgttct gccgtaaccg acagggaaac ggatgtataa tttttttttat agcgtgaagg 150720
atatgataaa aaatataatt gttgtattta tcccattcca atcaccttat atgattctgt 150780

```
aaaaaaatta tactgtaaca caataaagga gtcttataga tgtatagagg tcagatactg 150840
gtttgataaa ctgtttattc cacataagta tgtttgactt tatggttaga cccgcatact 150900
ttaacaaatc actgaaaatt ggagttaggt attgacctct cagaatcagt tgccgttctg 150960
gaacattaaa tgtatttttt atgatatact ccaacgcatt tatgtgggca tacaacaagt 151020
cattactaat ggagtattcc aagagtttta gttgtctagt atttaacaag agaagagatt 151080
tcaacagact gtttatgaac tcgaacgccg cctcattgtc gcttatattg atgatgtcga 151140
attctcccaa tatcatcact gatgagtagc tcatcttgtt atcgggatcc aagttttcta 151200
aagatgtcat taaaccctcg atcatgaatg gatttatcat catcgttttt atgttggaca 151260
tgagcttagt ccgtttgtcc acatctatag acgacgattt ctgaattatt tcatatatcc 151320
ctctctttaa ctccaggaac ttgtcaggat ggtctacttt aatatgttct cgtctaagag 151380
atgaaaatct ttggatggtt gcacgcgact tttctttaaa ggatgacgtt gcccaagatc 151440
ctctcttaaa tgaatccatc ttatccttgg acaagatgga cagtctattt tccttagatg 151500
gtttaatatt tttgttaccc atgatctata aaggtagacc taatcgtctc ggatgaccat 151560
atatttattt tcagttttat tatacgcata aattgtaaaa aatatgttag gtttacaaaa 151620
atgtctcgtg gggcattaat cgtttttgaa ggattggaca aatctggaaa aacaacacaa 151680
tgtatgaaca tcatggaatc tataccggca aacacgataa aatatcttaa ctttcctcag 151740
agatccactg tcactggaaa gatgatagat gactatctaa ctcgtaaaaa aacctataat 151800
gatcatatag ttaatctatt attttgtgca aatagatggg agtttgcatc ttttatacaa 151860
gaacaactag aacagggaat tactttaata gttgatagat acgcattttc tggagtagcg 151920
tatgccgccg ctaaaggcgc gtcaatgact ctcagtaaga gttatgaatc tggattgcct 151980
aaacccgact tagttatatt cttggaatct ggtagcaaag aaattaatag aaacgtcggc 152040
gaggaaattt atgaagatgt tacattccaa caaaaggtat tacaagaata taaaaaaatg 152100
attgaagaag gagatattca ttggcaaatt atttcttctg aattcgagga agatgtaaag 152160
aaggagttga ttaagaatat agttatagag gctatacaca cggttactgg accagtgggg 152220
caactgtgga tgtaatagtg aaattacatt ttttataaat agatgttagt acagtgttat 152280
aaatggatga agcatattac tctggcaact tggaatcagt actcggatac gtgtccgata 152340
tgcataccga actcgcatca atatctcaat tagttattgc caagatagaa actatagata 152400
atgatatatt aaacaaggac attgtaaatt ttatcatgtg tagatcaaac ttggataatc 152460
catttatctc tttcctagat actgtatata ctattataga tcaagagatc tatcagaccg 152520
aattgattaa ttcattagac gacaatgaaa ttatcgattg tatagttaac aagtttatga 152580
gcttttataa ggataaccta gaaaatatag tagatgctat cattactcta aaatatataa 152640
tgaataatcc agattttaaa actacgtatg ccgaagtact cggttccaga atagccgata 152700
tagatattaa acaagtgata cgtaagaata tactacaatt gtctaatgat atccgcgaac 152760
gatatttgtg aaaaatatta aaaaaaaata ctttttttat taaatgacgt cgcttcgcga 152820
atttagaaaa ttatgctgtg atatatatca cgcatcagga tataaagaaa aatctaaatt 152880
aattagagac tttataacag atagggatga taaatatttg atcattaagc tattgcttcc 152940
cggattagac gatagaattt ataacatgaa cgataaacaa attataaaat tatatagtat 153000
aatatttaaa caatctcagg aagatatgct acaagattta ggatacggat atataggaga 153060
cactattagg actttcttca aagagaacac agaaatccgt ccacgagata aaagcatttt 153120
aactttagaa gaagtggata gtttttttaac tacgttatca tccgtaacta aagaatcgca 153180
```

```
tcaaataaaa ttattgactg atgtagcatc tgtttgtaca tgtaatgatt taaaatgtgt 153240
agtcatgctt attgataaag atctaaaaat taaagcgggc cctcggtacg tacttaacgc 153300
tattagtcct catgcctatg atgtgtttag aaaatctaat aacttgaaag agataataga 153360
aaatgcatct aaacaaaatc tagactctat atctatttct gttatgactc caattaatcc 153420
catgttagcg gaatcgtgtg attctgtcaa taaggcgttt aaaaaatttc catcaggaat 153480
gtttgcggaa gtcaaatacg atggtgaaag agtacaagtt cataaaaata ataacgagtt 153540
tgccttcttt agtagaaaca tgaaaccagt actctctcat aaagtggatt atctcaaaga 153600
atacataccg aaagcattta aaaaagctac gtctatcgta ttggattctg aaattgttct 153660
tgtagacgaa cataatgtac cgctaccgtt tggaagttta ggaatacaca aaaagaaaga 153720
atataaaaac tctaacatgt gtttgttcgt gtttgactgt ttgtactttg atggattcga 153780
tatgacggac attccattgt acgaacgaag atcttttctc aaagatgtta tggttgaaat 153840
acccaataga atagtattct cagagttgac gaatattagt aacgagtctc agttaactga 153900
cgtattggat gatgcactaa cgagaaaatt agaaggattg gtcttaaaag atattaatgg 153960
agtatacgaa ccgggaaaga gaagatggtt aaaaataaag cgagactatt tgaacgaggg 154020
ttccatggca gattctgccg atttagtagt actaggtgcc tactatggta aaggagcaaa 154080
gggtggtatc atggcagtct ttctaatggg ttgttacgac gatgaatccg gtaaatggaa 154140
gacggttacc aagtgttcag gacacgatga taatacgtta agggagttgc aagaccaatt 154200
aaagatgatt aaaattaaca aggatcccaa aaaaattcca gagtggttag tagttaataa 154260
aatctatatt cccgattttg tagtagagga tccgaaacaa tctcagatat gggaaatttc 154320
aggagcagag tttacatctt ccaagtccca taccgcaaat ggaatatcca ttagatttcc 154380
tagatttact aggataagag aggataaaac gtggaaagaa tctactcatc taaacgattt 154440
agtaaacttg actaaatctt aatagttaca tacaaactga aaattaaaat aacaccattt 154500
agttggtggt cgccatggat ggtgttattg tatactgtct aaacgcgtta gtaaaacatg 154560
gcgaggaaat aaatcatata aaaaatgatt tcatgattaa accatgttgt gaaagagttt 154620
gtgaaaaagt caagaacgtt cacattggcg gacaatctaa aaacaataca gtgattgcag 154680
atttgccata tatggataat gcggtatccg atgtatgcaa ttcactgtat aaaaagaatg 154740
tatcaagaat atccagattt gctaatttga taaagataga tgacgatgac aagactccta 154800
ctggtgtata taattatttt aaacctaaag atgttattcc tgttatcata tctataggaa 154860
aggataaaga tgtctgtgaa ctattaatct catcagacat atcgtgtgca tgcgtggagt 154920
taaattcata tcacgtagcc attcttccca tgaatgtttc ctttttttacc aaaggaaatg 154980
cctcgttgat tattctcctg tttgatttct ctatcgatgc agcacctctc ttaagaagtg 155040
taaccgataa taatgttatt atatctagac accagcgtct acatgacgag cttccgagtt 155100
ccaattggtt caagttttac ataagtataa agtccgacta ttgttctata ttatatatgg 155160
ttgttgatgg atctgtgatg catgcgatag ctgataatag aactcacgca attattagca 155220
aaaatatatt agacaatact acaattaacg atgagtgtag atgctgttat tttgaaccac 155280
agattaggat tcttgataga gatgagatgc tcaatggatc atcgtgtgat atgaacagac 155340
attgtattat gatgaattta cctgatgtag gcgaatttgg atctagtatg ttggggaaat 155400
atgaacctga catgattaag attgctcttt cggtggctgg taatttaata agaaatcgag 155460
actacattcc cgggagacga ggctatagct actacgttta cggtatagcc tctagataat 155520
```

```
tttttaagc acgaaataaa aaacataatt ttaaaccaat ctatttcata ctattttgtg 155580
tgatcaccat ggacataaag atagatatta gtatttctgg tgataaattt acggtgacta 155640
ctaggaggga aaatgaagaa agaaaaaaat atctacctct ccaaaaagaa aaaactactg 155700
atgttatcaa acctgattat cttgagtacg atgacttgtt agatagagat gagatgttta 155760
ctattctaga ggaatatttt atgtacagag gtctattagg cctcagaata aaatatggac 155820
gactctttaa cgaaattaaa aaattcgaca atgatgcgga agaacaattc ggtactatag 155880
aagaactcaa gcagaaactt agattaaatt ctgaagaggg agcagataac tttatagatt 155940
atataaaggt acaaaaacag gatatcgtca aacttactgt atacgattgc atatctatga 156000
taggattgtg tgcatgcgtg gtagatgttt ggagaaatga gaaactgttt tctagatgga 156060
aatattgttt acgagcgatt aaactgttta ttaatgatca catgcttgat aagataaaat 156120
ctatactgca gaatagacta gtatatgtgg aaatgtcata gaaagttaat gagagcaaaa 156180
atatataagg ttgtattcca tatttgttat tttttctgta atagttaaaa aaatacattc 156240
gatggtctat ctatcagatt attatgtgtt ataaggtact ttttctcata ataaactaga 156300
gtatgagtaa gatagtgttt ttcaaaacat ataaatctaa aattgatgga tgagatatac 156360
agctattaat ttcgaaaata tataaatcta aaattgatgg ataagatata cagctattaa 156420
tttcgaaaat atattttaat ctgataactt taaacatgga tttttgatgg tggtttaacg 156480
ttttaaaaaa agattttgtt attgtagtat atgataatat taaaagatgg atataaagaa 156540
tttgctgact gcatgtacta ttttttacat tactacattg gctacggcag atatacctac 156600
tccgccacca acgggtcatg tgacaaggga gaatatcttg ataagaggca taatcaatgt 156660
tgtaatcggt gtccacctgg agaatttgcc aaggttagat gtaatggtaa cgataacaca 156720
aaatgtgaac gctgcccacc tcatacatat accacaatcc ccaattattc taatggatgt 156780
catcaatgta gaaaatgccc aaccggatca tttgataagg taaagtgtac cggaacacag 156840
aacagtaaat gttcgtgtct tcctggttgg tattgcgcta ctgattcttc acagactgaa 156900
gattgttgaa attgtgtacc aaaaaggaga tgtccatgcg gatactttgg tggaatagat 156960
gaacaaggaa atcctatttg taaatcgtgc tgtattggtg aatattgcaa ctacctacgt 157020
aattatagac ttgatccatt ttctccatgc aaactatcta aatgtaatta attatgattt 157080
tgatgataat gttaccatac attatatcgc tacttggtta gtgtattatt cagtatgaag 157140
acctattaat aattacttat cttttgacga tcttgttata attataatat aaaaacttat 157200
ggcatagtaa ctcataattg ctgacgcgat aaattcgtaa taatctgttt tgttcaaatt 157260
tttataagga atctacaggc ataaaaataa aaatataatt tataatatac tcttacagcg 157320
cgccatcatg aatagcagca gtaaattaat tgctgttatt aatggattta gaaatagtgg 157380
acgattttgt gatattaata tagttattaa tgatgaaagg ataaacgctc acagactcat 157440
cctatctgga gcctccgaat atttttccat tctgttttcc aataatttta tcgattctaa 157500
tgaatacgaa gttaatctaa gtcatttaga ttatcaaagt gttaacgatt tgatcgatta 157560
catttatggg atacctttga gcctaactaa cgataacgtg aaatatattc tttcaaccgc 157620
tgatttttta caaattggat ctgccattac tgagtgcgaa aaatacatac ttaaaaatct 157680
ttgttctaga aactgtatcg atttctacat atacgctgat aaatataata acaagaaaat 157740
agaatcagcg tcgtttaaca caatattacg aaatattttg agactcatca acgatgaaaa 157800
ctttaaatac ttaacagagg aatcaatgat aaaaatttta agcgatgata tgttaaatat 157860
aaaaaatgag gattttgcac cactaattct cattaaatgg ttagagagta ctcaacaatc 157920
```

atgcaccgtc gagttactta gatgcctcag aatatcattg ctttccccac aagttataaa 157980
atcactttat agtcatcaac tggttagttc aatctacgaa tgtataacat tcttaaacaa 158040
tatagcattc ttggatgaat catttcctag ataccatagc atcgagttga tatctatcgg 158100
tataagtaat tcgcatgata agatttccat aaactgctac aatcataaaa aaaatacatg 158160
ggaaatgata tcttcacgta gatataggtg tagtttcgca gtggccgtcc tggataatat 158220
tatctatatg atgggtggat atgatcagtc cccgtataga agttcaaagg ttatagcgta 158280
caatacatgt acaaattctt ggatatatga tataccagag ctaaaatatc ctcgttctaa 158340
ttgtggggga ctggctgatg acgaatacat ttattgtata ggcggcatac gcgatcagga 158400
ttcatcgttg acatctagta ttgatagatg gaagccatca aaaccatatt ggcagaagta 158460
tgctaaaatg cgcgaaccaa aatgtgatat gggggttgcg atgttaaacg gattaatata 158520
tgtcatgggt ggaatcgtta aaggtgacac gtgtaccgac gcactagaga gtttatcaga 158580
agatggatgg atgaagcatc aacgtcttcc aataaaaatg tccaatatgt cgacgattgt 158640
tcatgatggc aagatttata tatctggagg ttacaacaat agtagtgtag ttaatgtaat 158700
atcgaatcta gtccttagct ataatccgat atatgatgaa tggaccaaat tatcatcatt 158760
aaacattcct agaattaatc ccgctctatg gtcagcgcat aataaattat atgtaggagg 158820
aggaatatct gatgatgttc gaactaatac atctgaaaca tacgataaag aaaaagattg 158880
ttggacattg gataatggtc acgtgttacc acgcaattat ataatgtata aatgcgaacc 158940
gattaaacat aaatatccat tggaaaaaac acagtacacg aatgattttc taaagtattt 159000
ggaaagtttt ataggtagtt gatagaacaa aatacataat tttgtaaaaa taaatcactt 159060
tttatactaa tatgacacga ttaccaatac ttttgttact aatatcatta gtatacgcta 159120
caccttttcc tcagacatct aaaaaaatag gtgatgatgc aactctatca tgtaatcgaa 159180
ataatacaaa tgactacgtt gttatgagtg cttggtataa ggagcccaat tccattattc 159240
ttttagctgc taaaagcgac gtcttgtatt ttgataatta taccaaggat aaaatatctt 159300
acgactctcc atacgatgat ctagttacaa ctatcacaat taaatcattg actgctagag 159360
atgccggtac ttatgtatgt gcattcttta tgacatcaac tacaaatgac actgataaag 159420
tagattatga agaatactcc acagagttga ttgtaaatac agatagtgaa tcgactatag 159480
acataatact atctggatct acacattcac cagaaactag ttctgagaaa ccagaggata 159540
tagataattt taattgctcg tcggtattcg aaatcgcgac tccggaacca attactgata 159600
atgtagaaga tcatacagac accgtcacat acactagtga tagcattaat acagtaagtg 159660
catcatctgg agaatccaca acagacgaga ctccggaacc aattactgat aaagaagaag 159720
atcatacagt cacagacact gtctcataca ctacagtaag tacatcatct ggaattgtca 159780
ctactaaatc aaccaccgat gatgcggatc tttatgatac gtacaatgat aatgatacag 159840
taccaccaac tactgtaggc ggtagtacaa cctctattag caattataaa accaaggact 159900
ttgtagaaat atttggtatt accgcattaa ttatattgtc ggccgtggca atattctgta 159960
ttacatatta tatatataat aaacgttcac gtaaatacaa aacagagaac aaagtctaga 160020
tttttgactt acataaatgt ctgggatagt aaaatctatc atattgagcg gaccatctgg 160080
ttcaggaaag acagccatag ccaaaagact atgggaatat atttggattt gtggtgtccc 160140
ataccactag atttcctcgt cctatggaac gagaaggtgt cgattaccat tacgttaaca 160200
gagaggccat ctggaaggga atagccgccg gaaactttct agaacatact gagtttttag 160260

```
gaaatattta cggaacttct aaaactgctg tgaatacagc ggctattaat aatcgtattt 160320
gtgtgatgga tctaaacatc gatggcgtta gaagtcttaa aaatacgtac ctaatgcctt 160380
actcggtgta tataagacct acctctctta aaatggttga gaccaagctt cgttgtagaa 160440
acactgaagc ggatgatgag attcatcgtc gtgtgatgtt ggcaaaaact gacatggatg 160500
aggcaggtga agccggtcta ttcgacacta ttatcattga agatgatgtg aatttagcat 160560
atagtaagtt aattcagata ctacaggacc gtattagaat gtattttaac actaattaga 160620
gacttaagac ttaaaacttg ataattaata atataactcg tttttatatg tggctatttc 160680
aacgtctaat gtattagtta aatattaaaa cttaccacgt aaaacttaaa atttaaaatg 160740
atatttcatt gacagataga tcacacatta tgaactttca aggacttgtg ttaactgaca 160800
attgcaaaaa tcaatgggtc gttggaccat taataggaaa aggtggattc ggtagtattt 160860
atactactaa tgacaataat tatgtagtaa aaatagagcc caaagctaac ggatcattat 160920
ttaccgaaca ggcattttat actagagtac ttaaaccatc cgttatcgaa gaatggaaaa 160980
aatctcacaa tataaagcac gtaggtctta tcacgtgcaa ggcatttggt ctatacaaat 161040
ccattaatgt ggaatatcga ttcttggtaa ttaatagatt aggtgcagat ctagatgcgg 161100
tgatcagagc caataataat agattaccaa aaaggtcggt gatgttgatc ggaatcgaaa 161160
tcttaaatac catacaattt atgcacgagc aaggatattc tcacggagat attaaagcga 161220
gtaatatagt cttggatcaa atagataaga ataaattata tctagtggat tacggattgg 161280
tttctaaatt catgtctaat ggcgaacatg ttccatttat aagaaatcca aataaaatgg 161340
ataacggtac tctagaattt acacctatag attcgcataa aggatacgtt gtatctagac 161400
gtggagatct agaaacactt ggatattgta tgattagatg gttgggaggt atcttgccat 161460
ggactaagat atctgaaaca aagaattgtg cattagtaag tgccacaaaa cagaaatatg 161520
ttaacaatac tgcgactttg ttaatgacca gtttgcaata tgcacctaga gaattgctgc 161580
aatatattac catggtaaac tctttgacat attttgagga acccaattac gacgagtttc 161640
ggcacatatt aatgcagggt gtatattatt aagtgtggtg tttggtcgat gtaaaatttt 161700
tgtcgataaa aattaaaaaa taacttaatt tattattgat ctcgtgtgta caaccgaaat 161760
catggcgatg ttttacgcac acgctctcgg tgggtacgac gagaatcttc atgcctttcc 161820
tggaatatca tcgactgttg ccaatgatgt caggaaatat tctgttgtgt cagtttataa 161880
taacaagtat gacattgtaa aagacaaata tatgtggtgt tacagtcagg tgaacaagag 161940
atatattgga gcactgctgc ctatgtttga gtgcaatgaa tatctacaaa ttggagatcc 162000
gatccatgat caagaaggaa atcaaatctc tatcatcaca tatcgccaca aaaactacta 162060
tgctctaagc ggaatcgggt acgagagtct agacttgtgt ttggaaggag tagggattca 162120
tcatcacgta cttgaaacag gaaacgctgt atatggaaaa gttcaacatg attattctac 162180
tatcaaagag aaggccaaag aaatgaatgc actcagttca ggacctatca tcgattacca 162240
cgtctggata ggagattgta tctgtcaagt tactgctgtg gacgtacatg gaaaggaaat 162300
tatgagaatg agattcaaaa agggtgcggt gctacagatc ccaaatctgg taaaagttaa 162360
acttggggag aatgatacag aaaatctttc ttctactata tcggcggcac catcgaggta 162420
accacctctc aagaagaccg cgtgaataat gtactcatga aacgtttgga aactatacgc 162480
catatgtggt ctgttgtata tgatcatttt gatattgtga atggtaaaga atgctgttat 162540
gtgcatacgc attcatctaa tcaaaatcct ataccgagta ctgtaaaaac aaatttgtac 162600
atgaagacta tgggatcatg cattcaaatg gattccatgg aagctctaga gtatcttagc 162660
```

gaactgaagg aatcaggtgg atggagtccc agaccagaaa tgcaggaatt tgaatatcca 162720
gatggagtgg aagacactga atcaattgag agattggtag aggagttctt caatagatca 162780
gaacttcagg ctggtaaatt agtcaaattt ggtaattcta ttaattgtta aacatacatc 162840
tgtttcagct aagcaactaa gaacacgtat acggcagcag cttcctttta tactctcatc 162900
ttttaccaac acaaagggtg gatatttgtt cattggagtt gataataata cacacaaagt 162960
atttggattc acggtgggtt acgactacct cagactgata gagaatgata tagaaaagca 163020
tatcaaaaga ctttgtgttg tgcatttctg tgagaagaaa gaggacatca agtacacgtg 163080
tcgattcatc aaggtatata aacctgggga tgaggctacc tcgacatacg tgtgcgctat 163140
caaagtggaa agatgctgtt gtgctgtgtt tgcagattgg ccagaatcat ggtatatgga 163200
tactaatggt atcaagaagt attctccaga tgaatgggtg tcacatataa aattttaatt 163260
aatgtaacta tagagaacaa ataataggtt gtaatatcat atagacaata actaacaatt 163320
aattagtaac tgttatctct tttttaacta accaactaac tatataccta ttaatacatc 163380
gtaattatag ttcttaacat ctattaatca ttgattcgct tctttaattt tttataaact 163440
aacattgtta attgaaaagg gataacatgt tacagaatat aaattatata tggatttttt 163500
taaaaaggaa atacttgact ggagtgtata tttatctctt cattatatag cacgcgtgtg 163560
ttccaattct tccacatccc atataataca ggattataat ctcgttcgaa catacgagaa 163620
agtggataaa acaatagttg attttttatc taggttgcca aatttattcc atattttaga 163680
atatggggaa aatattctac atatttattc tatggatgat gctaatacga atattataat 163740
tttttttcta gatagagtat taaatattaa taagaacggg tcatttatac acaatctcag 163800
gttatcatca tccattaata taaaagaata tgtatatcaa ttagttaata atgatcatcc 163860
agataatagg ataagactaa tgcttgaaaa tggacgtaga acaagacatt ttttgtccta 163920
tatatcagat acagttaata tctatatatg tattttaata aatcatggat tttatataga 163980
tgcagaagac agttacggtt gtacattatt acatagatgt atatatcact ataagaaatc 164040
agaatcagaa tcatacaatg aattaattaa gatattgtta aataatggat ccgatgtaga 164100
taaaaaagat acgtacggaa acacaccttt tatcctatta tgtaaacacg atatcaacaa 164160
cgtggaattg tttgagatat gtttagagaa tgctaatata gactctgtag actttaatag 164220
atatacacct cttcattatg tctcatgtcg taataaatat gattttgtaa agttattaat 164280
ttctaaagga gcaaatgtta atgcgcgtaa taaattcgga actactccat tttattgtgg 164340
aattatacac ggtatctcgc ttataaaact atatttggaa tcagacacag agttagaaat 164400
agataatgaa catatagttc gtcatttaat aatttttgat gctgttgaat ctttagatta 164460
tctattatcc agaggagtta ttgatattaa ctatcgtact atatacaacg aaacatctat 164520
ttacgacgct gtcagttata atgcgtataa tacgttggtc tatctattaa acagaaatgg 164580
tgattttgag acgattacta ctagtggatg tacatgtatt tcggaagcag tcgcaaacaa 164640
caacaaaata ataatggaag tactattgtc taaacgacca tctttgaaaa ttatgataca 164700
gtctatgata gcaattacta aaaataaaca acataatgca gatttattga aaatgtgtat 164760
aaaatatact gcgtgtatga ccgattatga tactcttata gatgtacagt cgctacagca 164820
atataaatgg tatattttaa aatgtttcga tgaaatagat atcatgaaga gatgttatat 164880
aaaaaataaa actgtattcc aattagtttt ttgtatcaaa gacattaata ctttaatgag 164940
atatggtaaa catccttctt tcgtgaagtg cactagtctc gacgtatacg gaagtcgtgt 165000
acgtaatatc atagcatcta ttagatatcg tcagagatta attagtctat tatccaagaa 165060
gctggatgcg ggagataaat ggtcgtgttt tcctaacgaa ataaaatata aaatattgga 165120
aaactttaac gataacgaac tatccacata tctaaaaatc ttataaacac tattaaaata 165180
taaaatctaa gtaggataaa atcacactac atcattgttt ccttttagtg ctcgacagtg 165240
tatactattt ttaacactca taaataaaaa tgaaaacgat ttccgttgtt acgttgttat 165300
gcgtactacc tgctgttgtt tattcaacat gtactgtacc cactatgaat aacgctaaat 165360
taacgtctac cgaaacatcg tttaatgata aacagaaagt tacatttaca tgtgatcagg 165420
gatatcattc tttggatcca aatgctgtct gcgaaacaga taaatggaaa tacgaaaatc 165480
catgcaagaa aatgtgcaca gtttctgatt atgtctctga attatatgat aagccattat 165540
acgaagtgaa ttccaccatg acactaagtt gcaacggcga aacaaaatat tttcgttgcg 165600
aagaaaaaaa tggaaatact tcttggaatg atactgttac gtgtcctaat gcggaatgtc 165660
aacctcttca attagaacac ggatcgtgtc aaccagttaa agaaaaatac tcatttgggg 165720
aatatatgac tatcaactgt gatgttggat atgaggttat tggtgcttcg tacataagtt 165780
gtacagctaa ttcttggaat gttattccat catgtcaaca aaaatgtgat ataccgtctc 165840
tatctaatgg attaatttcc ggatctacat tttctatcgg tggcgttata catcttagtt 165900
gtaaaagtgg ttttatacta acgggatctc catcatccac atgtatcgac ggtaaatgga 165960
atcccatact cccaacatgt gtacgatcta acgaaaaatt tgatccagtg gatgatggtc 166020
ccgacgatga gacagatttg agcaaactct cgaaagacgt tgtacaatat gaacaagaaa 166080
tagaatcgtt agaagcaact tatcatataa tcatagtggc gttaacaatt atgggcgtca 166140
tatttttaat ctccgttata gtattagttt gttcctgtga caaaaataat gaccaatata 166200
agttccataa attgctaccg taaatataaa tccgttaaaa taattaataa tttaataaca 166260
aacaagtatc aaaagattaa agacttatag ctagaatcaa ttgagatgtc ttcttcagtg 166320
gatgttgata tctacgatgc cgttagagca tttttactca ggcactatta taacaagaga 166380
tttattgtgt atggaagaag taacgccata ttacataata tatacaggct atttacaaga 166440
tgcgccgtta taccgttcga tgatatagta cgtactatgc caaatgaatc acgtgttaaa 166500
caatgggtga tggatacact taatggtata atgatgaatg aacgcgatgt ttctgtaagc 166560
gttggcaccg gaatactatt catggaaatg tttttcgatt acaataaaaa tagtatcaac 166620
aatcaactaa tgtatgatat aattaatagc gtatctataa ttctagctaa tgagagatat 166680
agaagcgctt ttaacgacga tggtatatac atccgtagaa atatgattaa caagttgtac 166740
ggatacgcat ctctaactac tattggcacg atcgctggag gtgtttgtta ttatctgttg 166800
atgcatctag ttagtttgta taaataatta tttcaatata ctagttaaaa ttttaagatt 166860
ttaaatgtat aaaaaactaa taacgttttt atttgtaata ggtgcattag catcctattc 166920
gaataatgag tacactccgt ttaataaact gagtgtaaaa ctctatatag atggagtaga 166980
taatatagaa aattcatata ctgatgataa taatgaattg gtgttaaatt ttaaagagta 167040
cacaatttct attattacag agtcatgcga cgtcggattt gattccatag atatagatgt 167100
tataaacgac tataaaatta ttgatatgta taccattgac tcgtctacta ttcaacgcag 167160
aggtcacacg tgtagaatat ctaccaaatt atcatgccat tatgataagt acccttatat 167220
tcacaaatat gatggtgatg agcaacaata ttctattact gcagagggaa aatgctataa 167280
aggaataaaa tatgaaataa gtatgatcaa cgatgatact ctattgagaa aacatactct 167340
taaaattgga tctacttata tatttgatcg tcatggacat agtaatacat attattcaaa 167400
atatgatttt taaaaattta aaatatatta tcacttcagt gacagtagtc aaataacaaa 167460
caacaccatg agatatatta taattctcgc agttttgttc attaatagta tacacgctaa 167520
aataactagt tataagtttg aatccgtcaa ttttgattcc aaaattgaat ggactgggga 167580
tggtctatac aatatatccc ttaaaaatta tggcatcaag acgtggcaaa caatgtatac 167640
aaatgtacca gaaggaacat acgacatatc cgcatttcca aagaatgatt tcgtatcttt 167700
ctgggttaaa tttgaacaag gcgattataa agtggaagag tattgtacgg gactatgcgt 167760
cgaagtaaaa attggaccac cgactgtaac attgactgaa tacgacgacc atatcaattt 167820
gtacatcgag catccgtatg ctactagagg tagcaaaaag attcctattt acaaacgcgg 167880
tgacatgtgt gatatctact tgttgtatac ggctaacttc acattcggag attctaaaga 167940
accagtacca tatgatatcg atgactacga ttgcacgtct acaggttgca gcatagactt 168000
tgtcacaaca gaaaaagtgt gcgtgacagc acagggagcc acagaagggt ttctcgaaaa 168060
aattactcca tggagttcga aagtatgtct gacacctaaa aagagtgtat atacatgcgc 168120
aattagatcc aaagaagatg ttcccaattt caaggacaaa atggccagag ttatcaagag 168180
aaaatttaat aaacagtctc aatcttattt aactaaattt ctcggtagca catcaaatga 168240
tgttaccact tttcttagca tgcttaactt gactaaatat tcataactaa tttttattaa 168300
tgatacaaaa acgaaataaa actgcatatt atacactggt taacgccctt ataggctcta 168360
accattttca agatgaggtc cctgattata gtccttctgt tcccctctat catctactcc 168420
atgtctatta gacgatgtga gaagactgaa gaggaaacat ggggattgaa aatagggttg 168480
tgtataattg ccaaagattt ctatcccgaa agaactgatt gcagtgttca tctcccaact 168540
gcaagtgaag gattgataac tgaaggcaat ggattcaggg atatacgaaa caccgataaa 168600
ttataaaaaa agcaatgtgt ccgctgtttc cgttaataat actattttcg taactggcgg 168660
attattcata aataactcta atagcacgat cgtggttaac aatatggaaa aacttgacat 168720
ttataaagac aaacaatggt cgattataga aatgcctatg gctagggtat atcacggcat 168780
cgactcgaca tttggaatgt tatattttgc cggaggtcta tccgttaccg aacaatatgg 168840
taatttagag aaaaacaacg agatatcttg ttacaatcct agaacgaata agtggtttga 168900
tatttcatat actatttata agatatccat atcatcattg tgtaaactaa ataacgtctt 168960
ctatgtattt agtaaggaca ttggatatgt ggaaaagtat gatggtgcat ggaagttagt 169020
acatgatcgt ctccccgcta taaaggcatt atcaacttct ccttattgat tgaaaatgaa 169080
aatataaata gtttttatgt atagcagtat taccctatag ttttattgct tactactaac 169140
atggatacag atgttacaaa tgtagaagat atcataaatg aaatagatag agagaaagaa 169200
gaaatactaa aaaatgtaga aattgaaaat aataaaaaca ttaacaagaa tcatccaagt 169260
ggatatatta gagaagcact cgttattaat acaagtagta atagtgattc cattgataaa 169320
gaagttatag aatgtatcag tcacgatgta ggaatataga tcatatctac taatttttat 169380
aatcgataca aaacataaaa aacaactcgt tattacatag caggcatgga atccttcaag 169440
tattgttttg ataacgatgg caagaaatgg attatcggaa atactttata ttctggtaat 169500
tcaatactat ataaggtcag aaaaaatttc actagttcgt tctacaatta cgtaatgaaa 169560
atagatcaca aatcacacaa gccattgttg tctgaaatac gattctatat atctgtattg 169620
gatcctttga ctatcgacaa ctggacacgg gaacgtggta taaagtattt ggctattcca 169680
gatctgtatg gaattggaga aaccgatgat tatatgttct tcgttataaa gaattcggga 169740
agagtattcg ccccaaagga tactgaatca gtcttcgaag catgcgtcac tatgataaac 169800
acgttagagt ttatacactc tcgaggattt acccatggaa aaatagaacc gaggaatata 169860
ctgattagaa ataaacgtct ttcactaatt gactattcta gaactaacaa actatacaag 169920
agtggaaact cacatataga ttacaacgag gacatgataa cttcaggaaa tatcaattat 169980
atgtgtgtag acaatcatct tggagcaaca gtttcaaaac gaggagattt agaaatgttg 170040
ggatattgca tgatagaatg gttcggtggc aaacttccat ggaaaaacga aagtagtata 170100
aaagtaataa aacaaaaaaa agaatataaa aaatttatag ctactttctt tgaggactgt 170160
tttcctgaag gaaatgaacc tctggaatta gttagatata tagaattagt atacacgtta 170220
gattattctc aaactcctaa ttatgacaga ctacgtaaac tgtttataca agattgaaat 170280
tatattcttt ttttatagag tgtggtagtg ttacggatat ctaatattaa tattagacta 170340
tctctatcgc gctacacgac caatatcgat tactatggat atcttcaggg aaatcgcatc 170400
ttctatgaaa ggagagaatg tattcatttc tccagcgtca atctcgtcag tattgacaat 170460
actgtattat ggagctaatg gatccactgc tgaacagcta tcaaaatatg tagaaacgga 170520
ggagaacacg gataaggtta gcgctcagaa tatctcattc aaatccatga ataaagtata 170580
tgggcgatat tctgccgtgt ttaaagattc ctttttgaga aaaattggcg ataagtttca 170640
aactgttgac ttcactgatt gtcgcactat agatgcaatc aacaagtgtg tagatatctt 170700
tactgagggg aaaatcaatc cactattgga tgaaccattg tctcctgata cctgtctcct 170760
agcaattagt gccgtatact ttaaagcaaa atggttgatg ccattcgaaa aggaatttac 170820
cagtgattat cccttttacg tatctccgac ggaaatggta gatgtaagta tgatgtctat 170880
gtacggcaag gcatttaatc acgcatctgt aaaggaatca ttcggcaact tttcaatcat 170940
agaactgcca tatgttggag atactagtat gatggtcatt cttccagaca agattgatgg 171000
attagaatcc atagaacaaa atctaacaga tacaaatttt aagaaatggt gtaactctct 171060
ggaagctacg tttatcgatg ttcacattcc caagtttaag gtaacaggtt cgtataatct 171120
tgtggatact ctagtaaagt caggactgac agaggtgttc ggttcaactg gagattatag 171180
caatatgtgt aattcagatg tgagtgtcga cgctatgatt cacaaaacgt atatagatgt 171240
caatgaagag tatacagaag cagctgcagc aacttgtgca ctggtgtcag actgtgcatc 171300
aacaattaca aatgagttct gtgtagatca tccgttcatc tatgtgatta ggcatgttga 171360
tggaaaaatt cttttcgttg gtagatattg ctctccgaca actaattgtt aaccattttt 171420
tttaaaaaaa tagaaaaaac atgtggtatt agtgcaggtc gttgttcttc caattgcaat 171480
tggtaagatg acggccaact ttagtaccca cgtcttttca ccacagcact gtggatgtga 171540
cagactgacc agtattgatg acgtcagaca atgtttgact gaatatattt attggtcgtc 171600
ctatgcatac cgcaacaggc aatgcgctgg acagttgtat tccacactcc tctcttttag 171660
agatgatgcg gaatcagtgt tcatcgacat tcgcgagctg gtaaaaaata tgccgtggga 171720
tgatgtcaaa gattgtacag aaatcatccg ttgttatata ccggatgagc aaaaaaccat 171780
cagagagatt tcggccatca tcggactttg tgcatatgct gctacttact ggggaggtga 171840
agaccatccc actagtaaca gtctgaacgc attgtttgtg atgcttgaga tgctcaatta 171900
cgtggattat aacatcatat tccggcgtat gaattgatga gttgtacatc ttgacatttt 171960
ctttcttctc ttctcccttt cttctcttct cccttcctcc ctcttctccc tttcccagaa 172020
acaaactttt ttacccacta taaaataaaa tgagtatact acctattata tttcttccta 172080
tattttttta ttcttcattc gttcagactt ttaacgcgcc tgaatgtatc gacaaagggc 172140

```
aatattttgc atcattcatg gagttagaaa acgagccagt aatcttacca tgtcctcaaa 172200
taaatacgct atcatccgga tataatatat tagatatttt atgggaaaaa cgaggagcgg 172260
ataatgatag aattataccg atagataatg gtagcaatat gctaattctg aacccgacac 172320
aatcagactc tggtatttat atatgcatta ccacgaacga aacctactgt gacatgatgt 172380
cgttaaattt gacaatcgtg tctgtctcag aatcaaatat agatcttatc tcgtatccac 172440
aaatagtaaa tgagagatct actggcgaaa tggtatgtcc caatattaat gcatttattg 172500
ctagtaacgt aaacgcagat attatatgga gcggacatcg acgccttaga aataagagac 172560
ttaaacaacg gacacctgga attattacca tagaagatgt tagaaaaaat gatgctggtt 172620
attatacatg tgttttagaa tatatataca gaggtaaaac atataacgta accagaattg 172680
taaaattaga ggtacgggat aaaataatac cttctactat gcaattacca gatggcattg 172740
taacttcaat aggtagtaat ttgactattg cgtgtagagt atcgttgaga cctcccacaa 172800
cggatgcaga cgtcttttgg ataagtaatg gtatgtatta cgaagaagat gatggggacg 172860
gagacggtag aataagtgta gcaaataaaa tctatatgac cgataagaga cgtgttatta 172920
catcccggtt aaacattaat cctgtcaagg aagaagatgc tacaacgttt acgtgtatgg 172980
cgtttactat tcctagcatc agcaaaacag ttactgttag tataacgtga atgtatgttg 173040
ttacatttcc atgtcaattg agtttataag aatttttata cattatcttc caacaaacaa 173100
ttgacgaacg tattgctatg attaactccc acgatactat gcatattatt aatcattaac 173160
ttgcagacta tacctagtgc tattttgaca tactcatgtt cttgtgtaat tgcggtatct 173220
atattattaa agtacgtaaa tctagctata gttttattat ttaattttag ataatatacc 173280
gtctccttat ttttaaaaat tgccacatcc tttattaaat catgaatggg aatttctatg 173340
tcatcgttag tatattgtga acaacaagag cagatatcta taggaaaggg tggaatgcga 173400
tacattgatc tatgtagttt taaaacacac gcgaactttg aagaatttat ataaatcatt 173460
ccatcgatac atccttctat gttgacatgt atatatccag gaattctttt attaatgtca 173520
ggaaatgtat aaactaaaac attgcccgaa agcggtgcct ctatctgcgt tatatccgtt 173580
cttaacttac aaaatgtaac caataccttt gcatgacttg ttttgttcgg caacgttagt 173640
ttaaacttga cgaatggatt aattacaata gcatgatccg cgcatctatt aagttttttt 173700
actttaacgc ccttgtatgt ttttacagag actttatcta aatttctagt acttgtatgt 173760
gttataaata taacgggata tagaactgaa tcacctacct tagataccca attacatttt 173820
atcagatcca gataataaac aaattttgtc gccctaacta attctatatt gttatatatt 173880
ttacaattgg ttatgatatc atgtaataac ttggagtcta acgcgcatcg tcgtacgttt 173940
atacaattgt gatttagtgt agtatatcta cacatgtatt tttccgcact atagtattct 174000
ggactagtga taaaactatc gttatatctg tcttcaatga actcatcgag atattgctct 174060
ctgtcatatt catacacctg cataaacttt ctagacatct tacaatccgt gttattttag 174120
gatcatattt acatatttac gggtatatca aagatgttag attagttaat gggaatcgtc 174180
tataataatg aatattaaac aattatatga ggacttttac cacaaagcat cataaaaatg 174240
agtcgtcgtc tgatttatgt tttaaatatc aaccgcaaat caactcataa aatacaagag 174300
aatgaaatat atacatattt tagtcattgc aatatagacc atacttctac agaacttgat 174360
tttgtagtta aaaactatga tctaaacaga cgacaacatg taactgggta tactgcacta 174420
cactgctatt tgtataataa ttactttaca aacgatgtac tgaagatatt attaaatcat 174480
```

gacgtaaatg taacgatgaa aaccagtagc ggacgtatgc ctgtttatat attgcttact 174540
agatgttgca atatttcaca tgatgtagtg atagatatga tagacaaaga taaaaaccac 174600
ttattacata gagactattc caacctatta ctagagtata taaaatctcg ttacatgtta 174660
ttaaaggaag aggatatcga tgagaacata gtatccactt tattagataa gggaatcgat 174720
cctaacttta aacaagacgg atatacagcg ttacattatt attatttgtg tctcgcacac 174780
gtttataaac caggtgagtg tagaaaaccg ataacgataa aaaaggccaa gcgaattatt 174840
tctttgttta tacaacatgg agctaatcta aacgcgttag ataattgtgg taatacacca 174900
ttccatttgt atcttagtat tgaaatgtgt aataatattc atatgactaa aatgctgttg 174960
acttttaatc cgaatttcaa aatatgtaat aatcatggat taacgcctat actatgttat 175020
ataacttccg actacataca acacgatatt cttgttatgt taatacatca ctatgaaaca 175080
aatgttggag aaatgccgat agatgagcgt cgtatgatcg tattcgagtt tatcaaaaca 175140
tattctacac gtccggcaga ttcgataact tatttgatga ataggtttaa aaatataaat 175200
atttataccc gctatgaagg aaagacatta ttacacgtag catgtgaata taataataca 175260
cacgtaatag attatcttat acgtatcaac ggagatataa atgcgttaac cgacaataac 175320
aaacacgcta cacaactcat tatagataac aaagaaaatt ccccgtatac catcgattgt 175380
ttactgtata tacttagata tattgtagat aagaatgtga taagatcgtt ggtggatcaa 175440
cttccatctc tacctatctt cgatataaaa tcatttgaga aattcatatc ctactgtata 175500
cttttagatg acacatttta cgataggcac gttaagaatc gcgattctaa aacgtatcga 175560
tacgcatttt caaaatacat gtcgtttgat aaatacgatg gtataataac taaatgtcac 175620
gacgaaacaa tgttactcaa actgtccact gttctagaca ctacactata tgcagtttta 175680
agatgccata attcgaaaaa gttaagaaga tacctcaacg agttaaaaaa atataataac 175740
gataagtcct ttaaaatata ttctaatatt atgaatgaga gataccttaa tgtatattat 175800
aaagatatgt acgtgtcaaa ggtatatgat aaactatttc ctgttttcac agataaaaat 175860
tgtctactaa cattactacc ttcagaaatt atatacgaaa tattatacat gctgacaatt 175920
aacgatcttt ataatatatc gtatccacct accaaagtat agttgtattt ttctcatgcg 175980
atgtgtgtaa aaaaactgat attatataaa tattttagtg ccgtataata aagatgacga 176040
tgaaaatgat ggtacatata tatttcgtat cattattgtt attgctattc cacagttacg 176100
ccatagacat cgaaaatgaa atcacagaat tcttcaataa aatgagagat actctaccag 176160
ctaaagactc taaatggttg aatccagcat gtatgttcgg aggcacaatg aatgatatag 176220
ccgctctagg agagccattc agcgcaaagt gtcctcctat tgaagacagt cttttatcgc 176280
acagatataa agactatgtg gttaaatggg agaggctaga aaagaataga cggcgacagg 176340
tttctaataa acgtgttaaa catggtgatt tatggatagc caactataca tctaaattca 176400
gtaaccgtag gtatttgtgt accgtaacta caaagaatgg tgactgtgtt cagggtatag 176460
ttagatctca tattaaaaaa cctccttcat gcattccaaa aacatatgaa ctaggtactc 176520
atgataagta tggcatagac ttatactgtg gaattcttta cgcaaaacat tataataata 176580
taacttggta taaagataat aaggaaatta atatcgacga cattaagtat tcacaaacgg 176640
gaaagaaatt aattattcat aatccagagt tagaagatag tggaagatac aactgttacg 176700
ttcattacga cgacgttaga atcaagaatg atatcgtagt atcaagatgt aaaatactta 176760
cggttatacc gtcgcaagac cacaggttta aactaatact agatccaaaa atcaacgtaa 176820
cgataggaga acctgccaat ataacatgca ctgctgtgtc aacgtcatta ttgattgacg 176880
atgtactgat tgaatgggaa aatccatccg gatggcttat aggattcgat tttgatgtat 176940
actctgtttt aactagtaga ggcggtatta ccgaggcgac cttgtacttt gaaaatgtta 177000
ctgaagaata tataggtaat acatataaat gtcgtggaca caactattat tttgaaaaaa 177060
cccttacaac tacagtagta ttggagtaaa tacacaatgc atttttatat acattactga 177120
ataattatta ttattattta tatcgtattt gtgctataac gcgactatct aggtatttgt 177180
atctcactga tagagaacat ataaatatag actctattaa acagttgtgt aaaatatcaa 177240
atcctaatag atgtggatgt acggctttac atgagtactt ttataattat agatcagtca 177300
acggaaaata caagtataga tacaacggtt actatcaata ttatttatct agcgattatg 177360
aaaattataa tgaatattat tatgatgatt atgatagaac tggtatgaac agtgagagtg 177420
ataatatatc aatcaaaaca gaatatgaat tctatgatga aacacaagat caaagtacac 177480
aactagtagg ttacgacatt aaactcaaaa ccaatgagga tgattttatg gctatgatag 177540
atcagtgggt gtccatgatt atatagatga atcaattaat aaagtagtat atggaagaga 177600
gtctcacgta agatggcggg atatatggca agaacataat gatggcgtat acagtatagg 177660
aaaggagtgc atagataata tatacgaaga caaccatacc gtagacgaat tctacaagat 177720
agacagcgta tcagatgtag atgacgcgga acacatatct ccgataacta atgatgtatc 177780
tacacaaaca tgggaaaaga aatcagagtt agatagatac atggaaatgt atcctcgtca 177840
tagatatagt aagcattctg tctttaaggg attttctgac aaagttagaa aaaatgattt 177900
agacatgaat gtggtaaaag aattactttc taacggtgca tctctaacaa ttaaggatag 177960
cagtaataag gatccaataa ccgtttattt tcgaagaacg ataatgaatt tagaaatgat 178020
tgatattatt aacaaacata caactattga tgaacgaaag tatatagtac actcctatct 178080
aaaaaattat aaaaatttcg attatccatt tttcaggaag ttagttttga ctaataaaca 178140
ttgtctcaac aattattata atataagcga cagcaaatat ggaacaccgc tacatatatt 178200
ggcgtctaat aaaaaattaa taactcctaa ttacatgaag ttattagtgt ataacggaaa 178260
tgatataaac gcacgaggtg aagatacaca aatgcgaact ccattacaca aatatttgtg 178320
taaatttgta tatcataata ttgaatatgg tatccgatac tataatgaaa agattataga 178380
cgcatttata gagttaggag ccgatctaac tattccaaat aacgatggaa tgataccagt 178440
agtttactgt atacactcaa atgcagaata tggttataac aatattacta acataaagat 178500
aatacgtaaa ctacttaatc ttagtagacg tgcgtcacat aatctattta gagatcgagt 178560
catgcacgat tatataagta atacatatat tgatcttgag tgtttagata ttattagatc 178620
gttggatgga ttcgatatca atggttactt tgaaggacgt acaccacttc attgcgctat 178680
acaacataac ttcactcaga ttgctaagta cttattagat cgaggagctg atatagtcgt 178740
acccaacaca ttgattatac atcagtacat acagtaaata gcatagatat ggaggaggat 178800
acaaatattt caaataaagt tataaggtac aacactgtca ataatatatg gaagacatta 178860
cctaacttct ggactggaac tataaatcca ggcgtggtct cgcataaaga tgatatatat 178920
gttgtatgcg acatcaaaga tgaaaaaaat gttaagactt gtatatttag atataacacg 178980
aatacgtata acggatggga attggttacg acgacagaaa gcagattatc agctctgcat 179040
actattcttc atgacaatac cataatgatg ttacattgtt atgaatcgta tatgttacaa 179100
gatacattta atgtgtacac tcgcgaatgg aatcatatgt gtcatcaaca ttcgaatagt 179160
tatatcatgt acaatatact acccatctac taaatataat agaataaaat aaatgagtat 179220

```
gatcatttta gataacgatt gattttatca ttaccgcttc attcttatat tctttgctta 179280
cggaacctat atttagaaac atctactaac gatttttat gcttgcatta ttaatggtat 179340
gtaatatgat tgattgtgta cgcaatacca atttgttaag tatgaatacg ggtacaaac 179400
ataaactgaa atttaacatt atttatttat gatatatatc gttatcgtta ttgtttggtc 179460
tataccatgg atatctttaa agaactaatc ttaaaacacc ctgatgaaaa tgttttgatt 179520
tctccagttt ctattttatc tactttatct attctaaatc atggagcagc tggttctaca 179580
gctgaacaac tatcaaaata tatagagaat atgaatgaga atacacccga tgataagaag 179640
gatgacaata atgacatgga cgtagatatt ccgtattgtg cgacactagc taccgcaaat 179700
aaaatatacg gtagcgatag tatcgagttc cacgcctcct tcctacaaaa aataaaagac 179760
gattttcaaa ctgtaaactt taataatgct aaccaaacaa aggaactaat caacgaatgg 179820
gttaagacga tgacaaatgg taaaattaat tccttattga ctagtccgct atccattaat 179880
actcgtatga cagttgttag cgccgtccat tttaaagcaa tgtggaaata tccattttct 179940
aaacatctta catatacaga caagttttat atttctaaga atatagttac cagtgttgat 180000
atgatggtgg gtaccgagaa taacttgcaa tatgtacata ttaatgaatt attcggagga 180060
ttctctatta tcgatattcc atacgaggga aactctagta tggtaattat actaccggac 180120
gacatagaag gtatatataa catagaaaaa aatataacag atgaaaaatt taaaaaatgg 180180
tgtggtatgt tatctactaa aagtatagac ttgtatatgc caaagtttaa agtggaaatg 180240
acagaaccgt ataatctggt accgatttta gaaaatttag gacttactaa tatattcgga 180300
tattatgcag attttagcaa gatgtgtaat gaaactatca ctgtagaaaa atttctacat 180360
acgacgttta tagatgttaa tgaggagtat acagaagcat cggccgttac aggagtattt 180420
atgactaact tttcgatggt atatcgtacg aaggtctaca taaaccatcc attcatgtac 180480
atgattaaag acaacacagg acgtatactt tttataggga aatactgcta tccgcaataa 180540
atataaacaa atagactttt atcacgttta tctatgtcta aatattacaa atagtaatag 180600
tataaactaa agctgataat acttaaaaaa ataataatat catttacaat taatagtata 180660
aactaaaaat taaacaaatc gttattataa gtaatatcaa aatgatgata tacggattaa 180720
tagcgtgtct tatattcgtg acttcatcca tcgctagtcc actttatatt cccgttattc 180780
cacccattac ggaagataaa tcgttcaata gtgtagaggt attagtttcc ttgtttagag 180840
atgaccaaaa agactatacg gtaacttctc agttcaataa ctacactatc gataccaaag 180900
actggactat cggcgtacta tccacacctg atggtttgga tataccattg actaatataa 180960
cttattggtc acggtttact ataggtcgtg cattgttcaa atcagagtct gaggatattt 181020
tccaaaagaa aatgagtatt ctaggtgttt ctatagaatg taagaagtcg tcgacattac 181080
ttactttttt gaccgtgcgt aaaatgactc gagtatttaa taaatttcca gatatggctt 181140
attatcgagg agactgttta aaagccgttt atgtaacaat gacttataaa aatactaaaa 181200
ctggagagac tgattacacg tacctctcta atggggggtt gcctgcatac tatcgtaatg 181260
gggtcgatgg ttgattattg attagtatat tccttattca cacaaaaaga acatttttat 181320
aaacatgaaa ccactgtcta aatgtaatta tgatcttgat ttatagatga agatcagcct 181380
ttagaggatt ttaaccagta tgtttaatat gaaaaaaata aacataacat attttgagat 181440
taagcgctat tgtgcttaat tattttgctc tataaactga atatatagcc acaattattg 181500
acgggcttgt ttatgaccgg caatcatgaa tttacagaaa ttatctctgg ctatatatct 181560
tactgcgaca tgttcgtggt gttatgaaac atgcataaga aaaactgcgt tgtatcatga 181620
```

cattcaattg gagcatgtag aagacaataa agatagtgta gcgtcgctac cgtacaagta 181680
gtcaatcaaa gagaacgtag tagattgttg gctacattta attggacaga tatagctgag 181740
ggtgttagaa atgagttcat taaaatatgt gatatcaacg gaacatattt atataattat 181800
actattgctg ttagtataat tattgattcc acggaagaac taccaacagt tactccaatt 181860
acaacaacat atgaaccttc tacatataat tatactatcg atgatagcac tgttattact 181920
actgaagaac tacaagtgac tcctcatatg gatctccatc gatgatacat gtattaaaat 181980
actttccgaa taagtctttt aaatattgta ttaattatga aaaactatgc tatgcgagta 182040
tgatgcaaag atgtttaatg atacgatact agattttatc tctagcgaga gatgtcgtta 182100
gaatcattta tcataactac gtttaataat aattcatcaa cgaatatcga taacatgtgt 182160
catttatacg ttaaagtctg tccgtcttct ctattgttta gactgtttgt agaatgctgt 182220
gatataaaca aactagtaga aggtacgact ccgttacact gttatctaat gaatgaagga 182280
tttgaatcat ctgttttaaa aaacctatta aaggagtatg tcatgaatac gtttaatgtt 182340
catgacatcc attacacaaa tatttaactc atgatgaagt tgagaatgat atgctttctg 182400
atagtataga tagctttagc taatataaaa atatattaat ccactatata ttctagactt 182460
gatttaaaac cgataaacta ctactacgta ctgtataagt tgttaaaaaa aggagcagac 182520
cctaattatg tagatgatag aggtaatact tttcttcatt acttctgcat ctatatgtcc 182580
acttatgaga aaacgtcatt taataagatg catcgtgaaa agaaatttat taaagagttg 182640
gtaaaatatg aaaccgaaag taaataatat aggaaataca cctctacata actacgtatc 182700
tcaatatgat atcactctca ttcctcatcc acaacccatt aaaaaaatgg aaattaaagc 182760
cctctattag cataaacggc tacaggtcta cctttacaat ggcctctcct tgtgcccagt 182820
tcagaccctg tcattgccac gctactaagg actccctgaa taccgtggcc gacgtcagac 182880
attgtctgac tgaatacatc ctgtgggttt ctcatagatg gacccataga gaaagcgcag 182940
ggtctctcta caggcttctc atctctttca gaactgatgc aacggagctc tttggtggtg 183000
agttgaagga ttcacttccg tgggacaata tcgacaattg cgtggagatc attaaatgtt 183060
tcatcagaaa tgactccatg aaaaccgccg aagaacttcg tgcaatcatt ggactttgta 183120
ctcaatcagc tatcgtctct ggaagagtct tcaacgataa gtatatcgac atactactta 183180
tgctgcgaaa gattctgaac gagaacgact atctcaccct cttggatcat atccgcactg 183240
ctaaatacta aatctccttc atgctctctc actacacttt ttatcatctt atgaggaatg 183300
attgccttca tcatttttcg tgaaatagga ataattagca ccagaatagc tatggattgc 183360
acatgtattc tatgtcgtct actggatgaa gatgtgacgt acaaaaaaat aaaactagaa 183420
attgaaacgt gtcacaactt atcaaaacat atagatagac gaggaaacaa tgcgctacat 183480
tgttacgtct tcaataaatg cgatacagac attaagattg ttcgactgtt actctctcgc 183540
ggagtcgaga gactttgtag aaacaacgaa ggattaactc cgctaggagc atacagtaag 183600
catagatacg taaaatctca aattgtgcat ctactgatat ccagctattc gaattcctct 183660
aacgaactca agtcgaatat aaatgatttc gatctgtatt cgtatatgtc ttcggataat 183720
atcgacttac gtctgctaaa atacctaatt gtggataaac ggatacgtcc gtccaagaat 183780
acgaattatg caatcaatgg tctcggattg gtggatatat acgtaacgac gcctaatccg 183840
agaccagaag tattgctatg gcttcttaaa tcagaatgtt acagcaccgg ttacgtattt 183900
cgtacctgta tgtacgacag tgatatgtgt aagaactctc ttcattacta tatatcgtct 183960
catagagaat ctcaatctct atccaaggat gtaattaaat gtttgatcaa taacaatgtt 184020
tccatccatg gcagagacga aggaggatct ttacccatcc aatactactg gtcttgctca 184080
accatagata tagagattgt taaattatta ataaaggatg tggacacgtg tagagtatac 184140
gacgtcagcc ctatattaga ggcggattat ctaaacaagc gatttagagt aaccccatat 184200
aatgtagaca tggaaatcgt taatcttctt attgagagac gtcatactct tgtcgacgta 184260
atgcgtagta ttacttctta cgattccaga gactataacc actacatcat cgataacatt 184320
ctaaagagat ttagacaaca ggatgaatcc atcgtacaag ccatgttgat aaactactta 184380
cattacggcg atatggtcgt tcgatgcatg ttagataacg gacaacaact atcctctgca 184440
cgactacttt gttaataata atctcgtcga tgtaaacgtc gtaaggttta tcgtggaaaa 184500
taatggacac atggctgtaa atcacgtatc gaacaatggc cgtctatgta tgtacggtct 184560
gatattatcg agatttaata attgcgggta tcactgttat gaaaccatac taatagatgt 184620
atttgatata ctaagcaagt acatggataa tatagatatg atcgataatg agaataaaac 184680
tctactatat tacgcggtcg atgtcaataa tatacaattt gcaaagcggt tattggaata 184740
tggagcgagt gttacaacat cacgctcgat aatcaatacg gccatccaga aaagtagtta 184800
cagaagagaa aacaaaacga ggatagttga tttattactt agctaccatc ccactctaga 184860
gactatgatt gacgcattta atagagatat acgctatcta tatcctgaac cattattcgc 184920
ctgtatcaga tacgccttaa tcctagatga tgattttcct tctaaagtaa gtatgatatc 184980
tccggtcgtc ataaggaact aaagcgctat agagtagaca ttaatagaat gaagaatgcc 185040
tacatatcag gcgtctccat gtttgatata ttatttaaac gaagcaaacg ccacagattg 185100
agatacgcaa agaatccgac atcaaatggt acaaaaaaga actaacgtcc atcattacag 185160
aaactgtaaa gaacaatgag aggatcgact ccatagtgga caacattaat acagacgata 185220
acttgatttc gaaattaccc atggagatac tttattactc cattaaataa tttatcatgg 185280
agcgataatg tcctgtttca tttgtttcca tgacatatta caaaatcgat tccgtccaag 185340
atgataaaaa catttaccgg catcataaac acggagttta ttttatatgt ctcgcataaa 185400
cattactaaa aaaatatatt gttctgtttt tctttcacat ctttaattat gaaaaagtaa 185460
atcattatga gatggacgag attgtacgca tcgttcgcga cagtatgtgg tacataccta 185520
acgtatttat ggacgacggt aagaatgaag gtcacgtttc tgtcaacaat gtttgtcata 185580
tgtattttac gttctttgat gtggatacat cgtctcatct gtttaagcta gttattaaac 185640
actgcgatct gaataaacga ggtaactctc cattacattg ctatacgatg aatacacgat 185700
ttaatccatc tgtattaaag atattgttac accacggcat gcgtaacttt gatagcaagg 185760
atgaaaaagg acatattcct ctacaccact atctgattca ttcactatca atcgataaca 185820
agatctttga tatactaacg gacaccattg atgactttag taaatcatcc gatctattgc 185880
tgtgttatct tagatataaa ttcaatggga gcttaaacta ttacgttctg tacaaaggat 185940
ccgaccctaa ttgcgtcgac gaggatggac tcacttctct tcattactac tgtaaacaca 186000
tatccacgtt ctacaaaagc aattattaca agttaagtca cactaagatg cgagccgaga 186060
agcgattcat ctacgcgata atagattatg gagcaaacat taacgcggtt acacacttac 186120
cttcaacagt ataccaaaca tagtcctcgt gtggtgtatg ctcttttatc tcgaggagcc 186180
gatacgagga tacgtaataa tcttgattgt acacccatca tggaacgatt gtgcaacagg 186240
tcatattctc ataatgttac tcaattggca cgaacaaaag gaagaaggac aacatctact 186300
ttatctattc ataaaacata atcaaggata cactctcaat atactacggt atctactaga 186360
taggttcgac attcagaaag acgaatacta taataccgcc tttcaaaatt gtaacaacaa 186420
tgttgcctca tacatcggat acgacatcaa ccttccgact aaagacggta ttcgacttgg 186480
tgtttgaaaa cagaaacatc atatacaagg cggatgttgt gaatgacatc atccaccaca 186540
gactgaaagt atctctacct atgattaaat cgttgttcta caagatgtct ctccctacga 186600
cgattactac gtaaaaaaga tactagccta ctgcctatta agggacgagt cattcgcgga 186660
actacatagt aaattctgtt taaacgagga ctataaaagt gtatttatga aaaatatatc 186720
attcgataag atagattcca tcatcgtgac ataagtcgcc ttaaagagat tcgaatctcc 186780
gacaccgacc tgtatacggt atcacagcta tcttaaagcc atacattcag acagtcacat 186840
ttcatttccc atgtacgacg atctcaaacc cgtacccaga aataccttta actatatcga 186900
tgtggaaatt aatctgtatc ccgtcaacga cacatcgtgt actcggacga ccactaccgg 186960
tctcagcgaa tccatctcaa cgtcggaact aactattact atgaatcata aagactgtaa 187020
tcccgtcttt cgtgatggat acttctccgt tcttaataag gtagcaactt caggattctt 187080
tacaggagaa aggtgtgcac tctgaatttc gagattaaat gcaataacaa agattcttcc 187140
tccaaacagt taacgaaagc aaagaatgat actatcatgc cgcattcgga gacagtaact 187200
ctagcgtcga catctatata ctatatagta ataccaatac tcaagactac gaaactgata 187260
caatctctta tcatgtgggt aatgtagcca tatgcccggt agttgcgata tacataaact 187320
gatcactaat tccaaaccca cccgcttttt atagtaagtt tttcacccat aaatacaata 187380
attaatttct cgtaaaagta gaaaatatat tctaatttat tgcacggtaa ggaagtagaa 187440
tcataaagaa cagtactcaa tcaatagcaa tcatgaaaca atatatcgta ctggcatgca 187500
tgtgcctgcc agtcttcagc aatcatcctc atcgtgtacg gaagaagaaa acaaacatca 187560
tatgggaatc gatgttatta tcaaagtcac aaagcaagac caaacaccga ccgatgataa 187620
gatttgccaa tccgtaacgg aaattacaga gtccgagtca gatccagatc ccgaggtgga 187680
atcagtcgag gatgtagatc ctcctaccac ttattactcc atcatcggtg gaggtctgag 187740
aatgaacttt ggattcacca aatgtcctca gattaaatcc atctcagaat ccgctgatgg 187800
aaagactgtg aggtgtctat cgacatcaga tgtagcgaag aagagaaaga cagcgacatc 187860
aagacccatc cagtactcgg gtctaacatc tctcataaga aagtgagtta cgaagatatc 187920
atcggttcaa cgatcgtcga tacaaaatgt gtcaagaatc tagagtttag cgttcgtatc 187980
ggagacatgt gcaaggaatc atctgaactt gaggtcaagt atgtcgacgg atcggcatct 188040
gaaggtgcaa ccgatgatac ttcactcatc gattcaacaa aactcaaagc gtgtgtctga 188100
atcgataact ctattcatct gaaattggat gagtagggtt aatcgaacga ttcaggcaca 188160
ccacgaatta aaaaagtgta ccggacacta tattccggtt tgcaaaacaa aaagttacct 188220
ctcgcgactt cttcttttc tgtctcaata gtgtgatacg attatgacac tattcctatt 188280
cctatttcct ttcagggtat cacaaaaata ttaaacctct ttctgatggt ctcataaaaa 188340
aagttttaca aaaatatttt tttattctct ttctctcttt gatggtctca taaaaaaagt 188400
tttacaaaaa tatttttatt ctctttctct ctttgatggt ctcataaaaa aagttttaca 188460
aaaatatttt tattctcttt ctctctttga tggtctcata aaaaaagttt tacaaaaata 188520
tttttattct ctttctctct ttgatggtct cataaaaaaa gttttacaaa aatattttta 188580
ttctctttct ctctttgatg gtctcataaa aaaagtttta caaaaatatt tttattctct 188640
ttctctcttt gatggtctca taaaaaatat taaacctctt tctgatggtg tcactaaaat 188700

```
atttttattc tcattctcat tttctctttc tctcttcaat ggagtcataa aatattttta 188760
ttctctttct ctcttcgatg gtctcacaaa aatattaaac ctctttctga tggtgtcact 188820
aaaatatttt tattctcatt ctcattttct ctttctctct tcaatggagt cataaaatat 188880
ttttattctc tttctctctt cgatggtctc acaaaaatat taaacctctt tctgatggag 188940
tcgtaaaaaa gttttatctc tttctctctt cgatggtctc actaaaatat tttttattct 189000
ctttctgatg catcaactat ttcttaaaca ataacgtcca acaacatata ctcgtcgagc 189060
ttatcaacat cccctatgcc catctaggtt accagacaat tgtatatcat aaaataatgt 189120
ttataattta cacgttaaaa tcatataata aaacgtagat cgtataatat tttttggtat 189180
ataaatgatc tagtaaaatc catgtagggg atactgctca cattttttct ttggtacaaa 189240
atttcacaca agtttttata cagacaaatt cttgtccata tattttaaaa cattgacttt 189300
tgtactaaga aaaatatcta gactaactat ctctttctct ttctctcttc gatggtctca 189360
caaaaatatt aaacctcttt ctgatggagt cgtaaaaaag ttttatctct ttctc      189415
```

<210> SEQ ID NO 2
<211> LENGTH: 138203
<212> TYPE: DNA
<213> ORGANISM: Artificial Sequence
<220> FEATURE:
<223> OTHER INFORMATION: Synthetic Polynucleotide

<400> SEQUENCE: 2

```
ccggcgaagc cgcggatccg ctgttccggc gaaggcagga cagacatttt ttccagccca     60
taaattaaaa agaatcaaca gaaaattatc atgatgataa aaacttttag gattgtattt    120
agttgaacgt ttcgtcaata aatcaacctc aaattttttc acatgtaatt tcttgttctt    180
tttaatttat gggctggaaa aaatgtctgt cctgccttcg ccggaacagc ggatccgcgg    240
cttcgccggg gcggcggccg gctcccgcgg cggctgagcc gcgctgccgc gagaacgcgg    300
accaggagtt cctgcgggag gagctacggc agaggctgga actgctgaat gctttcgagg    360
acgggcgtcc gcgggaacgc gactccgcgg aggcggcacc ccgcagccgc gagacctcgc    420
tctggagtca gggagtcagg gagtcgggag tcagggagtc gggagtcagg gagtcgggag    480
tcagggagtc gggagtcagg gagtcgggag tcagggagtc gggagtcagg gagtcgggag    540
tcagggagtc gggagtcagg gagtcgggag tcagggagtc gggagtcagg gagtcgggag    600
tcagggagtc gggagtcagg gagtcgggag tcagggagtc gggagtcagg gagtcgggag    660
tcagggagtc gggagtcagg gagtcgggag tcagggaaac agaagtcaag tagtcgggta    720
gacaggagtc aggtggtcgg gtgaccgcgc cgtccgagtc ccgcaaaaag tttttagact    780
ctgagagagg ccgacctgcc tccaacggtt ccgcggaaaa gtttttataa aaagttttcg    840
ggagaggccg actgccttcc aacggttcct cctctcgcgt gccgcgggcg gccgctctcc    900
cgcgacggtc ccgccaacgc gtttacaaag ttttaaaagt tttcgagaga ggccgacctg    960
tcttccaacg gttgcgcgaa aaggttctgc ggaggtttgg aagagccgcc cgccctccga   1020
catcctccga aaagttttcg caaaaagttt ttaaaggttt cgcgaggagt tttcgaggga   1080
ggcgacctgc ctccgaggtt ccgcgtaaac gtttttacaa agcgtcggag gtgggggcga   1140
cctgcccttc ctctcctccg aaaagctctt gagagtgtgg gagaggcggc cggccttcgc   1200
ggtcgcgcga aaaggttctg cgggagttcg cgggagctga cccgccctcc gcgcccctcc   1260
gaaaagtttt tgcacgaagt cttttggcgt tctcgagagg acgcctaccc cgacggtaac   1320
gcggaacgtc tcgggaggtc ggcctctccg ctcccgcggt cgcgggcggc ggcccgtctc   1380
```

```
cggaggttcc gcgaaaagtt ttataaaaag ttttgaggga ggtaccgacc tcctaaagtt   1440
ttacagagag ttctcgcaaa agttttggga ggtcgacctg acctcctaaa gttatcgaag   1500
agttctcgcg aagagttctc gcaaagagtt tgagaggccg acctgcctcc aacggttccg   1560
cggaaaagtt ttataagagt tttgagagag gtcgacctac cttccaacgg ttccgcggaa   1620
aagttttata agagttttga gagaggtcga cctactctcc gaggttccgc ggaaagtttt   1680
ataaaaagtt tttacaaagt ttttgaggga ggtcgacacc ctccggatcc tccgcctcgc   1740
gtgccgcggg cggcctccaa gagttttacg gaacgttctg gagaggagag gccgacctcc   1800
caaagatttt gcggaacgtt ttggagagga ggactggcct cgaaaagatt ttacaaagag   1860
tttggaggga ggactggcct ccaacggttc cgcgaaaaag ttttgcaaga gtttggagag   1920
aggtcgacca ccctccgagg ttccgcgaaa gtgtttgcgg agagtccgag agaggcagac   1980
actgcctgcg aaaagttttc gcggacggtt gagcgggtca ccgacctccg acagtttaca   2040
aacgttttac ggagagttag agaggcagca gaccgacctc cgaacagttt agttttacaa   2100
agttttggag ggtgaactgt catcgggaaa gttttacgaa gagttttggg agaggccgac   2160
ggttagccga gcgagcgcgc gagcgagttt acgttctctc gctcgtgtgc gcgttaactc   2220
gcactggttc cctctctaac tcggagtggg cgagcgagtg gttgactcgt cctccgctct   2280
cactctgagt ggtgataact gttaaccatt aactcgtcct ccactctctc actctctcac   2340
tctgagtgag gattgacttg ttaactcgtc ctccactctc tcgctctctc gctctgagtg   2400
agtgaggatt aactgttcaa ctcgtcaact cgtcctctgc ctctcatcca agactgagtg   2460
ggtagttgac tgctcttgtt ctcttactcc gaggggtgat tgagttagca acagctactc   2520
gttctcttgt tctctcacac cgagtgagcg agtgagcaac gttacttgtt ctctcacacc   2580
gagtgagcga gtgagcaacg gttaactcgt tctctcgttc tctcgttcta ttattccgag   2640
gagtggcgag tgaggtaacg gttactgtta cttgttctct gttcccttcc tcggtgagcg   2700
gtgcgtcaac ttgttctcgt gagtgagtac ggtcacttgt tctctcgttc tctacctcga   2760
ggagtgagtc aacttgttct cgtgagtgag ttgaccgtaa ccgttccctt acctcaagtg   2820
agtggcggtc gcttgttctc gtgagtgggt taaccgcgtt cccttaccgg agtgagcggg   2880
cgggcgataa aaataatcaa ttgactgatt cgctcgtgag cgagcgaagg gcggcggaca   2940
agggcgcggg atgctggtct aatctactaa ggccgattac aaaaacggat gggagaccgg   3000
gagggagagg gtcacagctc cgagcggtgc atccgcgcca gctggcggcg ccactcggcc   3060
gcgggccgcg cggccgccca ggccgcgttg tagccgcccg ccaccgcgac gcaggtcagc   3120
tcgaactccg gcccgagcgc gcgcacgtcg tagatgtgca cggtcgcgac gttcagcagc   3180
agcgcgccct tgcgcagcga ggcgaaggtc gcgtgcatgc cggcggcgag cgggtacacc   3240
ggcgagagcg tcccgccgcc gtgcgcgacc accgccatgt gccgcccgtc gccgccgacg   3300
gtcaggcagg tcaccgaggc ggagccgttc gcgcggacgg ggcccgcctc cacgagggcg   3360
gccggcagcg gcggcgccgc ggggcggaag agcccgccga ggaggaagcc cagcgccacc   3420
agcgcgagcg cgccgagcag cctgcgcggc gaggggtgca tgcttgttgg ctgcggtgtt   3480
ggcgtctggc gggtggaagg cgggtgtggg gtgtccgcgg ctgcggcggg agggtctcga   3540
ctgctaggcg gtccttttc actttgctcc gtggcgcctg gtccggggca agggctgcgg   3600
cgggcgcccg ggcgggcggg ccgctacccc gccgcgcggc ccgcggccgc cagcgccgcg   3660
gccagccgcc gccaccgcgg gcccgccgcg cgcagcagcc ccgccgccga gcgccccgcg   3720
```

```
ccgccgcggg cgcgcgccga ggccgcggcc ccgcgccgcg ccagcagcag cggcagccgc   3780
gcgtccagcg ggccgccgcg gcgcagcgcc gcgcgcagca gcgccgccag cggcagccgc   3840
cccgccgcgt ccgggcccgc cgcgcgcgcg cccgccgcca gcagcgcgcg caccagcgcc   3900
ggcgaggggc gccgcgcgcg gaccaggtgc tccacgagca gggtggtgag caaggattct   3960
cgagaagtag gagtcatgtg tgacgacaag gagagacgtt atattaggcg cgtcctactt   4020
cactttgaag atggtgtaaa gtgttaaaac ttgaacaccg ttcactccac cactgccgtt   4080
accgtgtcct gccccaaaag caaccacagt gctttttcca ccacctgttc caaatccgtt   4140
ccaaaagctc ccatccattg ttgttagaac tttcagatgt ttctctaggt tgtttagttc   4200
cactgcaagt ttcgaccatt atcgttactg gacatgctgt tggtaatgag tttaataacc   4260
aatcataaaa atagttataa tttgttataa agctaataaa gtagcaaaca ctttaatgtt   4320
atattttgcc taaccctccg ttaacaccac cattaacacc accacttaag cttttactac   4380
caccactacc acctccaaca cacattcttt tctctaaagg tccccaaatt ccacctcctg   4440
aacttggacg ttttacagca cctccgggtg tacttgcgta ccctttagaa gttccactgt   4500
gactgtagat atgatactgt ccttctccag gcatgattaa agtgtgttgt aattagtgtt   4560
atctacgcaa ctgtgcgaga ctctcgaata aaaagaagct acattttaca attttgatta   4620
gctgatgtac cacgctgtat cgcggccacc acaagcaccc gatccagtag aaccaaatcc   4680
agagtcgccg cggtcagtgt tgtccaagca gttaacctct tgaactgctg ggcacgatat   4740
gcgttcgcat attagctgag ctatcctgtc tcccttctta acctcaaagt cactgtttcc   4800
aaagttaaac agcaccactc cgacgttgcc tcggtagtct tcgtcgatca cgccagcgcc   4860
cacgtcgata aagtgtttga ctgcaaggcc agaacgtggt gctatgcgtc cgtagcaacc   4920
agaagggggc tttatcagaa ggtcagtaaa tactacgcga ctgcaatgcg aagggatgac   4980
acagtcgtat gcactacata ggtctaatcc tgcggcacca ggagatcctc tggctggtat   5040
agtggcgttt tggctgaggc gaacaacctg aagagtttcc gtgtggcaga actccatggc   5100
tagggtggcg agcggccgat cgactacggg gtgtacaatt tacactttct ccagaaaaat   5160
caggggcggg tcagcatggc gcggcgcaag tccagcagcg agtcgtacga caggaagcac   5220
aggatggagg tcacgatctc cggcggcagg gcgcacgggc acatgaggcc ggcgatctgc   5280
tcggccagcg agacgcgcag ccgcatcatg cagatcttgc cgaagagcgc cgtcccgtag   5340
atggggaact cggccgcgcg ctccaaaaag gcgttctgca cgaagagcgc cttcgcgtcg   5400
tccgacgcgc gcagcacgtc caacagcgtc gcgtccgtgt ggcagcgcac cgcgcgcatg   5460
cttgcgatct cctgctcgca cgcgcggatc acggtcgcgt agtccgccag cgcgcgctcc   5520
gccagcatgc gcgcgccctc gccgcgcagc gccagctcct gcacgcacag cagcgcggcc   5580
tccgagcgtc ggaacacgtg gccccattgc tcggatgtga tcagcgcgcg cgcgagcagc   5640
tccgtcggcg gccggcgcgc gagcacggcc gccgtcgcgc gcacgttgtt gcggcgcagc   5700
atctccgaaa ccgcgcatag gcccgaggcc gacatgtgct cgagctccgc gcccatgcgc   5760
accagccggc agcaggcgcc gtggctgaac accgccgcgc ggtgcagcgc ggtctgcagg   5820
ttgttgttgc gcaggttcag gtccagcccg cgctcgagca cgaagtccac gacgccgcgc   5880
tcgcagctcc cgtaggtcgc catgtagtgc agcatggtgt tcccacacgc gtctacggcg   5940
gccgggtcca cgcctaggcc cgtgagcgtg cgcaccatgc cctcggagat cttggccgtg   6000
cgcgcgaggt ggtgcagcgt tgtgcgcccg tacgcgtcca cgacgcacgc gtccgcgccc   6060
gcgcgcagca tcatgtccac gagcgcggcg gagacgccgc cggagcacag cagcgccgcc   6120
```

```
agcggcgtca agccgttgca gtcgcaggcg tttgggttcg cgccgcgctc gagcagcagc   6180
cgcagcacgt cctcgcggat ccactggttc ttggcgtaca cgtgcagcgg cgttacgccg   6240
taggtgttgc cctcgttcac gcgcgcgccc gcgtccagca gcagccgcgc gacctcgagc   6300
tcggcgccgt cggggccgca gaaagccagg aaggaggaga gcacgctgtc gcagacaacg   6360
acgctggcgt cgcagaccac gtccgcgccc gcctccagca tgagcgcgac cacctccggc   6420
cgcacgccgt cgtactgcac gtaggcgtgc agcggcgtgc ggccgcagga gtccttggct   6480
ttcacgtccg caccggcctc cagcagcacg cgcacgatct ccgcgcactg ctcgtgccgc   6540
gcgaagtgca cgcagaggtg cagcggcgtg cgcccgtgct cgccgcggaa gttcacgtct   6600
gcgtcggtgg ctacgagcgc gcggaccgtt tcgaggtcca cctgcccgga ctccaggtag   6660
cggaagagca ggtccgcgtg cgggaccacg acggactccc gcgagagcat ggcggcgttt   6720
acaaatattg aaatcttttt tcactcatct ttatgggcgc tgaacgcgca ataagggtga   6780
gagtaaaaaa cttctacaaa aagcgtacaa aaggtacaaa aggtaaaaaa ggcggggcgg   6840
ggacgggctg gggtgctgcg agctgaattg gcctctacac agggacgccc tcgccggagc   6900
cggtgagccg gtagccggcg ccggcgatca tggtcaagcg ctgcacgagc tcgttgcgct   6960
tgacgccggc ctctgaaacg cacaccatgt ggtggatgta ccgctcgatg cactcgcagc   7020
gcgggagagt ggagtcaaga tcggatgcga gttgcagaat gtcatcccag agctcggaga   7080
acttgctgta cagttctcgg aggtctctct ccattcgagc cgtaagagag tcaggatgcg   7140
gtgttccttc gggagtctga gcgaacaccg cgaacaggct ggttatgccg tgttctagaa   7200
tagagtggtt ccgcgttaat gccgcagaca agggtcgtcg tccgcgcaac gactggcggc   7260
agagcgctgt ttgtgccgca ccgcccattc ctctggcgat cgcatccacc gacgcagtga   7320
tcatctgcgc gccgacgtca ttgtagcgcg cgttaaactc agtaatcatg attacgagat   7380
tgcagatttc atagtagcac ttttccaagt cgacgcgcag tttcacgatc tggttgacaa   7440
tcttgcacgc ctttcgccgc gtctccgcca cgttggcgac tcggacttgc gcttcctggt   7500
cgatggacgg cggaaacact tcaaacccaa ggtcgcacag ttcagcggtg ggactagcgg   7560
tcacgatgat gtactccgca tcgccaccca cttgcggcag gaagaacacc gaccgcgcgg   7620
cgggaacgac cagaacgtcg ccttcctgca tgttggtttt tagaaactta gtgttgttca   7680
cggagatgcc ggccatgccc tcgtttttga cacatattat ggtgacgtac gcggcgaccg   7740
tgggggccat gtggtggcgc atgtaccact cgtcgtgctt gagtttcaga ccgtgagatt   7800
cgccaacctc gaagtgcatg ttggcgtctc tgacgtagcg cgagaactcg ctgcgacaga   7860
ttcgcgcggg cgcccggtgg aacgtcgact cgaagagact gatggctgtc cattcgccca   7920
catgagtgac caccgaagaa gtgttttcga tccgagtctc gaacaccgag tccacgagca   7980
ccggacagtt ggttccgggc accgtcagca ccaagggccg cgcctccacg gggcgacgg    8040
acgaagccac ggagtcggtg tccccgtacc cgtagtcgtc gtcggagtcg ccgcctccgt   8100
cggccccgtc gcgcggcctc cgcagcggca tgcagccggc ggtgggaacg cactggtttc   8160
ggccacggcc gaagcggcca aacagtctcg ccagggctga catccttgga cggccacacc   8220
aaaaccaaaa aaacatattt tatcagttat ttgtcgattt tcaccggctc accgagggca   8280
ggacctcctg gatcccggac acccccgcca ggcagcgggc cgcgcgctcg cgcacccaaa   8340
agcggtcgta gccgtgccgg agcacgaagg ccgccgtggc gtggcagtcc acgcgctcga   8400
tgaagccgtg gacggcgcgg cgcgcgtagc tcgccgcgaa ggcgcggacc accgccgagc   8460
```

```
agcgccccga gggcgagtcg tccgtctcca gcgccagcgg catgctcgcg atgcgcgaca   8520
tcaggttgga ggtctgcggg atgttgagct cgcgcgtggc ggtcatctgc gcctcgagcc   8580
cggccttgag cacctcgtcg cagcggcccc actccagcgc gcagaccacg cggatctcgt   8640
accccttgag ccgcagcgcg gtctcgatgt ccacggaggt gagcaccgcg ctgaagcgca   8700
ggcgctcttc gtccgcgggg tcgaagagca cggggatctt aacctccgcg ctgcgcgtga   8760
cctcgcagag cgcgatcgcg agcagcccgc gcgtgagctt gctcaccatg cgcggcttgc   8820
ccacggggta cagctggctc gcgacctcgc gcagcgggta cgccagtcgg aagcagcgcg   8880
cgtccgcggg caccgggctc gcgcccgtct cctcgaggaa gagcgcggcc tcaaccatgt   8940
tcagcgcgga gaagtgcacc gggcaggcgg cgcagccgcg cgcggcgttc gcgagcacca   9000
tctcgcgcag cccgcggaag gccgccatgt cgcaggaggg gaagatgcgc gcgagcgcgg   9060
cctggtgcgc gagcgccgcg tccgagagcg cctgcgcggc cgcggcggcg gcctcctcgg   9120
cggcggccgc gctctcgtcc gcggagacca cgtcttcggg cacgtccacg cagacgccgc   9180
cccagaactc gcagtactcg gagaagagcg tcgcgggcgc aaagcgcgcg aggtccacga   9240
aggcgacgcg gttgccgagc ctggagagca gcgtgttctc cgagatgcgc gtccagccct   9300
tgccggcgag ctccatgacc tgccgcgtgt cgaagaggga gctgtagaag ccgtacacgg   9360
tgatgttttc cttgcacgtc gtcagccaca tgaggaagtc gcgcaccacc agcttcgcgc   9420
agtctccgga gaacacgggg ccggcgttcg tcgcgatgga gttcaggcgc acggtgccgt   9480
cactgccgaa gcggtacacg aaccaggcgg ccacgctgtt gccagagggc gtgtgaacgt   9540
gtggctgcgc ccaggagtcg gcgctcgcgg cggtgcgcac gtcgtgcgag agcacctcgg   9600
tgtcggggcg cgagtaggtg ctggggtctt tgatccagat ggcgtagctg cccacgcagc   9660
acacgttcat gaggtcgagc agcgtctgcc ggcgcagcgg cgtgccgagc cggcgcacgg   9720
cgtcgtgcga gaccatgcgc aggtcgtaga ggcccacgtc cgagagccac tggttgagct   9780
cgtccatgga cagggcgtcg cggggggcg ggctgtcttc gaaggcggcg cggagctcgg   9840
gctccgtctc cgcgcgctgc cgcaggatgt ccaggaaggg gctggaggag tcggggatgt   9900
agcagtcggg gtcgtgcctg gacactatag cgaaccgctg cgtcgcgggc ggcggggcta   9960
gcgcgtcggc gcgtgcgtcg atgaaggtgc acgatatacg cacggacttg agcgagggga  10020
ggacgactgc ggcggcgcgc gcgccctccg cgtcgaagat catcgtcttt ccgtccctcg  10080
cctttgcgag cgcgtattct ccaggcacga ggtccgtcgg cggcggctcg tcccaggcct  10140
gccggtcagg gacgccgccg cacacctttc cccagaaccc cagcatcctc caaaatacct  10200
ataaggacgg ccaatagcgg ggcttgcggg cgttcggacc ttccgcgctt taattttaat  10260
ttattggctt gcagaactcc gagcgccagt cccgctcgaa gaccgcggac aggtccttga  10320
cgatgtcgcc cttctcggcg ttcacgctca cgaaggcgtg gtagcggtag tgcgtgccgt  10380
cgaggttggc gaccgtgagg tgcgcgaagg tgtcgtccac gatgagcagc ttagtgttgt  10440
tcgcggcgtc gtcccggccg ggtaccacga acttgcgcac ggacatgtcc acgctgccga  10500
cgccaaagtc gtcgaggctg cgcgcggccg agaccgaaag cgggtccgcg ttcttccact  10560
cggtaatgat cacgcgcacg cgcacgccgc ggttgatggc cgcgcgcagc agcgcgtcaa  10620
tgatctgcgg ccagtactcc acggcgctgg cgtgcttgat caccggcacc atcgagagca  10680
gcgagaggtc gatgctgttc ttggcgttct cgatgcggtg cagcacgagg tcctcgtcga  10740
gcgtgcggta gaagcctagg aagcgctccg gcgagtccga gaagaatacg ccgcccccgg  10800
agtggtcgag gtggaagttc gtggccgtgg gcgtgacgat ggcgcagcag agccgcgtga  10860
```

```
acggcacctt cggctccacg atcatggagt agaaggtgtt gtagcggttc atgaggtccc  10920
aggccaggtg cttgttggtg gagtagagcc cgaggttctt gatggtggac acggacccgc  10980
ccgtgagcga ggcgcttccc acgtaccagt gcccggcgtc cgagagccag aagctgccga  11040
gaaggttgcc gacgccctcc ttggtggaca ccttgacctt gtagtagttg acgcccgcct  11100
cgcgcagctc gtccgcgtcc ttgtccttgc tctgcacgtc cacgagcagc gtgacgtcta  11160
cgccctcctt ggcgagcgtg cagagcttgt ccttgacgtc gacgccctcc ttggtggagc  11220
tcaggttgca gcagaagctg cagatgtaca agaacttctt cgcggactcg gcgatagcgg  11280
tgaagcagtc gagggtgctc atgttgccct gcgccaaaga cgccacctct gcgggcagcg  11340
tctccacgac gcggcagtcg gcgcccaggg ggatggagga gaacggccac atttatttat  11400
ctcacaaaaa taatagggct tcagggaaag tcttttagca ggcgggcgag ttcttcgagt  11460
tcgcttagga gttcttccat ttcttcggaa gtcagcaact ggagctcgga cttgatttga  11520
atatcttcga ggaaaccgtc tagcatgttc gccatgtctt ccggggagca ctgcgccaca  11580
tcttcgggga caggatcggg tgtgggcatt aggtctccgc ttacttgaac gtcgtccatc  11640
atcctgtcga tgaggtcttc gacttctaga cggggtccgt agatcagcat atttggtgat  11700
ggaggtagtt taaggtgcga gagttagtgt tatacgaccg ccaacgtgtg tttatcgcgc  11760
gtacattttc aataattaac aaactcccct tcctgcgcct gctcgagaag cagctcgtcc  11820
agctcctcct gtcggcgcgc ggccacgcgt ctttccgcga agagtaccat cagctccagc  11880
cccacgccgc acagacccag gacgccgaac accaccgccg ccgagatcga cagacccagc  11940
agcaccgaca tcctcacgcg ggcatccggc tatttaatcg ttctggaaac gtattaatat  12000
gggcgtcgtc atgtgcgggt gtctgtttgt gtgggcgggc tggatcgcgc gccgcgtgcg  12060
cggcctctgc gcggcgctgc gccagagggt gtcgcgcgac aagggctacg tggccgtcat  12120
ccagacctgc gacgacgact acttcacaga ggaggagttc gacgacggca agcaggtggt  12180
cgcgctcctg cgcgacgtct cgcgcgtggt tgccgcgccc gcgggcgtga cggaataagt  12240
taggataagg agtcgagggg agaaaaacag cggtcacact ataaactcgc gcgaggccga  12300
ttttgacgtg ctcatgtctg gaagctccgc tttctgcagc gcggagcggc acacgaagca  12360
cacttccgtg ttggtgggag ttatgcagtg gacgtggtag ccgtgcccgc acaccatgac  12420
ttggaacgga cacgcgccgg gacaggccgc gtttatgcat ccttccggcg agcgcttgtt  12480
gcagatgtag cacacgtctg agcacgccag cgtgcaggac acggccagct tccactgctt  12540
aaccttaacg ggcatggcta gttgaacacg accatgggcg agtcgcgagc ctcgagtcgg  12600
gggttcaggg caaaccgttt cacgccgtca acggttcttc tctttgcaat tttctctctg  12660
cacaggctcg tcagcgtcat ctcggccagg cgcgcgtcgt tgcctaggtg ccgcgcggcg  12720
tcctcgaccg tcacgcccgt cttgccggcc tcgtccatga gcacaatgca taccaggtgc  12780
gcgctagagc atatgacctc ctgctcgcgc ccgccggcag cggggatggt tagctccgcg  12840
cgcccgaagg ccgccagcgg cgccacgtcg taggcagtgt ctgctcgggc gagcgccgac  12900
tccacggcac cgcggagcga ctccggcggc gtcagcgcgg ccagcggcac cggcgtgggc  12960
acggtgtaca cgttcacggg catgagcacc atctccgggt cgtggtggcc gctctcttcg  13020
ccgtcgtgct ccatgggctg cggcggcggc agcagcggga gcagcagccg tccggacatg  13080
agccggcgca caaggtcgtt gagcgcggac gaggccatcg gcgggtacag ctccatggcc  13140
agcttcagcg ataggtgctt ctcgaggttg acgccggtgt agacgctctt cacgatgcgc  13200
```

-continued

```
gcgaaggcca cgcgcgcgaa ggccgccagc tcctcgcgcg gcaggcgctc gatgtaggag  13260
agcagcatgt cggtgtcgca cggcggcgcc gcgaccaccg cgccgtagag cgccttgccc  13320
gagagctttt ccagcgccct tgcgtgcagg ccgtgggtct tgagcacgtc cacgtagttc  13380
acgtacaggc agagcgcgcg atcgaggttg ctctccgcga cgtgcgtctc gatgcactcc  13440
acgatgagcg ggcccatgcg gtccttgatg aggtctatga gcccgccgta ggcgactcgc  13500
gcgctcatga ggcacgtgcg gcagtacgcc atcaggccct cgaggtccgc ggctatcacg  13560
tcctcgacca cgttcgccac gacgcgctgc cagagccgca ccttgctcac gttctggtgc  13620
cgcaccatgt ccacgagctc gtcgtacgag ccgccgggct cgtgcgcgcg atcgacgatg  13680
cacctcgcca tggtgcggct ctggcgcatg agctcgttcg tgaagcgcac gcacgcgtcc  13740
tcggagaaga gcgcgctcag gcaggagtag cagcggtccg cgacgaggtg cgggaagcgg  13800
cactccacga cgccgcggcc gatccgcagc acgcactcgc cgtacatctc gtccatggcc  13860
tcgcgcagac agtcgtccag cacgtccgcg ttgtgcgccc actggatcac gcagaggtag  13920
ggctcgatgt tctcgcgcgc gttttccacc tcctgcacca tgtactcgag cacggtcatg  13980
tcctcgtgga tgtcggtgcc cagcatgcgc ccgggcggca gccagctctt gcgcgcgatc  14040
gcctctcgca ggcacgccac cgccgtgaag gtgttgacgc ggagcttggt cagcagccgc  14100
cgcagtcggg agatgtgtgc cacggagagg tccatctcca tggcctgggc gatgaggcgc  14160
gtgagttcct cctccatggc ggcggctccg cgggcagata tacgcgaaca acggtaagcc  14220
gtgctatttc atttttggac aaaaagctag tcgtcgacgc gcatgttgtc gaggttccgg  14280
cacagcgaga gcacgtcgtc gcgcgcgcgc ctccggcgca gttgattgtt cgcgcgccgc  14340
gcgtccgcga gcgcctgtct gtacatcgcg gagtccgcgt acccgtgcag cggcgagcgc  14400
cgagcgccgg gcctcgggct cgcgcggcgc gggagcggcg ttggcgcgcg cctcgagcgc  14460
cgcgcgaagt gcgcctgcat ggccagcagg caaccgaacg gcaccatgta tcggtccatg  14520
aggcactggc tggccgcgga cggctcgcgc gggtgcatca cgccgccgcc cacgtcctcc  14580
atgacgtcgc gcagcacgca gcgcagcatg gtctccatgc cgtccacggg cttgaaccgc  14640
accggggagg cgtcgacgta gaagccgtcg gccacgaagt agagcgcgtc cagcccgccg  14700
agtttctcgc cgagaccgac gaagagctcg tccacgtgcc agtccaccac cgaggccttg  14760
aagagcacca cgtgccggat gtcgtgcgag cgcgcgagct cccaggtgtc ctcgccgatg  14820
ttgctggcgt cgatgcggcc tgtcatgcgc acgctcacgc acggcgtcat cccgttcttg  14880
tagcagaact ggcgcgcgag ctcctcctgg cgtacgatgt cgaccatgct ctccatgaag  14940
gaggtggaga gcagcatcgc gccgcgcgcg gcgcgggtcg cgttttcgtc cacctccact  15000
tccatcccgc cgccgatcct aatcatctat cgtatttaaa ttttcggcgg agcagacacg  15060
cggctgctcg ctgcgcgatc gcttcagccg cggcggcgtc acgcacgcgt tgcggcggcc  15120
ggcacgcacg gacgaccgcc ggggctcttc gctgagcgag cgccgcggcc gcgtgacgcg  15180
acagtcgcag gtgggttgcc gggagtcgct cgcgcgcctt cttcgcattt cgccggaacg  15240
ccgcgtttat gtaggggatt atattttcaa cgtaactaaa tggacggggg cgtgcacaaa  15300
cggcctttca tcgtgaacgt ggatggcatg ggcaaggtgc tcgtgctccg gtacttgcgg  15360
atgtgcgagg tgcccgaggc caagtgcgag ggctcgcgcg cgtcctgcgt gctcaagatg  15420
gaccctcccc gctcacccag ctgcgagcgc aggccgtctc tcccgccgtc ccccccatgc  15480
cccatgcgca cgcctcccgg gtcgccgctc caggctccct tgatgcgcac gcagatgctc  15540
caggggctgt tcgacgctgc caaaaacaac ggcgagcaga tgtgccgccg ccagtaacct  15600
```

```
aggctgcgca gtacgaaagt tagtgcgtga tcacgttttt tgcaatgtcg atcacgccgt  15660
gcgtgcccgt cttgcgctcg cgctccacca cgctagtcac gggccgcgcg tccgagacta  15720
gcgaccccag catcgagcgc acggcgccct ccgcggcggg gtggcgcgtc agcagcagga  15780
acatcacgat gtgcgcggag acgccgcgcc ggctcagatc gtgcacggcg tcgccgtcca  15840
tgagcacggt gttcgagaag tacgtgaaca gagtgttgtc tcgcaccagg aaggccgagt  15900
tcgagacgct ctcgaagtcc acgatctcgt cgtcctgcac gcccatgtcc aacagcgtct  15960
gcacgagcgc gggctcgtcc aggaacacca ctgcgcgcgc gaacccgcag tccagcgcgc  16020
gcgcgtccgc ctccaacacg cgcgaggcgc cgccctccgg cggcaggaag gcgcagggca  16080
gcggcgtgcg tccgtccgcc ggcgcctccc cgagctcctc gagcgcgaag gccagcagcg  16140
tctccatgcg cgcgcgcgcc ttgtcgaagt tgtccgcgag gtcgcggatg cggtctgtct  16200
gcgagaacat cttcagcatc gccatgagct gcacgaaggg gtgcagcacg tatatgttgt  16260
ccacgagcag cgtgggcagc gcgcgcagcg tggcctgccg cacgttgaag ctgtccagga  16320
tgtgcccgcc ctcctcgtcc tgcagcacca cgtagttctt caggtagggc acgcgcagca  16380
gcacggtctg ccgccccgtg acgaagtata tcaggaaggc gaggttgatc aggaacgggc  16440
gcgcgttcgt ctgcaccatg tcgatgtcgc cgtactctat ctcggggttc agcaggtgca  16500
gggcgtacga gccgtagcac acgcaccgct tgttgtgtcg gcgcaggtgc tccttcacga  16560
gccgcttgac cacctccacc aggtccgagt gcttgtgccg cgccatcggc gcggcctcct  16620
cgggcggcgg cagcactgcg tacgagttga gcgcgcggct ggcgagcgcg cgcgcgcggg  16680
gcgcgtccac gcgccgcacc gccgcgttga ttgcaggcgt cggcgtcgtg agagagccca  16740
gcgtgcgcgt gaactcgctc acgatcacgc tctgcagctc cagcaccgtc aggatctggc  16800
ccagcttctc caggcgccgc tgcctcgaga agtactcctc gatgcgcgcg gcgatctcct  16860
tctcggagcc gcctagcttc ttgaagaagc gacgacgact ctttacaaca agagagagaa  16920
aaagcttcct atcgaagttg aggacgcggg tcatgttgcg gcgctgcgcg cgcaggagca  16980
cgcagcgctc catggagggg cgcgagccga ggtactcttc gatcacgggt ggagccatga  17040
cagctatttt ctgaacccgc gattattgta cagcgcaagc cgcgcgcaga cctgctggca  17100
cagcagcgtc gtgtttcgca tgcacacgcg cgaggactcg atcgtgcgcg cgtccggtgc  17160
ccaggcgcgc agctccatca gttcctgctc gacgaagtcc acgggctcca cgaagcgctc  17220
tgcgcagagt ccgtccgtga acgcgttgac gatctgccgc acgagcacta ccacgtccac  17280
ctgctccacg aggcgcacgc ccatggcgac gtgcacgaag aggcagcgga agagcgcgtc  17340
catggccatc tggtggtccg agcagggccc gaccgcggtc ttgcagccca gcgcgaagcg  17400
cccgatgccg cggtactgca ccatctccga gggcgagaag gagagccgct ccatcttgag  17460
cacgggcggc gggcccgccg gcagtccgcg cgcgaggtcc agcaccggcg tccacccggg  17520
cgtgaacatg tccgggatca ggaagagccc gtagctggcc atgcgcgcga tgtcgaaggc  17580
gtggtccacg accttgttca cggcgctgtc cgcgcggttt acgcgcagcg cctgcaggat  17640
cacgtttccg gaagcgtgcc gcgtgatcgc gaggtccgcg gtcgcgtacc cgcgcaggcc  17700
cggcaccgcg tacgcggtca gacacacggc caggcgcgcg ctgtgctccg aggagaagat  17760
ctcctgctcg tagccctcct cgggctcctc gcactcgcga gggcgccgca cgtcctcgac  17820
cgagcgcagc cgcatctctc cctccgacac cagacagcca agcgactccc tcaccgccgg  17880
cgcgagcacc tccgtggcgc agagcgcgtc gtgcacgcgc ttgagtgtgt tcggcttcag  17940
```

```
cgcgtagccg aagagcagcc gcgtcatccg cgagcccgag aacgcgaagc ggcgcacgta  18000
ctcctccgcg agctcggggc ggtcgttgat ccacgaggta gagaagacgt ggtcggaggc  18060
gaaggggtct gcaccaaccg cgagcagtgt ggacagaggt acggtgtcga ggaagtccac  18120
gacgtcgggg aagttctggc gcacgcaggc ctcggcgacg cgtctggtgt gcacgcacat  18180
gtcggtgacg ggcacccggt ggccggactc cacgacggac acgcagacgt cctcggtgac  18240
ggcgtccacg ggcatggtcc gcagcagctt gccgagcacg tcgccgaacc cgccctcgag  18300
cgccttgcgc cacacgaacc ccgcgtcgaa cttcccgggg aagtccgcga tcaccgaaag  18360
ctccgcgtgc gagaggttgt ccacgttgag gtaggtggcg gcgtccacga agatgggccc  18420
gaaggcgccg gtgtcggaga cgcggtctct gaggtagtcc ctggcgtagt ggaggtactc  18480
ccgcacctgg ccggcgcgga tgcgctcgag cgcgaaggcc ttcatggtct cggagcagag  18540
cacggagtgc cgcagcccgt ccagtgtgcg ccgcacgtcg tagacgccgc gcatctgcgc  18600
gagcatctcg acggcgtccg ccggcgtcgc cgccgcgagc cccgggttca ctggaggtat  18660
cctgtgttct gcgagcatgc gcttgaggaa acagaggtcc agcggccgcg tggtgtacag  18720
cgcggaggcc atctcggggc gcgtctcgac gatgtcctcg atcatctcgt ccgtgaatgc  18780
cgcgttgatg ttgtgcacgc tgcgcgcgtt cacgtgcagg aggatgtcgc ccacgttgtc  18840
ggggaatcgc tcctcgatga gccggacgtc gtcctccgtg atgttcatgt agggaataca  18900
gcggcagagc agcgcgtagt ccgcgaactg cgcgatgtag ggcgtgtgga actcgatgtg  18960
tctggcgaag agcgcgccgc agcgccgccg cgagagctct tcgagcaggt cctcgggcgt  19020
gacgtgctgc gggcggaaga ggtgcaggtg cgtggggtgc tcggcggcca cgcgcgcgta  19080
cagccgccgc gggaggtgtc tggggtgcac gccggcgagc acgagatcca tggcctctga  19140
ggtagacagt gcggcgaacg cgcgctcggt gccgcccgcg gcgacagcgg cgccgacaaa  19200
tctcttgagc agctgcagca tcgcgtgttt gggctttcgc ggaaggcgct tattttaatg  19260
ttattggcgg tggccggtgc gagataaaaa ttagaactga tgccgcagtt gttgatgata  19320
tgatgattgc gctggccggc gcgagataaa aattagaagc tgatgccgca gttgttgatg  19380
aggatggtga gtgcgctgga gcaagcggtg tggcgcgcta gcttcttgct ggccccgtcg  19440
gccacggcaa cgacctttcc ggatatcgtg atggtgcagg tgaagcgcgg acagtgatcc  19500
tctccgccag cacgcgtctc gcagaactcc agaggtctgt gtgtcatcat gcagaactcg  19560
ttgaccgcgc tgaccgggtt aagacttttg aggcgtatca cggcagactg agtcatgatg  19620
tcgatgtcgc cgccgaaaag cgtatcgcac ccagcctcgg tctccatggg ctcggtgtcg  19680
gagttttcgt cctcctcggt gggcgcggag ggcgcgcact ctacgaacca gcggggcggg  19740
tttccgtcct cacagcaaac ctcgtccgag tccagcaggc ggtacagctg gcggtttgcc  19800
tcgtgtttgg atatgccgag ctccttcgcg atttgcttgg ccggcagctt gtcgtcggat  19860
tttctgagaa gctcgaggat cagagacgcg cactcgcagg ccattgtggc gatttacggg  19920
gcgtgcgttt ttttaggatt ttggcttgcc tttcttttcg cagaacttgg gaggattgaa  19980
actcttttgg caatttttgc aggcgtactt gatcaagggc ggctcgtccg ccgagcgcgt  20040
ctggatcatc atcggcatgg tgttcttgct ctggcacgag gggcagggca ggttgaactt  20100
ctcgtcgagc acgttgaagt acccgctgta gtcgtggtcc ggcacctcct cgatgtcgta  20160
gggcacgcgc gcggccacgc acttgaccgc gaagagcagg taccgcagcg cgtcgtgctc  20220
cgcgccgctg gtcgcgcgga tctgcgcgca caggtccgcg tagtcctcgt tcgcgtccac  20280
ctccaggctg cgcttgttct tgtacgagag ccggttcttg gcgtccttcg agtactcgat  20340
```

```
gccgatgttg tgcgcggggt caaagttggt ctcgtcggtg ttcgaggtct tggtgttcac  20400
gatgttcttc agcgcgaagc gctgcgcgca gtccagcgcc catcgcgcga tgcgcgcggc  20460
ctccgccgcg tcggtgtgct tcgccgcgag gtcgcgcagc cggtcttcgt ccatcgcccg  20520
attttaggtt gggtatatta tctcaattcc gctcttccgc gggccgcggg cgcgcgcccg  20580
cggcaaatta ggcgttacaa atggacttcg tgcggcggaa gtacatgata cacgccatcg  20640
accgcaacct cgacttcatg aaggccgagg tccagcagaa ggtctccatc ttctccctcg  20700
ggcacgtgct cgcgctccac tacctggtca ccgcctttcc gcaggcggtc atcaccaagg  20760
acgtgctcgc gagcacaaac ttcttcgtgt tcgtgcacat gtcgcagcgg cacgaggtct  20820
tcgacgccgt gctcaaggcg gccttcgacg cgcctcagct ctttgtgcgg gcgctctcgc  20880
ggcacttcga ggccttcgtt gccgccatcc gggcctaccg cgcgacctgc gcggagctgc  20940
tggccgacgc gcgcttcatg gaggtggctg cgcgcgcggc cgagctcgcg gaggtcattg  21000
gcgtgaacca cgacatcgcc gcgaacccgc tcttcgcgga cggcgagccc gtgcgcgacg  21060
cggagctcat tttcgcaaag accttccgca agaccgagtt ccgcgccgtc aagcgcctcg  21120
ccgtgctgcg gctgctggtc tggccttcc tcgtgaagaa ggaccttggc ggcgagtacg  21180
cggacaacga ccgccaggac ctgtttacgc tgctgcagaa ggccgcgggg cccgtgcgcc  21240
acagcgcgct cacagagagc atccgcgagt acctcttccc cggagacagg cccagccact  21300
gggtctggct gaacgcgcgc gtggccgacg acgcagaggt gtaccgcgac cggcccgcgc  21360
gcacgctcta cgagcgcgtg ctcagctacg cgtactcaga ggtcaagcag gggcgcgtga  21420
acgccaacac gctcaagctc gtgtaccggc tcgaggacga ccccgacatc aagggtctgc  21480
tgctgcagct catctacgac gtgcccgcgg acatcgtcgg cgtcgtggac tccgcgaacg  21540
aggagtggcg gagctacttc gtgagtctgt accgcgagaa cttcgtcgac ggacgcacct  21600
tcacctcgga cgcgcgcttc cgcgacgacc tcttccgcgt ggtcgccgcc gtcgatcccg  21660
acttcttcga gcccgagcgc atccgcgagg ccttcagcgc agacgcgcgg ctgcgagagc  21720
gcttcacgga catggacctc aacaacgcct tcatgtcgca cctcatctac gactccgtgg  21780
accccgacgt cgccgccgcc gagcgcgggc tcgcactgcg cgtgcacaac gaggactccg  21840
actacttcat ccgggagtac aacacctacc tcttcctcag cgagaaggac ccgctggtgc  21900
tggaccgcgg ggcgctcacg cggctctcgg acgtccccgc cgagcgcttc cgcgacctct  21960
tcagcgacag tgtgctgcgg tacttcctgg acgcgaagct gggcacgctc gggctggtgc  22020
tcgaggacta ccgcgaggac gtggtcgccg ccatgcttcg gcacctgcgc cgcgtcgagg  22080
acgtgtcttc cttcgtgacg tacgccgcgc gcaagaaccc cgcctgcgtt cccggcgtcg  22140
tgcgcgcggt cgtgagcaac ttcaaccccg cggtggtcgc ggccatgcgc cccttcctgc  22200
gcgagcacat gacgcgcgtg gacgcgctgc tggacggaat gccgcacctc tcggaggccg  22260
accgtcggta catccgccgc gtggtgctgc agggccgcgc ctgattcgcc gtcaataaat  22320
cgcgatggtg gacagcggca cgcacgacgt ggactccgcc gcgcaggagc gcacgcccaa  22380
ccagcagacc ttcttcacca aggggctcag tccgctgatg cgccacacct acatctacaa  22440
caactacgcc tacggctgga ttcccgagac cgcgctctgg agcagccgtc tgggcgacta  22500
ccgcgtcacg gacttctacc cgatctcgct gggcatgctc aagaagttcg agttcatgtt  22560
ctcgctgctg gcggaccccg gcggcgcctg ccccgcgtac gagcccaagc tcaacaccga  22620
gttcctgaac cgcggctcct tctcgggacg gtacgtgaac cccttccacc gcttcgcggc  22680
```

```
gctgcccgag cgcgagtaca tatccttcct gctgctgagc tcggtgccca tcttcaacat  22740
cctcttctgg tttaagggcg agaccttcga cactgccaag cacagcctgc tcggcgccgt  22800
gtacaccacg cccgagcggc acatcgagct cgcgcggtac ctgcggcgca cgggcgacta  22860
caagccgctg ttcagccgcc tgggcaacga cgacacctac tcgaagccct tctctgggtt  22920
cacgcgcatc agcaacccca cgcccatcgg gcggctgccg ccctcggact tcgagacgct  22980
ggccaacctg agcaccattc tctactacac gcgctacgac ccggtgctct gtttcctggt  23040
cttctacgtg ccggggctct ccgcgaccac gaagatcacg cccggcgtgg agttcctcat  23100
ggagaagctc tcgctcgcgc ccgagaacgt ggtgctgctg tagcctcaaa cataaaatat  23160
aggcgccttt gatcgcactg cttcagttca gacagagcta agatggcttc ctacatcagc  23220
ggcgctagcg ccagcgcgaa caccgcccag ggcggcgatt ctcagtaccc acagtactat  23280
tatcacacac gcacctccca aggcgacatc cgcgacgaaa gcgaaggttg cttccacacc  23340
acggacgacg agcacttgga tctgtccgac gactacctcg gcgatggcgc accacactgc  23400
ggacacagcc acaaccacag tcgcagagat ggagatcggc accgccagcg cgcaccgcgg  23460
ctctatgagg acccggtgcc cgcgaacatc atggtgccca cgctcagtct agagcagctg  23520
ctggaggaaa cctcggtcgc ggggggcctt ctcggcggca ggacagagag ggacgtggaa  23580
cagctcctgg aggagttctc cgcactctgt cccggggacc agatcaccgc gctgcgctgc  23640
atggcggcct ccttttaccg cgacgcgctg ttcgcgccgt acgcctgcat gcacctcatc  23700
gccagtcgga tgcgcgtgca ctacgcgcgc gaggtcgtgc acgtggccga ggacctcgcg  23760
gacgcgatgt ctgcgaacag cggcgtctgc ttccggcggt accgaaagcg cgtgctagag  23820
gacatgctcg cggaggagat gggcgtgtac aattacctcg cgcgcgccaa cgcggacatc  23880
tgcgaggaca acctgctatc ggccgtggag acgctgctgc ggcgcttccg tcggatgggc  23940
tgctaccgct ctctgtgcat gctcaagatc ctcgcgctgc agcacgagga cctggccggc  24000
ttcatccgcc gcagcataag aaaaacctgc aacttggcac acgcgcgcac gcacacggtt  24060
tacgtgtagt taccctgtaa agacgggctt gctcccgaac aagcgctcga agaagagcgt  24120
gcacatagcc ttattgtcca gcaagttgac tatctctgta cacagcctct tgaagtacac  24180
ctcgtacatg atccgctcgt ttttatccag tctgaaggtc ttgtcgacca cgcgctcgta  24240
ggacttcacg ttcgcgatcc ggcgccgcca ggggccctcc tcgcacacgt acgcgaagaa  24300
gtagcgctcg ccgatctcga tggcctccgc gttcgccgcg ttgtaccgcg tcactagcgc  24360
cacgttgggg ttgtcggggg acttgaagtt cttgtggtgc gttcggctca gcaggaacca  24420
gtccagcggc atgctgcgcg cctcgaactc gaaggtgagc tcgtcctcca gcgagcgcag  24480
gatctccacg cccacgttcc cggagccctc ctccgccagc gcgcggcaga gcatgtcctt  24540
gtacttgcgg atcatgagct tgtggaaggg cgccacgtcg cggcgcgtct cgctggtgcc  24600
cttgctcacg cgctcgctgc cgccgccgtc gctcaccgca aacttgatcg tggtgtactt  24660
cttcttggac tgcatgatca ggttgcagta caccgcttcg aactccacct tgaagttcgc  24720
gaagagcacg tgctcgttga tcacgcgctc cagacagcgc cccacgcgcc gcgagaacgc  24780
gatgtcggag gcgcccacct ccaggaacac ggagtcggtg tcgccgtaca cgctgcggaa  24840
gcccacgcgc tccgtgcgct cgccggccac cgccgcgtcg atctctagct ccgcggcgcg  24900
gcccgcgaag gcctcgtcgc gcagcagcgg gttgtccggc gccgccgcca gcgacagccg  24960
cgtgccgcac accgacgcgc cgtctagcgt gcgctccagg tacgcgatca tggtgcgccc  25020
gatggccgtg cagctcttgg ccgaggcgta cgagaagagc gcgctgttgc ggaagcccat  25080
```

```
gagcccgtac acggagttgg ccgtgatctt gtacgtgtac tgcatcgagt tgtagatctc  25140
gcggtccacc gcggtctccg cggccttcat cagcttcttg tacttggcgc gcgcgtccag  25200
gaaggagcgc agcagcatcg ggatgatgcc cttggcctcg cggtcgaaga tggccacctc  25260
ggcgacgagc tccggcgagc gcggctcgca gggcaccgcg atgtaccgcg gcgccgggaa  25320
catccgccgg acgtccacgg ccgcgacctc cgcgtcgagc cggttgtccg agacgaccac  25380
gccgacaagc gtctccggcg acaggttcgc gtagatgcac acgttcgggt acaggctgtt  25440
gtagtcgaag atgagcacgt gcttgttgtg catcttctgc ttgggcgcca tcacgcggcc  25500
gccctcgtag aagaacttgg acttcgtgtc cgcgcgcacc atcaccgtgc ggttctccag  25560
cagcagcttc atcagcgggc ccttgatgca ggtgctcgcg cggtactcga agaccacgct  25620
ctgcggcagc aggtacgtgg acgcggcggc cgcgatcttg gtctccacgc cgtagtgcga  25680
ccagaggtag aggcagaggc aggcgtcgtg caggcagtac cgcgccatgt ccagacacac  25740
gtccagcgag tagttcgcgt acatgtccgc gaggctgacg tcgtccttgc cgaaggccag  25800
cgtgacgcgg tcgccgggcg cgcgcgccgc ggggtccgcg aggtccacgg tgaagccgtc  25860
ctcgtcgacg cgtttgtgca gcacgcggca cacgcgctcg tccacggtca cgtagttgcc  25920
ggtgctgagc acgcgagcga acacggccgc gttcccgtcg gcgtcggtgc tgcggtcgcc  25980
gcgaaagcgg accgcgtccg gccgcgcgtc ctccacgacc gcggtgcagt ggaaggcgtt  26040
cttggatatg gcgtccagct tgtaggagtc cagcttctcg gtgcgctgga tgaaggcgta  26100
caggtcgaag tagatggtcc cgttgttgtt gttgatgtgg aaggtggtgc tcgagacgcc  26160
gccgacgccc ttgtggctgg acttcgtgcg ctcgtacacg cagaagttga ctgtctcggt  26220
cccgtccggc agccggaagc ggatgtgctc gcccgtgagc agcgacagcc gcgagtccag  26280
gtaccgcagg tcgaagttgt ggccgttgaa ggtgaccacg aagtccagcg gcatctcgag  26340
caggcgcttg gccacgcgca gcagcgtcac ctcgggacac agcgtgacct ccgcgtcgaa  26400
cttcacgtcc gccgggtcca ggcagaccgg gatctcgcgc cgtgccgcct cctcgaggtc  26460
cgcgtcggag agcatatcgg agttcgtaag cgtgaatcgc cgctccgcgc cgtccttgtc  26520
caccacgcag aagctgatgt gcgagacggc gttcttgaag acggaaggaa actttttctc  26580
gaagtggcac tctatgtcga ggaagagccc cgagcgcgtc acgttgaagc gcgggatctt  26640
ctccgcgaag cacgcgccgg ggtcgtcgca gtggaagcag ttgctcccca ggtcgcgcag  26700
cagcgcgggg tccacgcggt agcacccgtc agggtcgatg tcgtgcgcca cgaagaacca  26760
ggacacgttc agaaagtcgg acatgaagac ctctggcggc gcgagcttgc gctcgctggc  26820
caccagacac agctctatct ccgagcgctg gcgctccgga atcttcgccg agcgcgctac  26880
gatctcgtcg atgctgacca cggacatggg cccgagcgcg cgcgtccacg ccagcggctg  26940
ggcgatgtcg gccaccgcgt ccgcgcgcac cacgtagtaa aagtgctgca cgaagcgcag  27000
gtacacgacg gcgttgtcgg cgcggcgcgc cttgaggaag aggaaccggc tgtcattgcc  27060
gcggttctcg aaccagttca aacatttcag ctccatttca aagagcataa taacatttca  27120
tttaaatgga gcctcgcttc tggggccgcg ccatgtgggc ggtgatcttc atcgtgctgc  27180
ggcgcttcga ggagcaccgc gacctcgagc gctgcaagcg gcagctgtac gtgatctgct  27240
ccacgctgcc ctgcatcgcg tgccgacgac acgccaccgc cgccatcgag aaaaacaacg  27300
tcctctccag cgaggacccc aactacgtgc tcttcttctt catcaagctc ttcaacaacc  27360
tcgccttcga cgacagatac aagatcgacc ccgcgaaggt gcgcccgctc gtctagagca  27420
```

```
tgccctcgta cgcgcgcgag ttgtccgagt acacggtcac cgcgatgccc tcgcgcggcg  27480
tcacgtgcac gtgcatggag tccgtgatca cgaagcccac gcccgtgacc ggctcctcgc  27540
ccgcgtcgtc cgtgaagagc agcccgtggt tgaagaggta gaactcgttc tctgcgagcg  27600
aaagccgccc gcggtcgcag aggtagtaga agatgtcgta gtcgcgcacg gccagcgtga  27660
acgtggactc gctcaccacg atgtacttgt ccagctcctc cagcacggac gcggccgcgc  27720
ggcgcgcggt ggcgcggcac tgcgtcgggc actcgcacgt gtctgcagag tacaggatgc  27780
gcgttcgccc cgaggcggtc tcgagaaaaa cgttaatcgc ctccatcgcc cagaagcgac  27840
tcgaggatcg cgagcaccgt gcgcagcacg agcccgatgg tgcagaaggg aacctctccc  27900
gactccgagc actcgcggat ctccgtctcc acgcggtcgt gcacttttat ggagggagcc  27960
gtcgttccag tggcctccat cgcgacggac accaccttgg ccacgaactc gcggatcttg  28020
ctcatgcgcc ggagcacggt cacgcggaag aagacggccg cgagcaggta ctcggccacg  28080
cagctcacgg cgatgagcgc ctgcgcgtgc ctggtgttga gcacgtgcgc gtcgggcacg  28140
aagtccgaga tcttcaggtg cgagagccgc acgagcgcgt tggtgtcctt gacgccgtcg  28200
caggaaatgt tcgcgaagat gagcttctcg tagtcgagcg cctcgaccac gcgctgcgcg  28260
tccatgtgcc gctcgcccga gagcgcgcgg ctcaaagggc cccagcacac cgagcccgcg  28320
aagcaggggt ccaccacgcc gtgcatcgcc agcagcgtca cgtcggccac cgccgcgagg  28380
atggccgcgt cgtcgagctc gttcgcgggc gtcgcgcccg tcagggacgc gctgcgcagc  28440
gcggacccgc ccggcgccgc gtgccgcgcg cagaactcgc acccgcagcc cggcggcagc  28500
ggcggcttcg agagcagact tatgagcccg cccacgtgcc cgtgctcggt gatcagaagc  28560
gccaggatgc tgtcggtgct gccctctatg gcggctgtgg ccgcgctaga aggctctccc  28620
gtgacctgcc atccgcagac aaccttgagc atcttgcgct tgagctcgtt gggcgcctcc  28680
gaggccagca tcgtgcgcgg gaacgtcgcg ttgaggcgga agtcctgcag cagcttttcg  28740
agcgtcgcgg tcttggcgtg ccgccctttg cgccactcct cccccaggtg ccacatgagc  28800
tcctcggccg tgtccagcgt cggcgagacg cgggccttgg gcacgcgcgc cgcgctgcgc  28860
atcagcggct ccgaggcgcg gaagctgccg cgcgcgtgca ggcgcatgga cgcagacgag  28920
gaccgcatcg agggtctctg gtggaagctc gtcatcgtga agcgccgcgt gagcggacct  28980
acctcgtcgc gcgactcgtc gaagtccggg tcagggtccg tcgtgtcggt ctcggcgctg  29040
tgcgtgctgg gcgcgctgct gcgggcgctg cgcgtgctgc gcgtgctgcg ggtgctctgc  29100
gtgctgaagc tgcgcgagca ggagtccgcc gtgtccgctt cctcgtagtg gaagtccacg  29160
tgctcctccg gcagccggcg cgagcgcgac ttggagatgc cgaccatctt gtccgcgccg  29220
accgggcgca cgcagagcgc catcgcgccc tcgcgcaccg cctgcgcgaa ctcgcggctg  29280
gcaaccatgc tggggttgag gaacttgatg atgttgaagt atggccactc gcagacgagc  29340
cgcgcgcagg tcgcgacgtc gtcgacgctt ctgagggccc tgttcagcgg ggggatgttg  29400
ctgccgtcgg ccagtgcgac gaggtcctcg gggagatct cgagcttggg aatcatctcg  29460
ttcacgagcg cggggtcgat ggcgtggcag acggtctcta cctcggtgcg cgagagcttg  29520
agctgcgcgc aggccgccca cggcgcgcac gtgagcgcga acaccgcgga gactcggccc  29580
ttgccgacca tcgccacaac ctcgggctcg tagaccaggc cggccttgag cagagcctcg  29640
agcacctcta tgtcgtcggc ggcgagcagc gcgcgcctgt ggaagcacac cgcgggcatc  29700
atcttcttgc agatgccgcg ggtgctcttg agggccgtga taaggtcggg gagcctgacg  29760
tgctgcggct ggaagaacat gacgttggcg gggctcgcgg ccaccgcctc gtcgtacacc  29820
```

```
gacatcggca ggtcgccgtg gagcccgcac ggcagcaggc tcagcagctg cgcgcgcgag  29880
agcttctcgg cgcagaagtt cttcttggcc agggcggccg ccgcgtcgcg ggccttcttg  29940
gggtataaca acatggcggg ctttaaacac gaaacaaaaa tccgggttgt aacatttcaa  30000
ttttgcatgt tctgggcctc ctcgcagagt ttctccaggc cgccggccac gatggcgtcg  30060
acgaagaggt cggcctcggt gaagcggtgg ttgccgcgca ccgccaccag cgcgttctcg  30120
gtgaccacca ccgacagctg ctgcgcagcc gtgcgcaggt cgaagtgtcg gcacgcgagc  30180
ccgtggccca gagtctggtc cagcgccgcg agcacctcct ccaggctctc ctcgcggtgg  30240
ttgtagaacc acatcagcac gaagtaggcc acgtaggtgt agaggtagtg cgcgaccgcg  30300
cgggcgcgca ccagcggctg gttgcagcgc gcgaaggcca ttccgctggc gatgaggtcg  30360
tcgtccagcg tggcgtagtc gccccagttg agcgcgctga actgcacgct gtagaccgcg  30420
cgcacgaacc cggactcgag gatgtcgatc tgcgacggcg cgccccaggt caccagccgg  30480
tacacgatgc cgcgctgcat cagccgcatg aggtcgccgc cgacctcgcg caggcggtgc  30540
gtcagcgagg cgaaggccag cttccgctgc gtgtactgca ggcccacggc cacgcacccg  30600
tccgactcca ccagcacgag cttgtggtcc gtgcagccgt cgctgcgcag gccgccctcg  30660
cgcgccatca tgtcggtgac gaacatgtac ttgcgcgcgc gcggcccgac caggatgcgc  30720
ttcttgcctt ccatgcgcag caccacgtcc tctagcagcc gcgtgctgtc cacgcgctcc  30780
acctgcgggt ggatggtggg ctggtagttg tacagcagcc gcggggacca gttgtaggcg  30840
aacgcgaaga ggtgcgtgtc caggagagag atggggaaga cgccgccttc ggtggcgcgc  30900
cggaggatgg cgagcttggt ctccgcgggc agcaggctcc cggtcaccgc gccgaagaac  30960
atggggtggt tgcggaactt gagcgcgtac gcgctcagca cctcctctcg cgagaatatc  31020
gagtccgcgg ggttggagct cgcgggcagg agcacgtcct ccacgctcag cacctcgtcg  31080
atgaagggca gcaccatgtc cacgttggag gcggtgaacc actccatgtc cacggcgttg  31140
cgctccacga tcacccggat cgtctcctcg gatatgttct cggcgaaggc gctctgcagc  31200
tcgatcaggt tctcggtggc gtcgatgctg agcccgaggc gcatgccctg ttgcagcacg  31260
tcgttgatgg ggttcacgta catggccacc gccatgcacc cggccggctg cacgcgccag  31320
aggttggagt acgcggacac gtccgtgatg cgcagcgtct ccagcacgtt gtacatcgcc  31380
gcgcgcattt ccagcgtgtc cacgtacacc tccgcgtgct cgaagatgat gtcgagctcg  31440
aacgcggaca gcggcagact cacgtagatc tggcaggcgt caaagagttc ctgcgcgtac  31500
tcagagaagc acgcgtacgc gatcacgccc gcgcggttga cgatgtagtc cgccttgaac  31560
atcttcgtga ggtaggcgta cagcgaccgg caggccacgt gcggccttag ctcgtcgagc  31620
acggcgtcca gcacctcgcg gtgctgcagc acggaggggt gcaggaactg cgtgaagtcc  31680
accgcggtct catccatgaa gtcggggatg gtctcgacca ccaagcggtg gttccgcacc  31740
gcgcggaagc cggtgttcat cggcgcgatg ctgtgctggt cgtggacctc cagcaggatc  31800
tcgtagccga tctctcggca gctcagcgcc gcgcgcgcct ccgtcacgct cgcgttccgg  31860
aagaactgcc gcaggtgctc gtccgtgcgg cagagcgtga cggattgggg gatgcgggaa  31920
aggtcgcaaa gagggctgtg gacggagatg cgccgcagcg cgtggtctac gaactcaaaa  31980
ccgcgcctcg acatcgtgaa gtcgcggagg gcgtacatgt tgtaggaaca gaggcggaag  32040
aggcagtcta tgtctagcat gttggaaacg cagtacgcgt gtctgtggag gtgcgggagc  32100
atggcgggca cgacctcggt cgtgttctgg agcatggtgc atacgaggtc gggcgctgtg  32160
```

aggtcggggg tgacgatgag gatgcaggag ctggagaact tgctgagctc ggaggccagc 32220
cggtgaaggt tgtagtcgtg gcgctggctg aagttgctgt ttatcgtgcc cgtgaagccc 32280
atgagcgccg ccagcgtcag gtcctcgcgc tcgatggccc agatgtctag gccggaggct 32340
atcatgcagc gcaccagcgc ggcggcgcgg tcgctcgtgg ggtagctcat ggtgctgtcg 32400
gtcgtgcgaa tcagcatggg ataatgcttc atttttacgg tcgggggttg cggactgtgg 32460
ggcgcacagg gcctgcgggc ggctcgtgcc ggtccgcggc gttcgccgaa cgcaggaacg 32520
ggcccatgcg cgcccaggcc atccacagcc ccgccgtcag cgccagcagc cagacgaata 32580
ccacgatcat cttttatgta gctggaactc gcgctcactc cccgccgcac ggcgacgggg 32640
agagcccaga gccgagctcc atgcgcgtgc tctgcacggt gagcgactcc acgagcttgg 32700
acacgttcat gcgcgtgttg tcgggcacca ggtgcgcgag gcgcgcgtac acgtcatcgt 32760
gcatgcgctt gctgcagcgg tccaggctcg cggagagcgc ggagactagc gcggtgtgct 32820
tcgcgtacac gaagtcgccg agacacacgg tctcgagccc gagcacgtcg gcgctctccg 32880
cgtccttgag cgccacgaat atcttctgct cctcgcgcgt catcgagcgc atgaggtagt 32940
cgtgcagccg cgagcgcgag atgagcccct gagagatctg cgggctgcgc atgaagcgcc 33000
ggcgcatcgc gcacagcagc tcctcgtcga cgacgtacat gctgtccttg atggagctct 33060
tctcgtcgat cacgagcaga ccgtcgttgg cgaccacgtt gatgaaatcg tccacgtgcc 33120
gcgcgtctat gtcgtagcgc gtgccgccgc actcgatgtg cgagggcggc gacttgagcc 33180
ggttcgcgag cgccttcacg tcggagacgt cgatgtacag cgaggactcg cgcgggacgc 33240
agccgaggat gcgcgtctcg agcggcgtga ggatgagcac gcgctcggcg ccgtcgacga 33300
gcttgccgtc gtcgggggaa aagaagttgt tctccacgat gctcgagacg aggctggcga 33360
gcacgccgtc gcggtaggcg ccgagcgcaa actcctgcac aaagggcgcg tgcagcaagt 33420
ccacgggaat gcgcatctcc acgcggcgcg cgaccgactt cttcttctgc aggtgccgcc 33480
ggtccaccat ctcgtccacg atgtccgata tgcgggagca gaggtacgcc ttgaggacgt 33540
tggcgtttac cttgttgaag atgagccgtt cgtcctccat ttaagctgct cagacgagct 33600
ttaaatagtg gaaacacagc agcacgccga tcgccgccgc tatcaggccg attagaaaaa 33660
cggtggtcca ggggacgccc ttgggcctat cgcacgccgg cttttcggtc attacggtgc 33720
gcacgatgtt taggaactcc tcgaagtcct cgtccgagtt ggagaggaag gagccgaaga 33780
cgccggtgta cagtttgtcc atttactact agatattaaa cggcgcttcc aactcctcgt 33840
cctcgaagcc cgcgccaggc tcgacgacgc ccaggccgcg cacgtcctgc tcctcgttga 33900
acgtggtctg agtctcgctc atgcgcacac acgtctgctc gccctcgaga ccgagcacgg 33960
tcagcgagca ctcgcgcggc atggtgatct tcttaaccgc gaaggtgact ttgccctcgc 34020
cgcccgagcg gtagaacacc accggcgcca ggatgagcgt cgccatctgc gcgtcgcggg 34080
ttgcgaggtt ttctatctct cgcgtcagcg gacatatctg cggctgggtg tcgtcgtcgc 34140
tggtgaactc caggagagcg ccggtcaggc ggttgagata cagacatccg gacttaaagg 34200
tgttgtcgat ggccgtttcg gtgttgaagt tgcgcagcga cggcggaacg cgagcgccgg 34260
ttttgatgtt gtcgtatatg ttctccagca gctggtagag cagcggactg gcgctcacgg 34320
gcttgaggcg accgaagtac ccgctgtcgt tctgccgctg catgtcggtc ttcttgctcg 34380
ggtagatctt aaactcgccc ttcacgacga tgagcggcga gacgagcttg gatgctagac 34440
tttcgacgag acacacgttg atgttggagc agctcgggta ctgcgacgga gttagagtca 34500
cggcctcgat gaccttggtt tggctcgacg agagcgactt agcgaagttg atcgcgtcgg 34560

```
tgcacgacat cgcctggttc tcgccgaacc gcctggcgga cgctgcatcc tcctgctgag  34620
gagcgcggtt agacgcgacg gtggttttgg atacagcgcg tttcattatt gcggcgattt  34680
taaagtacgt gtatactttc agttttgtcg ccgagcgttc agcgcctgca tgcagaggaa  34740
gtacaggatg atggtgcacg ggatcgtggt cagcagcgat acgaagtcca tcactgtgag  34800
gacgcgcagc gccccgcgcg agcggatgcc cagcgagggc gcgccgcggc gcgcgatggt  34860
ggccccgttc gtcaccacta ccagcagcat taggatggtc gcgcccacgg cgacgcccag  34920
gtcccgcgac tccatttata gtacagtata gagcgaccgc gtcacgaact ctcggctggc  34980
caacacgcgt ccgtcgggcg ggtgtccgcc ggccttcccg cggaactccg ggacctcgaa  35040
gctggacttc gtcacgcggt acgtgtactt gccgcgccag accaggtttt ccttctggaa  35100
gacgccgtcc atggtcacgc ccgccatgaa ggcgtccttg acgatgacca gcaccgcgtc  35160
tagcttgcgc ccgttgatgt gcgtgacgaa gtccgtgccg ctgcggctcg cgcagcggat  35220
gtccacgccc gagggcaggt ccaccacgaa cacgaagcgc ttcggcgcgt agagcaccag  35280
gtccgaggac ggcgacgccg aaggcgccga ggggaactgc cggtggtcaa aagggtgcac  35340
cacgcccacg atggacgtga cgcggtcgtc cgggaactgc gtcgcggcgc cgccgccgcg  35400
gtgccgcgtg accgtgcttc tgcccacgtc gtcgcagacc acgtgcagct ccgacacgat  35460
cggcagcagc gtggccagca tgcggtcggt ctctgtgcgc gtcgcgcagc ggtacgcgat  35520
cccgcagtgc gcgtcctgcg tgcgcccgaa gaagagcacc agcacgctcg cgtcctggtc  35580
gaagggacac acggccatca cgcccaccgg cggcggcccg tggcctgcgt acgcggagga  35640
gaactcctgc acctcgacca cggcgtcctc gcgcgcctcg ccgggcacca tcgccgccgc  35700
cggccgcagc gcccgcacgg tctgcttaac cgcacgcgcg gcggaggccg cgctcggcgc  35760
gactacgcgc acggccgcgt gcgcgcccgg cggcggcgcg gttccggcca tccagcccac  35820
cggcgagaag aacacgtcgc agacgtgcac gcccgcggcc tgcagcgcgc gcgcgagcgc  35880
gcgcacggcc tcccactcct cgcgaaaggc gctcgcgacc gcgagcgcct tcagcaccgt  35940
gtccacggag ttgacgggct tctggaagag gttctcgttg ttgtagatga actcggggag  36000
ctccacgggc actgtgaaca gcctaatctc gtgcgcgccg ctgggcgtga gccgcgtcgc  36060
gggcttgcgc acgccggcgc cgatctgctt gaagaagtgg ttcatggcgc cgccggcttc  36120
tcgggctccg gcgggagcag actatttatt cgggaggtta tcctttccga aagcacctgc  36180
acggacttcc gcgtccagcg ctccatcttc atgtactcct tcatgccgtc gctgagcacc  36240
tcgacggcct ccagcttggg cgctgtcggg tcgaagagga tgctcttgag cagcgtcatc  36300
ttcttgtccg cgaggaagcg gaagtaagtg tagatgcagc gcagcgcgcg gaagttctcc  36360
gggtgcttga tggtgcacag gatcatgaag atgcaggtga acatgccgca ctcggactcc  36420
atgagctggt tgacctcgag gttgatgcag ccgcgccgcg ccttgaagtt gtccacgaag  36480
aagcgcatga gcacgtccac gtcgcagttg cggttgtcca ggtccgcggt ctcggcgttc  36540
acgttgaagc cgtccgagaa ggagtagaag tagaagtact tgcaggggtg gaactccgag  36600
gggctgttgc cgccggagtc gtagaaggac acgagccgcg agacggtgtc gaagatgcag  36660
cacttccagt ggaacatgta gcagaagccg aacatcacgt agcgccgccc ggcgcgctcg  36720
atcttgtcct tgagcgtgag gctgaccatg ttgcagcgga agcggtccgc cttttcgtgg  36780
atggccgcgc cgttgaggaa gttcaggttg aactggccca ggtacgcgac ctcggtgccg  36840
aacgcgaagg gcgccaccag actctggatg ctcacgttgc tcatccaggc gctgcggtcg  36900
```

```
ggctttatgg cgatgggcac taccttggtg ttcacgcccg tgctgacgcc cgcgcgcgcg  36960
aggtcgtcca cgttcagcgg catctgcgag aagtccacgg cctcggacac cttctcgcgc  37020
aacgagggct tgaagaagaa gcccagcggg accttccact ccagcgcgat cgcctcgcgg  37080
aagccgtagc gacccttgag gctggccagc aacgcggtct tctgcgcgac ctcgtccttc  37140
tcggtgtccg gcggcgcggc gtcgatgagc ccgcgcttcg cgaagtccag cagcgccgcc  37200
agcgggatgc acgagacgcg accggccgtc gcggattcgt cgaagcgccg caccacgtac  37260
ccgttgcagt tggtcttgaa gttggacacg tccaggtgcg cgctgagccc caccaccgag  37320
tagatgtggc acagaaggtt ggtgaacccc agctccggga ttttgctcac cactaaatcc  37380
gtgtacttgt ccatttatca tggagaatca tctgccggac atgctgatgt ttcccaactg  37440
cgtttctgtg tttccctttg agtactcgct ggaggacgtg ttccgcctcc ccgaggagcg  37500
acggcgcgcg ttcgccatgg ccgtgttccc gctctccaag caccgctgga ggggcgcgcg  37560
gctccagcgc gacgagcgaa gcgtgtggct cagcgtcgag gaggaccgcg ggcgcgcgct  37620
ggacgagcgg aactgctcct ggctctcgga cgtggccgcg cgcatggtcg acgacgaggg  37680
ccgcgcggtc acgcccgagg cgtacgcctt catgcgcgcc gcgcccggcg cgcgcgtcgc  37740
cgagctcgcc gcggacgcgg gcgtgctagc gggccttgtc gccggcggca acgcgctgcg  37800
cgtcttctcc tcggagtcca cgcaggcgcg cgagggctgg aaggcgcgca gcgtgggcgt  37860
gctcggcaac gcggcgccgc tggcgcccgt gccgctggca tcgctgcgtc cggaagtgca  37920
gcgcgagctc ttcgccgcct ggatcggccg ccgccccgtg gtgctcacgg gcggcacggg  37980
cgtggggaag acctcgcagg ttcccaagct gctgatgtgg ttcaactacc tcttcggcgg  38040
cttcgagcgc ctggacgccg tccgcgagtt cgcggagcgc ccgctcgtgc tctcgctgcc  38100
gcgcgtcacg ctggtgcgcg cgcacaccgc gacctacctc gcctcgctgg gcttcggctc  38160
ggccgacggc tccccggtct cgccgcggta cggcgccatc ccggacgccg agcggaacac  38220
ggccccgcgc gcctacgggc tcgtggtggc cactcaccgg ctcacactga ctgccatccg  38280
ccgctacgac acggtcgtag tggacgagat ccacgagcac gaccagatgg gcgacatcgt  38340
ggtcgcggtc gcgcggaaac tgggctcgaa catgcgatcg ctggtgctta tgacggccac  38400
gctcgaggac gaccgcgcgc gcctggagga gttcctggac cggcccgcct ttgtgcacat  38460
agagggcgac acgctcttcc ccatccgcga ggtctacgtg aagaacacgc aacagccgcc  38520
gctctcgcgc aagtacgcgg aggcggagct gcagaacgtg gcgcaggcgc tgggcacctt  38580
cgtccccgag cagggaaagt gcggcatcct cttcgtagcc acggtggcgc agtgcgcgct  38640
cttcgcggag accatcgagg ccaagcaccc cgggctgctg gtgcgcgtgg tgcacggaaa  38700
ggtgccctcc gtggccgcgg tgctcgagga ggtatacgcc gcggaccggc ccgcggtgct  38760
ggtttccacg ccgtacctgg agtccagcgt gaccgtgcgc accgccacgc acgtctacga  38820
cactgggcgc gtgtacgtgc ccgagccctt cggcggccgc gagaccttcg tctccaagtc  38880
catgtacacg cagcgcaagg gccgcgtggg ccgcgtggcg cccggcacct acgtgcgctt  38940
cttcgacacg cggctcgcgc tgccgctgaa gcgcatcgac tccgagttcc tgcacccgta  39000
cgtgctttac gcgcgcatct tcgggctaac gctgcccgac gacctgctcg tgcagcccag  39060
cgacctcgcg ctgctgcgcc gcaccgagga gtacgtcgac ggcttcggca tcagcctctc  39120
gcgctggacg cagctgctgg accggcacta catgcacatg gtcgagtacg cgaaggtgta  39180
cgtgcgcggc gggcgcctcg ccgccgcgct ggacgccttc gagcgcaccg gcgtgatgac  39240
gcacgaggcc accgaggcca tccgcgccgt ggacatgctc gcggccgtcc taaacgtgcg  39300
```

```
caagtccaag gaccgctacc gcgcggagtg caaggtgctc ttcgggccct tcgcgggcaa  39360
aaagttcgtg gtcgccgggc ggcgtccgcc cggctcgcac gtgctcatgg tcacagaccg  39420
cgtcttcatc gaggccgagc cccattctg aggaccacct tcttggagac gcccgagaag  39480
tcgtcggcga cgccgcggcg cgccaccaca aggcagtacg aggtcacgtg cgggcagcgc  39540
gcgatgcagc ggaaggcttc ctcctgcgac agcgagaagg cgaacacgta gaaggtgtgc  39600
ggggacttca gcggcgtgtg gtccatcgag tagatgacac cgagcttctt catgcgccac  39660
ataagcgcgt tgatgtggtc ggcgcgcagc gcgcggccct tgagcacgcc gcagacgaag  39720
ctcgagcagg ccacgacgtc gtagcgcgtg ttcctgccga agaccaggtg cggcgcgccg  39780
gcggcgcgcc gcgcggccgc gcgattctcc acgatgtcct ctatggagcg ctcgctcgca  39840
aagaagtcca ggaacatgta ctggtaggcc acggccgggc gcgacttgct gaacttcatg  39900
aaggcgtccg agtccatgat ggcgtccatg tcctcagcgg cgagccggtg ctgcagccgg  39960
atgccctcga aggtgtggaa gagccgcgcg tccgcgtgca tggacagcgc gagagtgacg  40020
aagttgagaa ggtccgcgtc gccaaagcgc acgagcacgt taccgggcgt gcgcgtcttg  40080
cgcatgagcc gcgcgggcgc gccgtcgttg tggctgcggc ggcgcatttt gtcgccgggg  40140
gactcgggcg gcaggtcgat catgaccagc cggtgccgct gcgcgtcctc ggcgttgaag  40200
atcgaggacg tgaagcccgg gtacagcacc acgcagtcgc gctccgagat ggcgtgcagc  40260
acgtcgcgct tgagcccggc caccagccgc tccgcgttct cgacgaagta gttctcgtag  40320
tccaggatgt cgtgcgccat ccaggggaag ttcaggtacg cgttcatggc gtagtcctcg  40380
gcgtcgaagc agatgcgcgt gtctggcgtc gccgcgatcg gaaggtcctt gatgccgcgg  40440
agcagcccgt cgtagtcgga ctcgtccacg aaggagagca ccacaaagag gtcctcgccc  40500
acggtttcgt agtcgaagag gtggtaaagc tctcttagcg ccagcacggc gagcgcgttg  40560
tccagcgagg cgtgcacgcg cgccaggatg ctgtagaagg gcgtggccat catcacggcc  40620
ttgccgccct cgcaggcaac ggcgcgcggg aaaatgacct ccggcgtgcg cggcagccgc  40680
ccgaacgtcg cgttcagcag cgcgaccgtg gccgcgtcgc tctggcgcag gaacactacc  40740
accgaggggc ccgagatgct gagcatgcgc tcgcgcatgc gcgctggcag gtccggcgtg  40800
gtcacgaggt ccgcgaagcg gccgccgttg tagaggtcgc cgccgccgag gaaggtgagc  40860
acgtcgaagc agtgcagcac ctcgttgcgg aagtagtact cgttctcgag ctccttggcg  40920
tacgcgcgta tgtccacgtt ctcgaagttt gttcgcagac cgccgccgtc gaagaaccag  40980
gacgcgagct cgcggacggc gtccgcgggc ctgttgcggc ggctcttgca ccagaagctc  41040
atgtagttgc gcgaggtgga ggcgttcgcc aggaagaagc ggtggtcgaa ggagatgagc  41100
acatgctcga gcaggtgcgc gagccccagg accgcgccca cgtcgcgccc aaaaccgaag  41160
tttgatatcc ccaggtagac gtcccgtttc atagacggcc tcaggaacac cctgacgccg  41220
ttttccaaca ctatcattct ccggtattta cttacccaaa agtagtatgg ggagaagtgt  41280
ttgaacgtcc cctcgccttt ttaaatcaaa agtagacttc tcgcgcccgt gcgccaccgt  41340
cacgcgcgcg cggcgcgagt ccataccggc gatcaccgcg ctgctctgcg gtgcgtccgg  41400
ccgcgggaag agcacggtct cggagatccc gtccagctgc gcgtcggtgc gctgccgcca  41460
cgcgtgcgcg tccgcgagct cgcgcacggc cagctgcatc ttgttcgtcg gcaggaacgt  41520
gaacacgtac gccgccgcca ggaaggctgc gaagagcacg aactcaaccg cccatgacat  41580
ttagggagct gattttgttc cacgcggcga cgcacgtcgt gacgggcgac cccgaggcgc  41640
```

cgcggcgcgc ggcctcgctg tgccgcggct tcggcgtgga cttccgcgcg attcacgcgg 41700
agttcgcgcg gcggtacccg cgcaccgcgg ccgccgtgga gcgcgcgcag ccgctgcccg 41760
aagtcgatgc cgcctttccg ccggacgcgc gccggcaagt cgtgcggctg cgcctcgagg 41820
ctgcggcgct ggtcgtcaag gagtcgcgtg cgctatcggc ctccatgcgc ggcgtggcgg 41880
tggtcgacgg ctgctgcgtg cgcgtgtgcc gcgccaacga cgagctgcta gagttcctcg 41940
cgcggcgcta cgaccccgcg gtctaccgct acgcggaggt gccctcgccg agcgtgcgcc 42000
cgggctcgaa agtcttcgcg tgcgcgggcc gcagcgtcac ctttgcggcc gcgcaccgga 42060
gccgcatcac ggccaaccgc ccgctgcgcg tggtcgtgac cgaggcctgt gtggacggcg 42120
tgctcgcgcg cggcgccgcg gaggtcttcg accgcggctc cggcgtgctg ccccgcgcgc 42180
tgcgcgagat cttctaccgc ctcgacgagg acggctgtcc cacgggccag acgccaggct 42240
tcgcggacag tatggcgtcg cgcagctgat ctatgtccac ctttttctcg tcgatctgcg 42300
ccacgaccac gaaactgcga atgtccacag cggccatggt cttggccacc gggtcgtact 42360
tgaggagcag cacgtactcg ttgccgaagt gctcggtgac ctcggtgatg agccggtaca 42420
cgcccatgcc gagcacgttc accgcaccgt ccttggcgaa gagcgagagg atgttcacgc 42480
acttcagctc catctcgccc tcgaggcgcg cgagcatgcg ccgggtgacc tcgcatactg 42540
aacaaagagg cttacctagt aagataagcg ttagcttagc cgcggtcggt gacgcgtcgg 42600
aggccattta tggggatcaa aaacttaaag gcgttgctgc tcagccacgg cgcgctgacc 42660
ccgcacgagc cgggcggcga cgagcgcttc cctgccgtgt tcgtggacgg cttcagcgtc 42720
atgatgacca tggcgtactc gtgcgcggac gaagacgagt tccgcgcggc cgtcgaggag 42780
cgcgtgcagc actggatgag cgtgtccgag agcgggcgga tcgtggtctt cctcgaccgc 42840
ggcgagattc cgatcaagca gccgctgcgc gaccagcgcc gcaaagccac gcgcgaccgc 42900
gccgcgcgcc accgcgagtt catcgccgcc gcggaggcag acgcggcggc agaggccgtt 42960
ggcgcccgcg aggacaaaca ggaggacgag cacgcggagt tcgccgagga gatccgcgct 43020
gagaagcagc taaagctgca gcgcatccgc ttccagctca gcatcgccaa ccacgaggtc 43080
gttaagtcgc tgatagagtc cacgctcgcg cgcgctggcg atgccgtgga gatcgtcttc 43140
tgcgacggcg tcgacgcgga gatggtcatg tgcgcgcgcg gacgcgccga ggccgagcgt 43200
cgcgggcgct ggccgctgct cgtgaccacg gaccaggacg cgcttttgtt cacgtccacc 43260
gatcgcgacg agaagatagt gagcaccgtc tccgcctgct acgcgttcag gcccaccgag 43320
acgaccgagt acctgtgcaa acttgcggcg ctggccaacg gctgcgactt cttccccggg 43380
ctcggcggca tatgcgtgag tgtggagtcg ctgcgccgcg ccacgctttt cccggaattc 43440
tccgtgcgca acgccgccgt gagtctgtgc acgcggccca tgcggctgtc cacgcaggac 43500
gcgctggagc cagaggccgc cgccgaggtc gtggaattca tcaggcggta cgccgccggc 43560
gacgagcgca tctaccgcga ggtgccgccc ggcgcgtgct gcggacgcgc gtttgtgcgc 43620
ggagcgctcg cggccgagtg ggccgacgcg ctgccggcgg ccacgggtct gagcgtggtc 43680
gcggacatga tcgcgtgtct gcccgcgcgg cgggaccccg cgcccgagga ggtagagcgg 43740
ctgctggcgc tggaggcgcg cgcgcgaggc gcgcgcgtca cggatgcgat gctcgcgcag 43800
actgcgcagc tgctgggtta cggcgcgagt gcgggcgccg acggcgcctc cgccttcgcg 43860
gtctcgggcg ccaagggcct gatgtgtcgc ctgcgcggca cggccatgtt cttcaacgcg 43920
gagtacgtgg aaattgaaag cgaacccaga ctgttaaagc tgcggtagca tggtgttccc 43980
gatcgtgtgc tcaacgtgcg gccgcgacct gtcgcacgag cggtttctgc tcatcgtgcg 44040

```
acagcggccg ctaaaggttg ttttgcggac ggtgcgcaac gtctgctgcc gtataaagtt  44100
gtctacacaa atagagccgc accggaacct gacggtgctg cccatgctcg acataagctg  44160
atttttcttt tccgctcgta tgcgcgagtt cggactcgcg gcgcgcatgg cccgcgccat  44220
cgaggacgtg tgtccgcgcg gcgcggtgat attcgtatcc agcgccgcgt ccatgaccga  44280
ctgcctgaac ccgtcggtgt tcaagcacgc ggcgatatac gcggggcgcg tggaccgcgc  44340
gccgctgccg ccgccctcgc cggtcccggc ggaggccgtg acggagccct gtgcgataga  44400
cgccatagcg ccttacggcg cgcgcgtggt cctgctctcg gagctgctgc ggagctgcgt  44460
ggccgttcag gcctaccgcc tggcagtccc cggcgccctc gcgctcatga acctcgcggc  44520
cgacgcggcc ttcgagctcg tgggcacgcc ctacggcttt aacagcgacc gaacgtactg  44580
cttcaagctc gttgccgact gctttgctag cgtgggcgtg acaacgaaga ccaggcgcat  44640
catgggtcgc gacgtcgtgc tcagccagga cttcctggag agcggcatgt ggaccaaggt  44700
gctggactcc gccgcggagc cgccgtggct ggtctagaac agcggcggcg cgcgggtccc  44760
gagcacgggc cgcgccacct gcagccgctg ctgcagcgcg cggcactgcg cctcggcgtc  44820
ggccgtctcg gcggggtcga cgggcgtcgg agttgcggag gtggtcctga acggctgcgt  44880
gttcaccgag acgcggatgc gctccttgca ggagcgctgc tcgatgcagt tggccagcat  44940
cttcatcacg tgcaggtact ccagcaacac gaacttttcg agggtgatgc cgtcgaaggg  45000
cgacgacccc accacgccca gcgggctgga caccgcgccg tcgagcacct cgccgcggga  45060
ctccttgcgc gcgcgctcga gcaggtcctc tgtccgagcc accacactgc cgaagtcggc  45120
ggccgcgggg gcgggaacag gcgcagcagc gctgtccgcg tccgccggca tctcctcgat  45180
cttgagaccg gccgcgaact ccgaggccgc gtgcacgggc gaggcgccgc gccgcaccat  45240
gaagtcgcac agacgcgata gcgcggagga gcgcaccggc atgtcgagca ggcgctcggc  45300
ctccatctcg gcgaccgagt cggcgcacgc gtccggcgcg cccgcccgca cgagctcgtc  45360
gcagcacccc gcctccttca tgagcgcggg catgagcttg tactgcgcca tgttcaccag  45420
cccgtacttg agctcgagca ggtccgcgag ctcggaggcc atgggtcggt tttggtgta   45480
gatgacgcgc tccacggcct ccgccatgtc cacggcctgc atgagctcgc cgacgagcac  45540
gctggccacg agcgtggcca gcgtgacgcg cacggtgggc acgcagaccg cgaagaagga  45600
ggtggagtgg gtgaagcgca tgagcgcgcc gtgcagacgc gcgaggtccg cgctgttgcc  45660
cgcgtgcacg aagcgccggc gcagccgcgc cagcgcctcc acaaggtcct ctcgcgtggt  45720
cacgcgcacg ttcgcgatgc acaggtcgtg gatcgcgttg gcgatctgcg cgcggcgctg  45780
cggcgagctg ccgggcagca gccgcgcctt ggcctcgacg tcgacggtgc tcgagagaca  45840
gccgcaggcg gcgccgcgga cgacgaactt caacaacgac tcgaacacgc gcgcgcccgc  45900
gcggggcgct tgcttggacg actccattta ctttaaataa tttacgagat caaaataaaa  45960
tgactctgcg catcaaactc gagaagctca agcagatcgt aacttacttc tcggagttca  46020
gcgaggaggt ctcggtgaac gtggacgtcg gcgatggcct catgtacata ttcgcggcgc  46080
tgggcgggtc cgtgaacatc tggaccatcg tgccgctcag cgcgagcgtg gtatacgacg  46140
gcgatgtcag ccgcgtgttc aacctgcccg tgctcaaggt gaaggcctgt ctgtgcagct  46200
tccaccccga ctcggtggtg agcctggagc ccgacctcga ggacaacgtg gtgcggctct  46260
cgagccacca cgtggtcagc gtggactgcg acaacgagcc cgtggcgcac cgcacgaaca  46320
ccgccatctg cctgggcatt aaccagcgca agtcctacgt gttcaacttc cggcgctacg  46380
```

```
aggagaagtg ctgcggccgc accatcgtca acctggacct gctgctgggg ttcatcaagt  46440
gcatccacca gtaccagtac atcacggtct gcttccgcga caagaagatg gtgctgcaca  46500
cgcccgggaa ggtggacaac ttcttccgcg agtactccat gaccgagtgg gcgcccgacc  46560
tcgagcgctt ctcgttcaag atccccatct cctccgtgaa caaactccgc ggcttcaaga  46620
agcgcgtggt catgttcgag tcgcgcgtgg tcatggacgc cgacgacaac atcatcggca  46680
tgctcttcac cgaccgcgtg ggcatgtacc gcgtgaacgt gttcatgtcc tttcaggacc  46740
ggtctctttc atgcgactaa atactcatgg gcgggtcggt gagcctgccc tcgcgggacc  46800
tgccgccgcc ggtgcgcacg ccggagatga acatcgtgcc cgagcgcgac ctcgcggaca  46860
cgatggcgcg cctctccacc gcagacccgc cgcagccgct gggcgtcggc gacgacgcgc  46920
gcatggccgt gctgaagacg accttccccg agttcgcgat atcgcggccc gcgacgggca  46980
tgctcgccgc gcagcgaatc aggtacgacg gcgacccgcg cgtctgctgc ggcgggttcg  47040
ggatctcgca ttactgggag aagggggcgc gccgatcgaa cgtcgcgttc gagggcgcgg  47100
cgctgcgcac ctgcgacccc acgcgcttcg acgcgggcgc gtgcgacgcg ctgctcttcc  47160
gcgagtgcgc cgccggcggc gtcgacgcgg acttctgcgc gcactggatc aacgcggccg  47220
tgacgcggcg cacggaccga cagtcgcgcg cgcggctgaa cgacatgttc gtgcgcgatt  47280
gccaaaacga cgccgcccgg cctcactgcg tggcctggat ccgcgcgatg cgaagcgcgc  47340
gcgcgacggc ggacgacggt ctaatagacg ccgtgctctc ggtgcagagt cccgagttca  47400
agggcaagca catgcgctgc agctacccct cgccggccac tctcgccatg gccgcgaacg  47460
tggacgagcc gcgcgagtgc tgggaccccg agtgcgtggc cgggaacgtg gacttcatgc  47520
taagcgataa ctacacgaac ctgggcttgt gtcggctctc gcgctgctcc atcggcgtca  47580
cacacctgcg gattgacgcg cgttcgcggc tgcgcatgcg gtgcgccggc gcgcttgccg  47640
ggctcacgaa ggcgcccgtg aaccagactg tcgtcgtcgg cgacaacctc gcgcgcgcct  47700
tcgagccgcg cgtggaaacg ctcagcgtgt tggcgctgtg cgtggtgtat ctgctaattg  47760
tctggctcta aatgggggcc gccgccagca ttcagaccac cgtgaccacc gtcagcgagc  47820
gcatccgcaa cgagctcgag cagagcgcga gcgctagcgc gaccgccgac tgcgacgtca  47880
ccatcgggag tctgattatc cgcaagaacc taggatgcag cgtttccgtc cggaacatgt  47940
gctcggccaa cgccggcgcg cagctggacg ccgtcatgaa ggccgtgagc agcaccttca  48000
acgacctctc gtcggaccag aaggcctacg tgcccgggct gctcacggcc gcgctcaaca  48060
tccagaccac ggtgaacacc gccgtcaagg acttcgagac gtacatgaag cagacctgca  48120
cggcggacgc ggtcgttcac aacaaaatca agatccaaaa catcgtcatg gaagagtgcg  48180
cctctctgcc agggagtccg gccacgcacc tggatttcgt gaacaccggc acggccgtgg  48240
gcaactgcgg cgtgaaggcc gtgatggacg tgctcgcgaa ggccagcacc accgtgcgca  48300
acgaccagga ggccggcaag ggctaccaga ccatcatcat cgcgatcgtg gtcgccatcc  48360
tggcggccat cttcgcctgg tacgcgcggc acatgctatt catgtccacc tccgacaaaa  48420
tcaagctcga gctcgccaag aagcccgtgg tgcactggac cacctacctg gacaccttct  48480
ttacggaatt tccgccgtcc gtctagatac gcgcaacatt gaaacattat atccacctct  48540
caaacggcgg tatggtccga cgcgtcctcc tcgagcgcgt ggacggcatc gtcgagcact  48600
cgcgcgcaga ccgacgctac ttggaggcca ttcagcgaca cctcgagggg tctacgcccg  48660
ggctgcggca gatgtggcgc ttcctctacg acctgctgct gacggtgttc gtcgtcatgt  48720
acatcgtctt ccgcctaatc gtgcgcaacc ccggcatctg cgccatcctc gcgctcgcgg  48780
```

```
ccgcggtgta ctacctgttt ttgtgtctct ttagcatgga ctgatggcga tcacagacag  48840
accatcgccc gcgcgcgcgt gaccagctcc ggcgccgcga agacgtcctg caccgggaag  48900
tcgtcgatct cgaacacgga gccgtccgcg gaccagatca cgcgcacgtt gtcgctcacc  48960
gagacctcgg tcagcgtcac gcccagcaca accgcgtcgt tggtgctcac cagcaccagc  49020
gcgccgggct ccgcgcgccg gtgcagcggc ggccccgaga ctgagcgccg ctgcacgcgg  49080
aacatgtccg cgaactgctt cgagagcaag tccaggtggt tgcggatgat ccactcgaag  49140
aagtacgcgc aaccgccgcc gccgcacagg aagcgcgaac ccgcgggcat cagcagccgc  49200
acaacgtcca tgtagcaggc ctgcggcagg ctcgcgcggt acagccgcgt cttcggcgag  49260
agcaccacca ggctggaggt gctcatctgg aagaccagct ggctaacgga gacggtgagc  49320
gtgcacgcgg gcacggaaac cacgtccagg cagatgtcgt ccagaaagat gctccgctgg  49380
tagaggtggt acaggatggc cacgatctga aaggccgtgg cgtcgctgat ggcgcagggg  49440
cggtcggcgc agcgcatctg cgcgcaggac cagcccccga aggactcgaa gcagacggtg  49500
agcatgcccg tgctcggaca gtgtggcgag cgccgacaca ccggaaagcc cacggccttg  49560
cggcagcgca ccatggtcga gagctctatc cagcagcctg cctcctcctc gcccatgccc  49620
atggctaccg gcgtgaaggc cgtgacgtcg tcgcagatgc gccgctccag aaaccccacg  49680
cccgaggagg ggtgcgcggc cggcggcgag gtgatgcgcg ccgggacgcg gctcggagcg  49740
ggctcgggag gcgagctgcg ctcgacccgg gcagtcgccg ccggccgcga tgccctgcgc  49800
gcgggcgcgc gctcgcgcaa cttgtttgac ttgctggcct cgtcgctagc gtcatcgaag  49860
cggtcgttcc tgtcgccgcg gacgtccgcc tcgtcgcccg tcggctgcgc ggcgggcgac  49920
gtgccgtccc gcgtacggcc cgcgttcggc gcgaatgtca cgcgccggtg cacgtacggc  49980
tccgtagagc ccgtgggggc gccgcgcccg cgcccgcggc ggaaggcctg ccgggacgcg  50040
ccgaagcggg cgaactcccc cttcgcccgg cccctttttt cttccatgat atttatcaca  50100
aaaaaaactt ctctaaatga ccaatctgct ttcgttggtc gacccggagg acctggcctt  50160
ctgcgccggg ttcccgtcct tcgacgagac catgctcgtg atcgcggggg cgcgagtgcg  50220
cttcccacgc tcgctgctct cgctcttcaa cgtggtgccg cgcaccatga cgcgctacga  50280
aaccgagctc gtgggcaccg agatggtggt gggcgccgtg ttcaccaccg cgtacaacgt  50340
ccgccgcaac ctaggcctcg gcgaggagcc cgtgaccatg cgcgacatcg agaagtactt  50400
cctggactcc gagaacgagg tgctcacgct catcgtgcac aacaccgact tttccgccat  50460
gagcggcgtg cgccggcgcg gcggccggcg catcgccaac cccgtcatct tccgcagcgg  50520
gtccacgccg ctgctcatcg tgatggagtc gcgcaagaag accaacatct accgcgagcg  50580
caccgcggag caggccaacg cctcctacag ggaggtcggc tcctcgctcg cgctggtcac  50640
tcggtacgcg ggtctgcagc tggttgacgt gcacacgccc agctccgtgc taacggtctc  50700
cgccgtctac ggcttcaccg aggacaaggg gctcaagaag ctgggctccg acaaggagct  50760
cgcggactac cagtccacgc cgctcaccga ccccatccgg ctcagcgact tctccaatat  50820
attcgacggc gtcaagaaga gcatccagct cacgaacgtg cccgtgccct ccaccggcgc  50880
cgaggccgcg ccgtaggctt tcatgcgcga taaatcggat ggcggcgccg acgacgcccg  50940
cggtgcacct cacgccggtg ttcgtggagc ctacgatcgc gcactcgctg ctgcgcgcag  51000
agtcctacct cgcgatcgcg gtccttgagc tcgtgctcgc gctcgcgctc gcgctcgtct  51060
tcttccgcga cgagctaggc tcgctattcc gctgcgcgcc gcgagcgcct tcgccgctgg  51120
```

```
acgcgtacct gcaggcgagc ctcgtctgcg acggcgacgc gctgctgatc gagctgcccg  51180
agggccgggt gccggcgctc gcgctggacg ggcggcccgt cgcgttcccg gggtgcgaga  51240
gccttttgta ccgcataaat ggaccacgaa aagtacgtct tgtcgatgtt cttggaggaa  51300
gataactcct tcttctcgtt cgtcgccgcg ctgtccgatg acgaggcgct cggcgccgtg  51360
cagtccgctg ccgccctcct ggacttcctg ctctccgtgg tggtccgcgg caaggagaag  51420
ctcgccgccg cggggcacca ctacgactcc atcgcggacg gacgcgcgcg cgccgcgttc  51480
gagttccgag acctgcgcga gctggcgcag ctcttcgacc ggcggccctg cggcgtccag  51540
gaccgcgtgc gtgtgcgcga cggcccgcg cgcgccttcg tggacgcggc actggggctc  51600
atgcgcgagc gaggcttcga cggcacgcag gccgcggagc gcgcgcgcta catcgcgccg  51660
aacgatctgc ccgcgctggg ggcaatatcg gccacgctct cgccgggtct ataacgtaaa  51720
aaatattagt aaaattctga aggtccgtgt gtttcgcggg cggccaacaa accagtcgct  51780
taaatggagg gggtggaaat ggacaagccg ctcctctact tcgacgagat cgcgggcgcg  51840
cgcgactacg acgcggcctt cgcggagaag cacgagccgc ccaagatccc cggccgcgga  51900
cagatgaagc tgctggtctg cgagctcgtg tttctcaacc ggctgcacct gcacggcatg  51960
ctcgacggca gcgtcatcgt gtacgtgggc tccgcgcccg gacggcacat ctgctgcctg  52020
cactcgcact tccaggagct cggcgtctcg cttaagtggg tgctcattga cgggcgcaag  52080
cacgacccct gtctctcggg gctgcggaac gtgaccacgg tgacgcgatt cgcggacgag  52140
gcctacctcc gcgagctgcg cggcgagctg cggcgcgcca agatcgtgct catttcggac  52200
atccgctcca accgcgtgga cacagagccc accaccgcgg acctgctgcg cgactacgcg  52260
ctccagaaca ccatggtgag cgtgctcaag cccgtggcct ccagcctgaa gtggcgctgc  52320
cccttcccgg actcctggga gaaggacttc tacgtgccct gcggcaagga gatgctgcag  52380
ccgttcgcgc cgccgttctc cgcggagatg cggctgctca ccgtgtactc ggagacgcgc  52440
ccgaagctgc gtctgatcac gctcagcgac gcggtcaact atgaaaagag gatgttctac  52500
ctcaatagcg tggtccgcca gcgcgtaatt ctgaactttg actatcccaa ccaggagtac  52560
gacttctttc acatgttctg tctgctctcg tcggtggtgt gctcgtgcga atttaaatcg  52620
cccaaagaga aggtgctgag cctgcagaac cgcttcttcc gcttcctgcg catcccgccc  52680
tccatcacgc tcgggctgcg ccggcacgat gaaccgccac aacacgcggt acctggccaa  52740
gatcctctgc ctaaaggccg cggtaagaag cgaccccttc gcggtggtaa gtagggacac  52800
cgtgcgcatg tacgacatcg aggtcgagta cggcgacctc gtgacggtgg tcaccgtcac  52860
gcacaaactc gagaccagcc gcaccgtctt ccaggtcttc aacgagacct ctgtcgcgta  52920
ctcgccgctg ccggacgact acggcgagcc catcgtgctc accacgtaca tgcagcgcga  52980
gcacaccaag ttcccgctct ccatgctcta catcgacgtg gtcgcctcgg acatgttccc  53040
cacgtttaag cgccccaccg aggaggaggc cgcggtggtc gcggccatgc agcgcgtggg  53100
cgggcgccgc gagcccgtgc tcaagctccc gcgcatgctg gacaccgagc tcgtgtgcaa  53160
gatactgcac ctgcccgagc acccgctgcg cgtggtgcgc ttcctgcgcc gaaacatgtt  53220
cacgggcgtg gaggtcgccg accgctcggt gtccgtggtc ctcgactgac gaagggcagc  53280
acggtcagcg aggccgccgc caccaagcac agcggcagcc acgcgcgcgg gtccgccacg  53340
ggcacgaaga cgtgctggtt caggtacttc gcctggaagc gctccgcggt ggagtccacc  53400
ttggacccgc aggcgttggt gaggcgcacg accgcgtccg cgacgcgcac gtccccgagc  53460
gatatcacgc agtcagagac gttgcacccg gcgatgtttt tcttcagcgc gcgcggcagc  53520
```

agcgcgtccg cgcgcttgca gggcgcgtac cagcagtagt agggcaggcg cgtgtcgcgg 53580
ccggtgtcga ccacggcctg gctgggcttg aggcacgcgc agcgctcgtc gtccgggtgc 53640
gcgtcgcaga aggcgtaaat ctcctcgtcg ggcgcgtccg gcccgggcgc ggtcggcggc 53700
gccgcgcgac ggcggaagaa catctctgaa aaaatacttc gaccagaaaa cgaccaccga 53760
tcttatttca aagataaaaa tactattaat acgcactcgg agaatcatgt cggtggtggc 53820
gcgcgtgtcg tacagcctgt actcgcagag cgagataagc gccacggacg tggtcatcag 53880
ccagttgaag aacgacgagg acctgggcac ggtgaaggac ccgcgcctgg gcgcctcgga 53940
cgggtccata tgccgcacct gcgggctcac ggagatggag tgtttcgggc actggggcaa 54000
ggtgcgcatc tacgagtcct acatcgtgcg ccccgagtac atccccgagg tggtgcggct 54060
gctcaaccac ctctgcgtgc gctgcgggct gctgcgctcg cgcgacccgt acacgacgga 54120
cttggccgcg ctcagcgtgc acgagatgcg caagatgaag gaccggatga tgtccaagaa 54180
gaaggcctgc tggaacagca agtgtctgca gccgtaccag aagatcgtct tctccaagaa 54240
gaagatctgc ttcgtgaaca aggtggacga gatacccgtc cccaacgcgc tcatctacca 54300
gaagctgacc tccatccacc gcaagttctg gccgctgctg gaggtgttcc aggaccccgc 54360
gaacctgttc tacaaggagt acatgcccgt cccgccgctg ctcatccggc cggcgatcag 54420
cttctggata gacaacatcc ccaaggagac caacgagctc acctacctgc tgggcatgat 54480
cgtgaagtac tgctccatga acgccgagga gcaggtcatc cagcgcgccg tgatcgagta 54540
cgacaacatc aagatcatct cctcgaactc gagcagcatc aacctctcct acatcatcgc 54600
gggcaagagc aacatgctgc gcagcttcgt ggtcgcgcgg cgcaaggacc agaccgcgcg 54660
ctcggtcatc gggcccgact ccgcgctctc ggtgtgcgag gtcggcatcc ccgactacat 54720
ccggaacacg ctcacgcaga aggtgttcgt gaactacctc accagcaagc gcgtgcgcgc 54780
gctgttcgag gaccgcgcgg tcaagttcta cttcaacaag cggctgcgcc agctcacgcg 54840
catcaaggag ggcaagttca tcaaggacaa gatccacctg ctgcccggcg actgggtgga 54900
gatccccatg tccgagggca cgaacgtgat attcggccgc cagccctcgc tgcaccgaca 54960
caacgtcata tcctcgaccg cgcgcgcctc gcccggctac accatcaaga tcccgcccgg 55020
gatcgcgaac tcgcagaacg cggacttcga cggcgacgag gagtgggccg tgctcgagca 55080
gaaccccaag tccgtgatcg agcagagcgt gctcatgtac ccggtgacta tcttcaagca 55140
cgacgcgcac ggcgcgccgg tgtacgggtc catccaggac gagatcgtgg ccgcgttctc 55200
gctgttccgg caccagaacc tctcgctgga cgaggtgctg aacctgctcg ggcgctacgg 55260
gcgagacttc gcgccggagc ctggccagaa gaccttctcg ggcgccgacg tcttccgatt 55320
catgataggc gcggacataa acttcaaggg cgtgctcgag aacgggcgcg tggtggcgcc 55380
gaacgtcgac agcgacctcg tggtggccat gcgcgcaacc tcgctagcgg ggctgatcgc 55440
ggactacgcc acgaacgtgg agggcgtgcg cttcgtggac atggcctcct acgtgtacaa 55500
gcggtacctg gccatctacg gcttcggcgt gaccttccgc gacctgcgcc cggacccgag 55560
tttggttcgc cggctgcacg cgctgaacac cgagaagata gagcagatca aggacgcgta 55620
ctcgcggtac ctgcaggacg tcgcggacgg gaagctggtg ccgatggcgc ccgcggacga 55680
ggccgacgcg ctggactcgc tgctggccaa cctgaccaac ctcaacgtgc gcgagatcaa 55740
cgagtacatg cgcgagacgc tggagcgcaa ccccgataac agcctgctaa agatggcgcg 55800
cgccgggtac aaggtcaacc ccacagagct catgtacctg ctgggcacct acgggcagca 55860

```
gcgcgtgaac ggcgccgtcg ccgagaccaa gatatacggg cgcgtgctcc cgtacgcgtt  55920
ccccgactcc gcggacccgg aggcgcgcgg ctacatcatc aactcgctca tgaacggtct  55980
ctccggctcg cagttctact tcgcgatgct ggtggcgcgc tcgcagtcca cggacatcgt  56040
ctgcgagacc tcgcgcacgg gcacgctcgc gcgcaaggtc atcaagaaga tggaggacac  56100
ggtcgtggac gggtacggac agatcgtgag cggctcggta ctgctcaagt acgcggccaa  56160
ctacgcgaag atcccggggt ccaccaccaa gcccgtggag ctgctcttcc cgcacgagag  56220
catgacctgg ttcctggaga taagcgcgct ctggacgaag atccggcacg ggttcgtgcg  56280
catgcaccgg cagcgcctgg ccaccaagat cctggcgccg ttcaacttcc tggtcttcgt  56340
gaaaccggcg ccctcggagg cggaggcgct ctccgcgcgg gacctgtacc acatgatcca  56400
gcgcgtgatg aacgacgtgc gcgagaagta cttcttctcg ctggcgaacg tggacttcat  56460
ggagtacgtc ttcctcacgc acctgaaccc ctcgcgcgtg cgcatcacgc gcgcgaccgc  56520
cgagctcatc ttccgcaagc tgtaccagaa gctgaacgcg ctgctcggcg gcggcacgcc  56580
cgtgggcatc atgtccgcgc aggtgctctg cgagaagttc acgcagcagg cgctctcgag  56640
cttccacacc accgagaaga gcggcgccgc gaaggtgaag ctgggcttca acgagttcag  56700
caacctcatc agcatgagcc gcaaccacac cgagatagtg gcgctgaccg cgccgagcgc  56760
ggacaagctg atgccgctga aggtaaactt cgagttcgtg tgtctgggcg agctcgtgcc  56820
cgagatcgag acccggccct cgggacggcc ctccgtgcac cgcgtggaca tcacggtgca  56880
ccgcctgcgc atcaagcgcg cgcacctgac cgaggtcctg gtggacacca tcatcgagcg  56940
cttcgtgtcc ttcaacgtgc tcgtgaagga gtggggcagc gacatgaccg tggagggcga  57000
ccgcgtcacg tacacgctgc tgctgcgctt cgtggagccg gagcagctca acttccacaa  57060
gttcatgctg gtgctgcccg gcgccgcgaa caagggcaag gtgagcaggt tcaagatccc  57120
gatcaccgag accacggtct acgacgactt cgacgccgcg cgcaaggcct accgcatgaa  57180
catcgagctc atgagtctga aggagctggg gatattcgac ctcgaggacg tgaacgtggt  57240
ccccggcatg tggaacacct tcgacatatt cggcatcgag gccgcgcgcg ggcacctctg  57300
cgagagcatg ctggacacct acggcacggg cttcgactac ctgtttccct cctgcgacct  57360
gctcgcgagc ctgctctgct ccgggtacga gcccgagtcc gtaaacaagt tcaagttctg  57420
gaacgcgagc gcgctgaaga aggccacctt cggcgacggc cgcgcgctgc tgaacgcggc  57480
gctgcacaac cgcaccgacg cggtcgcgga caacagcagc tgccacttct tcagcaagac  57540
gccctgcgtg ggcacgggct actacaagta cttcgtgaac gtggagatgt tcatgcgcat  57600
ggagcgcgag atccaggcgc gcgtggcggc gcgcaagatg gaggagatcg aggaggccgc  57660
cgaggaggag ttctaggcgc gacggcgcct tactttgcga ccgtgtcacg acgacacgac  57720
acggttagga cggcgagtcg cagacgaaca tttttatgag ctggtagcgg aagttggcgt  57780
tttccaggaa ggcgccgcgg aggtcccgga tctcgtagta ggttttgagg aagtacacga  57840
agcgcgcggg ctgcgtcata gtcgggttct ccgcaagccg cttgtgcatc acgtacccca  57900
tggcggcggc gccgctgcgg ttgacgccgg ccacgcagtg cacgagcgtg ggcttctgct  57960
cggcctcgag gcgcgccagc agcttcacga gcgcgggcat gatggaagcg atgttcgtcg  58020
tgtcgtcgtc tctcagcgga atgtggtacg ccgttatccc cgcgggcgtc gagtacttgg  58080
acatggtcat gttaaccaga cacttgaagt cgacgccgga gtccccccgc agcacggcgc  58140
gcgcgtcctc ggcgctgccc aagtacacgt ggtccgtgag ccgcgtcatg cccgagggca  58200
gggccagcgg cggccccgcg cgcgtgcacc gcagcaggag cctggcgtac cactcgctct  58260
```

```
tatcgcccat atttatttat atgatacaaa tggcagacgt cacaacactg acggccaacg  58320
gtctgaccct ggagttcgcg cgcgagcgcg ctctgcgcag tctgcgcgcc gcgcgcacct  58380
ccacgctggt gttcttcacg ctcacgctcg cggcctcgct gttcgtgctc tggctgcagc  58440
taaccgagtt tcccgtcttc gaggagctcg gcaagtacgc gcgcatcaag agcgcggtgc  58500
ggtcctggcg cccgctggtg gaggctaaga cagagatcga gtccgacctc ggccggcaga  58560
agaccgccga ccggcccgag ctcttcgagt tcaggtgcgt ggacttcggc aagttctacc  58620
tgccggtgag gtacagcccc acgaccttcc tgccgcaagc cgtgcgccgc ggcgcgggcg  58680
atggctggat ggtgcacaag gcggcggccg tggacctcgc cgcgcagcag ttctgcgagt  58740
ccgtgctgcg gcaccgcgcc aacaacgtca tcacatgcgg gtcagagatg atgcggctgg  58800
tgggctacag cggctacttc gaggacgacc actggtgcgc cgcgacgtcc ggcgtgctga  58860
cgtgaacgat cacacgatgg ccgtgaccag cagcccggcg atgaaccaca gcagccgcga  58920
gttcggcagc agcagcacga gcaccagcag gtacgccagg atgaagatgt cgaccacgtc  58980
cacgtcgaag agccccatga aggagaagag cggcgtggtg aggaagtaga tggcgccggg  59040
ccagaagcgc gccagccacg tggcgagcag cgaccacagg gagggcgcgc cgctgagccg  59100
cgtcttcacc tgtatgtagt actcggggta gaccacctgc tcggcgccgg agagcaccac  59160
gcgcgccaga gagagccgct tctccagcgt gaacacctcg gtgagcaggc cgctgcgcag  59220
ccctccctcc ttgatgatcg cgtcgtagag cttcttcatg ccgccgacgc tgatgatgta  59280
ggcgtctagc gagacgtcgt acccgccggg gtagaccatg agctcggggt cgccggtgcc  59340
ggggacgttg gtggccagcg cgccggtcat gtaggtctcc ttgagctgcg tcatgtacca  59400
gccgttcgcc ttcatcgcct cgatgagcgg cttcaccatc tcgggcttgc ggaaggtcat  59460
gtcgttgtcg accaccagga tgaagtcatc gtcggagtac ttggtgggga cagtgccggc  59520
cgatatgctc tcccagaggt tgaggtggtg cgctgcgcgg cgctgcatct ccttcggaca  59580
cgtggacttg cacatgtccg tgaagaagtg cgggtagtct ttggagtcca cgtctttcca  59640
ttccaccgcc ttgagcacgt ggtcgccctt ggggtgcggc gcgggaggag atggcttggg  59700
tgccggcgcg ggggccggtg cgggggctgg ggcaggagag ggagcaggcg cgggttgagg  59760
cttgggcggg tcgtcggcga ggcccaccag gtacggcagc gtggggaaca cctccttggt  59820
cccgcggcct tcggcaaccc cgattatgta ggccgtgatt tcgggtggat ccatttagtt  59880
attaaaatta atcatataca actcttttat ggcggctatg gattcggcta tccagtcctt  59940
gaccgagccc acgatgcccg ccaggaacag gaagaaggcg aactccaggt ccacgcggtt  60000
cagagagtcg ctgaagtaca cgaagacgtc gctgtccggg aagaagctgc gccggaacat  60060
gttgtacccg ttgaccttgt gcgcgacgtg ctccgcgctc agcagcgtct cgtcgaaggg  60120
gtacgggtcg ctgaagcgga acacgtacat ggccgggttt gcgtagtagt acttcatggt  60180
gtttgtgacg aagaggctcg ccagcgagat gatgattttt ttcttctcga tctcgatctt  60240
gatgtggtcc tcgaagcgct tcatgttgta ggcgttggtg tcgtgcacgc ggatgagcac  60300
gcgcgagtcc gacatgatgt cctggaactc cgcgcgcgcg tcggggctct cggcgggcgt  60360
ctccgcgggc cgcgccacct ccgcgcacac cgtcggccta gcgcgcggcg gcgtgcgcat  60420
gggccgcgcc cccacgcgct gcgaagcgaa aaactccacg gcgcgagcct cgcccgcgtc  60480
cgcgtacgac tccaccaggt agttgcggct gcgcgtggtg cggccgatgg tgttcagccg  60540
gtgcagctcc gcgaccagcc ggcggtagtg cgcctccagc tcctcgggca tgatggaggt  60600
```

```
gtacacctcg gtgagcagca tcacggtgtc gaagtcctcc ttgccgcaga cgcgcgtctt  60660
cacgaggaag tggtgcacag ccgtcgcgat agagagccgc agcgtggact cggtgacctc  60720
gacgctggcg tccttggtct tcttcgcgct ccgcgaggcc atgaacgaga cgaggaagtc  60780
cgcgctgctg ttgagcacga tgaccagcgc gacgatgaag ttgaggttca gcgtcttcgc  60840
ggactggaac agctcggtgg ccgacgcgtg cacgtcgagc aggttcgcgg agagccgcag  60900
gaagaacacg ccgcgcttga tctcggccgc gaagcgacgt tcgtactcct gccggcgcgc  60960
gttgatcgcg atgaggaagt tcaggatgag ccggttgatg ttgtacttca cggcccaggt  61020
ctgcgtcttc atgatggtgt cgaaggacat cacgatgttg aagatgaagc gctggctgtg  61080
cgagaagtag ctgtagggct cgctgaggaa gatggacttg ttggtcgcgg gcaccaccac  61140
gcccgcgcgc gcgccggacg cgtcggtgtt caggtccggg atgttcatgc cgcagatgcg  61200
gcagtaggcc atgccgtcct caaagtacac gaactcctcc acgaactcgt tgatcttggc  61260
gaagtagtcc acgtccacgc gcatcgcgac cgcgagccgg atctggtgct cgcagggcgg  61320
cgactcgaag cgcacccccct cgccccagcc cggcggctcg cgcacgacca gcgcggtgcg  61380
cgaggccggg cggaacttgg cgtcgcgcgc gttgagcagc gccgggaaga ggtcgcagag  61440
gtgccggctc gagaggaaca cgtacttgta cagcagccgg cgcgcgtccg cggccatggc  61500
gtccacgaag gcgcggcccc actccgcgac cgcgggctgc tcctccgcaa agttgttcgg  61560
gtagaccttg tccgtggccg cgaggaacac cttcttcacg tcgaggaagt cgcggatcac  61620
gatggggacg cgcgcgccgt cgagctcgta catgaacacg tagcgcaggt tgagcttgcg  61680
ccgcgagacc gggatgccga tgtgccgaca caggtacgcg aactcgaggt acttcttcga  61740
gaagcggatg cggtccaggt tcttggagac gtactgcagc atgttgcgca tgttgaaggg  61800
gatctcgcgc acggcgggct ccgcggcgtc gtcgaaggcg gtgcgcagat cgctggtgcg  61860
ctgtacgacc acggcttcgc cggtggcgtc gtcgtgcacc agcacgttaa cgcgccgctg  61920
ccggatgacc atgtcgaagg tgttgaagaa catctcgtac atgctgtgcc gagtgtcgtc  61980
cgcgatgcgc tcgcccaccg agaggctcgc ggtggcgtcg tcacgcacct gcttctcgaa  62040
cttgtacccg atgtaggaga atatcgagat cagcgtggcg tcgtcggcgt cggggttctg  62100
ctccatggtc gcgaagagca ggcggatgtc gtcctccgtg atcgcgtcca cgttgtacag  62160
gttgaccacg aagatggact tgttctcggc gatgaagtcc gtgtaggact tggtggccgt  62220
gttcgggtcg cgcatgtacg cgcggatctt cggcacgatg ctcgcgagga tggactccct  62280
ggaatccatt taaggacggc aagggcgcgc gagaccgtct caaaactgaa atcgtataaa  62340
ctcttaaaaa atcggtattg aaagtacgca ccaccaaata aagcgtcgag gtcgggcatg  62400
tcttcgtggc gactcaaaat gagcaagtgt tcaggttcca gcagcgtcca gactctcgag  62460
gatctgcgta atcgtcttcg ctccgaggcc ttgggcaacg attgccaaga gccccgcgac  62520
gacctcttcc ccagcggcga ggagtgtctg gacatcgacg ggccctgccc ttgcgatgag  62580
gcggagcagg agatcgacca ggagcagttg cccgtgcccg aaaccgtgcc cgaaccgccg  62640
gccaagactc ctaagcgccg accagtgaag aaggataagg cagataaggc agataaggac  62700
aagtcgacca gaggcgcaaa gaaaccgtgc ccttcggacg acaaggatga cgagctcaag  62760
agcaacgacg tcgacaacaa cgaagagtcc ggcgacacag acggcggcgc gagcgcccga  62820
agccccagcg acatcgacaa cgtggacgaa atggacgact ccgacctcat ggtggcgttc  62880
tccaccatcc tcgcagactt caaggacctt acccaacgag tgaaagctct ttcgtccgtg  62940
ctcacggacg tgcaggcggc cggcatacgc aggagcttct cgacgctcgg caaggctctg  63000
```

```
acggaggcgg cccacatcgc caacaccgga tctaagccag tcactgcgcc tcgcaagaag  63060
aaggccgccg cctgcaagaa gtaggcgcac taaatagcga ggctcggtat gcgggcgctg  63120
cacctgtcag acggcaaact tttttttgac aaggagctga cgcagccggt ccccgacgac  63180
aaccccgcgt acgctgtcct tgcgaagatc cggatcccac cgcacctctc ggatgtggtc  63240
gtgtacgagc aggacctcga gtctgcgcag cagggcctca tcttcgtcgg gcgcgacgcc  63300
aagggccgaa agcagtactt ctacgggcgc ggacacgtgg agcggcgcac ggccgtccgc  63360
aacgccgtgt tcgtgcgcgt gcaccgcgtc atgaacaaga taaacgcctt catcgacgac  63420
cacctcgcct ccggcagcga ggccgaggcg cagatggccg ccttcctgct catggagacg  63480
agcttcttca tccgcgtcgg caagacgcgc tacgagcgcg agagcggcac cgtgggcatg  63540
ctcacgctgc gcaacaagca cctcgccgag gccgagggcg gtgaggagat ccgcgtcgcc  63600
ttcgtgggca aggaccgagt cgcgcacgag tttgccgtgc gcgaggggca gcggctcttc  63660
gcggcgctgc gtcggctctg ggacccgggc gcgcccgaca ggctgctgtt cgaccggctg  63720
agcgagcgcc gcgtgtacac cttcatgcga cgcttcggca tccgcgtcaa ggacctgcgc  63780
acctacggcg tgaactacac cttcctgtac aacttctggt ccaacgtgcg ctcgctggag  63840
ccgcgtccct ccgtgaagtc gctcatctgc acctccgtgc ggcagaccgc cgagacggtg  63900
gggcacacgc cctcgatctc gcgcagcgcc tacatggcca ccgcggtgct cgagctcgtc  63960
agggacggcg cgttcctgga cagagtcgcc gccaccgaca cgctcgacga cttcgtggac  64020
atcgtcgtgg actatgtaaa taactctgag caggtaaatg gatgaggcgc tgcgcgtggc  64080
ggcgcgcgtc gtggacgggc tccggccgct ggacgtggcc gtgtgtctcg cgcagctgcg  64140
cggagccgcg cccgagcgcc gcttcccggc gctcgacgag tgctccggcg aggccttcct  64200
ggactttgag ttcgccggcg gggacgtggc gtcgcggtac ctctccgcgc acacgcgcga  64260
gctccgtgcg gcggagcggc gcgagcacat ggccgcgatc gcgcgctgcg tcaccgaggc  64320
cgacctggcg ctcgcagacc gcccccgggg caaggcgcgc gcggcgctgc gcgtgtgccg  64380
caaccgcgag aaagtcgcgc gcttggcgag gctgctgcgc gacgccgaga gcagcggcgc  64440
ggacttcgcc ttcatacgcg cggccgtggc gtagcaaaac gtaaaaacaa cacattccct  64500
aaatcgccat ggacgcgcca agtctcgact gcatgctcgc cgcactcgcg gcgaaggcgg  64560
cctcggtgga ccgaggcgct cccgaggacg aggtgcacca cgaagtggag ctcgtgctcg  64620
tggacccgcc gctgtccacc ctggccgcca cgctgcgcct ggcctcggag acggagtcct  64680
tcatcctctt cacggtgacc gcgctcgcca aggaggaggg caagctgcgc gcgcgcgtgc  64740
ccatgtcgcg cgtcgtcggc ctggacgtga agaacgtgca gctggtcaac gccatcgaca  64800
gcatcgtctg ggagcgcaag gcgctcgtgg aggagaccgc gctgcaggaa ggctgtctgc  64860
tgcgccactc caccgagcgg cggcacctct tcgtggacta caagaagtac ctctcggcca  64920
tccgcgtgga gctggtaaac cgcgtgcgcg tgcgctccaa agaagtcgtc gcggacttca  64980
agttcaagta ctttctgggg tccggcgcgc aggccaagag ctcgctgctg cacgcactca  65040
accaccccaa ggtgcggccc tcgcccacgc tggagttcga ggtcgtcccc gcgggcgagg  65100
ccgtggacga ggccgccgtg ctcgcggagc tgcgcgccgt ggcgaaggcg ctcttcatgg  65160
cgcccaccga cgccgtcttc ctggcgccgc cggccgagat gccggtgcgc acgctcatgc  65220
tgcagaagca ggagatcccc gcgctagacc tcgacggcct tttcgcggtc tccaagacgg  65280
acggcgtctc cgcgagcgtg tgcgtggacg aggacggcgt cttctgcgcg ttctcgcacc  65340
```

tcgcgtacac catccggtac ccgctcgcgc gcgaagtgca gggccggtac cggctctggt 65400
gcgaggccgt gcggcccgtg ggcgagcgcg tgtggtccat gttcgtgctg gtcgtggagg 65460
agcctgcggg cgatgaccgc gtcgcggccg tggccggcgc cgtggaggcg ctgcgcggcg 65520
tgtgtgcacg cgtcgagttc aaacctaagc gcgtggacgg gcccttctcg gcgacctccg 65580
agctggtgga gcacatcaag agcgcgctgc agacggagcc agagggcgtg gtgctcttct 65640
acgcgcgcgg agagaagtcc aagcgcgacc tcaaggtcaa gcgcgacaac acggtggacc 65700
agaccacgaa cgtgatgttc cggtacatgt ccagcgagcc catcgtcttc ggcgagggct 65760
ccaccttcct ggagttcaag cggtacagca acgaccgcgg gttccccaag gagtacggcg 65820
cggggcgcat cttcctgcgc gaggacgtgg tctaccacaa caacatctac tgcatcgagt 65880
tcacgaagac gcacctggag gtgggcctcc gcagcgtggt cgtgcccgtg aagttcatcg 65940
gcgagttctc gcaggagggg tacctgctgc ggccgcgcct ggccaaaacg gagtgctact 66000
tccgcaaccc ctcattctac gggaaccagc actcggtggt gctcgagcac actcgcgacc 66060
agctgctctc ggtgggggac gtgttcgacg agagccgcat ggccgccgtc gggcagacgc 66120
tggccaacga cgccttccgc ctgaacccgg acacgcccta cttcaccaac cgacgcacgc 66180
gcgggccgct gggcgtgctc tccaactacg tgaagacgct catgatatcg ctgtactgct 66240
cgaagacctt cctgaacaac gccgagcgac gcaaggtgct ggccgtggac ttcggcaacg 66300
gcgcggacct ggagaagtac ttcttcggcg agatcgcgtc catggtggcc acggacccgg 66360
acgcgcgcgc gatcgagcgc gccatggagc gctacaaccg cctcaacgcg gggctgaagt 66420
cgcgctacta caagtttaac tacatccagg agaccatccg atccgagacc tacgtggaga 66480
gcatccgcca ggtcatgtac ttcgggcgct tcaacatcgt ggactggcag atggccatcc 66540
actactcctt ccacccgcgg cacttcgcca cggtgatgcg caacctgcgc gagctcaccg 66600
cgcccggctg caaggtgctc atcaccacca tggacgggga cttcctgtcg acgctctccg 66660
agaagaccag cttcgtgatc aaccgcaacc tgcaggagag cgaaaacttc atgtcgatcg 66720
agcgcgtggc cgatgaccag gtcatggtct acgcgccctc gaccatggcg cagcccatga 66780
cggagtacat cgtgcgccgc gcggacatcg tcaagctctt cgcggacaac ggcttcgacc 66840
tcgtggacca cgcgaacttc gagaccgtga tccggcgcag ccgccgcttc gtcgagggcg 66900
tctcgcggct ggagacgcgg ccctccacca agaacttctt cgagctcaac cgcaacgcgc 66960
tcacggagat ggacagcacc gacgtggccg cgctgctaaa gatctacgtg ctgtacgtct 67020
tcagcaagcg gtaggcagaa ccagggcgtc gattccgcgc ccgcgccggc gcggaaggcg 67080
ttgaacagct ccgccagcca ggctgcggtc tcgcgcgcgt cgatcgggcc gccgtcgtcc 67140
ggcggcggct cgcgcgccgc gcgcaacacc agcgtctccg cgggcggcag aggctccaga 67200
gcctcgaaga ccgcgcggct cgggaacagc gcgcgcatca tgcgcgcgcg gtggccgaac 67260
accgccttga ccgcgcgcag tgccgagcgg ttgtccagcc gcagcgctcg gtcaaaacga 67320
tgcacgcgcg cgggcgcgcc gcggtggtcg cgctccacga gcacgtgccg ccacgccagc 67380
gccgcgccga cgcggtccag gctgggcgcg agcgccacca ggcttttcag cgcatgtaaa 67440
tctccgcgca tggccgacgg ctccatttac tactgcggag gaacgcacgt ggtcgcggcc 67500
gcgccgggcg ccgcgcttgt ggtgctggac gcgcccggtg cggcggcggc ggccgcgccc 67560
gcggggcagc gcgtcttctt cgccgagtac ggcctcgaga agcgggccgg cggcccgatc 67620
acggcgcggc tgcgccgctc cgggttccgc ggcgccgcga acgcctgggc ctccgtggcg 67680
gacttcgagg ccggcggccg tccctccgcg tggacgctgc gcgcggagga ggcttcgcgc 67740

```
gtgccgctgc cgacggacgc ggcgctggtc ctggcctggg gcgcgcgcga ggagccgctg  67800
cgggcgtgcg tgctggcgcg cgcggcagac gcggaggcgc cggtgggcgc cgcgctcaaa  67860
gaagccgcct tcgacgcgcg ggcgccggcg gccgcgctgt tcgcggcgct gggcgcgccc  67920
gcgctcgcgc ccccgctgcg ggcgcggcta gtggcgccgc cgggcgcgcc gccgcggacg  67980
cggctctgcg agaacccggc catgctgcgc gcgttcgcgg tgggctggtt cggcgcgcag  68040
ctgggcgagg cctccgaaaa tgaaaaggta tttgccgcct ttgataaggc gaggtcgtgt  68100
ttggacgacc gctgatggcg acgcccgcga acgcgcccgc gctgctcgtc gcggcgctgc  68160
gacaccgccc gtaccgcgtg gagtaccacc cggactggga gccggtcatc gagacgctgg  68220
tggacgagta cgacgcggtc gcgccctggc tgctgcgcga cgcgacgagc cccgagcccg  68280
agcgcttctt cgcgcagctg gcgaagccgc tggcggacaa gcgagtgtgc gtgtgcggca  68340
tcgacccgta cccgcgcggc ggcaccggcg tgcccttcca gtccccggac ttcagcaaga  68400
agaccatccg cgcgatcgcg agctcggtcg cgcgcacgac cggcacgcag ggctacgcga  68460
actacgacct ggacgcggtt ccgggcgtgc tgccctggaa ctactacctc tcctgccgcg  68520
agggcgagac caagagccac gcgatgtact gggagcgcat ctcgcggctg ctgctgcagc  68580
acgtggccaa gcacgtgagc gtgctctact gcatggggcg cacggacttc cagaacgtgc  68640
gcgcgcgcct ggacgtgccg gtgacgctgg tggtgggctt ccaccccgcg gcgcgcgacg  68700
ggcagttcgc gcgcgagcgg gccttcgagg tcatcaacgc cttattggag ctcaacggga  68760
agtctcaagt ggactgggcg cgaggatttt ctttttatag tgaaaattaa tccgtggtcc  68820
taaatggcgg cgcccatatg cgataactct cacgtgttcc tcctcaagcg cctgggcgtg  68880
ccgtcttcct gccggcgctc ggaggacccg cgcttcgtgg agatcctgac tcccttcgag  68940
ctctcaaact acatcgagcg gcacccggga tgctgcctct tcgagacgct gcgcgacgag  69000
gaggactgct ccgtcgtgcg cgtcttcgcg gacgtggaca tggacagcgt gctcgaggag  69060
gaggacttcg tcgcggcgct ggaggacctc atcgtggagc tcgcggcctt cttcgaccgc  69120
ttcgcgagcg gctcctgcgg caccgtgccc ggcgaggtca agcgcgccat gctcgcgaac  69180
ttctcggtca cgcgatccac ggccgagcac aagaccagct tccacctgat cttcacggag  69240
acgtacacca cgctggacac gctggtggcg gcgaagcgcc cgctgctgga cctgtgccgg  69300
cgctcggaca acgtgctgct gcgcgcgctg gacacggccg tgtaccgccg cggcgcgacg  69360
ctgcgcgtgg tgggcacgcg caagacgccg gagtcgagcg cggtccaccg catgcagtcg  69420
cccgacgacg acatcaagga ctacctgttc acgttcgtgg agctctcgga cgcgagcgtg  69480
tacttcgagc tcgcggagcg cgagcagcac acgctgagca ccgtctgctg ggagacctcc  69540
tacatcccct tcggcgacgc gatgcggcgc gtgtgccagg cggtggtcaa cgacatcgtg  69600
aacctccgcg acatcaccga ggacaacttc ctcgacacgc cgctggtcat cgactacgcg  69660
acgcgctgcg cgctgtgcaa gaagcccaag cacaagcacg cgcaccacat caccatgggc  69720
aacggctgcc tgcgcctggt caagggcggg aacgcgcaca gctgcaaggt caagatcatc  69780
cagctcgagg gcaaccggct cttcacggcc gcgcagatca tcatcgcgtc cgaggtcgtg  69840
aagctcaccg agcgcaacga ctacatcgtg tggctgaaca actcctggcg cttcagcgcg  69900
gaggagtcgc tcatcaccaa gctcatcctg gacgtgcggc actcgctgcc cgcggactac  69960
gccaacgaca tgctgtgtcc gcgcaagcgc aaggtcgtgg agaccaacat ccgcgacatg  70020
ctcgtggaca tctccgagac ggacacgcag tacgacaagc tgcccttcac gaacggcgtg  70080
```

```
ctggacctgg ccacgggcga gttcctcacc ggcgaccgcg cgaaggcctg cgtgtgcacg  70140
gtctccaccg ggtacgcctt ctcgcgcgag gagttcgcgg ccgcggcgga ctcggaggcc  70200
atgcgccggc tggtcggcgt catcgacgac atccagccgg acacgcccga gaacgccgat  70260
aaccgcgcgc tgtacgagcg cgccatgtcc agcgcgctct gcggcgccac gaagacggtc  70320
atcgtcttct tctacggcga caccatgacc ggcaagtcca cgagcaagcg tctgctcatg  70380
tccgcgctcg gcggactctt catcgagacc gggcagaccg tgctcacgga cgtgctcgac  70440
aagggcccga accccttcgt ggccaacatg cacctgcggc gcgcggtctt ctgcagcgag  70500
ctcccggact tcgcctgcaa caacgcgcgc aagctgcgct ccgacaactt caagaagctg  70560
accgagccct gcatcgtggg ccggccctgc ttctccaaca agatccacaa ccgcaaccac  70620
gccaccttca tcatcgacac caactaccgc ccggtcttcg accgcgtgga caacgcgctc  70680
atgcgccgcg tggcgctggt gcgcttccgc acgcacttct cctcgtcggc cactcgcgcg  70740
gccgccgcgc acaacgtcga gtacagcgcg gtcaaggaga tggacgagag cctggacacc  70800
aagatccagc gcaactactt ccgctacgcc ttcctgcgcc tgctcgtgca gtggttcggc  70860
aagtaccacg tcccgcaggt ctcgctggcg cccacgcccg acgcggtccc cgacttcgcc  70920
ttccaccgcc gcgtggccga gctggtggtg gccagcaacg acgcgcaccg ccgcgcgatg  70980
gagtcgctgt ccaagctggg gtacgtgctc gtgggcggca acgtggccat gcccgcggac  71040
gccttccggc agcggctggc cgcgcacttc aacgcgcgcg tgcacggcgg cgacatagac  71100
gccttcatgt tcaagcacaa gaaggtcgtc aacgtaacgg aggagtacgt ggagtacgta  71160
ttcatcgaag atgtcgagaa taaatagacg ggtatgaact cggacgtgat aaagctgttc  71220
gtcgggcacg acgagtccgt gcccggcatc ctgccgcacc agctcgcgac cgtggacttc  71280
ctgatacgcc gcgttctaga cgacaacgtc agcgtgcttc tcttccacat catgggctct  71340
gggaagaccg tcatcgcgct gctgttcgcg atggtggcct cgcgcaccaa gaaggtgtac  71400
atcctggtgc ccaacgtgaa cgtcatgaac atattcaact acagcatggt catggtcgct  71460
aacctgttca acgcgccctt cgtggccgag aacatattcg tgtactcgac gactagtttt  71520
tattcgctaa actgcaacga cggcgtcata aactacaacg gcctcggcaa gtacgagaac  71580
tcggtcttcg tggtcgacga ggcgcacaac atcttcggga acaacaccgg cgagctcatg  71640
atggtgatca agaacaagac gcgcgtgccc ttcctgctgc tctcggcctc gccgatcacg  71700
aacacgccgc tcacgctcag cagcatcatc agcctcatgt ccgagaagga cgtggacgtc  71760
ggcgacatcg tggtgcaggg caagaaggtg ttccagatcc tgctgaacga gcacggcgtg  71820
cgcgtgatcc gcgaggtgct caaggggcgc atctcctact acgagatgcc ggacacggac  71880
atgcccgagg tgctctacca cgggcgccgc ttcctggaca cgcgcgtggt ctactgccgc  71940
atgtcgcgcc ggcaggagga cgactacctc accgtgcgcc ggctctgcaa caacgagatg  72000
ttcgagaaga acatgaacaa cgtgtccatg gcggtgctgg gcccgctgaa cctggtgaac  72060
aacctggacg tgctcttcca ggcgcaggac aaggacctgt acccgaacct gcgcatcagc  72120
aacggcgtgc tctacgggaa cgagctcacc aagctggaca tcagctgcaa gttcaagttc  72180
ttcatctcga aggtgggcgc catgcgcggg aagcacttca tctacttctc caactcgacc  72240
tacggcagcc tggtcatccg caacgtgatg ctcagcaacg ggtactcgga gttcggcggc  72300
tcgcagagca acaatccgca caccacgccc gacgggcgcg ccaagacctt cgcgatcgtg  72360
accagcaaga tgaaggcctc gctggaggag ctgctcgagg tgtacaactc cgcggagaac  72420
aacgacggtg gcaagctcat gttcctcttc tcctcgaaca tcatgtccga gtcctacacg  72480
```

```
ctcaaggagg tgcggcacat ctggttcatg accatccccg acaccttctc gcagttcaac  72540
cagatcctgg gccgcgccgt gcgcaagttc tcctacgcgg acgtggccgc gcccgtgaac  72600
gtgtacctca tggcggcggt gtactcggac ttcgacgagg acatcgtctc gctggaggac  72660
tacagcgtgg aggacatcaa cgcgctgccc ttcgacgtga agaagctctt ctacctcaag  72720
ttcaaggcca aggaaaccaa ccgcgtgtac gccatcctgc aggagctctc ggacgcgtac  72780
tccgcgcgcc cgcacccgca gctcgtggac gtggtgctgg gggagatcgt gcgccagttc  72840
ttcgcacggc actgccgcgt gcccgccgag gacgccgcgc tcgtggccgc cgtcgaggcc  72900
gttctcggca cgcgcgaggc agcggccgag tacatccgcg cgatagtgga cggacacttc  72960
ttcgtgacca acaagacctt cgggaagtgc ctgctcttcc ggcacgagcg cgacatcgtg  73020
accgtgccct tcgagctcga gcacgacccc ttcgcgtggg cgatcaactt ccgcaaggag  73080
gtcagtgtgg tgaatatata acggcaaaca taaatagaaa gactgtcctt ttgcgcgatg  73140
tcgaccttcc ggcagacggt gtacctggcg gtgacgctgc agccgcacga gctcacgctc  73200
gacttccgcg gcaacgtcgc ggaggcggtc atgcgcgagt acctctacaa ggagaagggc  73260
gggctcatgg ccaccgacat cgaggtctgc ctcggaaacg agatgccgct ggggcgcatc  73320
gtgaacaacg cggttgtggt ctcggtgccc tgcaacgtga ccttcaagta ctaccgcgtc  73380
ggcgacaccg tgagcggcac gctcaacgtc gaggacgaga ccaacgtctt cgtggactgc  73440
ggagacctca tctgccagct cggcaagagc tcgggcggcg tgaccttcaa cgagtccaag  73500
tactgcctcg tgcgcaacgg agtcgtctac gagcacggca gccgggtctc ggctgtgctg  73560
cgcgaggcgc gctccggacg cgagtccgcg ttcgtgttct ccgcagtgct gctggacggc  73620
gtccccgccg aggagaagga cgagaagaag gacgagggcg agaaggccgc ggaggaggag  73680
acgcccgcga gccccgccgc caaaaactag cattattggg ccgcgcgaac cttcgataaa  73740
tgcgcacgta cacgtcgctg ctctcgaagc tgctcaagag caaccggcgg ctcgggagca  73800
cgcgcgtctt ccgcgacccg ctgcagcaca tcagcgcgac cgcctttgtg caccggcgca  73860
tcgaccggca ccggcgcgtc tccatctgcg ccgtgctcac caccaccgac gggctcgtgg  73920
tcgcgtgccg gcgccggtac tcctttttgt cctccgagct cgcggagacg cgctcgcccg  73980
cgcggcgcgt gctgctcgca accaagcacg cggacgctct cgcgcgcctc ggcgccgcgc  74040
gcccgcgcga cgacgtcatg tttccgggcg gcgccccgct gtccggggag tcgccgctgg  74100
cgtgcgtgct gcgcgaggtc gaggaggaga ccgggctgcg cggcgaccag gtcagcgtgg  74160
acgagcggct gttcgtgcac gccttcatcg acgacctggt ctcgggccgc gacttcgacg  74220
cgatcatctt cacgggcgca gtcgcgcttt cgagcgcgga ggtggcgaag cagttccggc  74280
ccaacgacga ggtcaagggg ctggtcttcc tgcaccccga ggacgcggag ggcgtgggcg  74340
tgatggcgcg gctggcggcg ttcgcgcgct gcgcggcgcg cctgcgctgc tggggcgcgg  74400
ccgtcacgcg atagaggcgg ggtccaccac gtacacgagg cgcccgccgc tcacgcgcac  74460
ggtgggcggg tcgcccagcg cggtcaggaa gttcccgtcg tcgtcgaaga ggcgcccgcc  74520
gcgctcgagg aagcccttgc gcaccgtgac cagcgccgtg gaggtggagt accacacgct  74580
ctgcccgtcc gcgagccgcg ccgcgcgcgc gggcccgcgc gcgtccgccg ggcgcgccac  74640
cagcgcggac cagccggagt cgtcctccag cggcgcgaag tccgtgaagg cctcgcgcac  74700
ccactccagc gagcagcgct tgagcacgcg gaagagctgc gtgaactgcc gggacttgtc  74760
gcggatgagg gccagcaggt cctcgtccac ggtggcggcg ccggagtcct ggcgcgcgac  74820
```

cacgaagtgc acgttcacgt agcggcggtc gggcggcgtc atctcgtggc tgttcaggcg 74880
caccgcgcgg cccacgatct ggcgcagcga ggcctcgttc caggtcatgt ccaggatgaa 74940
gatgtcgttg atggagagga agctgaggcc ctcggagccg ctcagcgaga acacacagac 75000
cttgatcttc tcgccgtcgg tgttgtcgca ggcgttgaag gcgtccacga gcttggcgcg 75060
cgtgtcgcgc gtgcgcgagg agaactccac gctggagacg ccgaaggcgc ggaagtagag 75120
cagcagcatc tcgatgccgg tcacgttgac gaagggctcg aagaccagac acttgcccgg 75180
cgaggccagg atgcgcaggc agacctcggt gtacttgcag ctgcgctcgc gcagctccgc 75240
gagcagcgag acgtccgcgg aggtcatgcg gtcgccgctg acgggcgcgc cgctgcggaa 75300
gagccgcatg gccgcctccg agaagacgcg gtccttgacg gcgcgcgcga agtccaggaa 75360
gagcgcggcc acggcctcgt cgtactcctg cttggagagc acggacttgt cgggcgcgtc 75420
ctcgaaggcg aaggtggccg cgatgcgccg gtacacgcgg aagaccgcgg cgccggactt 75480
gcgctccatg gcggccgcgc ggcggtaggc ctcggtctgc ttcgcggtca tgtccacgta 75540
catcatgcgc acgcgcttgc gcgcgaaggc ggcggagccg tcgacgtcgt cgaagatgga 75600
ggcctcgttg gtgactaagt acgagcacag gccgccgagc ttgtccacga ggtcctcggg 75660
gttcgcgagc gcgccgccgt tgaagagcgg cgtctgcccg accacgccgg ggcgcagcag 75720
gttcacggcc atggagaact ccttgacgct gttcaccacc ggcgtggccg tgaggcagag 75780
cagcttcccg cggcccatgg ggatgttctt cgcgaggtag ttgtacaccg tgcgcgcggg 75840
ccgctggcgc ccgtcctcct tggtcagcga catcgagatg aagttgtgga actcgtcgat 75900
gaccacgcag acgcggctgc tcgacgaggc ggtcttcatc agcgtgaaga agcggtggtg 75960
gaagcgcggg tcgtcgtagt tgatgaaggt gcacccgggc acggcctcgg gcgcgaagcg 76020
catcatcgtc gaggtccagg gctgctccac gagcgccttc ttcacgagca cgaccaccgt 76080
ccagtccgtg aagacgtcgc gcaggtgctt gagcacgtac accgcggtca cggtcttgcc 76140
cacgcccgtc tcgtggaaga gcagcagcga gtgcatgctg tccaggccca ggaacacgcg 76200
cgccacgaag agctggtagt ccttgaggcg cacggactcc tccacgccct gcatctcgga 76260
gggcatgtgc gcggtgcgcc gcagcgcgta gtcgatgtag gccgcgtgcg cgctggtcat 76320
ggcgacggtc ggcgctcctt ttacggggtc tgtcgtctat ctattgtcgg cgcgggtctg 76380
atttaggggc agtagttaca aaaacgtttc cgctgctcgg cgcggcgttt ggaggagcgg 76440
ttgcggccgc ggcggcgcag gcgcgcgcgg cgcgtcttcg tggtgcggtg gccgaaccag 76500
cgccggtgca tgaccgggtg cgagaccgcg gccgcgcgat ccgcgctcat gcaggttgcg 76560
taggtgcggc acatgctgcg cagcacgcgc cgcgtgcgcc gctccacggc gtcgagccgc 76620
ctcgcgacga tgggaaagag ccggcgccag ccgcgcacgg cgaagagcgg gcgctcgcag 76680
accgggcgcg cgagcgcgtg gtaggcgccc agcagccgcg ggtccagcga gcgcacgtag 76740
gtctccacga agccgttgcc gaagacgatg gcctgtgcgc atagcgggtt cgtcatctcc 76800
ctcttggagg cgatggcgtc gcccacgaag gcgcgcacgc cgcagtgccg cagcaccagg 76860
cgccgccgcg ggaagtgcag gtgcgggccg agcgccgcgc gggcggcggg gatgtgcagc 76920
cgcggagaaa aacgcgcgcg tccctccatg gcatctaagc gctccgtctg ttttcagtta 76980
tatcgccgcg ggcggctact gcagcagcag cttgagcttg cgctggctct cgttctcgat 77040
gctcttggac tcggaggtca tgctctcgta gagcagcgag tgcgtgacgt agagcgcctc 77100
gtacacgcgg ctggcgaagg ccacgaagcg gtccacgaac tcgctctcta cggggtcctt 77160
gagcacgcgg aagggcacgg ccagcgcgtc gcgccaggcg gcggccttgg tgcgctcgcg 77220
cacgtgcgtc acgaaggcgg cgatggccgc gcgccgcggc tcgctggcga ccatgacggc 77280
gctgtccttg agccagctgt cgctcacgca cttgaagagg cgcacggtgc cgaagaggct 77340
gcagtacacg cgcagcgcgt gcaccacgtc ggtgccgaag agcgtgggca gcttgagcac 77400
cacgaagcgc tcctgcgtga tctcgagcag cgggcgcatc accgcgaagg tgatcgcgtg 77460
gtagtcagcc acgtagaggt tgttctcggt gaggtggttg ttggagcgga tggcgccgcg 77520
ctccttgcgg tagagccggt tgcgcgcgct gaggtcgagc acgaccgcgt cggccctgcc 77580
gcgcgctctg gagcgcacgc tggtgatgcc gtgcgcctcg agcaccttct cgacgtcgcg 77640
ctcgtcgatc atgaggtcgt gcgtgtacag actcagcatc tccgtgggca tgcggttgat 77700
gtcgttcacg cgcgagcact gcaggaagta gttggtcccg taggccaggc tgggcaggtg 77760
cccgacgccg agctgcaggt ccagcgcggg cgtcgagtcg aaggtgggca gcgtcacgct 77820
gagcccctcg cggatgctgc ggcgcacggc ctccaccgcg tccatggccg atttattgga 77880
cgcacagtct gttttcattt cgcggctact gcgcagtcac cttctcggcc acgatccccg 77940
cgtcgtagct gagccggtac acctcgttgc acaccacgac catctgccgc ggcacgtaca 78000
tgagcgggtt gtgcgcctcc atgtgcgcgg tggtcacgcg caccgccagc ttgtccttgc 78060
ccctggagac gttggagttc agcgcggtgg gcgagaagaa ggtgctgggc gtaaagttga 78120
actgcagcgt gcgcacgccg ggcgtcttgc cgaggatctc gccgaagacg cgcgagactg 78180
cgctgttctc cgagtacagc acctcgttgc cgaagcgcac gtccatgcgc gcgatgacgt 78240
cgatcttgtt cttgaagtcc acgcccttga ggaaggggtc ggccacgaag aggtccttgg 78300
cgcgcgcctc cggcgagcgg ttgtcgccgt tgtacacgtt gcgctggcag gtccacacgc 78360
ccacgggcac ggaggcgtcg ccgatgttca cggagtggat ggcggtcgtg aagcggatgc 78420
gggaggtcgc gcggctgtag gcccccgtga tggcggagaa cttcttggac atgttgtaca 78480
cgacggagtt cttcctggtg gcgaacacta ggatgttcgt gtgcaggaac acgcgcatgc 78540
ccacgggcac gtcgtcgatg cgcacgaaga cgtcggtgtc ctggatggac acgacgcccg 78600
acgggggcac ctcgactatc tccgcggtct cggggaagcc ctcggggtag cagttcgaga 78660
cgatcaccat gtcctccagc aggcgctcca cgaaggccat cacgaagtcg ccctcggact 78720
gctggaagcc ggggtacgat atgaagcggt tgttggcgtc gctgagcacg ggcttcatgt 78780
acacggacag ggaggtgcac gcgtgcacgt ccgtgatcac cgcggtggtg tggttgatct 78840
gctccacgcg ccgccgcggc atctcgatga aggccgggcg cgggcacagg ttcttgacca 78900
tgtagccgat gaagctcagc tccatggagt aggggaactc cttggcgagc ttggcggcgt 78960
cgaaggtctc gtcgtagacc atgacgcagg cgacggggtt cagcgtgacc gtgaccgtga 79020
ccttgctgtc gctgagcttg agcgtgctga aggtcttgtc cgcgtcaaag ggcgtcttga 79080
tgtaggcgtg cacgcaggcg gcctccttga tgacgtcgtt gggcgagctc ccggtggaga 79140
ggtcgttgag ctcgcgcgag aagcccgaga gctccatcac gcgctcgttg tccaggcagg 79200
agtcgaacag ctcctcgccg gaggtctccc agatggtgtc cgcggcggag ttcacggcca 79260
cgtggcggat gagcttgtac gcgatgtagg gcacgtagca catcttgccc acgcccttta 79320
tctcgggcag gtccacgctc agcacgaagt tgttcatggc cgagatgtac ttgtcgcgga 79380
tctcgaaggt cacggtgacc gcgtcgctgg tggtgtccac cacgccctgc gtggtgatgt 79440
actgcggcat gtacaccgtg ggcgcgcggt ggtccgtggc gaacacgctg gcgcgccgca 79500
cggcgtcgtc gccgcccacc aggctcacca cggagttatt catttattcc ctgggaaaac 79560

```
cagttaaata aggctcttca gagccatgcg caccgtccgg ccgtcgggct ccaggtagca  79620
gcgcccgtag acgccctccg tggcgcgcgt ctcgttgatg agcgcgcgca cgcggtcggg  79680
gtccgcgtac atctccagcg gcagcagctc gatcttgggc tcctcgcgca gcgcgacgag  79740
gtgccggatg gagcccgcga aggagtcgcg gcacaaccgc gagcagaact cgcccacggc  79800
gccgccgtcg agcgtctcca cggccagcgc ggccgtgccc acgcgctgac ggcagaacca  79860
gcacgtgccg tccgcggcgc gcagcgccag ccgctccgcg gacaccgtgt tgaagtactt  79920
cggcagcacg tactcgatgc ggcacgccgc cggcggcgcg caggccgacg cccgcggcgc  79980
ggatatgtcc acccgcgaga gcgcgatgcg cttcatgggc ggcggtggct gctatttatg  80040
tcgcccgcgg cttttcaaag gtcgagcgag cacgccgcga agcgcgcggg cgagaacacg  80100
tactcgtggc cgaactccgg gatctgcgcg gcgcgcttgc gcgcgcgcat gtgcgcgagg  80160
aagttctccc aggtgagctg gttgctgttg ttcttcgcgt agttcttcac ggtctgcgga  80220
cgcaggttgc gcgtcacgcc cgtgacctcg aagatcttgt ccaggaagaa ggagtagttg  80280
atggttttgg tgggcgtgat ctcctggcag aagaagacca gctgcttgaa tatctcgatg  80340
acctcgttga tcttctcggt gctgaggtcc agcttctcgt tttgacctg gttgatgatc  80400
tcgaagacca gcttgtagtc cttcttgttg atcatttcgc tgtccttgag gaagctggag  80460
acgtagttgg cgtccacgtc ctcgggccgg atctggtgcc ggtccatcat cgcgcgcagg  80520
tcgcggatga cctcctccga gcactgcttg gagagcagcc gccggagcac gttccgcagg  80580
tggatgagct tgttcgacac gtggaagttg gacctcttct gcacgcggat gcccatggga  80640
aacacggtct cgcagaacag gcagaactcg tagtccgcgt cggacacgag cccgttgcgg  80700
cggcagccgc cgcacatgcg caggttcatg cttgctccag ccccagcacg cgcaggatct  80760
cgcggtccag cactttagtg tccagcgtgc gggttctaca gaactggagg aagcccgcga  80820
gcgcgcgcgc gcgccctggc tgcgagagca gcagcatgcg cgcgttctcg gggtcctcgt  80880
tgatgacgcg cgtgaggttc agcgagcacc gcgtgcagcg ccgcggcggg tcgagctcga  80940
ccgagtacgc cgcgaaccag acgttgtcgc ccatgtatta tttattaaca cagaacgtcg  81000
cacatgttgc gcgaggacat gtacgggtcg tactcctgcc cgtagatgag gatggtgcag  81060
taccgcgaga tcatgagcat ggcctcctcc atggtgagca ggtcgtcctc gaacatggcc  81120
ttgtgctgca tgtgctggct ctgcttggcg gccatcgcgg ccgcgccgtc gccgcgcagc  81180
cactcgttca gacactggcc gtcgccgccg gcgccgctct cctgcgcgaa ggtgttgcgc  81240
atggcgcgca tgagcctggc ctccctggcc gagcggctga gcacggtcat ggggtcgtag  81300
agccaggggc ctgcgtccgt gaacaggatg gtgcagtacc cgttggcgaa ggcgtccgcg  81360
ccgctgcagt tgtcgatgcc gtcgccgacc ctgtagcaca ccgcggagac cagccggtac  81420
atgatgccgt tgagcatcat gtcctgcgac acctcgatgg gaatgtcgct gatcacgggc  81480
cgcatgttcg tgaagcagtc gcccgtgctg gccatgcccc cgcgccggtt caccaggaac  81540
accagcacgc cgttcgtgat cacgggcgcg cggtcgcgct cgtagaggta gccgctcgcc  81600
gcgcacacgg cggacgccac gtccgtgcgc gagaccgcgc ccatgttctg ggcgggcatg  81660
tacagcactc gcccggcctc cgcggtgcac gagaagggct gctccccgcc cacgtggatg  81720
ggcgccgtcg atgtcgtgat catcttgctg gagtccacca ccaggtaggg caccgtgtgc  81780
atggccatgt cgcccatgcc cccgatcccc gttccgaacg acggccgcga cacgctcacg  81840
agcgtcggct tgaacgagac tatggagaag atggaggcca agatctgctc ctcgtcggtc  81900
atgatggagg cgcacgaggg gtggatgatc ttcattaggg cgttgtcgat ggactcgtcg  81960
```

```
ctctcgcagt agaagacgcc catgcggagg ttcaggatgc accgccgcag gttggtgtgc  82020
agcaccgcgc gctggatctc catggacacg gagtcgccga cgccgggcat cacgatgggc  82080
gtttcctcgg tgagcttgtt caccagcagc tggtagttgt tgggtcgcac gcggctgttg  82140
tggtggagct gcgccaggag cgagaggctg tccccgttga cgaacgcgga ctcgatggcc  82200
ggcagcttta cgccgaacag cgccatggcg atggggtgca cgaagcccac ggagtcggac  82260
gacttgaacg agaagagcag gtcgcccgag gagctcatgt ctttgaagtg cacggactgg  82320
aactgcgtgg cggagagcaa gttctggtag ctggacatgc tctgcaggtc gtcgatctcc  82380
ttcatctgct tgtttacgcg ggtcgagttc ctcccgtaga tgatcaccag cgggtgcgtc  82440
tggctcacgg atagccccga gtccgtcatg gcggcgcgca cgctgttcag cagatcgaac  82500
agctccgacc ggtctctgtt ctggatcccg acctttgcca tcacagacat gagctcctgg  82560
atggtcatgt tcttgtggtc tcggcgcgtg gaccgcaggt agtcggcgat catctcgccc  82620
tccttacgga tcttcatctg ccagtcgtgc atggaggtca tgcggtccac aggcatgagc  82680
acgctgtcgg aggacgactg cgcggcgctg ccggactggc gcgagccagg gcgcgcggac  82740
gacgggcgcg cggagctgcc gcggctggag gaggacctgg acctccgcga ggatcttcgc  82800
tgcgaagagc tgcgcacggg ccgctgggcg cgcgccccgg cggaaaccat gtcctcgcgg  82860
tttatgctga ggagcgagct gcagaccgcg cacgacagcg actgctttgg aatgtggatg  82920
tggtcgcact ccagggacat gcccgcattg tcgtagcccg ggaccaagtc gaactttgca  82980
ttaaaaaaat ctgatgcgca cgcgggcgat tccatttata ccggaagttt ttatgaggtg  83040
ccggtattat ccacgcgatc tcgcagtgtg ctgggagact ctagcgtagc cacggacccc  83100
gtgagcagac gacgcaagtc gttgatggcc gactgcgtga cggacttcgc cgtctcgatg  83160
tcgcgcgtaa ggctgagcga ctcggcgttg aggtcgcgca cgctgtccgc gatgtcggcc  83220
agctcctttt tgatgaaatc cttatcatta tcggcgttga tgactttgtc cggcactcta  83280
gactctagaa ccggtgacgc ggcgggcgcc ttgatcgtcg ggcagctgga cgccgggtac  83340
tggggcggcg gcaatgattg ctgtaggaag atgggcttag cggcaggcgc cggttttgtc  83400
ggcaagggcg gcgccggcgg gcactgtcgt gtagacggcg ggcacgccgg cgcggggcac  83460
gccgccggtg gcggacatgt cggcgcagtt gcgggtggac acgcgggcgc gggcgccggc  83520
gcgggacacg tcgcggcagg agccgggcac gcgggagccg gagctggagc cgggcacggc  83580
gcggcaggag ccgggcacgt cgcggcaggc gcagggcacg cgggagccgg agccgggcac  83640
gccggcgcag gaggacatgc cggcgcagcg gcaggacaga ccaccgctgt cgcggagcac  83700
gcggcaaccg gcgtggagca cgcggcgggc attacgttca gaggcgtcga ctggaccttg  83760
gcaccgcggg gcagtagcga tggcgctagg ggcgactgtc cggtggttgg acgctgcatg  83820
caggcagtcg cagatttcag acgggactgg taatacctgc ccgcttcctt caccgtgtac  83880
ttgtcgacgg agtctacctc ctcatctgga ggacatggct gctccggtgc gggaacgact  83940
gtttgaggac acttggtgaa cagactggag ctggtctccg atagcaccag tttagacttg  84000
gccaagtcgg aggcaaacct tcttctgaga tccatttaag ccttcaaaat tgaacgtgta  84060
cgccgaccgc taaatggaag aatcggtggc cgtcgagtac gcggacgagg acgaagatga  84120
gattgaggag tacgaggagg aggacgatga cgaggaggaa gagtctgccg agggcgccgc  84180
cgcctcctcg gtcagcgacg tagcgctctc tgccgccgag aagctggtgg cctcggaggt  84240
cccggacgac gcggctgccg cggacaccaa cgtgcgtcaa cgcgtcaccg cgcgcgtgga  84300
```

```
ggagcttaag gcgcgctaca cacggcggat gagtctattt gagctcaccg gaattgtagc  84360
agagagtttc aatcttctgt gtcgcgggcg gctgccgctc gtggcggacg ccgcagaccc  84420
ggcgctcgac aacgagctaa aagtggtggt tcgggagctc gaggagggcg tctgccccat  84480
cgtcatcgag aaaaacggcg agttcctctc gccgggcgac ttcgaccccg agtgcctgcg  84540
ctaccacctg acgtacatga ccgacctctg gaagtcccag ggcgcatgt agccgcggct  84600
acgccgactc ggcggcctcc gcgatttttt cttttatcat gtccagcagc tcgcgcacca  84660
cgatggggcg gccgcagtac gtgatgccgt tttcggatat cacgctctgt gcgatgtcca  84720
ccagcgagcc ctcgcgctcc cagtactcgc gcgcgagcac ctccttgtac aacgcgcggt  84780
ggttggccac gtaccgcacc agcgtctgga tgttcttcac gcccacgctc ttgaggtcct  84840
gcggcgagaa cttctcgcgc agcgacacga agacgtcccg gacgagcttg ccgatctcca  84900
cgttggtctt gaactcgttg tacagcacca cgtagagctt gcacacgacc gtagcgaact  84960
tcgcgggctt gagatccttg ttctggaaga ccagcatgct gctcatcacc ttcttcatga  85020
aggccaggta cttcgcgcgg tcgccctcga cgctcacgct cccgacctcg aggtcggaca  85080
cgcagcggat tccgtgctcc gcgctctccg cggagacgcg cagcagctcc tggtactcct  85140
tgagcttctg cttgtccgtc atcagcgagt tgtcgaatac cgccaccagc ttgagcacgt  85200
agttctcgtc cgagaagacc ttgttcagac acttcaccag gaagctgtag tggctctgca  85260
ggatcttcat gaccgcgttg gcgccgctgg ctccgcggac gtgcgatatc atctccatga  85320
tcttcttaga gtcgtcgatg atctcctcgg tgtcgttgcg catgttgcgg tacattgcgt  85380
tcagcgagac cagcgtctgc gcggccagga gcacgtcgcg gaacacgcgc gcgaactcgc  85440
gcttctcctc cgcgtcggtg atgctgttgt acacggactt cgccaccgcg ttcgacttca  85500
ggaaccagaa ggagagcgcc tggtagttga agtgcttcat cagcgccagc acgtccgcct  85560
cgctcatttc cggcgcaatg gggcacaccg agctctcgag cacgggcacc atgctgacga  85620
gcgtgtccac gtccgtgtcg aagtccaggc agtccacgca gagcccggtg ccgcggctca  85680
ggtgatcgcg gctgatgtcg tagaagcgct cgtagcaggt gcggaggcgg tccatgtcgg  85740
ctgcgtttta gagagacaca cactcttgaa ttatggctgc gggtagaact cctgcagcag  85800
cgccggcgca cgcgcggagt ccggctccac tcccagcttc agcgcgcagt tcacggacca  85860
ggtcttcatg aagcggtcgg gcgcgtccgt gaccacgtgc cggaagagct tcgcgaagtg  85920
gcggctcacg gcgttgggca cggtcgcgtt gcgcacgaag gccgtgaagc gcgaggtcag  85980
cttcggcgcg aagcgcttgc cgtccacgaa gaagcccgag gtggtgagcg agagcccgtt  86040
ctcctcgcgc accacgcgtc gcgcggcctt gtgcggaaac atgctcgcga ggcgcccgct  86100
cgcgtcctgg tctaggtgga tggcgtccgt ggccgcgtcc ttgcggatgc gcaccacgtc  86160
gtgcacgatc tcctggatga ggatgcgcgt ggccgcggtc tccgccagcc gcatggggaa  86220
gtagaccatg tccccggaga tgagcacgtt cccgctagcg tttacgtagc tcactatctc  86280
ggacacggtg cgcagacgca cgatcgcgcc ttcgcagcag tgcaccacgt agtacccagc  86340
ggtggcgcgc aggcgcttgt tgtccgcctc gaagtccgcc tccaacccct cgttgaagta  86400
cttgtcgaat atgatgggca ggaaggatag ttttgactcg gtgaccacct ttccgaagtt  86460
gaggatgtac gggttcagcg cgctgcggtc gacctcttcg tcgtacacgc aggacttgaa  86520
ggtgtcggtg tgcgcctggc tgcgcaggaa gcagcacgga atgcagatgc gctgcaggcg  86580
gtggaagatg gagaggaagc ccacgctgtt gtagcgcccg tcggggtcca tgcacgaaaa  86640
catgacgccg tttccgttta cgaagacctc gcgcgtctcg gacttgaaga agttgttgct  86700
```

```
gaccttggcc atgttcgcgt ccagcgactg cacgatcacg ggcttgcggt tcttggtctt  86760
ggtgttctgg cagatgcgcg accagtacac ggtctccacc ttggtgaagt ccgaggactg  86820
cttcacgttg ttgaacatca cgctgatggc cacgatcaag aacgtgaagt acttctcgat  86880
gttcgggatg tagttcttta ccttcacgga cacgtgcgac ttcgcgagga tgatcgagat  86940
gcgcttgtcc gtggagagca ggatgttgtt ggtcgccgtc tccacgaaga tgaagctcgt  87000
ttccatgtcc agcttcatct tagacgtgat ggtcgtgttc agcgacacct tgtaggtgat  87060
gtcgcccttg acgcggtcca tctttacgtc catgctctcg atgagcttcg tgaacagact  87120
cacgtcgttc accgtgagcg tcttcccgtc gctcgagatg accaggtcgc cttccgggcc  87180
ccacaccgag aggttcagcg gctcgtccac cagcaggaag cgagtccccg tcatcgacac  87240
gaagaagtcg tccgtcttcg agagcaggat gtcgaagtcg cccacctccg ctcgcttgtc  87300
cggcgactgc tgcgcgatcg cgcggagccc ggactcgcgc aggttcgtgc ggaagatgtt  87360
gttgaacttg gtctccacgt tcatgtttag gtcgaggttc gcgaactcgc ggatgagccg  87420
ctcctcgaac ttgaggatgg agtcgttggg ctcctcgaag gagccgaact ccggcgcgga  87480
ggtgtccgcc gcgcgcgcca cccagaccac caggaagttg cacgcgtccg cgtacgcgtt  87540
gtagaggatg ccgtccgtgc ggatgagcgt tttcttttgc gtgggcgaga acgggttgaa  87600
gatggtgttg tccacgtagc tgtactccag gttgttcttg tgcgagtaca cgatgatctc  87660
gtcctgcagg cccagcaggc tccccaagta ccccttgagc tgccgcacgc gcatggtcag  87720
caagatgtgt ctgcgcacgt gctcggggtc cttctggatg tactgcttcg cgaagaagta  87780
gatcggcgag gcctcgtcca cggagtcgta cagcgatagg tacagcacgc gctcgatctc  87840
ctggtggcgc cccaccagca ccaccagctg cggcgcgacg gtgtagagca tgttcgcgcg  87900
ggcgtattta tagccggcgt taaactgaaa taaaatacgc gggtcgcgag gcagcgccat  87960
gttccagccg gtgcccgaca tggccgccga ggccgacatc gacctcggcg acgtcagcgt  88020
ggacgcgacg cgcgcgggcg cgcgcgagaa gaccgtcttc ttcgcgcgca acaagcgcat  88080
gtacccgcac cgcagcaagg acgaggagcg caagctgtcg ctgggcttct tcttgcagcg  88140
gctggacttc ctcacgtcgc gcgaggtcaa cctgcagttc cggtcgctgg acgcgctgcg  88200
caccgagaac gtcatgaaga agaacaacgt gctcgtggcg ccgtacatcc tcatcgcgac  88260
gctcgcgggg cgcggtttcc gcatgacgga gaccatggtc gagctctact tccccgagct  88320
gtaccgcgag accagcaagc gcttccgctt ctgcgcgcag ataaaggtca tccaggactt  88380
cctggggttc gcccacgaca gctaccacac ttacgacttc gagacgtact tcgcgttcgt  88440
ggcgctggtg ctgcgcggcg cggactctgc ggccgaggcc ttcgacgtcc gcgccgagag  88500
cgggcttgtg cgcagcctca ccgagatcac gtaccggctc tacgtgatgc agctgcgctc  88560
cgacgccgcg cagtggagcg tgagcaccgg cgccgtagtc tcgcaggcgg tgaacaccgt  88620
gctgtcggtc gtcggcgacc tcgctgcgcg cgcggaggcc gagcggctca cgcccgtgtg  88680
cgacctcgcg cgcgagaacc cgctctcgct cgaggacctg cgcaagtacg gcccgcggct  88740
gcgctcgctg ctcacgacca tggcgcgcgc gcgatccttc aagacgaacc ggcgggacaa  88800
ggacgcgctg tcccggttct gccgactgac ggcgggccct agcccgtctg cgtgccgcgc  88860
gtcgccatag gcgtcggcgc gcgctcgccg ccggaacact cggggtcgct gaacatgtag  88920
atgagcgcga cgcctagcag caggtacatg atcatgctga tcacggtttt gaacacgacg  88980
gcggcgaacg tgttggaccg cagtcggtgc tcgcagaagt gcatgaacag gtgccgcatg  89040
```

```
aggtcgatgg ccccgttggc cacctggaaa agggcgaggc cgccgatgga cttgatcacc  89100
gtcacgtagc acggccgcat tccgacgacg ctatttactc actgtcaaaa gaaacggcgc  89160
catccgaccg gaggttgagg ttgcgcttca tgttgttcca gtacatctca ccgatgctcg  89220
agtagtacgc cgtcagccgc gatatttttt ctcgcaccag ctcgtaggcc ttctgcatct  89280
ccgcaacgcc gatctccgcg tcgcccacgt accggccgct gcggcgcacg atcagcagca  89340
gcgccttcag gttctccagc gcgatcatgt ccatgtacag cgacttcgag agctgcacga  89400
agaggttgta ccgctccagg atgctgttct tcacctcgtc cgcgatcggg actccgaaga  89460
tgcgctccgt ggtgtacacg gactgcgtga gctgcttgaa gagcgcggag atgcagcagg  89520
tcgcgcgctt gacggcgtcg agctgcttct cggagcgcgc gctcgcgatg ctcagcgcgc  89580
tgttcacgac gttgctcgtg tcgcgcacgt agcgcgtctt cagcgcggcg ttgatggcat  89640
ccgcgatctc gttgctgctc acgctcgagt cgtccgagct gcccgagacc tcgtccagca  89700
gccccgagat cgtgatgtcg ggcgagccgc cgacggtcac cagacggtcg agcaggttgc  89760
agggcatgga catgaggatg ccctcgctcg agaggcagcc ctcgtcgatc atgctctgca  89820
ggttgcgctt gaaggccgtg ttttcgggca tgaacccgtc cacgctcatg agctcgtcga  89880
ccgtgctcgc ggaaaagatg cccctcacgt tgatgcggtc cagcatgccc atgtcctgcg  89940
agcacagcac caccgactgg tcggccgtct cggcggcgtc cttggcgccg ccgtagatga  90000
tgcgcggaaa ccgccagctc gccggaaaag agaaggaggg aaaccggcac tgcgcgctcg  90060
ggcctcggta gccctgcgcg tcgcgcacgt tggtggccgt gaccatgaac tgcagcaggt  90120
cgtgcgcgga cgccatgatc ttctccacct cctccttgct gcagcagacc ttgcccaggc  90180
tgcgcgcgat gttcgttttg ctcactgagg gcgagaccgt gacggcggtg tgtcggcggc  90240
tgccgagcgt gtacgcgctc acgctaacgc ggtaccccat ggcgccgaag agcagcttca  90300
cgaagtccag gtagctctcc ttattgatgt agtgcggcgc gcccttgtct tccatcctca  90360
gcccggcgta ggccatgagc acttccttca tcgccgtctc ggggtccgag ttgcacacca  90420
gccgcagcat ctggaagaac tgcatgaagg cgcgctgcga gagcccgatg tggtggttgg  90480
gctgcgtcga ccggcgcggg aactccctgg gcgtcatggc gttgatgccc gagagcgtct  90540
ccatcacgag cgcgcccacg gtcttctggc ccatgacgcg cgggtaaaag cacacgcgga  90600
ggggctcctt gccggccgcg agcgcgtccg agagcagcga gcagtacgtg acgttgtcgt  90660
ggtcgaagag cgcgaaggtg tagcagacgg agctcatgaa gagcgagtcg gcggtgctca  90720
tggacttgaa ctccgtgtac gcgattccgt cccagaacag gctctttccg ggcgcgatca  90780
gcggggacgc gcggtcggcg cgcatcagca tggagagcag cgtcacgtag taacggatgt  90840
tggcggaaat gtctacgaac tgcatgccgg gcgaggccac gcgcagggtc gcgcccgagg  90900
tagtgagcac ctccaggctg tccatgagcg tcacgctggg gtgcagctgc gcaaggcgcg  90960
ccagctggct ctggtagaag atggacacgg cgaggctggc cacgctgccg cgtgccatgc  91020
gcaggttttg cccgttgaag gtgagctggc gcagcgagaa cacggagtcg aagtactgga  91080
agaaggtgag caggtacttg agcggcatgg tcgtcagctc ggtatccacc tgcggcgtct  91140
gtgcgagcac gattccgttc ttggccgcgg cgtcggggat gtcgtacatg gcgtccattc  91200
tggcgcggga ggcgtcggtg agcagcgcgc gcacgttgag cagcatgagc aggtcccgcg  91260
ctagcatggt cccgtcgacc agccgggcgc gaaagccgat ctcggcgggg ccggcgatgt  91320
tggggtagat caggttcagc aggtacgtgt tgtcgaagct cagcgagggg aaggagatgg  91380
gagacttcgc cgggaggccg gtggggtagc gcacgtagcc gccgcagatg cgcgcgtgcg  91440
```

```
cctcaaagct ggtcacgcga gtcttcagca ggttgcgggt gaagggcggc acgtccttga  91500
aggactgcgt gcagatcacg gggttggcgg tgtcggtcag cttgaggttg gtgggcttaa  91560
gctccgcgaa gttggggccc agcagcacgg ggacgaggtg cgagttggcg gcgctgtcga  91620
gcaggaagtt gatgccgaac tgcttcacgg cgacctcggt ttcctcgtcg ctggcgagct  91680
tctccgcgtc ctcgaggaag agcgcgtcca gcgggtgcac gtacgtgcgg ttgacgtcgt  91740
agctgggctt gaagtccgaa cacagcgtgg ggagcacggt ggagacgagc tggaacatgt  91800
attccgcgcc ctccacatgg tgcaaggcca tgtgcacgtt tggggccgtc atttatttag  91860
tattaaatga cggccgtacc ggtaaccgat attcctggag actacgggcc gacgtccttt  91920
tcggaggaca actacccgct gaacaagcac tacgagctca ccaaaggcca gctctcgatc  91980
ctgcgcacgg tcaacgacaa gctgctcgcg cgcaccgtgc agcactcgga cggggagagc  92040
gatgagagcg aaagcgagga ggacgacatc tccagtccgc tgccgccgga cgaggaggag  92100
ccggactcgt gcgtggcccg ggtcatgccg cgggacgcgg acctggcggc gccaaaaaag  92160
gccgacggct acatcattgc cgccgagcag cagcgccagc agcgcataaa cattctggta  92220
tccgatcgag aggccgtcgt ggagcgggag ccggttcaga cgtcgttcgc gcgcgtctcg  92280
gctatcccga tccacgggga cggcgcgcgc cgcaccaccg cctccttctc cgcgaccacg  92340
ccgtcgctgg gcgccgtgtt cgacgacgcc aagcgcgtgc ggctgctgga ggaggaggtc  92400
aaggagctcc gcagaaagtg cgcgacctct caggataacg gaaacctgga gaacttcacc  92460
aaggtgctgt tcggcaaggc gccgcgcgcg agcgagctga acaagcgcgt ggtcatcgtg  92520
aactacgcca cgctgaacaa cgtgacgctg tccatggagg acctcgagaa gtgctccgac  92580
gaggaagtgg accgcatgta ctcggtcatc cggcgctaca acgagacgcg gaagaagaag  92640
atcctggtca cgaacgtggt catcatcggg atcaccgtgc tcgagcacgt gctggtgaag  92700
cttggcttct cggaggtgcg cgggctcagc gccgacctct cgtcggagct catcgacgtg  92760
gagatcggcg aggactgcga gcacatcgcg gagcgcctgg ggttcgggaa cagcccggtg  92820
ctaaacgtgg cgctcttcgt ggtaaagctg ttcgtgcgga agctgaacct gatctgatca  92880
acacatgccg ccgtcgaggt ccatggcgtt catgaggttg gaggcgcggc ggcgcgcgcc  92940
ggtggaagcg gtggaggcgc tcgaggtcgt ggagcaggga gtgttgctgg aggaggcgcg  93000
gcggcgggag ctagaagcgg aactcgaggt tccgctggtg gtgctgcggc gactcgtgcc  93060
gctcgtgccg ctcctgctag tgccagtgcc agtgccgctg cggcgtgaag taccggtgcc  93120
ggacctgccg ctggagcttt tcttgcggcc gccgttaacg ctgtcgatgc cgagcaggtc  93180
ctcgcacacc tcgccgacgg ttccctgcac gtccaacttg ccgttcttga caaccccgta  93240
cacgatcttg ccgcagttgg acacagcctg gatggtggtc tcgtcgctgt caaaggcgtt  93300
cattccgccg cacccgccgt cgttgtttct tcgagaaggc gcgccgctgc ggcgactcct  93360
ggtgctgccg ctggaccgag ttccggagga cctggagccc gtggaccggc tgccggtcga  93420
cctggtgccg gtagtgcgct ttctggacga agaggaggag gcgcttccgc ggcgggtgga  93480
cgaactagcc tccagcgcac cggcgccgcc cacacaatcc acgtcggcgg cggcgcctcc  93540
gcgaatgacc tgctcgttgt tgagctgcgt caggagagat cgcagctgcg gcgcgatctt  93600
ctgcaaggtg ctcacgtagt cgtcgtagct gctctgcggg cgctgcgcca ttttttcgga  93660
cgccatttat tacgcggaat atctacgacg acgcagcact gaatcggttt ctcgcgacgg  93720
gagattccgc ggtcggcgcc ggtgcggggt tgtcaccggg cgacgaggta accagcgcgt  93780
```

```
ggaaggcgcg cacctggtcg tccgtcatct tgtcctcgaa cgaggacgcg cccgggggga  93840
gcaggtcctt gttgcgcgga acggcgggcg ccgagacgca cgaccggcgg tacatcatga  93900
tgacgatgta gcacacgatc gagatgacga tcacggtcag cagcgcgtcg aggagcccca  93960
tttattacct gtatatgccc gcgtttaccg ggcggtgagc tcaatgtcgg tgttgtttag  94020
ccgggcgtac gggacgctgc cggagcactt cctgtacatg ctgaacacga acagcccgag  94080
cagcagcacg gcgcccacta tgaagcaggt tacgcacagc gcgcgccaca cgtagtcggt  94140
gacgttgttg gtgttcttgc tgaaatccac gaaggcgaag acgcaggcgg ccgtcagcag  94200
cagcacgccg catatcagca ctccggagta gtaagagctc aaggtctcga atatgtccat  94260
ttatctgagg agaaatttaa attactgaat ggacgaagtg gaatagaaac cacgagaaca  94320
cgacggactg cagcacgaag atggtgctca gcttcgtctt catgggcatg cagaagttcg  94380
cggccagcgc catacagaag atgaacacga gcaccgccgg gtcgtagtcg gacaccattt  94440
acactacgct aaaaggcata tctcggcgcg cgacgtccac gagcaccagc acgcggacgc  94500
ccgcgggcgc gccggcggcg accgcggcga gctgcccggc cgtggggttc accagcagca  94560
gtgcgcgcgc ggttcgcggg acggggtctt cgtaggccat ggtcggcgtg gacccgggac  94620
gcagcggccg cccctgtctg tcgaagaggc cctcgggaaa cgaggtgccc ggaacggcca  94680
cgacgacggt gtcgctatct agaaacattt atggtcttgg tttccacgga tcgcctcgag  94740
tagaccgcca cgaagtagaa gatgacgccc gccgcgagcg ccgccaccag gaagggcggc  94800
acggcgggca ggttcgcgga cgcgttgtcg cgcacgccgg ggtccgggtc tgcgtagccc  94860
gcgcccacgg ccttgccgca gtcggcgatc atgtgcgcgc gcgagttctg catgaccagg  94920
ctgtccacgt cgatgcggca gcccacgtag cggcaccgcg agcgctgctc gtcctggctg  94980
aagaagagcc acttgcggtc gcgcgactgg tccgtgcact cgtgcgcgcg acagacgcgc  95040
gggcccaggt acttcccgag cgtggtgccc gcgacacacg cgcactccgg cgcggcgcgg  95100
tgcgcgtcgc agtagcgccg cagcgcggag tcgccgaagg cgaaggaggc gggccgcgcc  95160
acgcgcacga actccgagca gaagcgcgcg tccatgtgct tggcgcagag cgccgcgtag  95220
gtgtccagcg ccgcgtagcg gcccgtgcgc agccaggcca tgcactcggg cgcgtcaggc  95280
tccaccgcgc agcggctggc cataacgccg tcgcagtgcg cggtcttgta cccgttcgcg  95340
aacacggacg ggcacccggg ctccggattt gtgcagcagc gcgccatggc ggcgtccgtg  95400
ggcggcgccg aggcgccgat ctcgaacgcg cacatggtgc cctggcgcag gtacggcttc  95460
gcgatctcgg gaacgtagtc tgcgcgcagc agcgagcccg ggcggaagaa gagcgagtcg  95520
cagggcgggc ctcgcacgag ccgcgcgcgg ctcgccagct ctggcgagag gaagcgcccg  95580
cactgcccgg ggtccatggt cggcagcaga cagaaccgcg gccgtacggt cttcagcttc  95640
gggtcggaga aggtttctga ttcttccgcg aaggcgaagg tgtccgtggc gctcgtgtgt  95700
gtgacgcgca gcgcgtactc gcctggcgtc ggcgtgtcga gcacctccac cttggatacg  95760
gtgtccccca tttgaagacg ctatttacgc cgctgcctac tcggcgaaga ataggtcctc  95820
cgacttggcg cccgcgtaca ccgggcaggc gggcgcggcg gagcgagtgc gcacgatacc  95880
gcggccagtg aggcggaagg cgtagatggc gaacagcagg ccgagcacga tgtacatgaa  95940
agtggtggcg cccacagacc cggtcacgtg cgtcacgatg atggtgacga tggacatgat  96000
cgtgcacacg atggccatgc cggtgttgtt ggccgcgtag gggtgcatga tctgcatggc  96060
cgcacagtat ccgatgacca ggcacggcag cgggaggata agtgaggcaa tacctatcat  96120
tactagagcg agcacggggg tggacgtcaa ggccaataca aaaatcacaa tacctgttag  96180
```

tatgcggata tcctcgtact ggaggacgct gtaaggcgcg atattccctc cgggcactgg 96240
cctggggtta gccgggacta ggggggagtc ggcagtgccg gggtccttgg ggagaaaggc 96300
attctgctcc tccgggctga agagctcggc gtcctgaacg ccgccggcgg tgaactcgtc 96360
gttatagtaa ctaaagtagc tttccattta tatgttgaaa aatgtttgga ggcgtacagg 96420
tggacgacaa actctacgcg tacctaaaaa aactcgccgg acgcgggcgg ccgctgtgtc 96480
tgttccgcga caacggcgag ttcgtcgaag tcttcgcggg gtccgcgttc cgctttgtgc 96540
tgcccgtggg cctcttcgcg gacctgcgcg tgcgcacgcg cggcgtggcc ttcccgaaac 96600
tgcgcgactc cgcgcgcatg cgcggcgtgc gggtggacgc gcacacgctg ccctcgctgt 96660
accccaacca gcgcatcgtg gtggacgagg tgctcgcggc ccgcgaccag ttgctggccg 96720
cgggccgcgc cgtgtacgtg acgctgcatc tggcttgcgg cttcgggaag acgctgaccg 96780
cgtgccacct catcgccacg cacggccgcc gcgcggtggt gtgcgtgccc aaccgcatgc 96840
tggtgccgca gtggcgcgcg gccgtggcgg agctgcgggt gcccttcgcg gtctcctgtg 96900
acggcgcggc ctcgctgctg cgctcgggcg agctcgaccg cgccatggtg gccatcgtgg 96960
tcagccggca cttcgccaac gacgacttct gccgcgcggt gagccggcag tttgacgtgc 97020
tcgtgctcga cgagtcgcac acatacaacc tcatgaacaa caccgcggtc tcgcgcttct 97080
tgaccaagta cccgccgccc atgtgcttct tcctgaccgc gacgccgcgc acggccaacc 97140
gcatctactg caaccgcgtg gtgaacgtgt ccgtggtcag ccgcctcacc aaggtagtgc 97200
gcgtggtgga cgccttcttc gagccgtaca ccacgcccaa gatccgcacg ctcgagcgca 97260
gcctcgaggg accccagaac aagtaccacg tcttcaccga gaagatcctc ggcgaggacg 97320
tgcaccgcaa caagctcatc gtggacaccg tggtcgcggc catggccgcg ggcgaggcgc 97380
ggcgcgtgct cgtgctcacc aagctgcgcg aacacatggt cgggctgcac gccgcgctct 97440
gcgagcgcct cggtgcggag acggtctttc tcggcgacgc caagaacagg aagacgcccg 97500
aggtcacgcg cgcactgcgc gacaaggacc gcttcgtgct cgtgtccacg gtcttcttct 97560
cgggcacggg cctggacctg cccaacctgg acgcgctcgc ggtggccgcg gccgtgctca 97620
accgcatggt catggagcag atgatcggac gcgtgtgtcg cgagtcgcac gccaacacgc 97680
gcacgctgtt cgtgttcccg gactcctccg tgcgcgcgat ccgcgacacc gtgtctgcgt 97740
ttgcgcagcg gctcgtggcg ctggcggtgg acgggctggg cttcgtccgc gagcgcgccg 97800
ccgccggcgc gaagaacgag ccggcgctgt acagcgccat cagcgggcga gatctcgcag 97860
cggtgtaagc gcggacccgc acgccgcgca cgagagcgtg ctggagcagg cgagtcccag 97920
cgacagtgtg gacagcctgt ccacgtcctt gatgctcacc agccgcgagt tgcacgacga 97980
gcacacgggg tcgctactat catcgaccac cgtggtgacg cggcggcgtc tgcgcttttt 98040
gtttccagcg gcgacatcga ccacgcctcc cttagagccc cccttcgccc ccgccttagc 98100
tttcaccgcg ctcatctttt atttatcata aaaacacgtc tgcgtacgcg ttcgcgcaca 98160
cgtcccgcaa atccgcgcgc gcgccgcagc gcgtgaagcg cgcggcgtcc gcctccgcga 98220
tccgcgcgca cggcagcggc gcgcccttct cgtccgccat cacgcgcgca gagatcccgg 98280
tggcccccag cgcgtacgac accaccacgt cgccgacgca gcggtacacg ttgccggagc 98340
cggcgaggcg gtcgaacgcg gcgccctcct ggcgcagctt gtcgaatatg cgaggaacga 98400
ggatgttaaa aatgagaacg aaatagcaga tcagcaaaaa cagcgagatc atgacctccg 98460
agagcgattt atataccttg aaagagctaa tacgacttcg ggactcgctg cacctcgcca 98520

```
ccggcgccgc cgtcgagcgc tacaacgcgc tcgtggagtg ggccgcgcgc acgtactgga  98580
cggtcgcggt gctgccctcc gcgccgtgcg cctccatcga gaagtactac tgcgtgtgca  98640
aacccgactg cgcgctcgag cccggcgagt actccgtgag ccggctgcac ttcggactca  98700
cgcacgcctg ggtgcgcggc gccgccttca actcggccag cggcgccgag gtcgagccgc  98760
cagaggaggt gcgtagggcc tgcgaggcgc tcgacgccgc cttcgcggac ctcaccttcg  98820
tgcgcttctc ggtcttcggc cgcgagtgga cggtcgacga cgccgtcaca gaccactcct  98880
cgcgcgacga ggtgctcgcc gcgtgcgccg cctccggcgt gcgcgtcgcg cgcacgctgc  98940
gtgtgcgcgt gcgggcggga gagtccttcg cgcgcgcaga cttcgacgcg gtgcacgccg  99000
cgctgcgcgc ggagggcgac gtcgctcgcg gcaccgcggt ctgtctcgcg ctgcgcgggt  99060
catcgcgccg ctggatagcg gaccgcgcgc ctcgatgctt catgcgcgtg cgccgcgtgg  99120
agctcgagcc cgtggacgcg cggcaccact gcccggtgct gatctccgcg cgcggcgacc  99180
gggtgctctg ccgcggcgtg gggcacctcg cggacgcgcg cgcgcgcgag ggcgtcttcg  99240
tggccgtgcg caggtacccg gagtgtctgg tgctctgcga cgaggcggcc gccggcgcgg  99300
cggagtgctc gcgcgaggag gcgctgcggc tgctggtgcg ccgcttcggg cgcgacttcg  99360
ccgtcagcga ggagggctac gtcttccgcg tgcaggacat ggacttgcgc ggcgtgtccg  99420
cgcgactggg gctcgcgccc tgcgcgagcc tggaggagct gcgccgagcg gtggagcgcg  99480
accgcgcgct gatgaggcgg ctgcgcgcgg agggcgccgt gcgcctcgcg tgcgagtgcg  99540
tgggataccc gcgccagaac gcggtggagc tcataaataa tatgcgcttt caaataacgg  99600
aagaaggcgc ggtggcgaac tttgagctgg cgaacgcgag ctgtctcggc aacccgaccg  99660
cggagtccat cttcgcgagc ttcgcgcagt tcgtgccggt cttcaacgtg ctctcggcga  99720
tcgcgcgcgc gcagccatga tcgtggcggc cttcgacctt ggcacgcgca accccgcgcg  99780
caccgtgctg gaggtgctcg acggcacggt gcgcgtggtg gacgtggcca agctggactg  99840
gagccgcgac tgggagaagc gcgtgcaccg cgacgtgacc gccttccccg cgaacgtggt  99900
gctcgtggag cgccagtgca agatgtcgcc tttttctaag ttcatatact tcatacgcgg  99960
gctgctctac gacgggcggc gccgcacgcg cgtgctcgcg gtgccgccgg ccatgaccgg 100020
cagcacctac cggcagcgca agcgccgctc ggtgcgcacc ttcctcgcgc tcgcggagag 100080
cttcggcatc ctggacgccg tgcccgcgcg gaagaagctc gacgacgtcg cggacagctt 100140
caacatggcc atcaattacg tgctccgaac aaactgaaat acgactggaa cgaataagtc 100200
atgctggcgc tgttcgagtt cctgcggtcc gtggaggact gctaccggcg caccatcttc 100260
aacttccaca tcgcgcacag cgccgaggcg ggcgatgtct acggcgtgct gcgcgaccgc 100320
attttggcgg ccacgcgctt cgaggaggta gcgccgccag ggctcgcgga cgcgctggcc 100380
aaggtggtct actgcgacat aagcaccacc aagcacctgg tcaaccacgc ggccttcgcg 100440
gcgcgcgcgc ggccggcgcg gcgcggaggc agcctcgcgc agttcttcga cgtgcacgtg 100500
ggcgaggacg cggagagccg ccgcaccgcg gagatcttcg accgcgagcg ctcctcgctg 100560
gtctcgtacg tgaagaccac ggccaagcgc tgcaagatcg actacggcga gatcaagcgc 100620
accatccacg gcgggcggca gacctacttc tcggggcggc gctcggacga cttcctgagc 100680
accaccgtgc gcgcggaccc gagcaagccc tggatcaagt ccatctccaa gcagctgcgc 100740
gtggacatcc tgcaccacgc gatctgcacg cgcggcaaga gctccatcct gcagaccatc 100800
gagatcgtgc tcacgaaccg cacctgcgtg aagatattca aggactcgac catgcacata 100860
atcctctcca aggacgaccg cgagcgcggg ctcgcggacc tcgcggacaa gctcttcggg 100920
```

acctacgcga ccaccttccg cgtcatcgcg gccatcaccg gcaacgcctg cttcgcggcg 100980
gtggcggacg cggccgcgcg cgtggtcgcg ctcccggacg cggacgcgaa gctggcggcg 101040
gtgcgcgggc tcgcggagtg ctacggcgtg cgcaacttca aaatcggcat gttcaacctc 101100
accttcacgg gcgccatcga gcacacggtc ttcccctcgc tgatccccgc ggagagcaag 101160
atcaagttct tcaagggcaa gaagcttaac atcgtcgcgg tgcgctccac cgaggagggc 101220
cgcgagtgcg tggagcaggc gcaggcgctg ctcgcggcca tgcgcgagcg ctccgcgcgg 101280
ctcgcggccg cggacgtggc caccgcgagc gtggacttcc tcaaggagct gctggggcca 101340
tagtgaaata atactgattt cttaaatatg gagcaggcgc tcggatacaa gtttttgttg 101400
cccgacccca aggacgacgt ctactaccgc ccgctccact tccagtatga gtcatacgcc 101460
aacttcatca agcaccggct taaggacatc ctcacggtgc ggcgcacgct gctcaccttc 101520
aagaacggca ccgagtccat cgtgctcgag atcgacgacg tgaagatctc ggcgccggag 101580
ttctcgccca tcgtggccag catcaagggc cacagctacg aggcgctggt caccttcacg 101640
gtgaacatct accggcacgt gatgaccaag gacggcctca ccgttaccaa gatcaacagc 101700
tacgagggca ccgactcgca cctcgtcaag ctcccgctgc tcatcggcta cgggaacaag 101760
aacgcgctgg accccctccaa gttcgtggtc ccgaacgcca tcggcggcgt cttcatcaac 101820
aagcagtcca tcgagaagct cggcatcaac atgatcgaga agatcaccac ctggcccaag 101880
ttccgcgccg tgaaggccaa ctccttcacg ctctccttct cctcgatctc gcccgtgcac 101940
gtgatgcccg cgcggtaccg acactacaag atcctgctcg acgtgaacca gcccgacaac 102000
ttcgtgatct cctccgcgaa gaccttcatc accgtgaacg tgatcgtgat ggtgcagttc 102060
ctcgcggacg tcacgctcga gttcgtggcg cgcaacctct gcttcgacat gccgcccgag 102120
gccgcgcacc tggccaccgc gctcgtggag agcgcgaaga ccgtgcccgc gggcgcggac 102180
gtggccgagt acgtgaacgc gctcatcgcg gccgagcacg cgaagcagaa gtcgacgctg 102240
tccaaggagg agttccgcta cgagatgctc agcaacttcc tcccgcacat gcaggacagc 102300
gccaaccagc tcaagggcct gtacctgctc tcgctggtgc gcaagatggt cttctgcgtg 102360
ttcttcccga accggtaccc ggaccgcgac tcgctggtct gccaccgcgt gtacacctac 102420
gggcgctact tcgaggcgct ggccatggac gagctcgaga cctacatcgg gaacatccgc 102480
aacgacatcc tcgcgaacca caagaaccgc ggcacctgca ccgtgaacat ccacgtgctg 102540
accacgcccg gcttcaacca cgccttcgcg gcgctgctca gcggcaagtt ccgcaagtcc 102600
gacggcagct tccgcacgca cccgcactac tcctggatgc agagcatctc catcccgcgc 102660
agcgtgggct tctaccccga gcaggtcaag atctcgaaga tgttcaaggt gcgcatgtac 102720
caccccagcc agtacggctt cttctgcgcc tcggacgtgc ccgagcgcgg gccgcaggtc 102780
gggctcatct cgcagctctc cgtgctcgcc tccatctcga acatccgcac cgcggacttc 102840
gtcgagctca ccaagcgcgt ctgcgactac gtgcgctcct accccgcgcg cgacatcagc 102900
tacttcgaga ccgggttcgc ggtcaccgtc gagaacgcgc tcgtggcctc gctgaacccc 102960
gcgatcgtgg acgcgttcgt gctcgacctg cgccggcgca agcggctcgg cttcttcggg 103020
aaccgcgaga tcggcgtcgc gctcgtgcgc gaccgcatga acgaggtgcg catcaacttc 103080
ggcgcgggcc ggctcatccg cccgctgctc gtggtcgaga acggcgtgct cgtcatggac 103140
gcggaggcgg agcggctcga gcgcgacctc gccgcgatga ccttctcgga cgtgctgcgc 103200
gagttcccgc acgtgatcga gatcgtggac gtggagcagt tcagcttcag caacgtctgc 103260

-continued

```
gactccgtgc agcgcttccg cacgctgccg cccgaggagc gcgcgctctt cgacttctgc 103320
gacttcccgg ccgagttccg cgacgggtac gtggcctcct cgctcgtggg catcaaccac 103380
aactccgcgc cgcgcgccat cctcggctgc gcgcaggcca agcaggccat ctcctgcctg 103440
agcgcggacc tgcgcaacaa ggtcgacaac ggcatccacc tcatgttcgc ggagcggccc 103500
atcgtggtca gcaaggcgct ggagacctcc aagatcgcgg acaactgctt cgggcaccac 103560
gtcaccatcg cgctcatgtc cttccgcggc atgaaccagg aggacggcat catcctgaag 103620
cggcagttcg cggagcgcgg cgggctcgac atcctcacct gcaagaagta ccaggtcgag 103680
atcccgctcg agaacttcaa caaccgcgag cgcgtgcgct ccgcggcgta ctccaagatc 103740
gacgtcaacg gcgtggtgcg cctgaacgcc ttcctcgagc agggcgacgc catcgcgcgg 103800
aacgtgtcct cgcgcacgct cgacgacgac ttcgtcgccg acaaccagat cagcttcgac 103860
atcgcggagc ggtactcgga catctacgcc gcgcgcgtgg agcgcgtgca ggccgacctc 103920
accgacaagg tcaaggtgcg cgcgctgacc gtgcgcgagc gccgcgccat cctcggggac 103980
aagttcacca cgcgcaccag ccagaagggc acggtcgcgt acgtggccga cgagactgag 104040
ctgccctacg acgagaacgg gatcgcgccg gacgtgatca tcaactcgac ctccatcttc 104100
tcgcggaaga cgctctccat gctcatggag gtcatcctca ccacggccta cgggcacaag 104160
cccttcgccg aggacggctc caaccgcccg atctgcttcc ccagcaccaa cgagaccgac 104220
ttcgagacct acatcgagtt cgcgcggcgc tgctacgcgc tctcgcaccc cgaggccgcc 104280
gcggacgacc ccgagttcga gcaccgcgtc ttctgcgagc gcgtgctctt cgaccccgag 104340
accgacgagc ccttcgcggc gcgcgtcttc ttcgggccgc tgtactacct gcgtctgcgg 104400
cacctcacgc tggacaaggc cacggtgcgc tgccgcgggc gcaagaccaa gctcatccgg 104460
caggccaacg agggccgccg ccgcggcggc ggcatcaaga tcggcgagat ggagcgcgac 104520
tgcatgatct cgcacggcgc ggccttcacc gtcgccgaga tcctgcgcga ctccgaggag 104580
gacgcgcagg aggtgctcgt ctgcgagaac tgcggcgaca tcgcggcgcg gctcaacggc 104640
acgcacgtct gcatccgctg ctccaagatg agcctctcgc cggtgctcac gcgcatggac 104700
tccacgcacg tgagcaaggt cttcaccacg cagatgaacg cgcgcggcat aaagatccgc 104760
gtggagttcg agaagcagga cccctgcttc tacgggactc cgaaacggtt cagcctcgcg 104820
cccgacgagt cgctgttctc gccggaggac tgaacccgcc gtcgcgaccg cgtcgcgacg 104880
actagcttat cgttcgactg atgcgaaacg cgcggcggcg ccgcgactta gcttatctcg 104940
actgatgcga acgcgcgacc tctcgcgact ttctagcttc tcagactgat gctaccatat 105000
cgcggcgtgc tggccccacc accagggctt ctcgccgtgg ctgacgcggg gctggctgcg 105060
acgcgcgctg cagtagctgc gcgcgcccca gtcgccgcgc acgtgcgccg ggggcaggct 105120
cccgtccagc gcgtgccgcg tcacctcggc gccgggccgg cggcacgtgt gcacgtccgt 105180
cttgttggag acgagcaccg cgtactgccg catggtctct atgtgatgct ccaagtgctt 105240
gcccgccatc cggttggact cgcagcacgt ttttgcttcg gctaaggttt tttctagagg 105300
ggatagtagc ttatccacgc gctcgggcag gacgcacgcg gagccgtcga accctacttt 105360
gaacggggtc accttgatgt tcccgtcgta gcggtcccac agcatcctga ggtaggttgt 105420
accgtcgggg tctgggtctg tccacactct aagcttttcg ctacagcggc cgtcgtacgt 105480
aagacggtct ctacgctcgt agtagtttct gcttatgttg ttggggtctc catgctcgta 105540
gtagtataaa tcgtacgcgc ctggcttttt taagtcgttt tcgtcgttgc tgacgtgtat 105600
cacgtcggga taataggata tcctaactgc actacaatct atagtatttg gtctagtaag 105660
```

ctgttcgaga tcaccttgtt catcatgatc tactgatttg tacacggcac cgtcgtgttc 105720
cgacggacgt atgaatatgt ccatggtaaa cgatgtaccc actttggaaa acgtatccca 105780
tgcagtaaag catagtccgt ccattataaa ctcaggaaca ctcataacaa atcgaaatct 105840
gtgaagtttt tcgaacacca cttttacatg gtctttgtca cgaacatcat tgccgtttac 105900
ttcagacatg aattgaagga acgctaaaga gtttcttgtt tcttcatgaa tctttccatt 105960
atacgtccat ccagtttcta gaattctata tatgcttttt gcatcgaccc cgtaccacca 106020
gtacatggga actccgaaat atatagctgg gtttgagtac caatgggcaa gagtgcccat 106080
tgcgtttaaa aagtcttgac aaaaaaatgc agtttttctg tcgataactt gacttggact 106140
acgttcgtgg acatcgtaca tgtccataat tggttcattg gtaacggtta catgacccgt 106200
cattatcttt ttaacaatca taagatacag tttgcctaaa gtcgaaatat gtataacgtt 106260
aatttttaca tgttctccta acgtaattgc gtttttactt agccattcgt cgtctacaaa 106320
aatcttacga tacataggat ttctctctac gtatcttcta aagtatagat ttaccggtct 106380
accggcgaca ttagcgccat ctatagcagg agcaagctgt atgtatcgtc gtataatgtc 106440
tcgtataagc tttctgtctt ctctgggaat acacgacacg gaacttagag actggtgcca 106500
gtgtctttca accaaagact tgaacctagc aaccaacgcg ttgtcactct ccatttataa 106560
ttaaataatt atcccaactt cgtatgttaa tccttattac cagatagcac cgctccttcc 106620
tctccaccac gtactatcta aaggatacct gtaagggtaa tgtctggata acgggcgtgt 106680
gagccaagac gtgttatggt gtcttcccca ccaacggtcc acttctctaa ctaccggagt 106740
gctagacgtt gtcgatccca ctactgttgt ttctccatta cctgtaatct ttgaagcgca 106800
acaagtgtta gtctttgcca aatcttctaa cggcttaatt aggtcgttaa gtctgtcaat 106860
atccatgcac tgaggtgtat cgttaccagt ttccccaact ttgggaggaa cttcctgttt 106920
agtgtccaaa taacccataa acctgtctct aagcattctt ctgtacgtgc ttttgtcatt 106980
gtctatgtct cccaaaaacc tgtgatttac gcatccgttg tacgtaagtc tgtcccttcg 107040
ctctcgctcg ttatttccta cttcttctat tgtactgtaa tgttgatagt ccaagtaata 107100
gccactgttt tcatgatttc ttgtaaatat aatcggtgtt ttattattga catcgtgttg 107160
cctactgtac gtatcttcca tggatctagg aacttgtcta gaaaattgag gactagaaat 107220
acgccttcca aatcctggat gataaaccaa acgcaatgca ctacagtcga catcgtcact 107280
gtctctagtt atcccatcaa caactccttc tttgtgatgc tccactgttt taaagttaac 107340
tcctctgtat atgttgagtg ttaaaaaaat atccacattg aacgcagttc catattttgt 107400
tattttatcc cacgacgtat aacacaaacc atccataatg aattccggaa ccgatactac 107460
aaaattagta tcgaacttat caaacgaaat gtttactcgc ggttgtgctt cgtatttttt 107520
gtcatacaca tctgtcatgt attgtacaaa atctatagct cctctagcat cgggcatgct 107580
aacgtctgga aaatcatttt ttaactgttc tagtacgaac tgttgatttt ggtcatctct 107640
ccaccagtac attggcaatc ctatcacaag agacttattt ttataataat ttgctacaga 107700
agctatatgc cacatgaaat tatagcaaaa ataatccatc tgtatgttta aaaccggttt 107760
actagtctgc tgagagtagc tatccatgat agtgtttccc tcgccaatac ttcctgacat 107820
tattctgtaa acaaccatta acaaaaatct tcctaccgtt gttatgttgt caaaagttct 107880
tatgttttga gcactttcga gtaaccatat gttattttca aatatacttt tgtaaactgg 107940
atttctgtcc acataactct ttaaaaatag atttactgga aggccgcttg ggttatctcc 108000

```
ctgtataggc ggcgcttgct ttatgtattc gcgtaacaaa tctcttacaa cttttctagt 108060
tcttctaggt atacatgacc tattattcaa aggctttgtc cagttagcgt ttataaacgt 108120
tgtaaagtca ctgactagct tctccattta taattaaata attacagacg gcaacacagc 108180
ggttatctaa tatctgctgt atcctgtctg tacatctatt tttctgttga gatcaagaag 108240
agctttacgt agactctcca agtgtctttc tagtctgtct aaccggttac ctgtttctct 108300
gcagcaatca gttatagttt tgtaactgtc taacaagctt acgaggcgct cttccacact 108360
ttctttagtt ggagctccag ccgcgtacac tccgttggtt gaattgcctg tatcatcagg 108420
ctgagtcaat aggttttctc cgtcattttc atccatattg agtccaacga acacaaacga 108480
gtaagtgttc ctctatttaa agtattgatt ttagaaaaag gcaagcctcg ctgccctgat 108540
tcggcggcaa acacgggttg aacacgcgga agtcgctcgc ggccgtgaag atctcgtccg 108600
cgcacgcctc cacgctcgcg aagcgcccag gcgagacgcc gtcgtgcgag cggaacccga 108660
actccgaggc cgccaccgcc gcgcccttga agagcacgca gcgccacttc ttgcgcacgt 108720
cgaaggcctc gtcgttgggg tcgaacacgc gccggtccac gcgcgggccg cccgccgtgc 108780
gcgcgaactc cagcgccgcg ttcgccgcgt tgaactcgcg gatgttgtcg tagttctcgt 108840
agacggccca gagctgcagc gccacgaaca tggcggccgc cgccgcgagg gccacgcaga 108900
gcgcggacac cgcgtccatc ttttatgtgc agaattattc gttggcgcgg agctcgcgca 108960
gctccgcggc gcgcagccgc gcgaaggctg ctttgagcgc gcgcagcagc tcctcggtgt 109020
ccgcgcgcag catgtcgaag cggtggtagc tgtccaggcg cgcgcggcag ccgaagaagc 109080
gtgcgacgca cgcggtgacg atgtcgttca cgtagagcac gcccgaggcc gtgcagtaca 109140
cggagcgcgg ctcgcgcggg tccggcggca cgtccacggc gaccgcgtgc gcggccacgt 109200
cctcgagcac cttgcgctcg agcacggcga ggaagtcgcg cagctggcgg cggttgtcca 109260
gccaggcgta ggtggtcgcg aagagcgtga gccgcccgcg cggcgcgatc gcggtgtagg 109320
gcgcgtaccc gcggaactcc cgggggtgca cgaccttgac gttctcgtgc tcgcgacgga 109380
aggcctcggt gtcgagcagc gccgcgagcg cgtccacgag cttgtcggag acctccacgc 109440
ccgcgccgaa ggcgatgagc tcgatcttct gctcgctctt ggggcggaag tcgtggaagg 109500
tgtgcagcag catctcgcgg agctgcggcg gcttctcgac ggcctcgagc gcgtcgccgc 109560
ggacgaggaa gtagtcgagg tcgtgcagcg agacgtgctg cccggcggcg ctctgcacaa 109620
acttgaggaa gacgcagagg cccgcgcggc gctcgagcac gtcctcgacg tgcgcgtgga 109680
atacgtgccg cgagggcatg gcctcgatcg cggagagcca ctcctcgttg acgcaggtgg 109740
tggtgttctc cagcaccacg ccctgcgtga gcgcgggcca ctgcaggtgg aaggcgaact 109800
cgtgcttgat gagcgaggcc acggccgggt ccaggtccac ggccagcgcg gcctcgccga 109860
cgaggggagc gtccgccatc acgcggagga cgcctggccc atctcctttt tcgccttttt 109920
attcaggatc attattcttt cgttgacgag gtccatgagc atcttgatgg cggcggccgc 109980
ggccgccgcg tcgccgccgc acatctgcgc gatgcgcgtg agcatgtgca gcagcgcggc 110040
ctcgtttagg tcctcctcca tttagaggcc gtgagggcgc gcgtcgtcgc gacgagggga 110100
cgcctcccgc ggcagcgtgg tgcgcacggc gaaggcgagc agcgcgccgg cgcactgcgt 110160
gagcacacac tccgcgagcg cgacgaggag ctcggagggc gcgagcacca tttagaggcg 110220
cgcgcgggtt taattgccgc cgtcagagtc ggcatcatcg cccttgtcgc cgccgtcctt 110280
gcagtcgccc ttggtctcgg cgtcgacgat gtcggcgagc cgcgtcttca tgtgcgagaa 110340
ctgcgcgagc aggatgccgg ggtcgagaca gcgcttgacg acgctctcgt cggcgaagtc 110400
```

gtagcagatg cgctcctggt tctggcagaa caccgagtct tcgatgatca acaccctcct 110460
ggtcccggcc gaccgcatga tggccatggc ccggatgagc ctcttcttcg atccgcgtat 110520
ggacatggac cggagcacgt tctccacgtc ggagtcggag acgttgcagc agcagaggtg 110580
cgtgatgctg gcgcgcccgt tgacggggat gtgcttgtag gtctggcaga gcagcaccag 110640
cgacacgttg atgtgccgcc cgtagttcat gaggcccaag agtgtgggcg accgcgtctg 110700
cgtgtcgccc atatcgtcga gaatgatgag gaacttctgc ttcttcgtct gcgcgtgccg 110760
ctcgatcttg cgcttggcga ccgagaggtt gtactcgagc tcctcgtgcg tggtgacctt 110820
gtggatgtgg tccggccaca cgaagccgtc gtaggcggcg ttgtagacgg gcgtgaagag 110880
caggatgtgc ttgaagcggc gcacgagcgt gcggaagagc gagagcaggt aggcggtctt 110940
gccggagccg gagccgccga cgagcgccat cctgaagggc gcctcgatga gactctcccg 111000
cttgaagcgc acctcctgca cgacatccat cgtatattta ctgtcactaa attaccggct 111060
ccgagaaata tagaaattag agcctcctag agcacaccga ggcgcatcgg caagatggca 111120
cataacacgt tcgaaaacga tagcgagtcg gcagctaaca accagtacgt ggcgtcagtc 111180
aagcgccaga aaatgattcg gcgatacatt aagatgttct tccggttcgt tacggcgata 111240
gctatcattg tcctggctat tctagttgtg attctgtcgc tatctctaga cgaatgtctg 111300
cacagagaac accctcatga ctattcacat gtacaaaatt caacatgcga cggcattact 111360
ttaggtggtg aaaagtgtct cagacttaat ttgccagcaa cgtgggaaga tgctaataga 111420
caatgtggta atcttgggtt ttacctacca tctactggcc ttgaaaagaa atttccttgg 111480
cttgtgacct atctcgacgg aacttgggga aacactcaga actccgtatt tggaccaacc 111540
ggtgacttgc agaatgtcat aggaccgaaa gaatacaaat atttttgtgt gtccgattag 111600
atgattataa tctaataaat gggttgctgt aaggtcccta accgccagtc tataaggact 111660
ttgaaaaagg cgtcctgtcc ggtcgccagt ctcgtcacca ttctctccct agtcaccagc 111720
ctcggtgcga tagtcagata caccaatttt tttctaaaag aagcatgtga cgaaggatgg 111780
atgcccataa aaaacatatg cattttaaac acgcactttg aagccaccaa tgacgatgcc 111840
cacaggatat gtgaaaacct agacggaaag ccgccggcca tccctaaccc tactctgtta 111900
aagggtgtca cagttctcac cggcgaaaag aaattttgga tgacccatca cgaagactat 111960
actactgtgt ttgagcatat agacgatagg acgactccta aaaacacaga ctatgacagt 112020
aaaaaacaca cttgtttgat gagcgaggac ggattgatac accataactg catgatgaac 112080
gtgactgtgg tatgcatgaa ggagatgcac ggataactga aaatatactg tttgaacgca 112140
aagacgccat gtcgcgactt caaatactga cctcatttgg acaaatcttc gcacccgacg 112200
aagctcggct gcgcgagatc gcgcgtgatt tgggaatatg caccataaaa cgcgcattcg 112260
gcgacatgct gtacggcttt atagacttcg acccggtgcc cctgacccaa gtaaacatgc 112320
tcatgtccaa ctgctacttc gcggtcaacg gcaacctgct tccgtgcacg gaggacttcc 112380
ggctcagact cccggcaacg gagatctctg cggcctacct gacgagaacg ggacggacga 112440
tcctgtgcgg caaagacttc aacatagtag cgccgtcggg gttcaagccg tccatgcggc 112500
tgcgcgacct cagtcacgtg tctgcgcttg tagagatcct ggaagtctac gacgagtccg 112560
gggagtacca attcgtgctc ggccccagcg cgcagttcat gctgcggctg atggagaagg 112620
agaacgtctg tctgttcggc agcgggtggt gcatagtgga cctgcgcaag ctggacgtac 112680
ccatataatc agcatccttg tttttatcct gtctttttat cagtttttta gctagttaaa 112740

-continued

```
acataaatag taaagctaaa aagaggagtt ctggagtctt gcaacaacca ggatgaaggc 112800
ggtgttgttg ctggcgttac tgggagcgtt caccaacgca gcgcctttgt tagaaagcca 112860
gcgttctaac agtgaggaaa aagcaaattt ctgctcgacg cataatgatg aagtgtacgc 112920
caggttcagg cttcagatgc gcgtgggtgt acgacacagt ccgctctaca ctcccagcaa 112980
catgtgcatg ctggacatag aagactccgt tgaggacata gaagagtcca cagaaaaaga 113040
atacgcgtct acggccacgg gtgaggcggc cggagtgaac gtgtcagtgg cactagtggg 113100
agaaggcgtg agcataccgt ttagttacat aggccttgga ttcaacccgt cgcttgaaga 113160
tagctacctg tacgtcaacg tctcgtcacg agctccttgg gttaaacaga cttcggacct 113220
atccgcgaac ggcggctggg gtatcaaaca ggttctagaa aaagagttac tggccatcca 113280
aatagggtgc gacaaccaaa aatttcccga agaacccaca actacacccc cctcacctgt 113340
cactacaacg ctttcctcaa caactccaga tctgaatgaa gaaaacacag aaaatacgcc 113400
gacgaccacc ggcgccagtg tagacagaaa gcgcaatcca gctgacattg acttctcgct 113460
gctcgtggac ccccgatgcg tgacctctgt agacctgcac gtcgagctca gggacgcgtg 113520
catagactac aaacaagagt cgccgttgtc gctgaagggg aaatatggag acggcgaact 113580
agtaaaaaag gagattaaag acgtgggaaa gaatcacaat atgtgcagtc ttaacctcaa 113640
ccctggcaat tgagctgttt ttattcggca atataatagg tgattattga acattaaaca 113700
aaacttatcc cacaacgccg caacaatgga agtgctggtg atcatctcta ttatcgtcgc 113760
cgtaatatgc ttgaccggag cggtaatgta cctccttatt gaactcggct tagccgccga 113820
gcgcgctaac aaacgcgcgc gcgtgaagaa aaatatgcgc aaattagcca ctcaattggg 113880
aaatggatct gtcgactccg gcataggcat aggcccgtgc ataatgtcgc gcaccatgga 113940
ctctggaccc agtcgctggg acagcgacag tgaggatgac ggggacagcc tgtccacgac 114000
gtccaccagc ggagggggga ctctcacccg agtgtgggtt gggagcgccg ggcctatgta 114060
cgaaaacttc tgcgggaacg gcacccgcca ctcccccacc aacgaccctg gctaccactc 114120
gcgggagact ctctgcagcg gacctccccg tcaggcgccg gcgctaccgc ccaccccgaa 114180
gcccgacgag gtaacggtgg acgtggggcc cggtcccgac gaccaacacg gtccgtacga 114240
ggaacctgat cccattcccc cgcaggaacc cgagccgccg gtgcagattg aggtaaccat 114300
caacgggccc ggtggagaag gcgaggcgga aggagaattt ttctacgacg agtagccgcc 114360
aaaactgaat aactatcggg cttcgtaaac gcgcagacat gccgctgttc cggaagctca 114420
tggtttcgcg ctccctggtc aaggaatgtc tgactctgga cttccggcag ggcgagcgtc 114480
tccctacgcg atgcttcctc ccggtgcccg cggggacgac attccacaga gtctgcgaca 114540
cctcgccgct gacggacgaa gtctcccggc acgtgcagga gcccgtcatg ggcaccggac 114600
gggtccagta ctactacttc gagagcggcc agggcatgat cggcgacaac gcgggcatgg 114660
cgcgcatgct cgtgtgcacg cggtcggcgt acaacggcgg cgacgtcgtc gtgcggtcca 114720
cgcggagcag agcagacaag accgtggtcg cgccctgcca gggcatggcg ctgctgctga 114780
gccccttctg cgccttcgac atcacgccgg tcgagagcgg ctccgcgata ttcgcggagg 114840
tcatcgtcac cgcgcccagc atggactacg tcgaggcggt caccggcacg ggcgaggcgg 114900
ccgtgcggat attcaactcg caccacccgc tctggccgcg acacggctcg aacgtctgct 114960
tcgcgctgcg gttgctgcga gacgtgcgca cgggcgagcg cgtggtcgag cagatgttca 115020
tggacgggcg ctggcacacc gtgctgagga cgtcctgcgg caacaaggtc tgcgtgcccg 115080
ccgacctcgt gggccagacg aacctcgagg aggtgccctt ctgcgacgtg acgcccgaga 115140
```

tcatgcgccg cgcgctggcg atcgacccgc cgtacgaggc cgtggcgcac ccgcaccgct 115200
gcgtgtacgg cgccatggac gtccggtgcg cgaacgagta cctcgtgtac tgcaccttca 115260
agacggagcc gacacggcgc agcacgtcct cgccgggccc ggacagcccg ctgtcgcccg 115320
cgactccgtc gacctcgcgg gccgcggccg cgcgcgtccc cacgacgccg caggaagtgg 115380
cctcgccgac cacgaggctc ctggagacct gtctgcgcga cgccctcgac ggactctgac 115440
ccgaaggacc caccgtccac tcacattcca ctgccagaca actcaagctt tttctgcatc 115500
tacctcgcta ataattgaat tgttatagga caaacaggcg cactcgagca caatggcgtg 115560
ttttatcgaa ttgttagact ccatcttcaa ccgacgccac cgtaatttcg ggccggagga 115620
catgtacagg ccctctgacg ccccgccccc caaatcgcac acgcctcgca ctccccgcac 115680
cccgcggacc cagtgtcccg gacacccgcg gcgacaaagc tcctctccca tctacggcgc 115740
ttatgtggac tccctgccga ggaacagaaa gcggttccag aatcaacaca gttgtcccgg 115800
agattacgag cggtgtcaac tctcggacac catcagcctg gatgcgacgc tactcacggt 115860
tacagtgacg tccatctcca gcatatccag ctctagtagc tcagactcta tctctctggg 115920
gcagtgcaga ctgtccatgg tgtccgcaac atcaacctcc acctccacaa ccttctcctc 115980
ctcggaatga gcgccacact tatttttgta taatagtttg tattgaacct tagagacatc 116040
cacaaatagt taggaagcat gagtagttca agtagcgaga ccacccctaa gcccaagccc 116100
atccctgctc ctcccatgac tcaggaggag tttaacaaag aagtgaagaa acgaaaagaa 116160
cagaaaaagg aaaaatctag aaccgttgaa cgtgagtcag aaaccgtaac tgtatcttcc 116220
gacggatcag agataaaaaa gacttacgag cgcgagtctg agagaacaac cgaaacagaa 116280
aagaacaaca cgtcaaccga tgataataag cagaacaccc ctgtagagaa accagaggaa 116340
accaagcctg cttctactcc tgaaggtgtg aagccagccg agactcctgc cccgactact 116400
gacccccaac ctactacaca accacccgca gaatcaaacc ctggaagtca acccgcacct 116460
gcttcagaac caaccccccgc acctgagcct gcaccggaac ccactcagcc tgcatcagta 116520
actcaacccg ctccaacacc agagccaagt ccagcccccta agcctactcc ggcttctgaa 116580
ccaaccccag catctgagcc tacttctgct ccagaaccta caccatccgc agaaccaact 116640
cctcaaccaa ctgtagaaac accaccatct gctccagcac caactcccga ggcccaacca 116700
cccgccaaca gcaatcccac tactgaaact accactggta ccagcacctc ctaagtgagt 116760
acgtaagcat ttcggagtaa cgtcgtagca agcgctagtc cgccgcgagc ggttctcgca 116820
agttttttcg ggtaaaaagc gtacaccgtc gccttgtcgc ggcggtgtac gctttttca 116880 cgccctttttt gcaaaattta aattgtaccc gcgccggctc taggaaagat ggcgtgcctc 116940
agagtgttcc tggcggtgct cgcgctgtgc gggagcgtgc actcggcgca atggatcggc 117000
gagcgcgact tctgcacggc ccacgcgcag gacgtcttcg cgcggctgca ggtgtggatg 117060
cgcattgacc ggaacgtgac cgccgcggac aacagctcgg cctgcgcgct ggcgatagag 117120
acgccgccga gcaacttcga cgcggacgtc tacgtcgccg cggccggcat aaacgtcagc 117180
gtgtccgcga tcaactgcgg cttcttcaac atgcgccagg tagagacgac gtacaacacg 117240
gcacgccggc agatgtacgt gtacatggac tcctgggacc cttgggtgat cgacgacccc 117300
cagccgctct tcagccagga gtacgaaaac gaaacgcttc cgtacctgct ggaggttctg 117360
gagctagcga ggctgtacat tcgcgtgggc tgcacggtgc ccggagagca gcccttcgag 117420
gtgatcccgg ggatcgacta cccgcacacc ggcatggagt ttctccagca cgttctacgg 117480

```
ccgaaccgcc ggttcgctcc ggcgaagctg cacatggacc tcgaggtgga ccaccggtgc 117540
gtgagcgccg tccacgtgaa ggcgttcctg caggacgcct gtagcgcccg caaggcgcgg 117600
acgccactct acttcgcggg gcatggctgc aaccatccag atcgccggcc aaaaaaccca 117660
gtaccgcgcc ctcagcacgt atcgtcgccg atctccagga agtgcagcat gcagacggcg 117720
cgctaagggc gctcaccgcg ctgacggcgg ccgtggtgtg cgcgatcgcc atcgcgctcg 117780
agcgcggggc ggaggccgac gccgtggacc ttatccttat aaaattttca atgatatgct 117840
agtttttatg cgaccttcct tagaaaattc ggaattcaaa aatgaaataa aacggcgttt 117900
agcacgcata ttattaatac cgaccaccat ggcaggcgtc cgcagctgcc agaagaaagt 117960
cccttctact gcgggctcca tgtcatttca acggggcaac cggagcatcc agccggcgat 118020
gtccgaggcg ttgcagaatg atttcagcta caacccgcga ccgcctccgc cgagcgcaga 118080
agagattgac ttcttctgcg tggacatgcg caaagtactg atggaaattg aggccaagcc 118140
cagcagctcc aagtaccccg atttcatcac ccggttgaca gcagcccgcc gtgcacgccg 118200
gcgcgcaagc gcaacggctt cggccgcaag gcactgaaca aaacccaggt gccgcagcag 118260
gccaagcgtg acggctactc ccgctaatgc agtccacaca cttcacacac tacatcagca 118320
ctcaagctta taatcactac acaatgaatc agcccaccac gtgcgaagca cacacataaa 118380
atcacccacc tgtcctgatc gttcccaata ctcccaatca ccgtgcttta cacgcacgtt 118440
aatcaccctt tccttccttc atgcgttcct gatcgttcct cctccttaat cacacacaca 118500
ccccgtaatt ttgtactttt gtactttaat ttgtacactt tacacactga ctttgtactg 118560
cctttgtact ttatttttgt actgaaattg gacgatactt atctttgtat tcacatccaa 118620
gttttgcaaa ttccacagcc ggtagcgaaa agtgaaatcg taccgtttta ggcttcgatc 118680
cccctcccgc gcgaagactc gccagcatgg actctcgtag gctcgctctt gccgtcgcct 118740
tcggaggcgt cctcgccagc atgacacagc gccgccgcct ggcttctctc atcgccagca 118800
tcggccaacg gctgatgggc ggcgacggca tgcgtcgcgt cgccgttcgg ttgatcgacc 118860
agctcatggc cggacccccg gacatcaacg acgaggcctt ccagcgcgag atccgcgtgg 118920
gcgagctctt ccaggcgctc caccgcgtgg tcgagcaggc acgccgagag aagtacttcg 118980
aggtctgcgg cgccggcaac gacgccgacg cgcccgtcgt cgagatggac accgcggccg 119040
cacccccgca gccccagccc gcgcccctcg tggtcacgcc gcagaacgcg ttcatgttcg 119100
tgccgcaagg cagccacgtg cacgtggacg agagcgtgga cccgttcttc ggcatgagcc 119160
cctccatctt cgggcgcgac ctccccccctc agccgcccga ggagctgctg agcgactacg 119220
acccgctcat gagccaggcc ggcgagccgc cgagcccgcg gtcgccctgc gaggccgacc 119280
tctggtgctt cgagacgctc ggcgacagcg acagcgattg agaccgcacc acaccctacc 119340
tcacccaccc cacactccac ctcacctcac cctaacaccc aacacccaac acctcaaccg 119400
gacaatgaag gagtcccaca tttcactgaa ggacgcggat gaagccgcac tcccccacat 119460
gaaggattgg caacggtcaa acatttcacc tgcaatgaag gacgatgcgc ggtcgcattg 119520
gcctgcgacc gacatcgcac acatgaagga cacaattggt ttgttaatcc ggacaatgaa 119580
ggacaaattg tttttgttaa tcaggacaat tagaacacaa tcaaattttt gtacgatcat 119640
aaaatcgata tttgatgcac atatattagt aagtatatta gactaaattc tccggggagg 119700
caagcagttg gatacggcgg ggcggggcac gacgtgcacg gagagttcgg gcgggtcccc 119760
cttcccccca cccccacgca ccacgatgcg cctaatctta gcgctcgtgg cctgcttgtt 119820
ggcggcgccg atgccgttat cgggtcgttc gacaagcact ccaaacacgt ccccctccgc 119880
```

actcggctcg acgagttcgg aaccaagctc ggaagacgct gtggcttcga gcacaacgac 119940
aagcacactc acaagcacta caagcacact cactatgtcc acaagtgtgg acaccactac 120000
tacctcgggc gctacaacgt ccgcaaacag cactcctgca gcgagtgtga gctcctccac 120060
acccgcaact accgaggcat cgacggcacc aacgacgccg tcgacgccga cgacagtgaa 120120
ggtaacgaag ggcaaggaag acacgaaggc gtctgcctac ctcgttttac taatcacgtt 120180
catggtcatg accacgctcg tgatggtcgt ggtcgtggtc gtggtcgtgt acaaacaggg 120240
actctgtaac tgctgctgta agtttccctg ctgcaaagag ctcaaggact acctcgacga 120300
ggaggagagc gccgggctgt acgacgcctt gacgtggagc cactcagact ccggcctccg 120360
gctcgtcgtg cgcgcggacc ccagatgatg aggatcggat aagatcggcg tgtttttccc 120420
gcccgtcgcg aacattatgc ctctaaatgc cgagaattaa ctgaaattca aacacgcttt 120480
gggactcaac tccgtgaccc acactcaacc atggctggct tcctaggcgc attcagaggc 120540
gtgtgctccg acttatggca gtcgctccgt ggacacggac accactcttc cagctgcccg 120600
cgacgacgcg ccaacagcat ggacgaccgc gaccggcgcc gacaccgcca ccgcgagatc 120660
cccaacagct cggcgtcgct gaacagcgac ccgatgccgc aacgcagtgc gggtgcgcgc 120720
cggcactacg actgccgccc ctcggaaaag agcagacact cctccgacaa gcaccactcg 120780
gcggaccgac accactcggc ggaccgacac caatcggcgg acagggacag acaccgtcgc 120840
agtcgcaaga actacgactc gcacccgtcg cgcaggaacc gcaactacga gcgggcggac 120900
taccagagac acccctcaca aacccaccca gacgccccg cgcagacctc gacgctcaag 120960
gtgacctccc taagcaccag ctgcagcacc ctgtcccaac atcactacga gaccccgac 121020 cacatctacg acatcccgga agacagtcgc ggggcgtcgg ctccccctcg cgcggacctc 121080
gcgctccccc cgctcgccat gcccaaatcc aagccgcgtc gcacgcgccc ggcgtccatg 121140
aacgactgcc tgatgaagca ctgcggcgcc ggcagaccca acctccaaga cgacatatgc 121200
acactatgta ctgatataga gacacagctg agcgcactag agaagtctct ggagtcagag 121260
ctcaacttct atcgtcgcta catacaagac actaagacat tgctcgccac gcgagcagca 121320
aacatcggca gcaaagctct gatctacacc gacgactaca acggcagtgg cgacgtcggc 121380
gaaaaggagc actgctcgga ggagtgctgc aaagtggagg aagttctgtg agaaagtgcg 121440
tttttctgta atgtgaaata agatagcctt atgtgtgcac agacatggcg aacaggctcg 121500
tgtttctcga ccccgagacc ctagccgagg ccgacggcat ccccggctat ggggtgttcg 121560
agcccggcaa gaagaaatgc atcttcacaa agatccgcac cagcgtcgca ctcgcgtgcc 121620
ggtacgccgt ctcggacggc ggcctcatcg acgagttcgt catggctaca tacgggacca 121680
gacgcgcgtg ccggctcgtc cggcacctga cgataggcgc ggagggcgtg atgacccggc 121740
ccgccagcaa ctgcgcgccg cacatggtgc tcatctgcct cagaggcgtg gccgccgtgt 121800
ccagcgagga catgggcttc ggtcgctgca tcatggagcg cggcaccatg ttcatggtca 121860
agtccgcgca cagcgccgtc gtctgcggca accccgcctg cgagctgctc gtcctcttct 121920
acgactactt cacccccatc ccccggccgc tctccggaga cgaggtgctg ttcacccgcg 121980
acctcgcgca cgtggactac gcccccgagt cggcggtcgt cttcaagatg gattacaacc 122040
tcgagaccga cgtggccacg ctgtttgtcg gggggtacat attccgcgcc aagggcctga 122100
tgatggagac gcgcgaacaa gtgggcgacg agtgcgactg ctgccgccac agctcgccgg 122160
tgctcgtcat ggatcgcgag aagatgatgt cgtcgctgcg catgatcccc agcatcgtgc 122220
ccggccagcg ggagatttgg cttcgcgagc gcggctgggc cgtcctcgag acggacgccc 122280
gcggacactg cgagcccggc gtcctgaggc tggcgctcgc cggcctgcgg ctgttcgcag 122340
gatgcctgcg ctccgtcgtg gggcggcgcg agctgtcgct gttctgctac ggcgtcgctc 122400
ccaagttcgg cggggagttc gaggacgcgc cgcgccccat ggagatcgac ggttagttgt 122460
ttttatccct gtacatacgc cgcaaactga aactttaggg caccgcgtaa tagtgcacga 122520
acgcccagtg gaccgcttcc gcagccatgg aaaacaacga cggcaacgaa cgcaacaacg 122580
aacacccgca cgttcgagaa ttcaaggagg cgtccctgta cgggtttctg gtggcggccg 122640
cggacgtgac cgtcgaagac gtgcaccggt accttcagtt cggcgcggac gtgaactaca 122700
ggggcgcgta cctgtgcacg ccgctgcacg cgtacctgca gtccggctgc gaaaagcgcc 122760
tagacgtcgt ggacgcgctg ctggacgccg gcgcagacat caacgccaag gagatctgcg 122820
gtctcacgcc cgtgcacctg tacgcgagct acgcggacgt ggacgtagag ttcatgcgcg 122880
ggctcatcga gcgcggcgcg agcgtgtgcg gcgagagctc ggtcacgggc tgcctgtact 122940
cgtacctgta cacacacagc gtggacggcg gcgcgcgcct ggacgtggtc gagctgctcg 123000
tgcaggcggg cgcggacgtg aacgtccgcg gcgaggcgcg caagacgccg ctgcacgtgc 123060
actgcgcggg cttcgaggtg gattcggaca tcgtggatct gctgctgcgc gcgggcgcgg 123120
accccgaggc gctcgacgaa cacgggctca cgcccgcgga cgtgctcgtg aagtccgtgg 123180
gcgccaacgt ggagacgctg cggctcttcc tcgacgcggg cgtgagcgtg gccacgtcgc 123240
gcgacgcgcg cggacgcacg ccgctgcacc accacgcaga ctccttccgg gcgagtgcgg 123300
gcatcgtgcg cgaactgctc gccgccggct gcgacgcggc ggccgccgac gacctcggaa 123360
acacgcccct gcacagcctc gccaccttct gctcgtgccg gcgctcggtg ctcgaccagc 123420
tcatcgccgg cggcgcggac atcaacgccc gcaaccacta cggccacacc tgtctgtact 123480
acgcgtccat ctacaacccc tccgtctgct cgcggctcat cgccgcgggt gcggacgtga 123540
ccgcgcgcac gccggacgga cgcacgccgc tctcgggcat gatcatgcgc aagcacacgc 123600
gcgccgtgcg cgccgccctg gcgacgcggc ctcccgcgga cgccgtcgcc gcgtcgctgg 123660
acgtcgcagt acagcccgag cccacggacg ccactcgcgc gtgcgtgcgg tacgtggtgc 123720
tctgcggcgg cacgctctcg gcgcgcgtgc ggtcgcgaca cgcggacttc gtgcgagagt 123780
gcgaaagcga ggtggtcgtg ctcagaacca ccgtggtggg gctgcccggc acctcgctgc 123840
tggacatcgt gcgtgcggcg cagccgccgc cggtactgct ctccccgcgc gtgcaccacg 123900
tgctgcagaa gctgtgcgtg tacgcggagt tggtggacgc gcggctgcgc gagatgcggc 123960
acaagaccaa cctcgtggac gcggtgtcgc ggctcgtgtg tccgtgcgcg ctgccgccgg 124020
aggtggtgcg cggcatcctc gtgcacgtgc cgatagacag cctgcggcac acgttgaccc 124080
tcggcgtggc gcaggcctcg cgtttccttc cctcgcataa atgaaatatt attttttgtg 124140
gtagaccgga tctccccgat ggaccccgcc ggacaacgac tgcgcgcgcc agggccgtgg 124200
cgcctgaacc cgccgaccgc ggccgcgctg gaaagcgcgc tgctgcggcc cgcggcgtcg 124260
gcgggcgccg accgctgcgc gaacgcgcac gtggaccgcc gcaacatggg cgtcggcgag 124320
ggccgcgagg tgcccgcgga cgtcgagggg ctcatgaccg agatccacct gcggtacgga 124380
atgacgcgcg tccaccggaa cgttcacttc gtgcagttct ggcacggcga gcacgtgcgc 124440
cggcgccccg cgcgacacgt gttcacggtc tggatctgcc tcagcggcga ggtgcgcatc 124500
tacgcagagt gctgccaggc ggggcacggc ttcgtgctct gccgacagat ggcggcaggg 124560
tacatgttcg tgaccgaacc cacggactcg gtcacggtct cggtgccgca ccgactgcgc 124620

```
aactcgcggt cgccggtgtg gctggcggcg gtcttcgcca cgcggcactt cgagccgctg 124680
ccgccgccca tgtacgccgt gcccgggcac gtggtgctcg cgcgcagcgc ctccatgctc 124740
tgcgactgct ggccgtcgga cccgcggcgc cgcaacgtga tcttctacat gcggctgtcg 124800
ggcgcgatgg tgcgcgtggt cgtgccgggc gcggagctcg agatcgagtg cacctcgggg 124860
ttccggccgg accacttctc catcaacgac gagtgcgtgt gctgcgagcg tccgcacgtc 124920
gcgcgaaccg cggtgtggac gctggcggag atttgccgcg gcgccacggt ggtgctcgcg 124980
ccgccactgc cccgcgaccg cgccgcgggg ctgctcgcgg agatccgcct ggcctcgctg 125040
cgatgggtgc gcgtgcgtgc ggtccgcagc ggcagagaaa gcgtgggccc gttcccctcg 125100
gtggtgtggg cggcggtctt ctccgccgtt cggctcttcc tggacggaac cgtgcctgcc 125160
ttcccggcgt gtgtggagaa tggacgcgcg gcgtacggca tggtgtacgt gcccccggag 125220
gagccgcgga tggacgggct ctgtgtgttc ccgacgcccg ccgagccggc ggcgctcttc 125280
gtccgcggag accaggtgct tgaggccggc gcggccgccg ccataatcgc ggccgctgag 125340
aagcgcgtcc aggccgccaa tgggtctcct gctgccgcgg aggaggacat aggtgcggcg 125400
gccgatgccg ccgcagagag cgtggagcag gaccagcgcg tcgagttcga ccttgggcct 125460
gggcctgacc ccagccaaga agcgcccgcg gacgcgcagc gtgccgattc ggacgacgac 125520
accggctccg agaccgagac cggcgacgag agtgtgggcg gcgaggatga cagcgactcc 125580
tcctcctctt actcggtgat gtcggacgac gaaaacgaca gcggcgacga gggctggggc 125640
gactctagcg actccggcat cgaggacgac gacggcggtg tcggccaggc cgccgaggaa 125700
gaagaggagg aagagcgcga cgtcctcggc gcagcggccc agatgctcgg agactgaccg 125760
gtggtgaaaa cataaaaata aactgttcaa cacttgtact ccgggcacca acactactat 125820
ccatacccac cctccctcca cacactacaa tggcaaacag agaagagatt gacgcctccg 125880
ccgtcatggc tgcctacctc gcgagagagt acgcggcggc tgtagaagaa cagctgacgc 125940
cgcgcgagcg cgatgcgctc gaagcccttc gcgtttccgg cgaggaggtc cggtcgccgc 126000
tgctgcaaga actctcgaac gcgggcgagc accgcgccaa ccccgaaaac tcgcacatcc 126060
ccgccgccct cgtctccgcg cttctcgaag cccccacctc ccccggccgc atggtcactg 126120
cgattgagct ctgcgcgcag atgggccggg tatggacgcg cggccgccag ctcgtcgaat 126180
tcatgcggct cgtgtacgtg ctcctagacc gtctgccgcc cacggccgac gaggacctca 126240
gcacctggct gcaggccgtc gcgcgcgtgc acggcacgcg gcgccgcctg caccgcgttc 126300
tcggcgtcgg ggccgtcatg gcaggcgtcg gtatgctgct gctcggcgtg cgcgtgttgc 126360
ggcgcacata actttttatc tcggctcaaa ctgaaatacg acattggact acgaaaccta 126420
tgattttgct cacggccgcg cgagatagga taataaataa cctttgagca actaacatgg 126480
ccgatgagag agaggccgac ggcgcgctgt tccggtacct ggagagcgag gaccgtccgg 126540
acgtggagca catgcgccgg ctgctggacg agggtgcgga cgtgaactac gcgggcccgc 126600
gcgggtacgc gccgctgcac atgctcatgc gcggcaaccc gctagacccc gacgcggtgc 126660
gactgctgct cgccgcgggc gcggacgtga acgcgacatc gctctgcggg ttcacgccgc 126720
tgcactccta catgtgcttc gggaccgtga cgccagacac gctgcgtgcg ctcatgcgcc 126780
acggcgcgag cgtcagcgac ctcgagcgca acatcaacgc gctgatcgag tacttcaacc 126840
gcgacggctg catgggcggc gcggaggcga ccgtgatcgc actgctggtg gagcacggcg 126900
cgcacgtgaa cgccaaagac gaccttggac gaacgccgct gcacatctac ctgtccggct 126960
```

```
tcttcgtgtc ggcaccggtg gcgctcgcgc tgatcgcgct cggcgcgaac ccgaacgcca 127020
cggacgcgta cgggcgcacg ccactgcacg ccttcctgcg ctcccgcgac gtggaccccg 127080
ctgtgctgaa gacgctcatc gccgcgggcg cagacccgct cgcgcgcgac atcatccggc 127140
gcacggcgct gcactaccac tgcgagtcct tcaagacgcg cgctagtgtt atagagacgc 127200
tggtggccgc cggctgcgac cccgcgagca cagacctgct cgacaacacg gcgctgcaca 127260
gcatggccat gggcagctcc tgccgcgcct cgctgatccg cccgctgctg gccgcgggcg 127320
tgtccgtgaa cgcgcgcaac gcgcggctgc agacgccgct gcacctcgcg gccgtgttca 127380
acccgccggc ctgcgcgcgg ctgctggccg cgggcgcgga ccccgcgctc gcggacctgg 127440
acgagacaac gccgctgctg agcatggtgc ggcacaactg cgcacgcgcg ctgcgcacgg 127500
cgctgccctt ggcgccggac gcgctggtgg ccggcgcggt gaaccgcgtg aacgcgcgca 127560
cgccgagcgc ggccacgcga gagtgcgtga tggcgctggc gctgcgcggc gcgctggacc 127620
tgctgagcgc ggagagcgtt gccacccacg cggccgcgat ccgcgcctgc gaggcggagg 127680
tcgcgctgct gcggcgcacg cgcctgggcg cgccgccgac gacgctcttc gcgctgctga 127740
caggacgacc gaacacgctg gtttccgcga aggcggcgcg acgcgcgatg gcggacgtgt 127800
gtgtctaccg cgcggcgctg gccgcgcgcg tggagcgcgt gcgccgcaag tcctcgctgg 127860
tcgagcgcct caccgccatg gtgtgtccgt gcgctctgcc gccagagcta gtgacgcgca 127920
tcctcgcgct cctgaccgtg gaggaactcg cttgcgcaat gcgcaaataa taatgaacta 127980
taactaggct tattagaggc actatttgtg cagagtcgtt agttatagtt agtgtactta 128040
caattggaat gtcgaagaac aaaattctgg tgtgttttgt aattattctt acttatacat 128100
tatacacaga tgcgtattgt gttgagtatg aggaaagtga ggaagataaa caacagtgcg 128160
gtagtagtag taattttcct gcgagtttac cgcacatgct tagagaactc agggcagcgt 128220
tcggaaaggt aaaaactttc ttccagatga aagaccaact gaacagtatg ctactcacac 128280
agtcgctcct cgacgacttc aaaggctacc tcgggtgtca ggcactttct gagatgatac 128340
agttttactt ggaagaggtg atgccgcagg cggaaaatca cgggccggac atcaaagagc 128400
acgttaactc gctgggagaa aaactcaaaa cgctgcgtct tcgactgcgt cgctgccacc 128460
gcttcctgcc gtgtgagaac aagagtaagg ccgtggagca agtcaaacgt gtgttcaaca 128520
tgctgcagga acgaggtgtt tacaaggcca tgagcgagtt cgacatattc atcaactaca 128580
tagaatcata catgactact aaaatgtaaa aatgtataca acttttagtt atcgttcgga 128640
ttctcgtatc gttctgcata ctatgtatat aaaatgtata ttaacatagt tacagttaca 128700
gttacagcta tatttttatg ctcacaagat gctatataat tgaaaggaaa ttgttcactc 128760
tctgtcaggg cgccatggac tttctaggcg ccgcgcttca cgactacgtt gccgatgcgc 128820
ccaaggtctg cgccgaggag gtgcggcggc tgctggccgc aggcgcctct gtggagtacg 128880
cgggcgagtt cgggaagacc gcgctgcacc agtacatggg ccgttccggc gcggaccccg 128940
ccgtcgtgcg cgcgctgctg gacgccggcg cgcgcgtgga cctcccggag acctgctgcg 129000
gctgcacgcc cgtgcacctc tgcctcatgg ccgccaatat cgacgtggag gttctccgca 129060
tgctcgtcca cgagggccgc gtcgaggact gcggccgcgc cgagctcgcc tccgtggtgc 129120
tcaaggagtt cgtggtgaac cgcgccttcg acgagaacgt caccgagcga gtgatgcgcg 129180
ttcttgtggc cgcgggcgcg gacgtgaacg ccgccagcgt ggtcgaccgc acgccgctgc 129240
acgtctgcct cacgggcatg tccacgcacc cgggcaccat cgccgcgctg ctgcgcttcg 129300
gcgcggacgt gaacgccgtg gacctctgcg gcatgtcgcc gctggcggtg ctcgtgcgct 129360
```

cgcgcgcggc gaccgcagag ctggtgcgca tgctgctcga cgcgggcgca gacgcacacg 129420
ctgtcgacag tcgcctggac tcgctgctgc accagcactt tcagtccgcg cgcccgcggc 129480
cggaggtggt gcgcgagctc atccgccacg gctgctcgcc gcgggcgcgg aaccgaatcg 129540
gcaacacgcc gctgcacgag gccgcaaaac actcctcctg caaacactcg ctggtggggc 129600
cgctgctggc tgccggcgcg agcgtggacg cgcgaaataa cacgggcagg acgccgctcc 129660
acttggcggt ggcgtccaac ccgcgcgcgt gccgccggct gatcgcgctt ggggcggacg 129720
tggtcgcgcg cagttacgcg ggcgtcacgc cgctggcgca gctgatcgcg gacaataact 129780
ccgcgctggt gaccgcggcg ctgaacacgc agcccgagcc gcgggccgtg gcagagtcgc 129840
tgcgagcgac cacgcccgtc ggcgagacag cgtgctcgcg gctctgtgtg gcgtacgtgg 129900
tggcgcgcgc gccgagcgag gtcctcggcg agcccgagcg cgccctgcac gcggccttcg 129960
tggcggagtg cttagcggag gtagcggcca tacacgccgt gcgctgcggc acacctccgg 130020
tctcgctgct ggagatcctg gtggccgcgc gcccgccgcg gagcctgctc tcgcgccgcg 130080
cgtggcggct ggccagccgg acgacagttt accgcgcgcc gctccgtgca cgcatcgcgg 130140
ccatgcgcca tcgctcgcga ctggtggagc gcgcgctgcg cacgctgcgc ggctgcgtgc 130200
tcccgcgcga ggtgctggag cgcgtgctgc ggtgtctgtc cacacaggac ctgcgggcct 130260
ccggactggc cgagtagctt tttctgagat aagtgaataa acatggtggg attcgatcgc 130320
gccgccaacg ccacgccatg gacgccgccg agatggagga tctcgacatc aacgcggagt 130380
cggcgctgta cgactacttc atcctgaacg cggacagagc ccgcgtgggc gaggtggtta 130440
tgcttctcgc acagggcgcg gaaataaact acgcggacag cttcgacaag acgccgctgc 130500
acctgtactt gcacacgcga cacccgcgct cggacgtgat tctggcgctg atggaggcgg 130560
gcgcggtcgt ggacacgccg gagcgctgct gcggcgcgac cgcggcgcac ctgtacatcc 130620
tcaacgcggc caaggtcgac ctgtcggtgc tggaggccat gctgacctgg ggcgtgcgcc 130680
agaacgacca gcactcggag cggctgctct cgagcttgtt gcgcgagtac gtggtgaccc 130740
gcgcctactc ggatcagacc gagccgatca tggacttgct catcggcatg ggcgccgacg 130800
tggacatgcc ggtcggcgtg agtcgcacgg cgctgcacgc ctgccttacg ggcctgaacg 130860
cgaacccgtg catgattcgc gcgctgcttc ggcgcggcgc cagcgtgacc gcaaaagaca 130920
cctacgagat gacgccgctg gcggtgctgc tgaagtccgc gagcgcgacg ccggagctcg 130980
tgcgcatcct cgtggaggca ggctccgacg tgagcgccac cgacttccgc ctcaacggca 131040
tgctgcacca gcacgcgcag tccacgcgcc cgcgcgcgag cgtcatgcgc gagctcatcc 131100
ggctggggtg cagcccagcg gccaaaaaca tgtttgggaa cacgccgatg cacatgctgg 131160
ccatggaaag ctcctgccgc cgctcactga tcctcccgct gctggaggca gggctttccg 131220
tgaacgagga gaacccgcac tacggcaccg tgcctctgca cgtggcctcg gggtacgaca 131280
acacgcaggg ctgcctcaag ctcctccggc atggaggaga ccccaccgtc gtgtcggccg 131340
ccggacgcac gccgctctcg aacatgctcg tcaaacgcaa ccacgtggcg gtcgccggcg 131400
cgctgtcgac gcacccgagc gcggcagtag tcgtgcaggc tctcgagcag gctctcgaga 131460
acgtgctgaa cgccgggccc agcgaggcct cgcggctcgc cgtggccttt gtggtggcgc 131520
gcgccggcgc atccgcgcta ccggaggccg tgcgccgtct gcacgagggc tttgtcgccg 131580
actgcgagcg cgaagtcgag ctgctttccc gcaccatgct cggcacaccg gccgtgagcg 131640
cgctggtcgt gctggtcagc aaggaggtct ttggcactgt tatctcctcg cgtgcgctgc 131700
gcgtcgtgcg ggaggtccgc gtgtacgcaa ggccgctccg cgaggcgctc ataaatctgc 131760
gccacaaatg ccgcttagtt tccagcctta aaaggcaggt gggaccttgc tcgctgcccg 131820
gcgaactggt ggagcgcgtg ctcgcgaccg tgccactgac cgacttgcgc cgctcgtgcg 131880
gccgccgcgc gcccgagtaa ctgcccgtcc cgttgctacg cgactcgaga ctgcccgctg 131940
tttttctttc cccgtttctt cttattagga gttgttgccc gcctccatga tcctcgcacg 132000
cgccggcggg caacctcgca cgcccgcggc ggccgcggcc gccgccgagg acggcgagca 132060
cagtgatcgc cggaagcgca agcgcaagac gcccaactgc gaagacgccg acaactccga 132120
cgacgagcta gcgcagacgc cgtgcgaccg cgagtggccg gactgtcgcg cgagctcgat 132180
cacgagctcc gactcggtct ctctcggcga cgagatctac ctgcgatacg tggcctcgca 132240
ggtggacttc gcgcagacct gggccccgcc agtgcggctg ctgcgcttct tcgggaactt 132300
ctcgaaggaa acgctcaacc gcatgtcgcg gcgcgggtac gtgaaccgct cctacttcca 132360
gatggcgcac gcgcgcttct cgcccaccaa cgacgacatg taccacatgg ccacgggcgg 132420
gtacggcatc gtgttccgct tcgaccgcta cgtggttaag tacgtcttcg agcaccgcaa 132480
cggcatgtcc gagatggacg cctctacgga gtacacggtg ccgcggttcc tgcgcaataa 132540
cctcaagggc gacgagcgcg agttcgtggt ctgcgcgctg gccatggggc tgaactaccg 132600
gctgggcttc ctgcactcgc tgtaccggcg cgtgctgcac acgctgctgc tgctcatgcg 132660
cgtggaggaa ggccagcggc cctcggtgga gatgtccaag aagccgctgc tgcgctggtt 132720
cgaggcgcgc aaggacagcg agtccttcgt gcgcctgatc tcgtacttct acccctcggc 132780
cgtgcagagc aacgtgaacc tgatcaacaa cttccaccac ctggtgcact tcttcgagca 132840
cgagaagcgc gcgcggtacg tgttcgaccg cggggccgtg atcgtgttcc ctctggcgcg 132900
cgggtccgcg gactcgatct cgccggaggc ggcggcggcg ctgggcttcg cgccgcactc 132960
ggagttcctc aagttcgtgt tcctgcagat cgcgctgctg tacctgaaga tctacgagct 133020
cccgggctgc acgaacttcc tgcacgtgga cctgaagccc gacaacgtgc tcatcttcga 133080
cagtgcgcgc gcgctcagcg tgaccgcggc cggcgcgact ttccgcttcg aggagcccgt 133140
gcgcgcggcg ctgaacgact tcgacttcgc gcgcgtggcc accatcgaga accgcaagat 133200
cgcgggcagc gtccgcgtgc cgcagaactg gtactacgac ttccacttct tcgcgcacac 133260
gctgctgcgc gcgtacccgc acatcgccgc ggaggacccg ggcttccacg cgctgctctc 133320
ggagctcacg gtctcgtgct cgcgcgggac ctgcgaccgc ttccggctgc gcgtgtcctc 133380
gccgcacccc atcgagcacc tcgcgcggct ggtgcgccgc gacgtcttct cccgctggat 133440
aaatgccgcc gcggacgccc ccgacgccgc cgcactctcc tgagcccacg cccgcggcgc 133500
cgggctcgct gtacgacgtc ttcctcgcgc gcttcctgcg ccggctggcc gcgcgcgcgg 133560
cgccggcctc ggccgcctgc gccgtgcgcg tgggtgcggt gcgcggccgc ctgcggaact 133620
gcgagctagt ggtgctgaac cgctgccacg cggacgcggc cggcgcgctc gcgctagcct 133680
ccgcggcgct cgccgagacg ctggcggagc tcccgcgcgc ggacaagctc gccgtcgcgc 133740
tcgagctggg cgtggacccc gagcacccgg agctgacgcc ggaccccgcc tgcgcaggcg 133800
agagcgcact cgcacagaac atcgacatcc agacgctgga cctgggcgac tgcggagacc 133860
ccaaaggccg ccgactgcgc gtggcgctgg tgaacagcgg ccacgcggcc gcgaactgcg 133920
cgctcgcgcg cgtggcgacc gcgctgacgc gccgcgtgcc cgcgagccgg cacggcctcg 133980
cggagggcgg cacgccgccg tggacgctgc tgctggcggt ggccgcggtg acggtgctcg 134040
gcgtggtggc ggtttcactg ctgcggcgcg cgctgcgggt acgctaccgc ttcgcgcggc 134100
cggccgcgct gcgcgcgtag ccgcgcaaaa tgtaaattat aacgcccaac ttttaagggt 134160
gaggcgccat gaagttgctc gtcggcatac tagtagccgt gtgcttgcac cagtatctgc 134220
tgaacgcgga cagcaacacg aaaggatggt ccgaagtgct gaaaggcagc gagtgcaagc 134280
ctaggccgat tgttgttcct gtaagcgaga cgcacccaga gctgacttct cagcggttca 134340
acccgccgtg tgtcacgttg atgcgatgcg gcgggtgctg caacgacgag agcttggaat 134400
gcgtccccac ggaagaagta aacgtgacga tggaactcct gggggcgtcg ggctccggta 134460
gtaacgggat gcaacgtctg agcttcgtag agcataagaa atgcgattgt agaccacgat 134520
tcacaaccac gccaccgacg accacaaggc cgcccagaag acgccgctag aactttttat 134580
ggaccgcaga tccaaacgat gatgcgatca ggtcatgcgg aagaaggcgc cacggagcaa 134640
agtgaaaaag gaccgcctag cagtcgagac cctcccgccg cagccgcgga caccccacac 134700
ccgccttcca cccgccagac gccaacaccg cagccaacaa gcatgcaccc ctcgccgcgc 134760
aggctgctcg gcgcgctcgc gctggtggcg ctgggcttcc tcctcggcgg gctcttccgc 134820
cccgcggcgc cgccgctgcc ggccgccctc gtggaggcgg gccccgtccg cgcgaacggc 134880
tccgcctcgg tgacctgcct gaccgtcggc ggcgacgggc ggcacatggc ggtggtcgcg 134940
cacggcggcg ggacgctctc gccggtgtac ccgctcgccg ccggcatgca cgcgaccttc 135000
gcctcgctgc gcaagggcgc gctgctgctg aacgtcgcga ccgtgcacat ctacgacgtg 135060
cgcgcgctcg ggccggagtt cgagctgacc tgcgtcgcgg tggcgggcgg ctacaacgcg 135120
gcctgggcgg ccgcgcggcc cgcggccgag tggcgccgcc agctggcgcg gatgcaccgc 135180
tcggagctgt gaccctctcc ctcccggtct cccatccgtt tttgtaatcg gccttagtag 135240
attagaccag catcccgcgc ccttgtccgc cgcccttcgc tcgctcacga gcgaatcagt 135300
caattgatta tttttatcgc ccgcccgctc actccggtaa gggaacgcgg ttaacccact 135360
cacgagaaca agcgaccgcc actcacttga ggtaagggaa cggttacggt caactcactc 135420
acgagaacaa gttgactcac tcctcgaggt agagaacgag agaacaagtg accgtactca 135480
ctcacgagaa caagttgacg caccgctcac cgaggaaggg aacagagaac aagtaacagt 135540
aaccgttacc tcactcgcca ctcctcggaa taatagaacg agagaacgag agaacgagtt 135600
aaccgttgct cactcgctca ctcggtgtga gagaacaagt aacgttgctc actcgctcac 135660
tcggtgtgag agaacaagag aacgagtagc tgttgctaac tcaatcaccc ctcggagtaa 135720
gagaacaaga gcagtcaact acccactcag tcttggatga gaggcagagg acgagttgac 135780
gagttgaaca gttaatcctc actcactcag agcgagagag cgagagagtg gaggacgagt 135840
taacaagtca atcctcactc agagtgagag agtgagagag tggaggacga gttaatggtt 135900
aacagttatc accactcaga gtgagagcgg aggacgagtc aaccactcgc tcgcccactc 135960
cgagttagag agggaaccag tgcgagttaa cgcgcacacg agcgagagaa cgtaaactcg 136020
ctcgcgcgct cgctcggcta accgtcggcc tctcccaaaa ctcttcgtaa aactttcccg 136080
atgacagttc accctccaaa actttgtaaa actaaactgt tcggaggtcg gtctgctgcc 136140
tctctaactc tccgtaaaac gtttgtaaac tgtcggaggt cggtgacccg ctcaaccgtc 136200
cgcgaaaact tttcgcaggc agtgtctgcc tctctcggac tctccgcaaa cactttcgcg 136260
gaacctcgga gggtggtcga cctctctcca aactcttgca aaactttttc gcggaaccgt 136320
tggaggccag tcctccctcc aaactctttg taaaatcttt tcgaggccag tcctcctctc 136380
caaaacgttc cgcaaaatct ttgggaggtc ggcctctcct ctccagaacg ttccgtaaaa 136440

```
ctcttggagg ccgcccgcgg cacgcgaggc ggaggatccg gagggtgtcg acctccctca 136500
aaaactttgt aaaaactttt tataaaactt tccgcggaac ctcggagagt aggtcgacct 136560
ctctcaaaac tcttataaaa cttttccgcg gaaccgttgg aaggtaggtc gacctctctc 136620
aaaactctta taaaactttt ccgcggaacc gttggaggca ggtcggcctc tcaaactctt 136680
tgcgagaact cttcgcgaga actcttcgat aactttagga ggtcaggtcg acctcccaaa 136740
acttttgcga gaactctctg taaaacttta ggaggtcggt acctccctca aaacttttta 136800
taaaactttt cgcggaacct ccggagacgg gccgccgccc gcgaccgcgg gagcggagag 136860
gccgacctcc cgagacgttc cgcgttaccg tcggggtagg cgtcctctcg agaacgccaa 136920
aagacttcgt gcaaaaactt ttcggagggg cgcggagggc gggtcagctc ccgcgaactc 136980
ccgcagaacc ttttcgcgcg accgcgaagg ccggccgcct ctcccacact ctcaagagct 137040
tttcggagga gaggaagggc aggtcgcccc cacctccgac gctttgtaaa aacgtttacg 137100
cggaacctcg gaggcaggtc gcctccctcg aaaactcctc gcgaaacctt taaaaacttt 137160
ttgcgaaaac ttttcggagg atgtcggagg gcgggcggct cttccaaacc tccgcagaac 137220
cttttcgcgc aaccgttgga agacaggtcg gcctctctcg aaaactttta aaactttgta 137280
aacgcgttgg cgggaccgtc gcgggagagc ggccgcccgc ggcacgcgag aggaggaacc 137340
gttggaaggc agtcggcctc tcccgaaaac tttttataaa aacttttccg cggaaccgtt 137400
ggaggcaggt cggcctctct cagagtctaa aaactttttg cgggactcgg acggcgcggt 137460
cacccgacca cctgactcct gtctacccga ctacttgact tctgtttccc tgactcccga 137520
ctccctgact cccgactccc tgactcccga ctccctgact cccgactccc tgactcccga 137580
ctccctgact cccgactccc tgactcccga ctccctgact cccgactccc tgactcccga 137640
ctccctgact cccgactccc tgactcccga ctccctgact cccgactccc tgactcccga 137700
ctccctgact cccgactccc tgactcccga ctccctgact cccgactccc tgactcccga 137760
ctccctgact ccctgactcc agagcgaggt ctcgcggctg cggggtgccg cctccgcgga 137820
gtcgcgttcc cgcggacgcc cgtcctcgaa agcattcagc agttccagcc tctgccgtag 137880
ctcctcccgc aggaactcct ggtccgcgtt ctcgcggcag cgcggctcag ccgccgcggg 137940
agccggccgc cgccccggcg aagccgcgga tccgctgttc cggcgaaggc aggacagaca 138000
ttttttccag cccataaatt aaaaagaaca agaaattaca tgtgaaaaaa tttgaggttg 138060
atttattgac gaaacgttca actaaataca atcctaaaag tttttatcat catgataatt 138120
ttctgttgat tctttttaat ttatgggctg gaaaaaatgt ctgtcctgcc ttcgccggaa 138180
cagcggatcc gcggcttcgc cgg                                         138203
```

<210> SEQ ID NO 3

<400> SEQUENCE: 3

000

<210> SEQ ID NO 4
<211> LENGTH: 12
<212> TYPE: PRT
<213> ORGANISM: Artificial
<220> FEATURE:
<223> OTHER INFORMATION: IgG4 hinge

<400> SEQUENCE: 4

```
Glu Ser Lys Tyr Gly Pro Pro Cys Pro Ser Cys Pro
1               5                   10
```

```
<210> SEQ ID NO 5
<211> LENGTH: 22
<212> TYPE: PRT
<213> ORGANISM: Artificial
<220> FEATURE:
<223> OTHER INFORMATION: IgG4 hinge (S228P) + linker

<400> SEQUENCE: 5

Glu Ser Lys Tyr Gly Pro Pro Cys Pro Pro Cys Pro Gly Gly Gly Ser
1               5                   10                  15

Ser Gly Gly Gly Ser Gly
            20


<210> SEQ ID NO 6
<211> LENGTH: 39
<212> TYPE: PRT
<213> ORGANISM: Artificial
<220> FEATURE:
<223> OTHER INFORMATION: CD28 hinge

<400> SEQUENCE: 6

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35


<210> SEQ ID NO 7
<211> LENGTH: 48
<212> TYPE: PRT
<213> ORGANISM: Artificial
<220> FEATURE:
<223> OTHER INFORMATION: CD8 hinge-48aa

<400> SEQUENCE: 7

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45


<210> SEQ ID NO 8
<211> LENGTH: 45
<212> TYPE: PRT
<213> ORGANISM: Artificial
<220> FEATURE:
<223> OTHER INFORMATION: CD8 hinge-45aa

<400> SEQUENCE: 8

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 9
<211> LENGTH: 129
<212> TYPE: PRT
<213> ORGANISM: Artificial
```

```
<220> FEATURE:
<223> OTHER INFORMATION: IgG4(HL-CH3) (includes S228P in hinge)

<400> SEQUENCE: 9

Glu Ser Lys Tyr Gly Pro Pro Cys Pro Pro Cys Pro Gly Gly Gly Ser
1               5                   10                  15

Ser Gly Gly Gly Ser Gly Gly Gln Pro Arg Glu Pro Gln Val Tyr Thr
            20                  25                  30

Leu Pro Pro Ser Gln Glu Glu Met Thr Lys Asn Gln Val Ser Leu Thr
        35                  40                  45

Cys Leu Val Lys Gly Phe Tyr Pro Ser Asp Ile Ala Val Glu Trp Glu
    50                  55                  60

Ser Asn Gly Gln Pro Glu Asn Asn Tyr Lys Thr Thr Pro Pro Val Leu
65                  70                  75                  80

Asp Ser Asp Gly Ser Phe Phe Leu Tyr Ser Arg Leu Thr Val Asp Lys
                85                  90                  95

Ser Arg Trp Gln Glu Gly Asn Val Phe Ser Cys Ser Val Met His Glu
            100                 105                 110

Ala Leu His Asn His Tyr Thr Gln Lys Ser Leu Ser Leu Ser Leu Gly
        115                 120                 125

Lys


<210> SEQ ID NO 10
<211> LENGTH: 228
<212> TYPE: PRT
<213> ORGANISM: Artificial
<220> FEATURE:
<223> OTHER INFORMATION: IgG4(L235E,N297Q)

<400> SEQUENCE: 10

Glu Ser Lys Tyr Gly Pro Pro Cys Pro Ser Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Gln Ala Lys Thr Lys Pro Arg Glu Glu Gln Phe Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205
```

```
Met His Glu Ala Leu His Asn His Tyr Thr Gln Lys Ser Leu Ser Leu
    210                 215                 220

Ser Leu Gly Lys
225


<210> SEQ ID NO 11
<211> LENGTH: 229
<212> TYPE: PRT
<213> ORGANISM: Artificial
<220> FEATURE:
<223> OTHER INFORMATION: IgG4(S228P, L235E,N297Q)

<400> SEQUENCE: 11

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Gln Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 12
<211> LENGTH: 107
<212> TYPE: PRT
<213> ORGANISM: Artificial
<220> FEATURE:
<223> OTHER INFORMATION: IgG4(CH3)

<400> SEQUENCE: 12

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
```

```
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105


<210> SEQ ID NO 13
<211> LENGTH: 21
<212> TYPE: PRT
<213> ORGANISM: Artificial
<220> FEATURE:
<223> OTHER INFORMATION: CD3z

<400> SEQUENCE: 13

Leu Cys Tyr Leu Leu Asp Gly Ile Leu Phe Ile Tyr Gly Val Ile Leu
1               5                   10                  15

Thr Ala Leu Phe Leu
            20


<210> SEQ ID NO 14
<211> LENGTH: 27
<212> TYPE: PRT
<213> ORGANISM: Artificial
<220> FEATURE:
<223> OTHER INFORMATION: CD28

<400> SEQUENCE: 14

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25


<210> SEQ ID NO 15
<211> LENGTH: 28
<212> TYPE: PRT
<213> ORGANISM: Artificial
<220> FEATURE:
<223> OTHER INFORMATION: CD28(M)

<400> SEQUENCE: 15

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25


<210> SEQ ID NO 16
<211> LENGTH: 22
<212> TYPE: PRT
<213> ORGANISM: Artificial
<220> FEATURE:
<223> OTHER INFORMATION: CD4

<400> SEQUENCE: 16

Met Ala Leu Ile Val Leu Gly Gly Val Ala Gly Leu Leu Leu Phe Ile
1               5                   10                  15

Gly Leu Gly Ile Phe Phe
            20
```

```
<210> SEQ ID NO 17
<211> LENGTH: 21
<212> TYPE: PRT
<213> ORGANISM: Artificial
<220> FEATURE:
<223> OTHER INFORMATION: CD8tm

<400> SEQUENCE: 17

Ile Tyr Ile Trp Ala Pro Leu Ala Gly Thr Cys Gly Val Leu Leu Leu
1               5                   10                  15

Ser Leu Val Ile Thr
            20


<210> SEQ ID NO 18
<211> LENGTH: 23
<212> TYPE: PRT
<213> ORGANISM: Artificial
<220> FEATURE:
<223> OTHER INFORMATION: CD8tm2

<400> SEQUENCE: 18

Ile Tyr Ile Trp Ala Pro Leu Ala Gly Thr Cys Gly Val Leu Leu Leu
1               5                   10                  15

Ser Leu Val Ile Thr Leu Tyr
            20


<210> SEQ ID NO 19
<211> LENGTH: 24
<212> TYPE: PRT
<213> ORGANISM: Artificial
<220> FEATURE:
<223> OTHER INFORMATION: CD8tm3

<400> SEQUENCE: 19

Ile Tyr Ile Trp Ala Pro Leu Ala Gly Thr Cys Gly Val Leu Leu Leu
1               5                   10                  15

Ser Leu Val Ile Thr Leu Tyr Cys
            20


<210> SEQ ID NO 20
<211> LENGTH: 27
<212> TYPE: PRT
<213> ORGANISM: Artificial
<220> FEATURE:
<223> OTHER INFORMATION: 41BB

<400> SEQUENCE: 20

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25


<210> SEQ ID NO 21
<211> LENGTH: 112
<212> TYPE: PRT
<213> ORGANISM: Artificial
<220> FEATURE:
<223> OTHER INFORMATION: CD3stigma

<400> SEQUENCE: 21

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30
```

```
Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 22
<211> LENGTH: 41
<212> TYPE: PRT
<213> ORGANISM: Artificial
<220> FEATURE:
<223> OTHER INFORMATION: CD28

<400> SEQUENCE: 22

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 23
<211> LENGTH: 41
<212> TYPE: PRT
<213> ORGANISM: Artificial
<220> FEATURE:
<223> OTHER INFORMATION: CD28gg

<400> SEQUENCE: 23

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 24
<211> LENGTH: 42
<212> TYPE: PRT
<213> ORGANISM: Artificial
<220> FEATURE:
<223> OTHER INFORMATION: 41BB

<400> SEQUENCE: 24

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 25
<211> LENGTH: 42
<212> TYPE: PRT
<213> ORGANISM: Artificial
<220> FEATURE:
<223> OTHER INFORMATION: OX40
```

<400> SEQUENCE: 25

```
Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
        35                  40
```

<210> SEQ ID NO 26
<211> LENGTH: 10
<212> TYPE: DNA
<213> ORGANISM: Artificial
<220> FEATURE:
<223> OTHER INFORMATION: Linker

<400> SEQUENCE: 26

```
gggssgggsg                                                            10
```

<210> SEQ ID NO 27
<211> LENGTH: 12
<212> TYPE: PRT
<213> ORGANISM: Artificial
<220> FEATURE:
<223> OTHER INFORMATION: IgG4 hinge (S-->P) (S228P)

<400> SEQUENCE: 27

```
Glu Ser Lys Tyr Gly Pro Pro Cys Pro Pro Cys Pro
1               5                   10
```

<210> SEQ ID NO 28
<211> LENGTH: 22
<212> TYPE: PRT
<213> ORGANISM: Artificial
<220> FEATURE:
<223> OTHER INFORMATION: HL

<400> SEQUENCE: 28

```
Glu Ser Lys Tyr Gly Pro Pro Cys Pro Pro Cys Pro Gly Gly Gly Ser
1               5                   10                  15

Ser Gly Gly Gly Ser Gly
            20
```

<210> SEQ ID NO 29
<211> LENGTH: 323
<212> TYPE: PRT
<213> ORGANISM: Artificial
<220> FEATURE:
<223> OTHER INFORMATION: CD19t

<400> SEQUENCE: 29

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
```

```
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg


<210> SEQ ID NO 30
<211> LENGTH: 245
<212> TYPE: PRT
<213> ORGANISM: Artificial
<220> FEATURE:
<223> OTHER INFORMATION: CD19 CAR

<400> SEQUENCE: 30

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125
```

```
Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
                245


<210> SEQ ID NO 31
<211> LENGTH: 37
<212> TYPE: DNA
<213> ORGANISM: Artificial
<220> FEATURE:
<223> OTHER INFORMATION: p33NC-TK LF1

<400> SEQUENCE: 31

gcgcatatga tctatggatt accatggatg acaactc                             37


<210> SEQ ID NO 32
<211> LENGTH: 28
<212> TYPE: DNA
<213> ORGANISM: Artificial
<220> FEATURE:
<223> OTHER INFORMATION: p33NC-TK LF2

<400> SEQUENCE: 32

cgtttaactc gtctaattaa ttctgtac                                       28


<210> SEQ ID NO 33
<211> LENGTH: 98
<212> TYPE: DNA
<213> ORGANISM: Artificial
<220> FEATURE:
<223> OTHER INFORMATION: p33NC-TK RF1

<400> SEQUENCE: 33

caggtaaaag tacagaatta attagacgag ttaaacgagc tcgtcgacgg atccgctagc    60

ggccgcggag gtaatgatat gtatcaatcg gtgtgtag                            98


<210> SEQ ID NO 34
<211> LENGTH: 39
<212> TYPE: DNA
<213> ORGANISM: Artificial
<220> FEATURE:
<223> OTHER INFORMATION: p33NC-TK RF2

<400> SEQUENCE: 34

gcggaattcg taattactta gtaaatccgc cgtactagg                           39


<210> SEQ ID NO 35
<211> LENGTH: 41
<212> TYPE: DNA
```

-continued

```
<213> ORGANISM: Artificial
<220> FEATURE:
<223> OTHER INFORMATION: p33NC-F14.5L LF1

<400> SEQUENCE: 35

gcgcatatgt agaagaattg ataaatatga aaccttttaa g                         41


<210> SEQ ID NO 36
<211> LENGTH: 29
<212> TYPE: DNA
<213> ORGANISM: Artificial
<220> FEATURE:
<223> OTHER INFORMATION: p33NC-F14.5L LF2

<400> SEQUENCE: 36

cctctctagc tttcacttaa actgtatcg                                       29


<210> SEQ ID NO 37
<211> LENGTH: 100
<212> TYPE: DNA
<213> ORGANISM: Artificial
<220> FEATURE:
<223> OTHER INFORMATION: p33NC-F14.5L RF1

<400> SEQUENCE: 37

gaataatcga tacagtttaa gtgaaagcta gagaggaagc ttgagctcga ggatccgcta     60

gcggccgctg aagaggatgc tagaatcaag gaggagcaag                          100


<210> SEQ ID NO 38
<211> LENGTH: 38
<212> TYPE: DNA
<213> ORGANISM: Artificial
<220> FEATURE:
<223> OTHER INFORMATION: p33NC-F14.5L RF2

<400> SEQUENCE: 38

gcggaattct ccgggcagtg actttgtagc tctcccag                             38
```

ONCOLYTIC VIRUS EXPRESSING A CAR T CELL TARGET AND USES THEREOF

CROSS-REFERENCE TO RELATED APPLICATIONS

This application is a U.S. National Phase Application under 35 U.S.C. § 371 of International Application No. PCT/US2018/046313, filed on Aug. 10, 2018, which claims priority to and the benefit of U.S. Provisional Application No. 62/544,707, filed on Aug. 11, 2017. The entire contents of the foregoing are incorporated herein by reference.

SEQUENCE LISTING

This application contains a Sequence Listing that has been submitted electronically as an ASCII text file named 40056-0034US1_SL_ST25.txt and is hereby incorporated by reference in its entirety. Said ASCII text file, created on Feb. 3, 2023, is 447,349 bytes in size.

BACKGROUND

Cancer is the second leading cause of death in the United States. In recent years, great progress has been made in cancer immunotherapy, including immune checkpoint inhibitors, T cells with chimeric antigen receptors (CAR T cells), and oncolytic viruses. Oncolytic viruses are naturally occurring or genetically modified viruses that infect, replicate in, and eventually kill cancer cells while leaving healthy cells unharmed.

Oncolytic viruses are naturally occurring or genetically modified viruses that infect, replicate in, and eventually kill cancer cells while leaving healthy cells unharmed (1, 2). A recently completed Phase III clinical trial of the oncolytic herpes simplex virus T-VEC in 436 patients with unresectable stage IIIB, IIIC or IV melanoma was reported to meet its primary end point, with a durable response rate of 16.3% in patients receiving T-VEC compared to 2.1% in patients receiving GM-CSF (3). Based on the results from this trial, FDA approved T-VEC on Oct. 27, 2015.

Oncolytic virus constructs from at least eight different species have been tested in various phases of clinical trials, including adenovirus, herpes simplex virus-1, Newcastle disease virus, reovirus, measles virus, coxsackievirus, Seneca Valley virus, and vaccinia virus. It has become clear that oncolytic viruses are well tolerated in patients with cancer. The clinical benefits of oncolytic viruses as stand-alone treatments, however, remain limited (5). Due to concerns on the safety of oncolytic viruses, only highly attenuated oncolytic viruses (either naturally avirulent or attenuated through genetic engineering) have been used in both preclinical and clinical studies. Since the safety of oncolytic viruses has now been well established it is time to design and test oncolytic viruses with maximal anti-tumor potency. Oncolytic viruses with a robust oncolytic effect will release abundant tumor antigens, resulting in a strong immunotherapeutic effect.

Vaccinia virus, the prototype member of the poxvirus family, was used as smallpox vaccine to eradicate smallpox that is estimated to have killed 500 million people just in the 19$^{th}$ and 20$^{th}$ centuries. It, thus, is arguably the most successful live biotherapeutic agent. The safety of vaccinia virus was well demonstrated in millions of people worldwide. Vaccinia virus is also the first oncolytic virus showing viral oncolysis in the laboratory. Vaccinia virus as an oncolytic virus has been tested in many clinical trials and has been shown to be well tolerated in patients with late-stage cancer (2). Several studies show that in terms of oncolytic activity vaccinia virus is superior to adenovirus (6), one of the best studied oncolytic virus species and the first oncolytic virus approved for cancer treatment in China (7). Besides vaccinia virus, other members in the poxvirus family were also tested as oncolytic viruses, including raccoonpox virus (8), orf virus (9), and myxoma virus (10).

SUMMARY

Described herein is a recombinant chimeric poxvirus comprising a nucleotide sequence having a sequence identity of at least 70% (80%, 85%, 90%, 95%, 98%) to SEQ ID NO: 1 or SEQ ID NO:2 (or having a having a sequence identity of at least 70% (80%, 85%, 90%, 95%, 98%) to SEQ ID NO: 1 or SEQ ID NO:2 that has been modified by deletion of the TK gene) and further comprising a nucleotide sequence encoding human CD19 or a portion thereof. The recombinant poxvirus is oncolytic and can infect and kill certain cancer cells. It can also cause the infected cells to express cell surface CD19 (or a portion of CD19 that can be expressed on the surface of the cell). The expression of CD19 renders the cells venerable to killing by CAR T cells targeted to CD19 ("CD19 CAR T cells"). Thus, various cancers can be treated by administering together or sequentially, the recombinant chimeric poxvirus or another oncolytic virus harboring a transgene encoding all or a portion of CD19 (collectively "oncolytic virus expressing CD19") and CD19 CAR T cells. In some cases, it is preferable to treat virst with oncolytic virus expressing CD19 and then, after time has passed such that cells can become infected and express CD19 (e.g., 1, 2, 3, 4, 5 or more days), treat with CD19 CAR T cells. One or both treatment can be repeated.

In one aspect is provided a recombinant oncolyic virus that includes a transgene, e.g., a transgene in an expression cassette wherein the transgene encodes all or a portion of human CD19 (UniProt ID P15391). The expressed portion of CD19 a portion that can be expressed on the cell surface and can be recognized by an anti-CD19 antibody.

In an another aspect is provided a method of treating cancer in a subject in need thereof, the method including administering to the subject a therapeutically effective amount of a chimeric poxvirus as described herein and, simultaneously or subsequently, T cells expressing a CAR targeted to CD19, thereby treating cancer in the subject. In embodiments, the cancer is, e.g., a B cell cancer, ALL, CLL or B-NHL, diffuse large B-cell lymphoma, follicular lymphoma, or mantle cell lymphoma.

In an aspect the nucleotide sequence having a sequence identity of at least 70% (80%, 85%, 90%, 95%, or 98%) to SEQ ID NO:1 or SEQ ID NO:2, includes: (i) nucleic acid fragments from at least two poxvirus strains selected from the group consisting of cowpox virus strain Brighton, raccoonpox virus strain Herman, rabbitpox virus strain Utrecht, vaccinia virus strain WR, vaccinia virus strain IHD, vaccinia virus strain Elstree, vaccinia virus strain CL, vaccinia virus strain Lederle-Chorioallantoic, vaccinia virus strain AS, orf virus strain NZ2 and pseudocowpox virus strain TJS; (ii) one or more anti-cancer nucleic acid sequences; or (iii) a detectable moiety-encoding nucleic acid sequence.

In another aspect the nucleotide sequence having a sequence identity of at least 70% (80%, 85%, 90%, 95%, or 98%) to SEQ ID NO: 1 includes: (i) nucleic acid fragments from cowpox virus strain Brighton, raccoonpox virus strain Herman, rabbitpox virus strain Utrecht, vaccinia virus strain WR, vaccinia virus strain IHD, vaccinia virus strain Elstree, vaccinia virus strain CL, vaccinia virus strain Lederle-Chorioallantoic, and vaccinia virus strain AS; (ii) one or more anti-cancer nucleic acid sequences; or (iii) a detectable moiety-encoding nucleic acid sequence.

In another aspect the nucleotide sequence having a sequence identity of at least 70% to SEQ ID NO:2, includes: (i) nucleic acid fragments from orf virus strain NZ2 and pseudocowpox virus strain TJS; (ii) one or more anti-cancer nucleic acid sequences; or (iii) a detectable moiety-encoding nucleic acid sequence.

In another aspect the nucleotide sequence having a sequence identity of at least 70% (80%, 85%, 90%, 95%, or 98%) to SEQ ID NO:3, includes: (i) nucleic acid fragments from cowpox virus strain Brighton, raccoonpox virus strain Herman, rabbitpox virus strain Utrecht, vaccinia virus strain WR, vaccinia virus strain IHD, vaccinia virus strain Elstree, vaccinia virus strain CL, vaccinia virus strain Lederle-Chorioallantoic, and vaccinia virus strain AS; (ii) one or more anti-cancer nucleic acid sequences; or (iii) a detectable moiety-encoding nucleic acid sequence.

In an aspect the nucleotide sequence having a sequence identity of at least 70% (80%, 85%, 90%, 95%, or 98%) to SEQ ID NO: 1 or SEQ ID NO:2, includes: (i) nucleic acid fragments from at least two poxvirus strains selected from the group consisting of cowpox virus strain Brighton, raccoonpox virus strain Herman, rabbitpox virus strain Utrecht, vaccinia virus strain WR, vaccinia virus strain IHD, vaccinia virus strain Elstree, vaccinia virus strain CL, vaccinia virus strain Lederle-Chorioallantoic, vaccinia virus strain AS, orf virus strain NZ2 and pseudocowpox virus strain TJS; (ii) one or more anti-cancer nucleic acid sequences; (iii) one or more nucleic acid binding sequences; or (iv) a detectable moiety-encoding nucleic acid sequence.

In another aspect the nucleotide sequence having a sequence identity of at least 70% (80%, 85%, 90%, 95%, or 98%) to SEQ ID NO:1, includes: (i) nucleic acid fragments from cowpox virus strain Brighton, raccoonpox virus strain Herman, rabbitpox virus strain Utrecht, vaccinia virus strain WR, vaccinia virus strain IHD, vaccinia virus strain Elstree, vaccinia virus strain CL, vaccinia virus strain Lederle-Chorioallantoic, and vaccinia virus strain AS; (ii) one or more anti-cancer nucleic acid sequences; (iii) one or more nucleic acid binding sequences; or (iv) a detectable moiety-encoding nucleic acid sequence.

In another aspect the nucleotide sequence having a sequence identity of at least 70% (80%, 85%, 90%, 95%, or 98%) (80%, 85%, 90%, 95%, or 98%) to SEQ ID NO:2, includes: (i) nucleic acid fragments from orf virus strain NZ2 and pseudocowpox virus strain TJS; (ii) one or more anti-cancer nucleic acid sequences; (iii) one or more nucleic acid binding sequences; or (iv) a detectable moiety-encoding nucleic acid sequence.

In another aspect the nucleotide sequence having a sequence identity of at least 70% (80%, 85%, 90%, 95%, or 98%) to SEQ ID NO:3, includes: (i) nucleic acid fragments from cowpox virus strain Brighton, raccoonpox virus strain Herman, rabbitpox virus strain Utrecht, vaccinia virus strain WR, vaccinia virus strain IHD, vaccinia virus strain Elstree, vaccinia virus strain CL, vaccinia virus strain Lederle-Chorioallantoic, and vaccinia virus strain AS; (ii) one or more anti-cancer nucleic acid sequences; (iii) one or more nucleic acid binding sequences; or (iv) a detectable moiety-encoding nucleic acid sequence.

DETAILED DESCRIPTION

Figure 1:
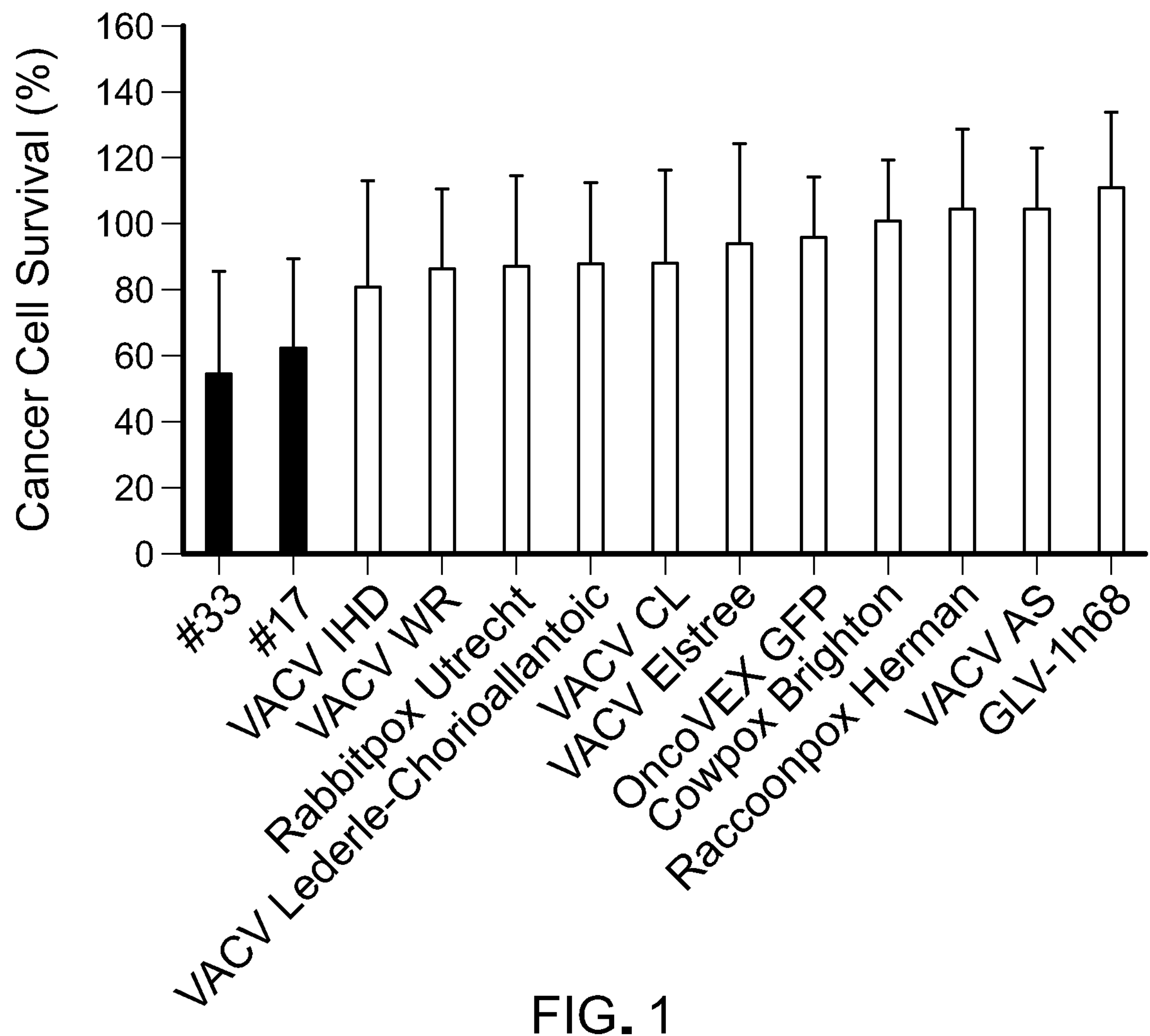
FIG. 1. Chimeric orthopoxvirus isolates #33 (SEQ ID NO:1) and #17 show superior cancer cell killing capability compared to the parental individual wild-type virus strains and the control viruses GLV-1h68 and OncoVEX GFP.

Described herein are recombinant oncolytic viruses that express all or a portion of human CD19. These viruses can be derived from chimeric poxvirus compositions which are oncolytic or other oncolytic viruses. Suitable recombinant oncolytic virus can be created by inserting an expression cassette that include a sequence encoding human CD19 or portion thereof into chimeric virus or other oncolyitic virus described in PCT/US2017/46163, filed 9 Aug. 2017 and incorporated herein by reference.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified.

The terms "virus" or "virus particle" are used according to its plain ordinary meaning within Virology and refers to a virion including the viral genome (e.g. DNA, RNA, single strand, double strand), viral capsid and associated proteins, and in the case of enveloped viruses (e.g. herpesvirus, poxvirus), an envelope including lipids and optionally components of host cell membranes, and/or viral proteins.

The term "poxvirus" is used according to its plain ordinary meaning within Virology and refers to a member of Poxviridae family capable of infecting vertebrates and invertebrates which replicate in the cytoplasm of their host. In embodiments, poxvirus virions have a size of about 200 nm in diameter and about 300 nm in length and possess a genome in a single, linear, double-stranded segment of DNA, typically 130-375 kilobase. The term poxvirus includes, without limitation, all genera of poxviridae (e.g., betaentomopoxvirus, yatapoxvirus, cervidpoxvirus, gammaentomopoxvirus, leporipoxvirus, suipoxvirus, molluscipoxvirus, crocodylidpoxvirus, alphaentomopoxvirus, capripoxvirus, orthopoxvirus, avipoxvirus, and parapoxvirus). In embodiments, the poxvirus is an orthopoxvirus (e.g., smallpox virus, vaccinia virus, cowpox virus, monkeypox virus), parapoxvirus (e.g., orf virus, pseudocowpox virus, bovine popular stomatitis virus), yatapoxvirus (e.g., tanapox virus, yaba monkey tumor virus) or molluscipoxvirus (e.g., molluscum contagiosum virus). In embodiments, the poxvirus is an orthopoxvirus (e.g., cowpox virus strain Brighton, raccoonpox virus strain Herman, rabbitpox virus strain Utrecht, vaccinia virus strain WR, vaccinia virus strain IHD, vaccinia virus strain Elstree, vaccinia virus strain CL, vaccinia virus strain Lederle-Chorioallantoic, or vaccinia virus strain AS). In embodiments, the poxvirus is a parapoxvirus (e.g., orf virus strain NZ2 or pseudocowpox virus strain TJS).

The term "chimeric" used within the context of a chimeric poxvirus, is used according to its plain ordinary meaning within Virology and refers to a hybrid microorganism (e.g., chimeric poxvirus) created by joining nucleic acid fragments from two or more different microorganisms (e.g., two viruses from the same subfamily, two viruses from different subfamilies). In embodiments, each of at least two of the nucleic acid fragments contain the essential genes necessary for replication. The chimeric poxvirus provided herein including embodiments thereof may include one or more transgenes (i.e., nucleic acid sequences not native to the viral genome). For example, the chimeric poxvirus provided herein including embodiments thereof may include an anti-cancer nucleic acid sequence, a nucleic acid binding sequence, a detectable moiety-encoding nucleic acid sequence or any combination thereof. In embodiments, the chimeric poxvirus includes a nucleic acid sequence including an anti-cancer nucleic acid sequence, a nucleic acid binding sequence and a detectable moiety-encoding nucleic acid sequence. In embodiments, the chimeric poxvirus includes a nucleic acid sequence including an anti-cancer nucleic acid sequence and a detectable moiety-encoding nucleic acid sequence. In embodiments, the chimeric poxvirus includes a nucleic acid sequence including a nucleic acid binding sequence and a detectable moiety-encoding nucleic acid sequence. In embodiments, the chimeric poxvirus includes a nucleic acid sequence including an anti-cancer nucleic acid sequence and a nucleic acid binding sequence.

The term "cowpox virus strain Brighton" is used according to its common, ordinary meaning and refers to virus strains of the same or similar names and functional fragments and homologs thereof. The term includes recombinant or naturally occurring forms of cowpox virus strain Brighton or variants thereof that maintain cowpox virus strain Brighton activity (e.g. within at least 30%, 40%, 50%, 60%, 70%, 80%, 90%, 95%, or 100%). The term includes recombinant or naturally occurring forms of cowpox virus strain Brighton or variants thereof whose genome has sequence identity to the cowpox virus strain Brighton genome (e.g. about 65%, 70%, 75%, 80%, 85%, 90%, 95%, 99% or 100% identity to the cowpox virus strain Brighton genome). Cowpox virus strain Brighton may refer to variants having mutated amino acid residues that modulate (e.g. increase or decrease when compared to cowpox virus strain Brighton) cowpox virus strain Brighton activity, expression, cellular targeting, or infectivity. Cowpox virus strain Brighton may be modified as described herein. In embodiments, the cowpox virus strain Brighton refers to the virus strain identified by ATCC (American Type Culture Collection) reference number ATCC VR-302™, variants or homologs thereof.

The term "raccoonpox virus strain Herman" is used according to its common, ordinary meaning and refers to virus strains of the same or similar names and functional fragments and homologs thereof. The term includes recombinant or naturally occurring forms of raccoonpox virus strain Herman or variants thereof that maintain raccoonpox virus strain Herman activity (e.g. within at least 30%, 40%, 50%, 60%, 70%, 80%, 90%, 95%, or 100%). The term includes recombinant or naturally occurring forms of raccoonpox virus strain Herman or variants thereof whose genome has sequence identity to the raccoonpox virus strain Herman genome (e.g. about 65%, 70%, 75%, 80%, 85%, 90%, 95%, 99% or 100% identity to the raccoonpox virus strain Herman genome). Raccoonpox virus strain Herman may refer to variants having mutated amino acid residues that modulate (e.g. increase or decrease when compared to raccoonpox virus strain Herman) raccoonpox virus strain Herman activity, expression, cellular targeting, or infectivity. Raccoonpox virus strain Herman may be modified as described herein. In embodiments, the raccoonpox virus strain Herman refers to the virus strain identified by ATCC reference number ATCC VR-838™, variants or homologs thereof.

The term "rabbitpox virus strain Utrecht" is used according to its common, ordinary meaning and refers to virus strains of the same or similar names and functional fragments and homologs thereof. The term includes recombinant or naturally occurring forms of rabbitpox virus strain Utrecht or variants thereof that maintain rabbitpox virus strain Utrecht activity (e.g. within at least 30%, 40%, 50%, 60%, 70%, 80%, 90%, 95%, or 100%). The term includes recombinant or naturally occurring forms of rabbitpox virus strain Utrecht or variants thereof whose genome has sequence identity to the rabbitpox virus strain Utrecht genome (e.g. about 65%, 70%, 75%, 80%, 85%, 90%, 95%, 99% or 100% identity to the rabbitpox virus strain Utrecht genome). Rabbitpox virus strain Utrecht may refer to variants having mutated amino acid residues that modulate (e.g. increase or decrease when compared to rabbitpox virus strain Utrecht) rabbitpox virus strain Utrecht activity, expression, cellular targeting, or infectivity. Rabbitpox virus strain Utrecht may be modified as described herein. In embodiments, the rabbitpox virus strain Utrecht refers to the virus strain identified by ATCC reference number ATCC VR-1591™, variants or homologs thereof.

The term "vaccinia virus strain WR" is used according to its common, ordinary meaning and refers to virus strains of the same or similar names and functional fragments and homologs thereof. The term includes recombinant or naturally occurring forms of vaccinia virus strain WR or variants thereof that maintain vaccinia virus strain WR activity (e.g. within at least 30%, 40%, 50%, 60%, 70%, 80%, 90%, 95%, or 100%). The term includes recombinant or naturally occurring forms of vaccinia virus strain WR or variants thereof whose genome has sequence identity to the vaccinia virus strain WR genome (e.g. about 65%, 70%, 75%, 80%, 85%, 90%, 95%, 99% or 100% identity to the vaccinia virus strain WR genome). Vaccinia virus strain WR may refer to variants having mutated amino acid residues that modulate (e.g. increase or decrease when compared to vaccinia virus strain WR) vaccinia virus strain WR activity, expression, cellular targeting, or infectivity. Vaccinia virus strain WR may be modified as described herein. In embodiments, the vaccinia virus strain WR refers to the virus strain identified by ATCC reference number ATCC VR-1354™ variants or homologs thereof.

The term "vaccinia virus strain IHD" is used according to its common, ordinary meaning and refers to virus strains of the same or similar names and functional fragments and homologs thereof. The term includes recombinant or naturally occurring forms of vaccinia virus strain IHD or variants thereof that maintain vaccinia virus strain IHD activity (e.g. within at least 30%, 40%, 50%, 60%, 70%, 80%, 90%, 95%, or 100%). The term includes recombinant or naturally occurring forms of vaccinia virus strain IHD or variants thereof whose genome has sequence identity to the vaccinia virus strain IHD genome (e.g. about 65%, 70%, 75%, 80%, 85%, 90%, 95%, 99% or 100% identity to the vaccinia virus strain IHD genome). Vaccinia virus strain IHD may refer to variants having mutated amino acid residues that modulate (e.g. increase or decrease when compared to vaccinia virus strain IHD) vaccinia virus strain IHD activity, expression, cellular targeting, or infectivity. Vaccinia virus strain IHD may be modified as described herein. In embodiments, the vaccinia virus strain IHD refers to the virus strain identified by ATCC reference number ATCC VR-156™, variants or homologs thereof.

The term "vaccinia virus strain Elstre" is used according to its common, ordinary meaning and refers to virus strains of the same or similar names and functional fragments and homologs thereof. The term includes recombinant or naturally occurring forms of vaccinia virus strain Elstre or variants thereof that maintain vaccinia virus strain Elstre activity (e.g. within at least 30%, 40%, 50%, 60%, 70%, 80%, 90%, 95%, or 100%). The term includes recombinant or naturally occurring forms of vaccinia virus strain Elstre or variants thereof whose genome has sequence identity to the vaccinia virus strain Elstre genome (e.g. about 65%, 70%, 75%, 80%, 85%, 90%, 95%, 99% or 100% identity to the vaccinia virus strain Elstre genome). Vaccinia virus strain Elstre may refer to variants having mutated amino acid residues that modulate (e.g. increase or decrease when compared to vaccinia virus strain Elstre) vaccinia virus strain Elstre activity, expression, cellular targeting, or infectivity. Vaccinia virus strain Elstre may be modified as described herein. In embodiments, the vaccinia virus strain Elstre refers to the virus strain identified by ATCC reference number ATCC VR-1549™, variants or homologs thereof.

The term "vaccinia virus strain CL" is used according to its common, ordinary meaning and refers to virus strains of the same or similar names and functional fragments and homologs thereof. The term includes recombinant or naturally occurring forms of vaccinia virus strain CL or variants thereof that maintain vaccinia virus strain CL activity (e.g. within at least 30%, 40%, 50%, 60%, 70%, 80%, 90%, 95%, or 100%). The term includes recombinant or naturally occurring forms of vaccinia virus strain CL or variants thereof whose genome has sequence identity to the vaccinia virus strain CL genome (e.g. about 65%, 70%, 75%, 80%, 85%, 90%, 95%, 99% or 100% identity to the vaccinia virus strain CL genome). Vaccinia virus strain CL may refer to variants having mutated amino acid residues that modulate (e.g. increase or decrease when compared to vaccinia virus strain CL) vaccinia virus strain CL activity, expression, cellular targeting, or infectivity. Vaccinia virus strain CL may be modified as described herein. In embodiments, the vaccinia virus strain CL refers to the virus strain identified by ATCC reference number ATCC VR-1774™, variants or homologs thereof.

The term "vaccinia virus strain Lederle-Chorioallantoic" is used according to its common, ordinary meaning and refers to virus strains of the same or similar names and functional fragments and homologs thereof. The term includes recombinant or naturally occurring forms of vaccinia virus strain Lederle-Chorioallantoic or variants thereof that maintain vaccinia virus strain Lederle-Chorioallantoic activity (e.g. within at least 30%, 40%, 50%, 60%, 70%, 80%, 90%, 95%, or 100%). The term includes recombinant or naturally occurring forms of vaccinia virus strain Lederle-Chorioallantoic or variants thereof whose genome has sequence identity to the vaccinia virus strain Lederle-Chorioallantoic genome (e.g. about 65%, 70%, 75%, 80%, 85%, 90%, 95%, 99% or 100% identity to the vaccinia virus strain Lederle-Chorioallantoic genome). Vaccinia virus strain Lederle-Chorioallantoic may refer to variants having mutated amino acid residues that modulate (e.g. increase or decrease when compared to vaccinia virus strain Lederle-Chorioallantoic) vaccinia virus strain Lederle-Chorioallantoic activity, expression, cellular targeting, or infectivity. Vaccinia virus strain Lederle-Chorioallantoic may be modified as described herein. In embodiments, the vaccinia virus strain Lederle-Chorioallantoic refers to the virus strain identified by ATCC reference number ATCC VR-118™, variants or homologs thereof.

The term "vaccinia virus strain AS" is used according to its common, ordinary meaning and refers to virus strains of the same or similar names and functional fragments and homologs thereof. The term includes recombinant or naturally occurring forms of vaccinia virus strain AS or variants thereof that maintain vaccinia virus strain AS activity (e.g. within at least 30%, 40%, 50%, 60%, 70%, 80%, 90%, 95%, or 100%). The term includes recombinant or naturally occurring forms of vaccinia virus strain AS or variants thereof whose genome has sequence identity to the vaccinia virus strain AS genome (e.g. about 65%, 70%, 75%, 80%, 85%, 90%, 95%, 99% or 100% identity to the vaccinia virus strain AS genome). Vaccinia virus strain AS may refer to variants having mutated amino acid residues that modulate (e.g. increase or decrease when compared to vaccinia virus strain AS) vaccinia virus strain AS activity, expression, cellular targeting, or infectivity. Vaccinia virus strain AS may be modified as described herein. In embodiments, the vaccinia virus strain AS refers to the virus strain identified by ATCC reference number ATCC VR-2010™, variants or homologs thereof.

The term "orf virus strain NZ2" is used according to its common, ordinary meaning and refers to virus strains of the same or similar names and functional fragments and homologs thereof. The term includes recombinant or naturally occurring forms of orf virus strain NZ2 or variants thereof that maintain orf virus strain NZ2 activity (e.g. within at least 30%, 40%, 50%, 60%, 70%, 80%, 90%, 95%, or 100%). The term includes recombinant or naturally occurring forms of orf virus strain NZ2 or variants thereof whose genome has sequence identity to the orf virus strain NZ2 genome (e.g. about 65%, 70%, 75%, 80%, 85%, 90%, 95%, 99% or 100% identity to the orf virus strain NZ2 genome). Orf virus strain NZ2 may refer to variants having mutated amino acid residues that modulate (e.g. increase or decrease when compared to orf virus strain NZ2) orf virus strain NZ2 activity, expression, cellular targeting, or infectivity. Orf virus strain NZ2 may be modified as described herein. In embodiments, the orf virus strain NZ2 refers to the virus strain identified by ATCC reference number ATCC VR-1548™, variants or homologs thereof.

The term "pseudocowpox virus strain TJS" is used according to its common, ordinary meaning and refers to virus strains of the same or similar names and functional fragments and homologs thereof. The term includes recombinant or naturally occurring forms of pseudocowpox virus strain TJS or variants thereof that maintain pseudocowpox virus strain TJS activity (e.g. within at least 30%, 40%, 50%, 60%, 70%, 80%, 90%, 95%, or 100%). The term includes recombinant or naturally occurring forms of pseudocowpox virus strain TJS or variants thereof whose genome has sequence identity to the pseudocowpox virus strain TJS genome (e.g. about 65%, 70%, 75%, 80%, 85%, 90%, 95%, 99% or 100% identity to the pseudocowpox virus strain TJS genome). Pseudocowpox virus strain TJS may refer to variants having mutated amino acid residues that modulate (e.g. increase or decrease when compared to pseudocowpox virus strain TJS) pseudocowpox virus strain TJS activity, expression, cellular targeting, or infectivity. Pseudocowpox virus strain TJS may be modified as described herein. In embodiments, the pseudocowpox virus strain TJS refers to the virus strain identified by ATCC reference number ATCC VR-634™, variants or homologs thereof.

In embodiments, cowpox virus strain Brighton is cowpox virus strain Brighton ATCC VR-302™. In embodiments, raccoonpox virus strain Herman is raccoonpox virus strain Herman ATCC VR-838™. In embodiments, rabbitpox virus strain Utrecht is rabbitpox virus strain Utrecht ATCC VR-1591™. In embodiments, vaccinia virus strain WR is vaccinia virus strain WR ATCC VR-1354™. In embodiments, vaccinia virus strain IHD is vaccinia virus strain IHD ATCC VR-156™. In embodiments, vaccinia virus strain Elstree is vaccinia virus strain Elstree ATCC VR-1549™. In embodiments, vaccinia virus strain CL is vaccinia virus strain CL ATCC VR-1774™. In embodiments, vaccinia virus strain Lederle-Chorioallantoic is vaccinia virus strain Lederle-Chorioallantoic ATCC VR-118™. In embodiments, vaccinia virus strain AS is vaccinia virus strain AS ATCC VR-2010™. In embodiments, orf virus strain NZ2 is orf virus strain NZ2 ATCC VR-1548™. In embodiments, pseudocowpox virus strain TJS is pseudocowpox virus strain TJS ATCC VR-634™.

I. Chimeric Poxvirus Compositions

In an aspect, is provided a chimeric poxvirus comprising a nucleotide sequence having a sequence identity of at least 70% (75%, 80%, 85%, 90%, 92%, 94%, 96%, 98%, or 99%) to SEQ ID NO:1 or SEQ ID NO:2 and a nucleotide sequence encoding human CD19 or a portion thereof that can be expressed on the cell surface. The sequence having at least 70% identify to SEQ IN NO: 1 or 2 in some embodiments includes nucleotide sequences ("nucleic acid fragments") from at least two poxvirus strains selected from the group including cowpox virus strain Brighton, raccoonpox virus strain Herman, rabbitpox virus strain Utrecht, vaccinia virus strain WR, vaccinia virus strain IHD, vaccinia virus strain Elstree, vaccinia virus strain CL, vaccinia virus strain Lederle-Chorioallantoic, vaccinia virus strain AS, orf virus strain NZ2 and pseudocowpox virus strain TJS, e.g, nucleotide sequences of at least 100 contiguous nucleotides The chimeric oncolytic poxviruses as described herein include transgene encoding human a truncated human CD19 (CD19t) that lacks a functional signaling domain, but includes the extracellular domain and transmembrane domain. The truncated human CD19 comprises the amino acid sequence (or a sequence at least 95%, 97%, 98% or 99% identical to) MPPPRLLFFLLFLTPMEVRPEE- PLVVKVEEGDNAVLQCLKGTSDGPTQQLTWSRESP LKPFLKLSLGLPGLGIHMR-PLAIWLFIFNVSQQMGGFYL-CQPGPPSEKAWQPGWTVN VEGSGELFRWNVSDLG-GLGCGLKNRSSEGPSSPSGKLMSPKLYVWAKDRPEI WEGE PPCVPPRDSLNQSLSQDLTMAPG-STLWLSCGVPPDSVSRGPLSWTHVHPKGPKSLLS LELKDDRPARDMWVMETGLLLPRATAQDAGKYY-CHRGNLTMSFHLEITARPVLWH WLLRTGGWKVSAVTLAY-LIFCLCSLVGILHLQRALVLRRKR (SEQ ID NO: 29). In some cases, the CD19t comprises or consists of amino acids 22-323 of SEQ ID NO: 29. Amino acid 1-21 of SEQ ID NO: 3 are a signaling domain and can be replaced with a different signaling domain. Thus, the oncolytic virus comprises a sequence comprising a nucleotide sequence encoding a truncated human CD19 operably linked to an expression control sequence (e.g., an early promoter).

In embodiments, the nucleic acid fragments are from cowpox virus strain Brighton, raccoonpox virus strain Herman, rabbitpox virus strain Utrecht, vaccinia virus strain WR, vaccinia virus strain IHD, vaccinia virus strain Elstree, vaccinia virus strain CL, vaccinia virus strain Lederle-Chorioallantoic and vaccinia virus strain AS.

In embodiments, the nucleic acid sequence includes nucleic acid fragments from cowpox virus strain Brighton and raccoonpox virus strain Herman. In embodiments, the nucleic acid sequence includes nucleic acid fragments from cowpox virus strain Brighton and rabbitpox virus strain Utrecht. In embodiments, the nucleic acid sequence includes nucleic acid fragments from cowpox virus strain Brighton and vaccinia virus strain WR. In embodiments, the nucleic acid sequence includes nucleic acid fragments from cowpox virus strain Brighton and vaccinia virus strain IHD. In embodiments, the nucleic acid sequence includes nucleic acid fragments from cowpox virus strain Brighton and vaccinia virus strain Elstree. In embodiments, the nucleic acid sequence includes nucleic acid fragments from cowpox virus strain Brighton and vaccinia virus strain CL. In embodiments, the nucleic acid sequence includes nucleic acid fragments from cowpox virus strain Brighton and vaccinia virus strain Lederle-Chorioallantoic. In embodiments, the nucleic acid sequence includes nucleic acid fragments from cowpox virus strain Brighton and vaccinia virus strain AS. In embodiments, the nucleic acid sequence includes nucleic acid fragments from cowpox virus strain Brighton and orf virus strain NZ2. In embodiments, the nucleic acid sequence includes nucleic acid fragments from cowpox virus strain Brighton and pseudocowpox virus strain TJS.

In embodiments, the nucleic acid sequence includes nucleic acid fragments from rabbitpox virus strain Utrecht and vaccinia virus strain WR. In embodiments, the nucleic acid sequence includes nucleic acid fragments from rabbitpox virus strain Utrecht and vaccinia virus strain IHD. In embodiments, the nucleic acid sequence includes nucleic acid fragments from rabbitpox virus strain Utrecht and vaccinia virus strain Elstree. In embodiments, the nucleic acid sequence includes nucleic acid fragments from rabbitpox virus strain Utrecht and vaccinia virus strain CL. In embodiments, the nucleic acid sequence includes nucleic acid fragments from rabbitpox virus strain Utrecht and vaccinia virus strain Lederle-Chorioallantoic. In embodiments, the nucleic acid sequence includes nucleic acid fragments from rabbitpox virus strain Utrecht and vaccinia virus strain AS. In embodiments, the nucleic acid sequence includes nucleic acid fragments from rabbitpox virus strain Utrecht and orf virus strain NZ2. In embodiments, the nucleic acid sequence includes nucleic acid fragments from rabbitpox virus strain Utrecht and pseudocowpox virus strain TJS.

In embodiments, the nucleic acid sequence includes nucleic acid fragments from vaccinia virus strain WR and vaccinia virus strain IHD. In embodiments, the nucleic acid sequence includes nucleic acid fragments from vaccinia virus strain WR and vaccinia virus strain Elstree. In embodiments, the nucleic acid sequence includes nucleic acid fragments from vaccinia virus strain WR and vaccinia virus strain CL. In embodiments, the nucleic acid sequence includes nucleic acid fragments from vaccinia virus strain WR and vaccinia virus strain Lederle-Chorioallantoic. In embodiments, the nucleic acid sequence includes nucleic acid fragments from vaccinia virus strain WR and vaccinia virus strain AS. In embodiments, the nucleic acid sequence includes nucleic acid fragments from vaccinia virus strain WR and orf virus strain NZ2. In embodiments, the nucleic acid sequence includes nucleic acid fragments from vaccinia virus strain WR and pseudocowpox virus strain TJS.

In embodiments, the nucleic acid sequence includes nucleic acid fragments from vaccinia virus strain IHD and vaccinia virus strain Elstree. In embodiments, the nucleic acid sequence includes nucleic acid fragments from vaccinia virus strain IHD and vaccinia virus strain CL. In embodiments, the nucleic acid sequence includes nucleic acid fragments from vaccinia virus strain IHD and vaccinia virus strain Lederle-Chorioallantoic. In embodiments, the nucleic acid sequence includes nucleic acid fragments from vaccinia virus strain IHD and vaccinia virus strain AS. In embodiments, the nucleic acid sequence includes nucleic acid fragments from vaccinia virus strain IHD and orf virus strain NZ2. In embodiments, the nucleic acid sequence includes nucleic acid fragments from vaccinia virus strain IHD and pseudocowpox virus strain TJS.

In embodiments, the nucleic acid sequence includes nucleic acid fragments from vaccinia virus strain Elstree and vaccinia virus strain CL. In embodiments, the nucleic acid sequence includes nucleic acid fragments from vaccinia virus strain Elstree and vaccinia virus strain Lederle-Chorioallantoic. In embodiments, the nucleic acid sequence includes nucleic acid fragments from vaccinia virus strain Elstree and vaccinia virus strain AS. In embodiments, the nucleic acid sequence includes nucleic acid fragments from vaccinia virus strain Elstree and orf virus strain NZ2. In embodiments, the nucleic acid sequence includes nucleic acid fragments from vaccinia virus strain Elstree and pseudocowpox virus strain TJS.

In embodiments, the nucleic acid sequence includes nucleic acid fragments from vaccinia virus strain CL and vaccinia virus strain Lederle-Chorioallantoic. In embodiments, the nucleic acid sequence includes nucleic acid fragments from vaccinia virus strain CL and vaccinia virus strain AS. In embodiments, the nucleic acid sequence includes nucleic acid fragments from vaccinia virus strain CL and orf virus strain NZ2. In embodiments, the nucleic acid sequence includes nucleic acid fragments from vaccinia virus strain CL and pseudocowpox virus strain TJS.

In embodiments, the nucleic acid sequence includes nucleic acid fragments from vaccinia virus strain Lederle-Chorioallantoic and vaccinia virus strain AS. In embodiments, the nucleic acid sequence includes nucleic acid fragments from vaccinia virus strain Lederle-Chorioallantoic and orf virus strain NZ2. In embodiments, the nucleic acid sequence includes nucleic acid fragments from vaccinia virus strain Lederle-Chorioallantoic and pseudocowpox virus strain TJS.

In embodiments, the nucleic acid sequence includes nucleic acid fragments from vaccinia virus strain AS and orf virus strain NZ2. In embodiments, the nucleic acid sequence includes nucleic acid fragments from vaccinia virus strain AS and pseudocowpox virus strain TJS. In embodiments, the nucleic acid sequence includes nucleic acid fragments from orf virus strain NZ2 and pseudocowpox virus strain TJS.

II. Chimeric Antigen Receptors (CAR) Targeted to CD19

A variety of CD19 CAR have been described and can be used, including those described in U.S. Pat. No. 7,446,179 and Park et al. 2016 Blood 128:4035. The CD19 CAR can include an scFv that binds CD19, e.g., FMC63 (Zola et al. 1991 Immunol Cell Biol 69:411) or SJ25C1 (Bejcek et al. 1995 Cancer Research 55:2346), both of which are commercially available.

Described herein is a nucleic acid molecule encoding a CAR comprising: an scFv targeted to CD19 (e.g., Asp Ile Gln Met Thr Gln Thr Thr Ser Ser Leu Ser Ala Ser Leu Gly Asp Arg Val Thr Ile Ser Cys Arg Ala Ser Gln Asp Ile Ser Lys Tyr Leu Asn Trp Tyr Gln Gln Lys Pro Asp Gly Thr Val Lys Leu Leu Ile Tyr His Thr Ser Arg Leu His Ser Gly Val Pro Ser Arg Phe Ser Gly Ser Gly Ser Gly Thr Asp Tyr Ser Leu Thr Ile Ser Asn Leu Glu Gln Glu Asp Ile Ala Thr Tyr Phe Cys Gln Gln Gly Asn Thr Leu Pro Tyr Thr Phe Gly Gly Gly Thr Lys Leu Glu Ile Thr Gly Ser Thr Ser Gly Ser Gly Lys Pro Gly Ser Gly Glu Gly Ser Thr Lys Gly Glu Val Lys Leu Gln Glu Ser Gly Pro Gly Leu Val Ala Pro Ser Gln Ser Leu Ser Val Thr Cys Thr Val Ser Gly Val Ser Leu Pro Asp Tyr Gly Val Ser Trp Ile Arg Gln Pro Pro Arg Lys Gly Leu Glu Trp Leu Gly Val Ile Trp Gly Ser Glu Thr Thr Tyr Tyr Asn Ser Ala Leu Lys Ser Arg Leu Thr Ile Ile Lys Asp Asn Ser Lys Ser Gln Val Phe Leu Lys Met Asn Ser Leu Gln Thr Asp Asp Thr Ala Ile Tyr Tyr Cys Ala Lys His Tyr Tyr Tyr Gly Gly Ser Tyr Ala Met Asp Tyr Trp Gly Gln Gly Thr Ser Val Thr Val Ser Ser (SEQ ID NO: 30) or a variant thereof having 1-5 (e.g., 1 or 2) amino acid modifications (e.g., substitutions); a transmembrane domain selected from: a CD4 transmembrane domain or variant thereof having 1-5 (e.g., 1 or 2) amino acid modifications (e.g., substitutions), a CD8 transmembrane domain or variant thereof having 1-5 (e.g., 1 or 2) amino acid modifications (e.g., substitutions), a CD28 transmembrane domain or a variant thereof having 1-5 (e.g., 1 or 2) amino acid modifications (e.g., substitutions), and a CD3g transmembrane domain or a variant thereof having 1-5 (e.g., 1 or 2) amino acid modifications (e.g., substitutions); a costimulatory domain (e.g., a CD28 co-stimulatory domain or a variant thereof having 1-5 (e.g., 1 or 2) amino acid modifications (e.g., substitutions); or a 4-1 BB co-stimulatory domain or a variant thereof having 1-5 (e.g., 1 or 2) amino acid modifications (e.g., substitutions); or both a CD28 co-stimulatory domain or a variant thereof having 1-5 (e.g., 1 or 2) amino acid modifications (e.g., substitutions) and a 4-1 BB co-stimulatory domain or a variant thereof having 1-5 (e.g., 1 or 2) amino acid modifications (e.g., substitutions); and a CD3ξ signaling domain or a variant thereof having 1-5 (e.g., 1 or 2) amino acid modifications.

In various embodiments: the costimulatory domain is selected from the group consisting of: a CD28 costimulatory domain or a variant thereof having 1-5 (e.g., 1 or acid modifications, a 4-1 BB costimulatory domain or a variant thereof having 1-5 (e.g., 1 or 2) amino acid modifications and an OX40 costimulatory domain or a variant thereof having 1-5 (e.g., 1 or 2) amino acid modifications. In certain embodiments, a 4-1 BB costimulatory domain or a variant thereof having 1-5 (e.g., 1 or 2) amino acid modifications in present. In some embodiments there are two costimulatory domains, for example a CD28 co-stimulatory domain or a variant thereof having 1-5 (e.g., 1 or 2) amino acid modifications (e.g., substitutions) and a 4-1 BB co-stimulatory domain or a variant thereof having 1-5 (e.g., 1 or 2) amino acid modifications (e.g., substitutions). In various embodiments the 1-5 (e.g., 1 or 2) amino acid modification are substitutions.

In some cases there is a short sequence of 1-6 amino acids (e.g. GGG) between the co-stimulatory domains and the CD3g signaling domain and/or between the two co-stimulatory domains.

Additional embodiment the CAR comprises: an scFv targeted to CD19; two different costimulatory domains selected from the group consisting of: a CD28 costimulatory domain or a variant thereof having 1-5 (e.g., 1 or 2) amino acid modifications, a 4-1 BB costimulatory domain or a variant thereof having 1-5 (e.g., 1 or 2) amino acid modifications and an OX40 costimulatory domain or a variant thereof having 1-5 (e.g., 1 or 2) amino acid modifications; two different costimulatory domains selected from the group consisting of: a CD28 costimulatory domain or a variant thereof having 1-2 amino acid modifications, a 4-1 BB costimulatory domain or a variant thereof having 1-2 amino acid modifications and an OX40 costimulatory domain or a variant thereof having 1-2 amino acid modifications; a CD19 scFv or a variant thereof having 1-2 amino acid modifications; a transmembrane domain selected from: a CD4 transmembrane domain or variant thereof having 1-2 amino acid modifications, a CD8 transmembrane domain or variant thereof having 1-2 amino acid modifications, a CD28 transmembrane domain or a variant thereof having 1-2 amino acid modifications, and a CD3ξ transmembrane domain or a variant thereof having 1-2 amino acid modifications; a costimulatory domain (e.g., a CD28 co-stimulatory domain or a variant thereof having 1-5 (e.g., 1 or 2) amino acid modifications (e.g., substitutions); or a 4-1 BB co-stimulatory domain or a variant thereof having 1-5 (e.g., 1 or 2) amino acid modifications (e.g., substitutions); or both a CD28 co-stimulatory domain or a variant thereof having 1-5 (e.g., 1 or 2) amino acid modifications (e.g., substitutions) and a 4-1 BB co-stimulatory domain or a variant thereof having 1-5 (e.g., 1 or 2) amino acid modifications (e.g., substitutions); and CD3ξ signaling domain of a variant thereof having 1-2 amino acid modifications; a spacer region located between the CD19 scFv or variant thereof and the transmembrane domain (e.g., the spacer region comprises an amino acid sequence selected from the group consisting of SEQ ID NOs: 2-12 and 42 (Table 3) or a variant thereof having 1-5 (e.g., 1 or 2) amino acid modifications); the spacer comprises an IgG hinge region; the spacer region comprises 1-150 amino acids; there is no spacer; the 4-1 BB signaling domain comprises the amino acid sequence of SEQ ID NO:24 the CD3& signaling domain comprises the amino acid sequence of SEQ ID NO:21 and a linker of 3 to 15 amino acids that is located between the costimulatory domain and the CD3g signaling domain or variant thereof. In certain embodiments where there are two costimulatory domains, one is a 4-1 BB costimulatory domain and the other a costimulatory domain selected from: CD28 and CD28gg. In various embodiments the 1-5 (e.g., 1 or 2) amino acid modification are substitutions, e.g., conservative substitutions.

Also disclosed is a population of human T cells transduced by a vector comprising an expression cassette encoding a chimeric antigen receptor, wherein chimeric antigen receptor comprises: an scFv targeted to CD19; a transmembrane domain selected from: a CD4 transmembrane domain or variant thereof having 1-5 amino acid modifications (e.g., 1 or 2) amino acid modifications (e.g., substitutions), a CD8 transmembrane domain or variant thereof having 1-5 amino acid modifications (e.g., 1 or 2) amino acid modifications (e.g., substitutions), a CD28 transmembrane domain or a variant thereof having 1-5 amino acid modifications (e.g., 1 or 2) amino acid modifications (e.g., substitutions), and a CD3ξ transmembrane domain or a variant thereof having 1-5 amino acid modifications (e.g., 1 or 2) amino acid modifications (e.g., substitutions); a costimulatory domain (e.g., a CD28 co-stimulatory domain or a variant thereof having 1-5 (e.g., 1 or 2) amino acid modifications (e.g., substitutions); or a 4-1 BB co-stimulatory domain or a variant thereof having 1-5 (e.g., 1 or 2) amino acid modifications (e.g., substitutions); or both a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions); and CD3g signaling domain of a variant thereof having 1-5 amino acid modifications (e.g., 1 or 2) amino acid modifications (e.g., substitutions). In various embodiments: the population of human T cells comprises central memory T cells (TCM cells) e.g., at least 20%, 30%, 40%, 50% 60%, 70%, 80% of the cells are TCM cells, or the population of T cells comprises a combination of central memory T cells, naive T cells and stem central memory cells (TCM/SCM/N cells) e.g., at least 20%, 30%, 40%, 50% 60%, 70%, 80% of the cells are TCM/SCM/N cells. In either case, the population of T cells includes both CD4+ cells and CD8+ cells (e.g., at least 20% of the CD3+ T cells are CD4+ and at least 3% of the CD3+ T cells are CD8+ and at least 70, 80 or 90% are either CD4+ or CD8+; at least 15%, 20%, 25%, 30%, 35%, 40%, 50%, 60% of the cells CD3+ cells are CD4+ and at least 4%, 5%, 8%, 10%, 20 of the CD3+ cells are CD8+ cells).

Also described is a method of treating cancer in a patient comprising administering a population of autologous or allogeneic human T cells (e.g., autologous or allogenic T cells comprising central memory T cells (TCM cells) or a combination of central memory T cells, naive T cells and stem central memory cells (i.e., the T cells are TCM/SCM/N cells) at least 20%, 30%, 40%, 50% 60%, 70%, 80% of the cells are TCM/SCM/N cells. In either case, the population of T cells includes both CD4+ cells and CD8+ cells (e.g., at least 20% of the CD3+ T cells are CD4+ and at least 3% of the CD3+ T cells are CD8+ and at least 70, 80 or 90% are either CD4+ or CD8+; at least 15%, 20%, 25%, 30%, 35%, 40%, 50%, 60% of the cells CD3+ cells are CD4+ and at least 4%, 5%, 8%, 10%, 20 of the CD3+ cells are CD8+ cells) transduced by a vector comprising an expression cassette encoding a chimeric antigen receptor.

The CD19 CAR can include a spacer region located between the CD19 binding domain (e.g., a CD19 scFv) and the transmembrane domain. A variety of different spacers can be used. Some of them include at least portion of a human Fc region, for example a hinge portion of a human Fc region or a CH3 domain or variants thereof. Table 1 below provides various spacers that can be used in the CARs described herein.

TABLE 1

Examples of Spacers

| Nam | Length | Sequence |
|---|---|---|
| a3 | 3 aa | AAA |
| linker | 10 aa | GGGSSGGGSG (SEQ ID NO: 26) |
| IgG4 hinge (S→P)(S228P) | 12 aa | ESKYGPPCPPCP (SEQ ID NO: 27) |
| IgG4 hinge | 12 aa | ESKYGPPCPSCP (SEQ ID NO: 4) |
| IgG4 hinge (S228P) + linker | 22 aa | ESKYGPPCPPCPGGGSSGGGSG (SEQ ID NO: 5) |
| CD28 hinge | 39 aa | IEVMYPPPYLDNEKSNGTIIHVKGKHL CPSPLFPGPSKP (SEQ ID NO: 6) |
| CD8 hinge-48aa | 48 aa | AKPTTTPAPRPPTPAPTIASQPLSLRP EACRPAAGGAVHTRGLDFACD (SEQ ID NO: 7) |
| CD8 hinge-45aa | 45 aa | TTTPAPRPPTPAPTIASQPLSLRPEAC RPAAGGAVHTRGLDFACD (SEQ ID NO: 8 |
| IgG4(HL-CH3) (includes S228P in hinge) | 129 aa | ESKYGPPCPPCPGGGSSGGGSGGQPR EPQVYTLPPSQEEMTKNQVSLTCLVK GFYPSDIAVEWESNGQPENNYKTTPP VLDSDGSFFL YSRLTVDKSRWQEGNV FSCSVMHEALHNHYTQKSLSLSLGK SEQ ID NO: 9) |
| IgG4(L235E, N297Q) | 229 aa | ESKYGPPCPSCPAPEFEGGPSVFLFPP KPKDTLMISRTPEVTCVVVDVSQEDPE VQFNWYVDGVEVHQAKTKPREEQF STYRVVSVLTVLHQDWLNGKEYKCK VSNKGLPSSIEKTISKAKGQPREPQVY TLPPSQEEMTKNQVSLTCLVKGFYPS DIAVEWESNGQPENNYKTTPPVLDSD GSFFLYSRLTVDKSRWQEGNVFSCSV MHEALHNHYTQKSLSLSLGK (SEQ ID NO: 10) |
| IgG4(S228P, L235E, N297Q) | 229 aa | ESKYGPPCPPCPAPEFEGGPSVFLFPP KPKDTLMISRTPEVTCVVVDVSQEDPE VQFNWYVDGVEVHQAKTKPREEQFQ STYRVVSVLTVLHQDWLNGKEYKCK VSNKGLPSSIEKTISKAKGQPREPQVY TLPPSQEEMTKNQVSL TCLVKGFYPS DIAVEWESNGQPENNYKTTPPVLDSD GSFFLYSRLTVDKSRWQEGNVFSCSV MHEALHNHYTQKSLSLSLGK (SEQ ID NO: 11) |
| IgG4(CH3) | 107 aa | GQPREPQVYTLPPSQEEMTKNQVSLT CLVKGFYPSDIAVEWESNGQPENNYK TTPPVLDSDGSFFLYSRLTVDKSRWQ EGNVFSCSVMHEALHNHYTQKSLSLSL GK(SEQ ID NO: 12) |
| HL | 22 aa | ESKYGPPCPPCPGGGSSGGGSG (SEQ ID NO: 28) |

Some spacer regions include all or part of an immunoglobulin (e.g., IgG 1, IgG2, IgG3, IgG4) hinge region, i.e., the sequence that falls between the CH1 and CH2 domains of an immunoglobulin, e.g., an IgG4 Fe hinge or a CD8 hinge. Some spacer regions include an immunoglobulin CH3 domain or both a CH3 domain and a CH2 domain. The immunoglobulin derived sequences can include one or more amino acid modifications, for example, 1, 2, 3, 4 or 5 substitutions, e.g., substitutions that reduce off-target binding.

An "amino acid modification" refers to an amino acid substitution, insertion, and/or deletion in a protein or peptide sequence. An "amino acid substitution" or "substitution" refers to replacement of an amino acid at a particular position in a parent peptide or protein sequence with another amino acid. A substitution can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The following are examples of various groupings of amino acids: 1) Amino acids with nonpolar R groups: Alanine, Valine, Leucine, Isoleucine, Proline, Phenylalanine, Tryptophan, Methionine; 2) Amino acids with uncharged polar R groups: Glycine, Serine, Threonine, Cysteine, Tyrosine, Asparagine, Glutamine; 3) Amino acids with charged polar R groups (negatively charged at pH 6.0): Aspartic acid, Glutamic acid; 4) Basic amino acids (positively charged at pH 6.0): Lysine, Arginine, Histidine (at pH 6.0). Another grouping may be those amino acids with phenyl groups: Phenylalanine, Tryptophan, and Tyrosine.

For amino acid positions in immunoglobulin discussed herein, numbering is according to the EU index or EU numbering scheme (Kabat et al. 1991 Sequences of Proteins of Immunological Interest, 5th Ed., United States Public Health Service, National Institutes of Health, Bethesda, hereby entirely incorporated by reference). The EU index or EU index as in Kabat or EU numbering scheme refers to the numbering of the EU antibody (Edelman et al. 1969 *Proc Natl Acad Sci USA* 63:78-85).

A variety of transmembrane domains can be used in the. Table 2 includes examples of suitable transmembrane domains. Where a spacer domain is present, the transmembrane domain is located carboxy terminal to the spacer domain.

TABLE 2

Examples of Transmembrane Domains

| Name | Accession | Length | Sequence |
|---|---|---|---|
| CD3z | J04132.1 | 21 aa | LCYLLDGILFIYGVILTALFL (SEQ ID NO: 13) |
| CD28 | NM_006139 | 27 aa | FWVLVVVGGVLACYSLLVTVAFIIFWV (SEQ ID NO: 14) |
| CD28(M) | NM_006139 | 28 aa | MFWVLVVVGGVLACYSLLVTVAFIIFWV (SEQ ID NO: 15) |
| CD4 | M35160 | 22 aa | MALIVLGGVAGLLLFIGLGIFF (SEQ ID NO: 16) |
| CD8tm | NM_001768 | 21 aa | IYIWAPLAGTCGVLLLSLVIT (SEQ ID NO: 17) |
| CD8tm2 | NM_001768 | 23 aa | IYIWAPLAGTCGVLLLSLVITLY (SEQ ID NO: 18) |

TABLE 2-continued

Examples of Transmembrane Domains

| Name | Accession | Length | Sequence |
|---|---|---|---|
| CD8tm3 | NM_001768 | 24 aa | IYIWAPLAGTCGVLLLSLVITLYC (SEQ ID NO: 19) |
| 41BB | NM_001561 | 27 aa | IISFFLALTSTALLFLLFFLTLRFSVV (SEQ ID NO: 20) |

Many of the CAR described herein include one or more (e.g., two) costimulatory domains. The costimulatory domain(s) are located between the transmembrane domain and the CD3ξ signaling domain. Table 3 includes examples of suitable costimulatory domains together with the sequence of the CD3& signaling domain.

TABLE 3

CD3zeta Domain and Examples of Costimulatory Domains

| Name | Accession | Length | Sequence |
|---|---|---|---|
| CD3ζ | J04132.1 | 113 aa | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (SEQ ID NO: 21) |
| CD28 | NM_006139 | 42 aa | RSKRSRLLHSDYMNMTPRRPGPTRKHYQPYAPPRDFAAYRS (SEQ ID NO: 22) |
| CD28gg* | NM_006139 | 42 aa | RSKRSRGGHSDYMNMTPRRPGPTRKHYQPYAPPRDFAAYRS (SEQ ID NO: 23) |
| 41BB | NM_001561 | 42 aa | KRGRKKLLYIFKQPFMRPVQTTQEEDGCSCRFPEEEEGGCEL (SEQ ID NO: 24) |
| OX40 | | 42 aa | ALYLLRRDQRLPPDAHKPPGGGSFRTPIQEEQADAHSTLAKI (SEQ ID NO: 25) |

EXAMPLES

Example 1. Novel Potent Chimeric Poxviruses for Oncolytic Immunotherapy of Cancer Described bellow are chimeric poxviruses that are oncolytic anc can be used to prepare recombinant chimeric poxviruses that express human CD19 in cells infected by the recombinant virus. Because the recombinant virus will infect cancer cells and cause them to express CD19. The infected cells can be targeted by a CAR directed to CD19.

A Chimeric poxviruses used to create recombinant poxvirus have potential to combine favorable features from different virus species, thus, are superior to individual wild-type viruses. Since orthopoxviruses and parapoxviruses are antigenically distinct the potent chimeric orthopoxvirus and the potent chimeric parapoxvirus generated in this study can be potentially combined into the same treatment regimen to achieve the maximum therapeutic efficacy. As explained in greater detail in PCT/US2017/46163 filed 9 Aug. 2017, chimeric poxvirus, including isolates #33 (SEQ ID NO:1) and #189 (SEQ ID NO:2) were generated from pools of chimeric orthopoxviruses and chimeric parapoxviruses. Several chimeric orthopoxvirus and parapoxvirus isolates, including isolates #33 and #189 showed superior killing capacity in a panel of the NCI 60 cancer cell lines compared to their parental individual wildtype viruses.

Generation of chimeric virus pools and isolation of individual chimeric viruses. A pool of chimeric orthopoxviruses was generated by co-infecting CV-1 cells with cowpox virus strain Brighton, raccoonpox virus strain Herman, rabbitpox virus strain Utrecht, and vaccinia virus strains WR, IHD, Elstree, CL, Lederle-Chorioallantoic and AS at a multiplicity of infection (MOI) of 0.01 per virus. To generate a pool of chimeric parapoxviruses, MDBK cells were co-infected with orf virus strain NZ2 and pseudocowpox virus strain TJS at an MOI of 0.1. Applicants' pilot experiments indicate that CV-1 cells are susceptible to all the orthopoxviruses used in this study and that both orf virus and pseudocowpox virus infect and form plaques in MDBK cells.

100 chimeric orthopoxvirus plaques and 100 chimeric parapoxvirus plaques were picked from CV-1 cells infected with the chimeric orthopoxvirus pool and MDBK cells infected with the chimeric parapoxvirus pool, respectively. These two hundred plaques were further plaque-purified two more times in respective cells to yield 200 clonally purified individual chimeric virus isolates. Viruses #14-113 are chimeric orthopoxvirus isolates whereas viruses #114-213 are chimeric parapoxvirus isolates.

Identification of novel potent chimeric poxvirus isolates by high throughput screening in the NCI-60 cell lines. Tumor cell-killing activity of 200 chimeric orthopoxvirus and chimeric parapoxvirus isolates, together with 11 parental virus strains and 2 control oncolytic viruses (GLV-1h68 and OncoVEX GFP) were evaluated and compared in a panel of the NCI-60 cell lines (Table 4). GLV-1h68 is one of the best studied oncolytic vaccinia viruses, and is currently in clinical development. OncoVEX GFP has the same backbone as T-VEC, an oncolytic herpes simplex virus-1 and the first oncolytic virus approved by the FDA. Each cell line was infected with each virus at an MOI of 0.01. Cell viability was measured at 96 h post infection using MTS assays. The virus amount used (MOI 0.01) in this high throughput screening experiment was intentionally kept low, and optimized to compare cell killing in adherent cell lines (the majority of cell lines in the NCI-60 panel are adherent cells) so potent new virus isolates can stand out. This amount of virus, however, was too low to see any significant and consistent cell killing in suspension cell lines. Therefore, the results from 6 leukemia cell lines were not included in the analysis for the purpose of virus comparison.

TABLE 4

Catalog of the NCI-60 cell lines

| Name | Species | Organ of Origin | Culture |
|---|---|---|---|
| BT549 | Human | Breast | Adherent |
| HS 578T | Human | Breast | Adherent |
| MCF7 | Human | Breast | Adherent |
| MDA-MB-231 | Human | Breast | Adherent |
| MDA-MB-468 | Human | Breast | Adherent |
| T-47D | Human | Breast | Adherent |
| SF268 | Human | CNS | Adherent |
| SF295 | Human | CNS | Adherent |
| SF539 | Human | CNS | Adherent |
| SNB-19 | Human | CNS | Adherent |
| SNB-75 | Human | CNS | Adherent |
| U251 | Human | CNS | Adherent |
| Colo205 | Human | Colon | Adherent & Suspension |
| HCC 2998 | Human | Colon | Adherent |
| HCT-116 | Human | Colon | Adherent |
| HCT-15 | Human | Colon | Adherent |
| HT29 | Human | Colon | Adherent |
| KM12 | Human | Colon | Adherent |
| SW620 | Human | Colon | Adherent |
| 786-O | Human | Kidney | Adherent |
| A498 | Human | Kidney | Adherent |
| ACHN | Human | Kidney | Adherent |
| CAKI | Human | Kidney | Adherent |
| RXF 393 | Human | Kidney | Adherent |
| SN12C | Human | Kidney | Adherent |
| TK-10 | Human | Kidney | Adherent |
| UO-31 | Human | Kidney | Adherent |
| CCRF-CEM | Human | Leukemia | Suspension |
| HL-60 | Human | Leukemia | Suspension |
| K562 | Human | Leukemia | Suspension |
| MOLT-4 | Human | Leukemia | Suspension |
| RPMI-8226 | Human | Leukemia | Suspension |
| SR | Human | Leukemia | Suspension |
| A549 | Human | Lung | Adherent |
| EKVX | Human | Lung | Adherent |
| HOP-62 | Human | Lung | Adherent |
| HOP-92 | Human | Lung | Adherent & Suspension |
| NCI-H226 | Human | Lung | Adherent |
| NCI-H23 | Human | Lung | Adherent |
| NCI-H322M | Human | Lung | Suspension |
| NCI-H460 | Human | Lung | Adherent |
| NCI-H522 | Human | Lung | Adherent |
| LOX IMVI | Human | Melanoma | Semi-Adherent |
| M14 | Human | Melanoma | Adherent |
| MALME-3M | Human | Melanoma | Adherent & Suspension |
| MDA-MB-435 | Human | Melanoma | Adherent |
| SK-MEL-2 | Human | Melanoma | Adherent |
| SK-MEL-28 | Human | Melanoma | Adherent |
| SK-MEL-5 | Human | Melanoma | Adherent |
| UACC-257 | Human | Melanoma | Adherent |
| UACC-62 | Human | Melanoma | Adherent |
| IGROV1 | Human | Ovary | Adherent |
| OVCAR-3 | Human | Ovary | Adherent |
| OVCAR-4 | Human | Ovary | Adherent |
| OVCAR-5 | Human | Ovary | Adherent |
| OVCAR-8 | Human | Ovary | Adherent |
| SK-OV-3 | Human | Ovary | Adherent |
| NCI-ADR-RES | Human | Ovary | Adherent |
| DU145 | Human | Prostate | Adherent |
| PC-3 | Human | Prostate | Adherent |

Figure 2:
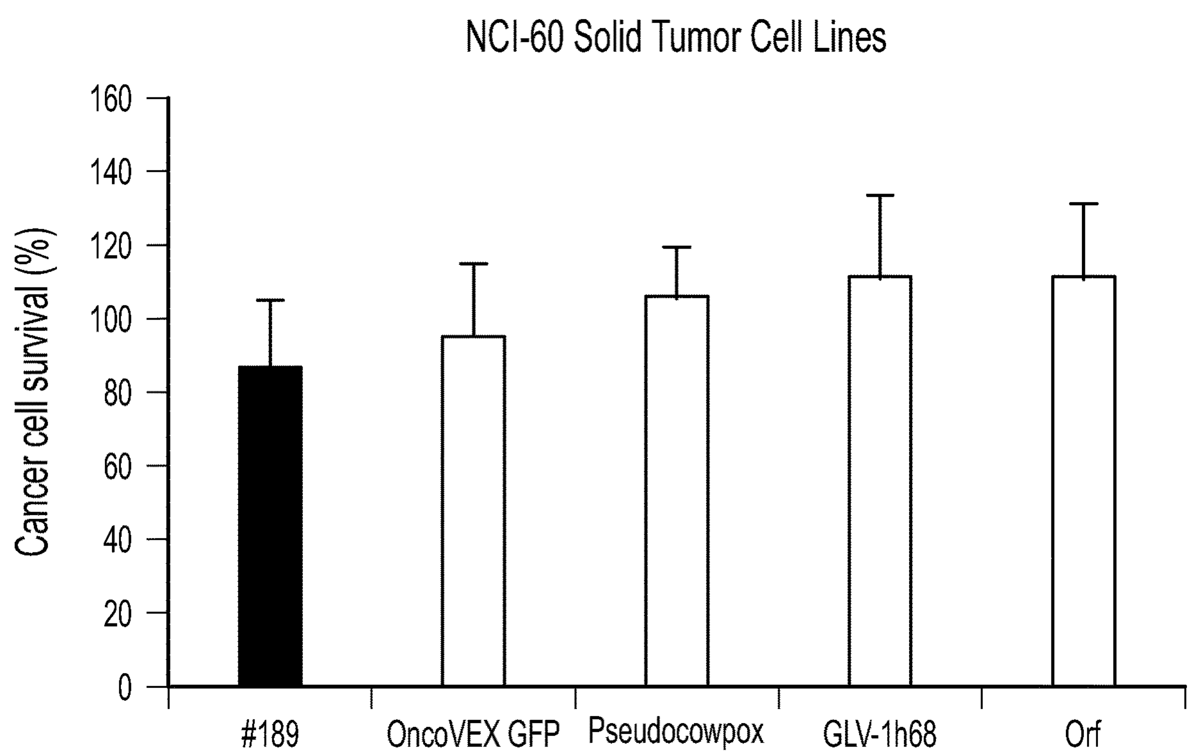
FIG. 2. Chimeric parapoxivirus isolate #189 (SEQ ID NO:2) shows superior cancer cell killing capability compared to the parental individual wild-type virus strains and the control viruses GLV-1h68 and OncoVEX GFP.

Among 100 new chimeric orthopoxvirus isolates, isolates #17 (SEQ ID NO:3) and #33 (SEQ ID NO:1) demonstrated significantly better cell killing in the NCI-60 solid tumor cell lines than did 9 parental orthopoxvirus strains and two control viruses (FIG. 1). Out of 100 new parapoxvirus isolates, isolate #189 (SEQ ID NO:2) stood out, showing the significantly better cell killing than did two parent parapoxvirus strains and the control viruses (FIG. 2). All three novel chimeric virus isolates (#17, #33, and #189) caused significant cell death in the majority of the NCI-60 solid cancer cell lines even at the low MOI of 0.01. In general, orthopoxvirus strains and chimeric orthopoxvirus isolates were more potent than parapoxvirus strains and chimeric parapoxvirus isolates in killing cancer cells at the low MOI of 0.01.

Genomic DNAs of novel poxvirus isolates #33 and #189 were isolated from purified virions and subject to next-generation sequencing using Illumina Hiseq 2500 with more than 1000× coverage. The gaps were PCR amplified and sequenced by Sanger sequencing. 189,415 base pairs (bps) of the #33 genome were fully sequenced whereas 138,203 bps of the 189 genome were obtained. Initial BLAST against GenBank indicated that the genomic sequences of both #33 and #189 are not identical to any genomic sequences in GenBank. #33 is more close to vaccinia virus strains than to any other orthpoxvirses. #189 is very close to orf virus NZ2 strain, one of the parental parapoxviruses. The nucleotide sequences of all ORFs identified in the orf virus NZ2 strain are identical to that in #189. There is one "G" insertion at position 6755 in the genome of #189 compared to orf virus NZ2. In the inverted terminal repeat regions there are one copy of a repeat element deleted and one copy of another repeat element inserted in the #189 genome. Overall, both #33 and #189 represent novel unique poxvirus isolates.

All cancer cell lines were grown in RPMI-1640 (Mediatech, Manassas, VA). African green monkey kidney fibroblast cells (CV-1) and cow kidney epithelial cells (MDBK) were obtained from American Type Culture Collection (ATCC; Rockville, MD, USA) and grown in DMEM (Mediatech, Manassas, VA). All media were supplemented with 10% FBS (Mediatech, Manassas, VA) and 1% penicillin-streptomycin solution (Mediatech, Manassas, VA). Cells were cultured at 37° C. under 5% $CO_2$.

Viruses: cowpox virus strain Brighton, raccoonpox virus strain Herman, rabbitpox virus strain Utrecht, vaccinia virus strains WR, IHD, Elstree, CL, Lederle-Chorioallantoic and AS, orf virus strain NZ2 and pseudocowpox virus strain TJS were purchased from ATCC. All orthopoxvirus strains were grown and titrated in CV-1 cells were parapoxvirus strains were grown and titrated in MDBK cells.

Generation of chimeric orthopoxvirus and chimeric parapoxvirus pools and isolation of individual clonal chimeric virus isolates: A pool of chimeric orthopoxviruses was generated by co-infecting CV-1 cells with cowpox virus strain Brighton, raccoonpox virus strain Herman, rabbitpox virus strain Utrecht, and vaccinia virus strains WR, IHD, Elstree, CL, Lederle-Chorioallantoic and AS at a multiplicity of infection (MOI) of 0.01 per virus. To generate a pool of chimeric parapoxviruses, MDBK cells were co-infected with orf virus strain NZ2 and pseudocowpox virus strain TJS at an MOI of 0.1. Infected cells were harvested at 3 days after infection. The initial chimeric orthopoxvirus pool was further passaged for three times in CV-1 cell at an MOI of 0.1 where the initial chimeric parapoxvirus poos was further passaged for three times in MDBK cells at an MOI of 0.1. 100 chimeric orthopoxvirus plaques and 100 chimeric parapoxvirus plaques were picked from CV-1 cells infected with the final chimeric orthopoxvirus pool and MDBK cells infected with the final chimeric parapoxvirus pool, respectively. These two hundred plaques were further plaque-purified two more times in respective cells to yield 200 clonally purified individual chimeric virus isolates.

NCI-60 cancer cell lines and a panel of pancreatic cancer cell line including PANC-1, MIA-PaCa2, BxPC3, FG, Capan-2 and Su.86.86 were dispensed into 96-well plates (3000 cells/well for solid tumor cell lines and 5000/well for leukemia cell lines) using an epMotion 5075 liquid handler (Eppendorf) under a sterile condition, incubated overnight at 37° C. under 5% (v/v) $CO_2$. Cells were then infected with 200 chimeric orthopoxvirus and chimeric parapoxvirus isolates, together with 11 parental virus strains and 2 control oncolytic viruses GLV-1h68 and OncoVEX GFP at an MOI of 0.01. Cell viability was determined at 96 h post infection using MTS assays (Promega). Absorbance at 490 nm was measured using an automated BMG PHERAstar plate reader (BMG Labtech). Each experiment was performed in duplicate. Cell viability for mock-infected cells was set to 100%.

MKN-45, OCUM-2M and KATO-3 cells were seeded into 96-well plates at a concentration of 3,000 cells per well, and incubated overnight at 37° C. under 5% (v/v) $CO_2$. Cells were infected with #33, #189, GLV-1h68 and OncoVEX GFP at MOIs of 0.01, 0.1 and 1. Cell viability was monitored daily for 4 days using MTS assays. 37° C. under 5% (v/v) $CO_2$.

Genomic DNAs of #33 and #189 were extracted from purified virions using Wizard Genomic DNA Purification kit (Promega) and fragmented by sonication. Libraries were prepared using KAPA LTP Library Preparation Kit. Sequencing was done using Illumina Hiseq 2500

Example 2. High Throughput Screening in Pancreatic Cancer Cell Lines

Figure 3:
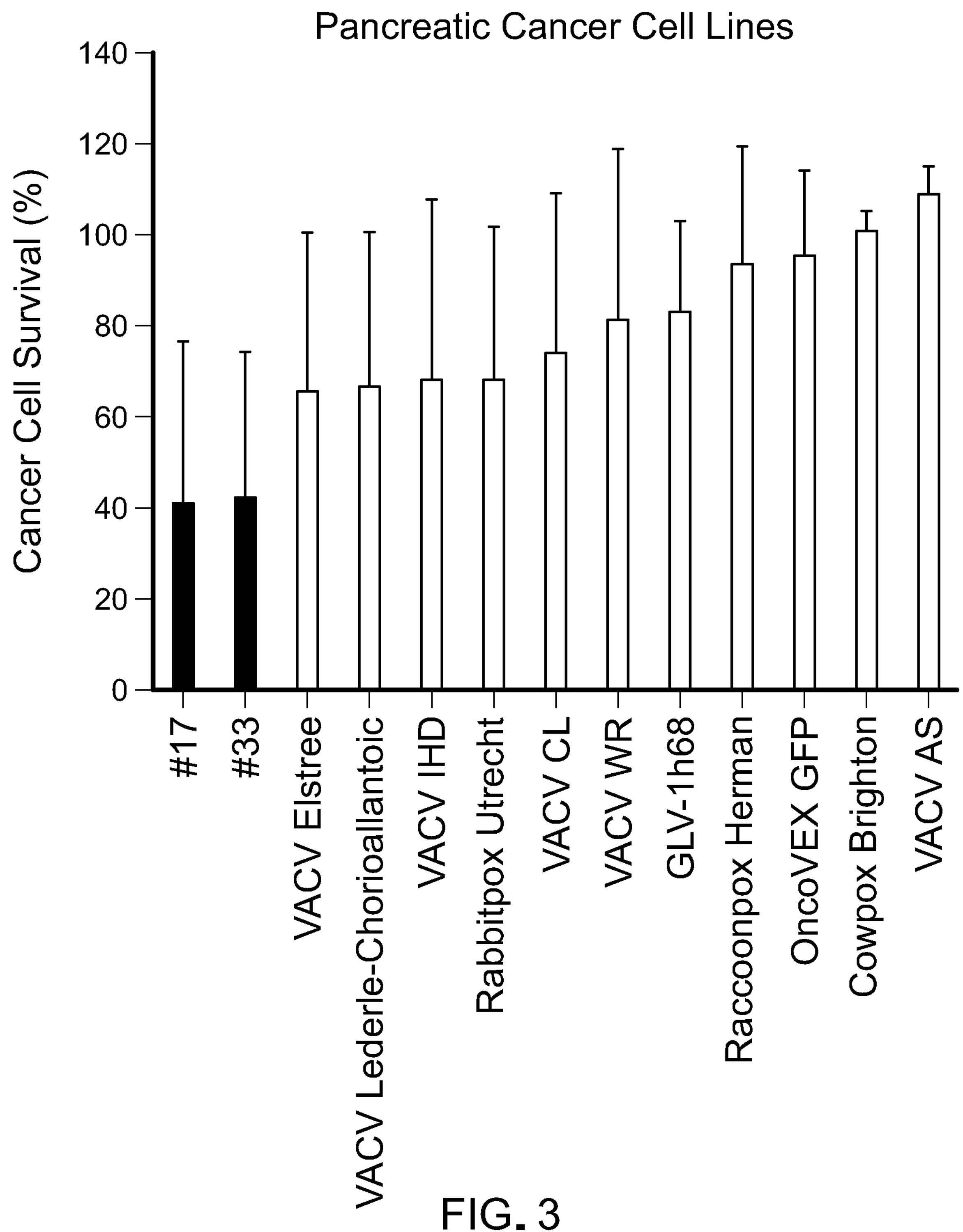
FIG. 3. Chimeric orthopoxvirus isolates #17 and #33 (SEQ ID NO:1) show potent cancer cell killing capacity in pancreatic cancer cell lines compared to their parent virus strains and the control viruses GLV-1h68 and OncoVEX GFP.
Figure 4:
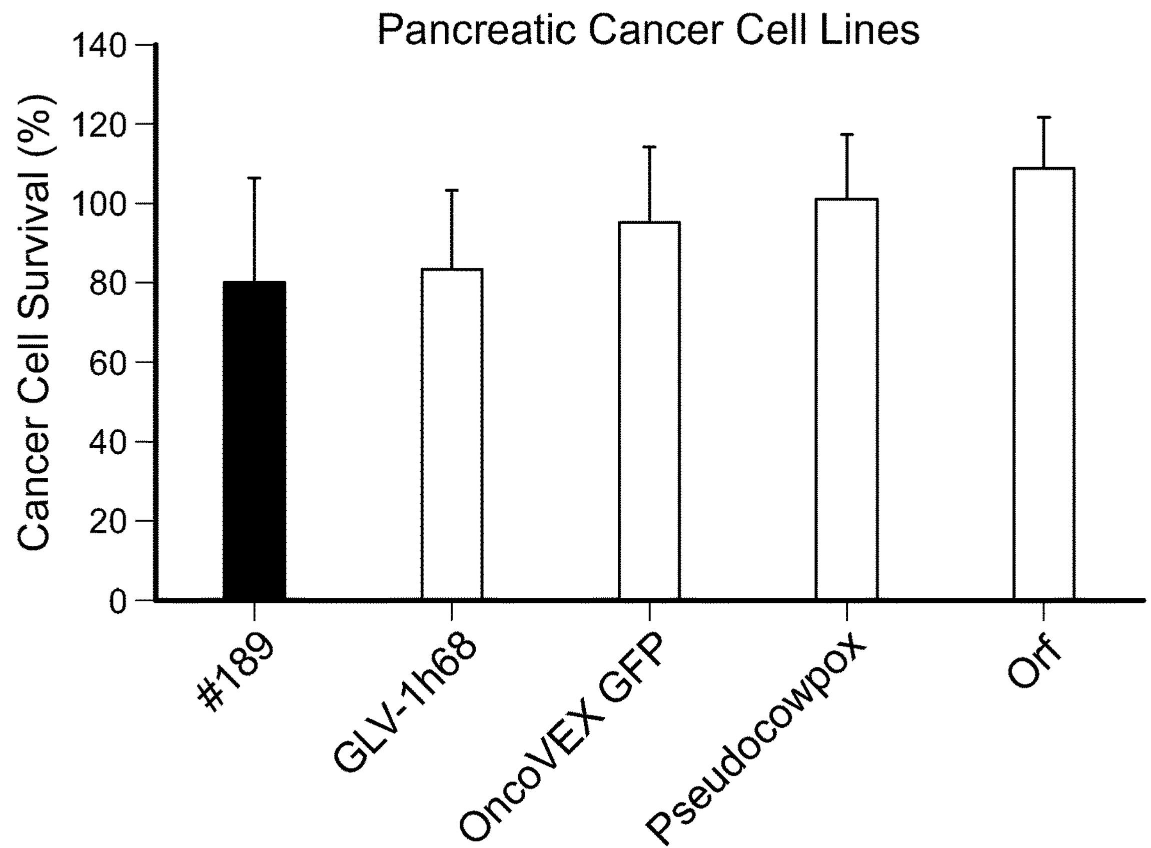
FIG. 4. Chimeric parapoxvirus isolate #189 (SEQ ID NO:2) shows potent cancer cell killing capability in pancreatic cancer cell lines compared to its parent virus strains and the control viruses GLV-1h68 and OncoVEX GFP.

NCI-60 cancer cell lines only contain solid cancers from 8 different organs (see Table 4). To investigate if the results from the NCI-60 cancer cell lines would be reproduced in solid cancers from other organs. Six pancreatic cancer cell lines (BxPC3, FG, MIA PaCa-2, Capan-2, PANC-1, and SU.86.86) were infected at an MOI of 0.1 with the same viruses used in the high throughput screening in the NCI-60 cancer cell lines. Cell viability was again measured at 96 h post infection using MTS assays. Chimeric orthopoxvirus isolates #17 and #33 showed the best cell killing among all the chimeric orthopoxvirus isolates whereas the chimeric parapoxvirus isolate #189 demonstrated the best cell killing among all the chimeric parapoxvirus isolates. They were all better in killing pancreatic cancer cell lines, as shown in Table 5 and FIG. 3 and FIG. 4, than their respective parent virus strains and the control viruses GLV-1h68 and OncoVEX GFP. Thus, the results from the NCI-60 cancer cell lines were very well reproduced in a panel of pancreatic cancer cell lines.

TABLE 5

Pancreatic Cancer Cell Survival.

| BxPC3 Ave. | FG Ave. | MIA PaCa2 Ave. | Capan 2 Ave. | PANC-1 Ave. | SU.86.86 Ave. | Ave. | stdev | Virus Name |
|---|---|---|---|---|---|---|---|---|
| 20.38 | 18.22 | 24.06 | 109.76 | 20.31 | 52.27 | 40.83 | 36.09 | #17 |
| 4.46 | 26.75 | 52.88 | 85.75 | 13.93 | 69.41 | 42.20 | 32.29 | #33 |
| 31.01 | 60.98 | 102.04 | 113.08 | 57.20 | 30.54 | 65.81 | 34.93 | VACV Elstree |
| 20.78 | 40.62 | 104.90 | 104.86 | 68.57 | 60.23 | 66.66 | 33.91 | VACV Lederle-Chorioallantoic |
| 18.21 | 33.81 | 93.44 | 106.36 | 45.64 | 109.87 | 67.89 | 40.05 | VACV IHD |
| 16.40 | 66.23 | 90.91 | 93.81 | 43.05 | 100.69 | 68.51 | 33.31 | Rabbitpox Utrecht |
| 19.57 | 50.96 | 97.52 | 108.60 | 68.27 | 101.81 | 74.46 | 34.78 | VACV CL |
| 17.51 | 75.42 | 102.31 | 123.05 | 68.27 | 103.55 | 81.69 | 37.29 | VACV WR |

TABLE 5-continued

| Pancreatic Cancer Cell Survival. | | | | | | | | |
|---|---|---|---|---|---|---|---|---|
| BxPC3 Ave. | FG Ave. | MIA PaCa2 Ave. | Capan 2 Ave. | PANC-1 Ave. | SU.86.86 Ave. | Ave. | stdev | Virus Name |
| 50.01 | 79.85 | 89.31 | 97.55 | 78.14 | 106.86 | 83.62 | 19.70 | GLV-1h68 |
| 61.29 | 96.76 | 122.32 | 112.34 | 62.99 | 107.42 | 93.85 | 25.91 | Raccoonpox Herman |
| 63.81 | 99.06 | 114.44 | 80.60 | 108.15 | 104.16 | 95.04 | 19.14 | OncoVEX GFP |
| 106.79 | 95.12 | 101.38 | 102.37 | 95.09 | 103.55 | 100.71 | 4.71 | Cowpox Brighton |
| 101.00 | 106.93 | 118.90 | 111.92 | 107.05 | 108.34 | 109.02 | 5.99 | VACV AS |

Figure 5A:
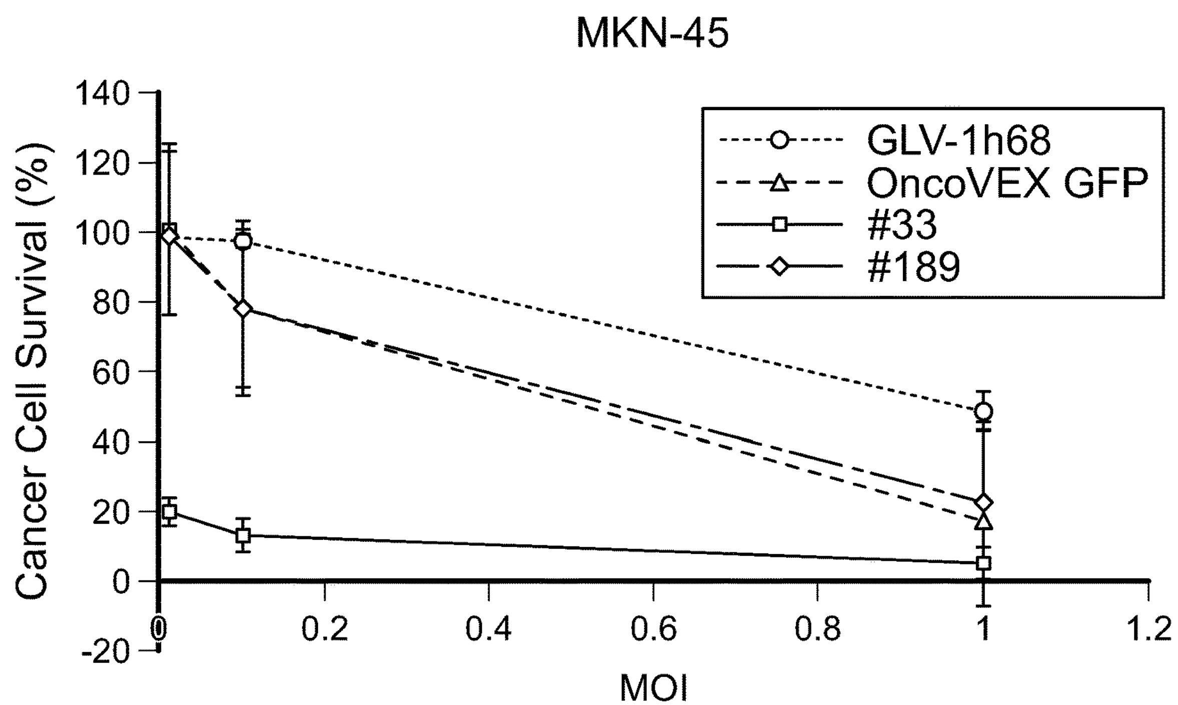
FIG. 5. Chimeric virus isolates #33 (SEQ ID NO:1) and #189 (SEQ ID NO:2) show superior cell killing activity in gastric cancer cell lines. Cancer cells were infected with each virus at MOIs of 0.01, 0.1, and 1.0. Cell viabilities at 96 hours post infection were plotted against MOIs in MKN-45 (A), OCUM-2M (B), and KATO-3 (C) gastric cell lines.
Figure 5B:
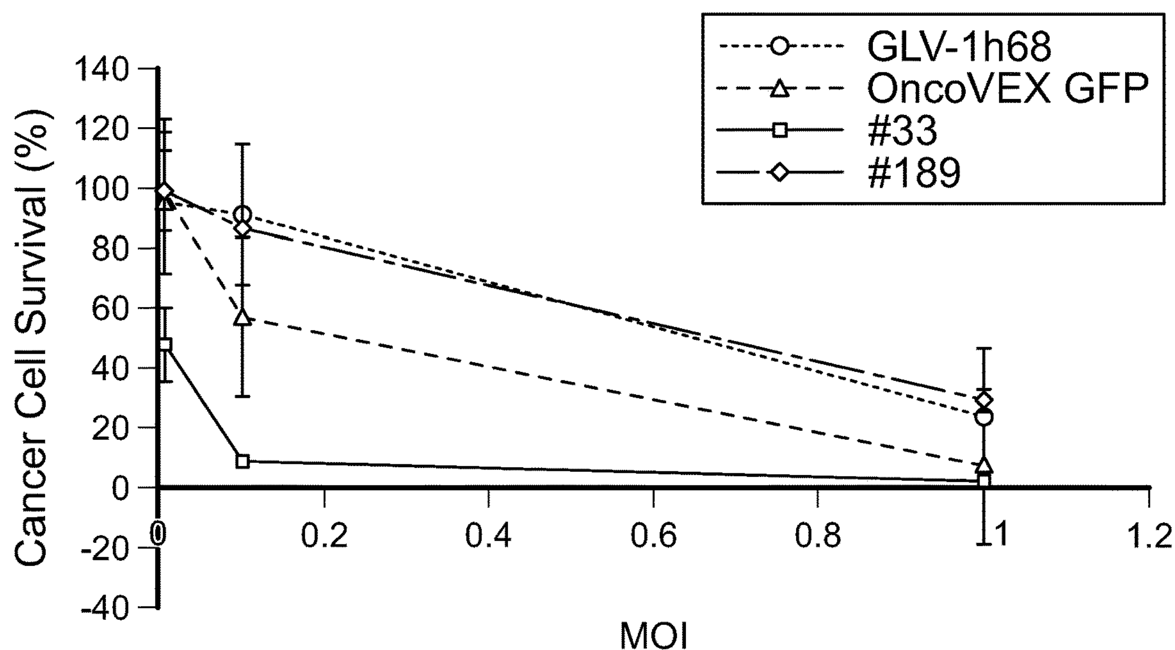
Figure 5C:
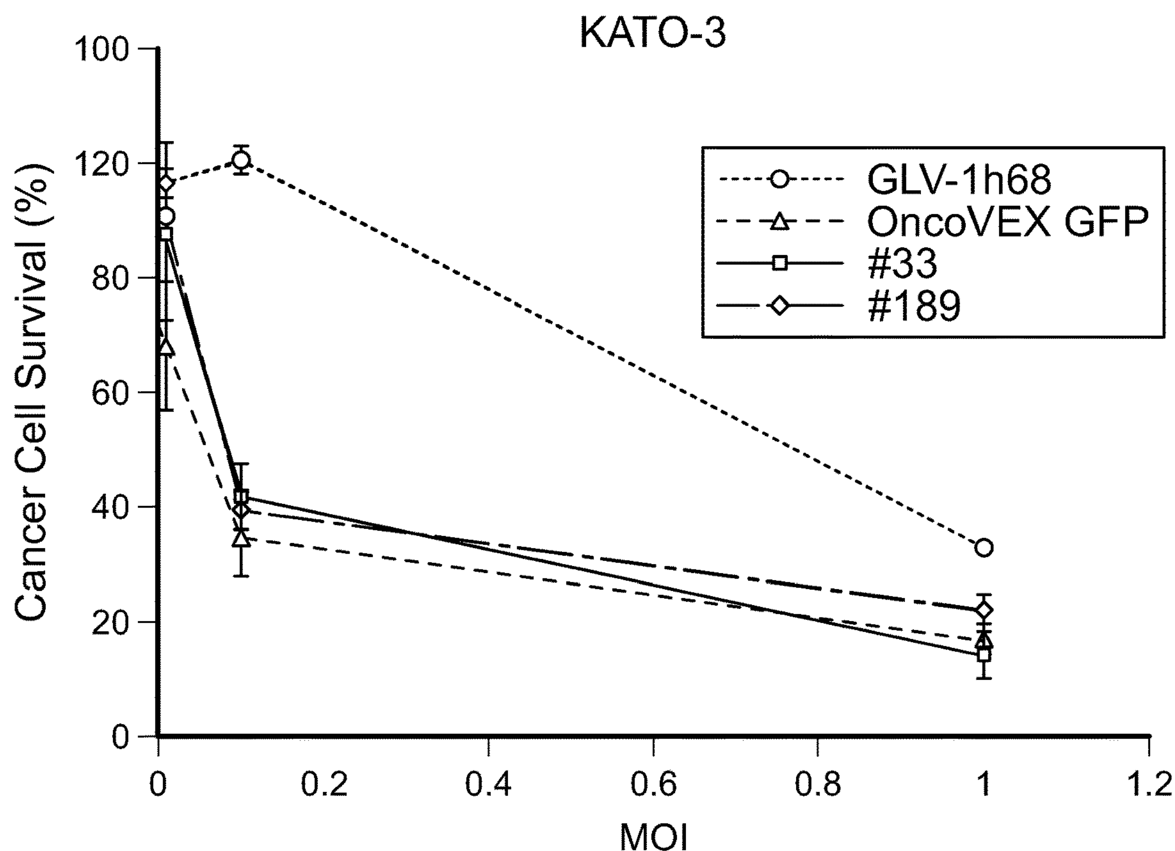

Example 3. Novel Chimeric Orthopoxvirus Isolate #33 and Chimeric Parapoxvirus Isolate #189 Show Potent Cell Killing in Gastric Cancer Cell Lines Based on the high throughput screening results from the NCI-60 cancer cell lines and the panel of pancreatic cancer cell lines, novel chimeric orthopoxvirus isolate #33 and chimeric parapoxvirus isolate #189 were chosen for further characterization. Tumor cell killing activity of the isolates #33 and #189 were further investigated in three gastric cancer cell lines. MKN-45, OCUM-2M and KATO-3 cells were infected with #33, #189, GLV-1h68 and OncoVEX GFP at MOIs of 0.01, 0.1 and 1. Cell viability was monitored daily for 4 days using MTS assays. MKN-45 and OCUM-2M cell lines were most sensitive to #33, intermediately sensitive to OncoVEX GFP, and least sensitive to GLV-1h68. While KATO-3 was most sensitive to OncoVEX GFP at the low MOI of 0.01, #33, #189, and OncoVEX GFP killed KATO-3 cells equally well at higher MOIs (0.1 and 1). KATO-3 cells were least sensitive to GLV-1h68. Overall, #33 killed gastric cancer cell lines most efficiently while GLV-1h68 kill gastric cancer cell lines least efficiently (FIGS. 5A-5C).

The 90 genes that are present in all sequenced ChPVs are listed together with their function when known, as reported in Table 6 (Abbreviations: IMV, intracellular mature virus; IEV, intracellular enveloped virus; EEV, extracellular enveloped virus). Genes are named after their VACV-COP counterpart. The asterisk, *, indicate genes also present in the two EnPVs. Table 3 is adapted from Gubser et al. (Gubser, C., Hue, S., Kellam, P., and Smith, G. L. (2004). Poxvirus genomes: a phylogenetic analysis. J Gen Virol 85, 105-117) and which is incorporated herein by reference in entirety and for all purposes.

TABLE 6

| Minimal Gene Complement of Chordopoxviruses. | | | |
|---|---|---|---|
| ORF | Putative function | ORF | Putative function |
| F9L* | Unknown | H6R* | DNA topoisomerase I |
| F10L* | IMV serine-threonine protein kinase | H7R | Unknown |
| F12L | IEV protein | D1R* | mRNA capping enzyme, large subunit |
| F13L | EEV protein/phospholipase | D2L | IMV core protein |
| F15L | Unknown | D3R* | IMV core protein |
| F17R | IMV core phosphoprotein, VP11/DNA-binding protein | D4R* | Uracil-DNA glycosylase |
| E1L* | Poly(A) polymerase catalytic subunit | D5R* | Nucleoside triphosphatase |
| E2L | Unknown | D6R* | Early transcription factor small subunit, VETF-1 |
| E4L | Poly(A) polymerase catalytic subunit, rpo30/VITF-1 | D7R* | RNA polymerase subunit rpo18 |
| E6R* | Unknown | D9R | 29 kDa mutT-like protein |
| E8R | Unknown | D10R* | 29 kDa mutT-like protein, negative regulator of gene expression |
| E9L | DNA polymerase | D11L* | Nucleoside triphosphate phosphohydrolase I |
| E10R | IMV membrane-associated protein | D12L* | mRNA capping enzyme small subunit, intermediate transcription factor, VITF |
| I1L | IMV core/DNA-binding protein | D13L* | IMV protein, rifampicin resistance |
| I2L | Unknown | A1L* | Late transcription factor/VLTF-2 |
| I3L | Phosphoprotein, binds ssDNA | A2L* | Late transcription factor/VLTF-3 |
| I5L | IMV structural protein, VP13K | A2-5L | Thioredoxin-like protein |
| I6L | Unknown | A3L* | IMV major core protein, P4b |
| I7L* | IMV core protein | A4L | IMV core protein |
| I8R* | Nucleoside triphosphate phosphohydrolase II, RNA helicase, NTPase | A5R* | RNA polymerase subunit rpo19 |
| G1L* | Metallo-endoproteinase/virion morphogenesis | A6L | Unknown |
| G2R | Late transcription/IBT-dependent protein | A7L* | Early transcription factor large subunit, VETF |

TABLE 6-continued

| Minimal Gene Complement of Chordopoxviruses. | | | |
|---|---|---|---|
| ORF | Putative function | ORF | Putative function |
| G3L | Unknown | A8R | Intermediate transcription factor, VITF-3 |
| G4L | Glutaredoxin 2, membrane protein, virion morphogenesis | A9L* | IMV protein, role in morphogenesis |
| G5R* | Unknown | A10L* | IMV major core protein P4a |
| G5-5R | RNA polymerase subunit rpo7 | A11R* | Unknown |
| G6R* | Unknown | A12L | IMV core protein |
| G7L | IMV core protein, VP16K | A13L | IMV membrane-associated protein/p8 |
| G8R | Late transcription factor, VLTF-1 | A14L | IMV protein, p16 |
| G9R* | Myristyl protein | A14-5L | IMV protein |
| L1R* | Myristylated IMV protein | A15L | Unknown |
| L2R | Unknown | A16L* | Myristyl protein |
| L3L* | Unknown | A17L | IMV membrane protein, morphogenesis factor |
| L4R* | IMV core protein VP8, DNA and RNA-binding protein | A18R* | DNA helicase, DNA-dependent ATPase, transcript release factor |
| L5R* | Unknown | A19L | Unknown |
| J1R | Dimeric virion protein | A20R | DNA polymerase processivity factor |
| J3R* | Poly(A) polymerase stimulatory submit, VP39 | A21L* | Unknown |
| J4R | RNA polymerase subunit rpo22 | A22R* | Holiday junction resolvase |
| J5L* | Unknown | A23R* | Intermediate transcription factor, VITF-3 |
| J6R* | RNA polymerase subunit rpo147 | A24R* | RNA polymerase subunit rpo132 |
| H1L | Tyrosine-serine phosphatase, virion maturation | A28L* | Unknown |
| H2R* | Unknown | A29L* | RNA polymerase subunit rpo35 |
| H3L* | Immunodominant IMV envelope protein p35 | A30L | Unknown |
| H4L* | RNA polymerase-associated transcription specificity factor, RAP 94 | A32L* | ATP- and GTP-binding motif A, DNA packaging |
| H5R | Late transcription factor, VLTF-4 | A34R | EEV glycoprotein |

Example 4. Construction of Recombinant Chimeric Poxviruses

Construction of Shuttle Vectors for Insertion of Foreign Gene Expression Cassettes into the Genome of the #33 Chimeric Poxvirus To construct thymidine kinase (TK) shuttle vector, the left and right flanking sequences of the TK gene of #33 chimeric poxvirus were PCR-amplified from #33 genomic DNA using Q5 High-Fidelity 2× Master Mix (New England Biolabs Inc., Ipswich, MA) and the primers: 5'-GCGCATATGATCTATGGATTACCATGGATGACAACTC-3' (SEQ ID NO: 31) and 5'-CGTTTAACTCGTCTAATTAATTCTGTAC-3' (left flank, SEQ ID NO: 32), 5'-CAGGTAAAAGTACAGAATTAATTAGACGAGTTAAACGAGCTCGTCGACGGATCC GCTAGCGGCCGCGGAGGTAATGATATGTATCAATCGGTGTGTAG-3' (SEQ ID NO: 33) and 5'-GCGGAATTCGTAATTACTTAGTAAATCCGCCGTACTAGG-3' (right flank; SEQ ID NO: 34). The two fragments were joined together using the method of gene splicing by overlapping extension. The resulting fragment was digested with NdeI and EcoRI and cloned into the same-cut plasmid pGPT to yield p33NC-TK. The flanking sequences of TK in the shuttle vector were confirmed by sequencing. p33NC-TK contains the left and right flanking sequences of TK separated by SacI, SalI, BamHI, NheI and NotI, and *Escherichia coli* guanine phosphoribosyltransferase (gpt) gene driven by the vaccinia virus (VACV) early promoter p7.5E as a transient dominant selectable marker.

The F14.5L shuttle vector was constructed similarly. The left and right flanking sequences of the F14.5L gene of #33 chimeric poxvirus were PCR-amplified from #33 genomic DNA using Q5 High-Fidelity 2× Master Mix (New England Biolabs Inc., Ipswich, MA) and the primers: 5'-GCGCATATGTAGAAGAATTGATAAATATGAAACCTTTTAAG-3' (SEQ ID NO: 35) and 5'-CCTCTCTAGCTTTCACTTAAACTGTATCG-3' (left flank; SEQ ID NO: 36), 5'-GAATAATCGATACAGTTTAAGTGAAAGCTAGAGAGGAAGCTTGAGCTCGAGGAT CCGCTAGCGGCCGCTGAAGAGGATGCTAGAATCAAGGAGGAGCAAG-3' (SEQ ID NO: 37) and 5'-GCGGAATTCTCCGGGCAGTGACTTTGTAGCTCTCCCAG-3' (right flank; SEQ ID NO: 38). The two fragments were joined together using the method of gene splicing by overlapping extension. The resulting fragment was digested with NdeI and EcoRI and cloned into the same-cut plasmid pGPT to yield p33NC-F14.5L. The flanking sequences of F14.5L in the shuttle vector were confirmed by sequencing. p33NC-F14.5L contains the left and right flanking sequences of F14.5L separated by HindIII, SacI, XhoI, BamHI, NheI and NotI, and *Escherichia coli* gpt driven by the VACV early promoter p7.5E as a transient dominant selectable marker.

Example 5. Recombinant Chimeric Poxvirus Expressing CD19t Provide a Target for CAR Targeted to CD19

Figure 7:
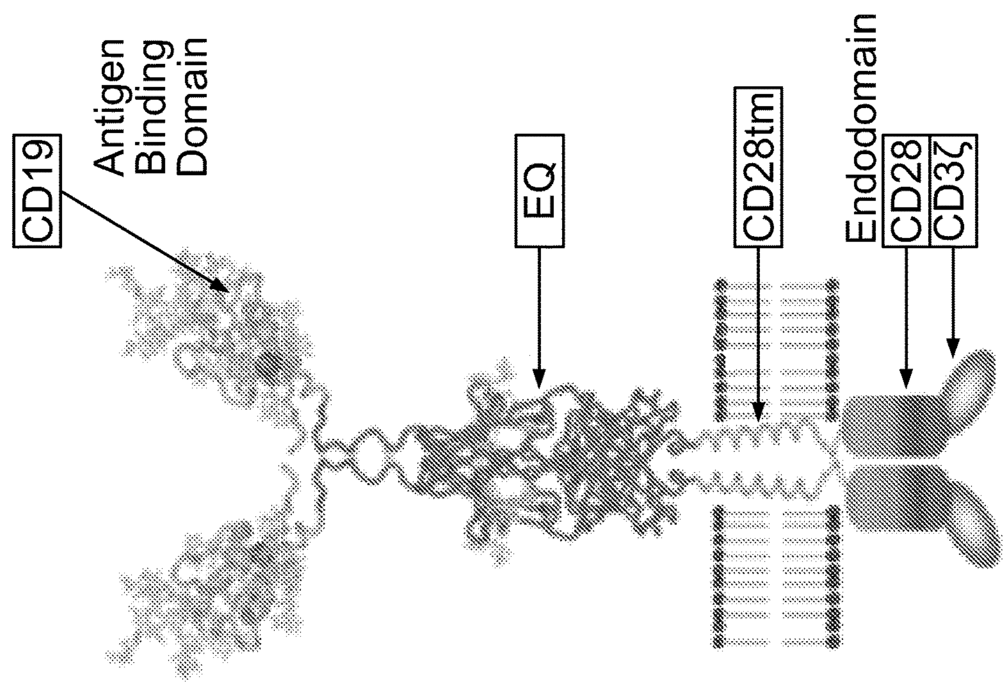
FIG. 7. Schematic depiction of CD19 CAR used in the studies described herein.
Figure 6:
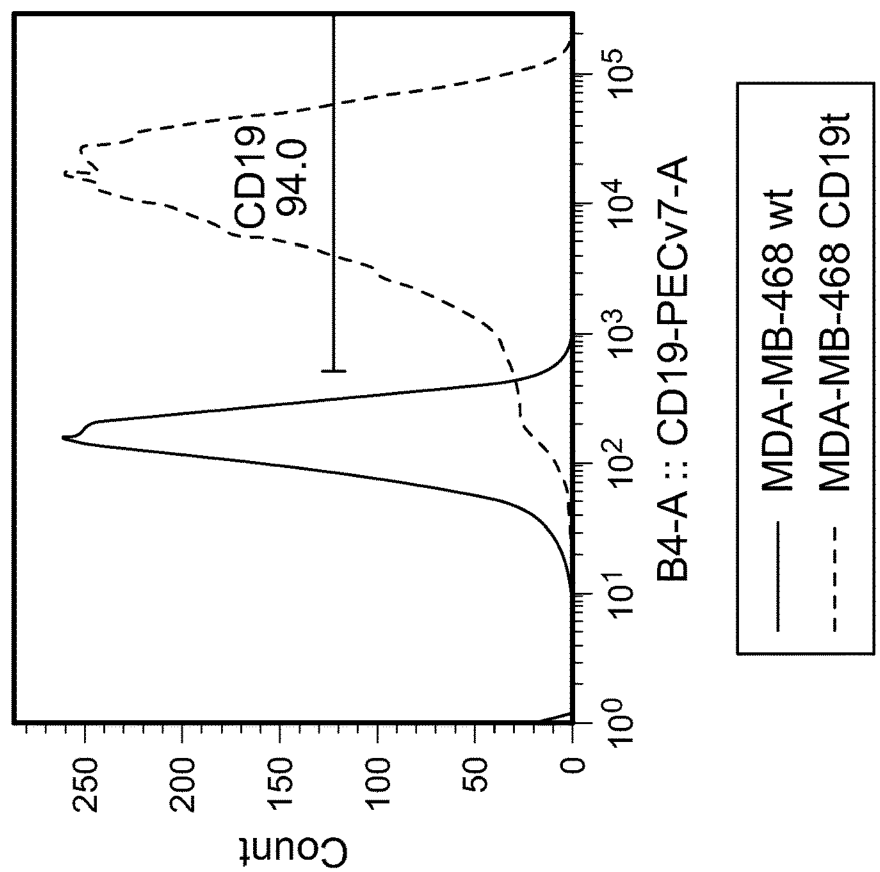
FIG. 6. CD19 expression of MDA-MB-468 parental and CD19t lines as determined by flow cytometry.
Figure 8:
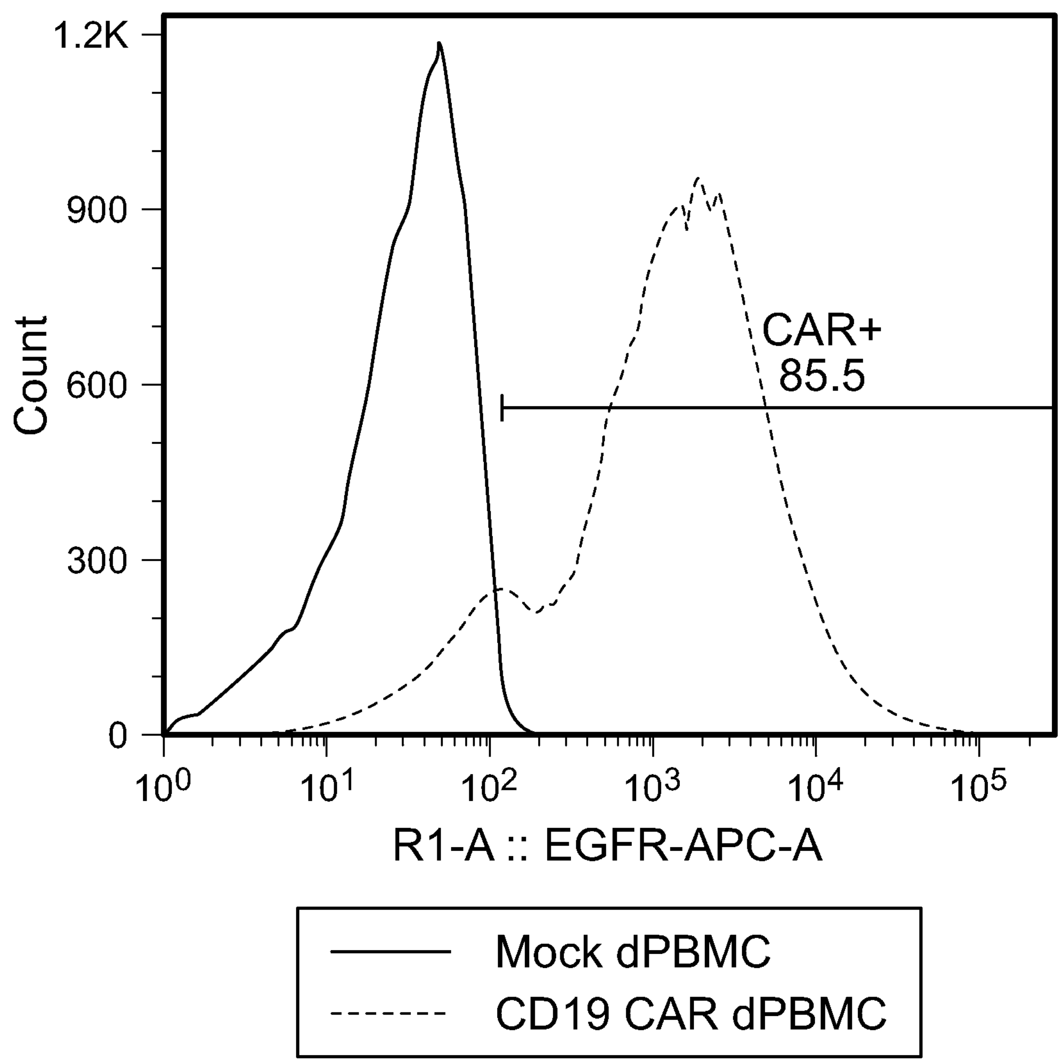
FIG. 8. Truncated EGFR expression, which indicates the presence of CD19 CAR, as determined by flow cytometry.

Two breast cancer cell lines, MDA-MB-468 wt (a triple negative breast cancer cell line), the parental line, and a variant of MDA-MB-468 modified to express a truncated human CD19 lacking a signaling domain (MDA-MB-468-CD19t) were used in the studies below. As shown in FIG. 6, MDA-MB-468-CD19t expresses CD19t. T cells modified to express a CAR targeted to CD19, described in greater detail below, were also used. The CAR expressed by these T cells is shown schematically in FIG. 7 and includes: a scFv targeted to CD19, and IgG4 spacer, a CD28 transmembrane domain, a CD28 co-stimulatory domain, and CD3zeta. A sequence encoding this CAR and a truncated EGFR was inserted into a lentiviral vector and this recombinant vector was used to transduce PBMC. The truncated EGFR can be used as marker for expression of the CAR. As shown in FIG. 8, which compares EGFR expression by mock transfected PBMC and PBMC transfected with the recombinant lentivirus expressing the CD19 CAR and truncated EGFR, show that the transfected cells express effectively express the transgene.

Figure 9:
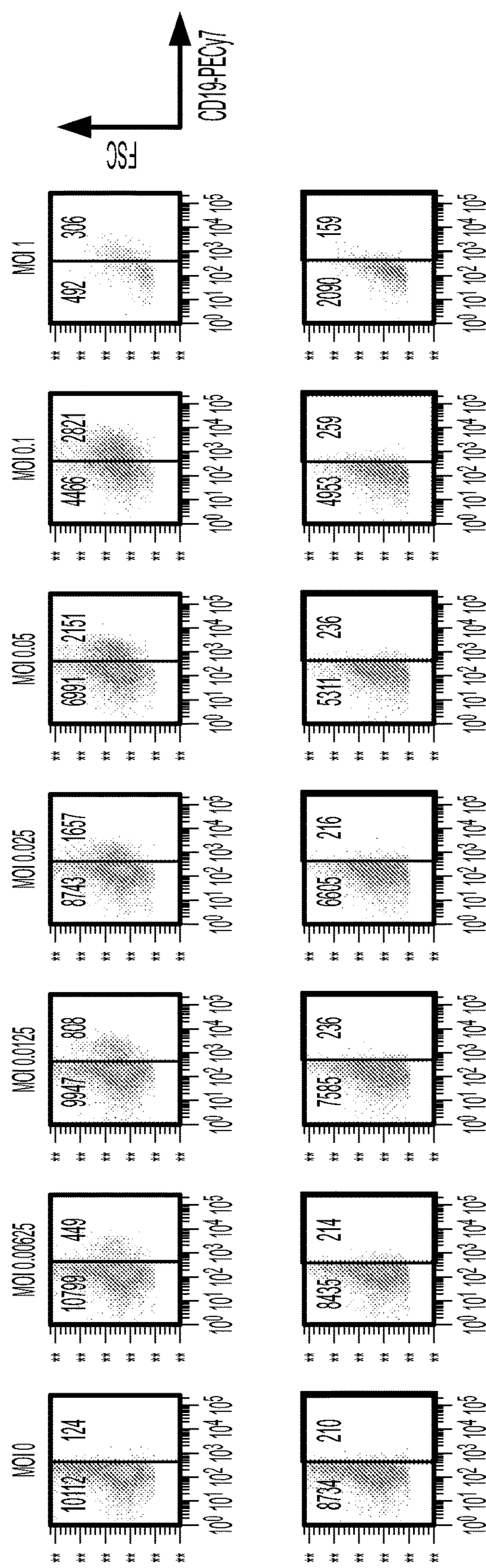
FIG. 9. The co-cultures of MDA-MB-468 tumors, either Mock or CD19 CAR T cell, and 33-CD19t virus were stained and analyzed by flow cytometry to determine CD19t expression on target cells. Top: without CD19 CART cell treatment. Bottom: with CD19 CAR T cell treatment.

Chimeric poxvirus #33 was engineered to express truncated CD19 recombinant oncolytic virus (33-CD19t). MDA-MB-48 tumor cells, which do not express CD19, were exposed to recombinant oncolytic virus 33-CD19t at various MOI and to mock transfected T cells. As shown in the upper panels of FIG. 9, increased levels of recombinant oncolytic virus 33-CD19t increased CD19 expression and reduced cell number. The lower panel of FIG. 9 depicts the results when the MDA-MB-48 tumor cells were exposed to recombinant oncolytic virus 33-CD19t, at various MOI, and to transfected T cells expressing the CD19 targeted CAR. As can be seen, the number of CD19t-expressing MDA-MB-468 cells was greatly reduced.

Figure 10:
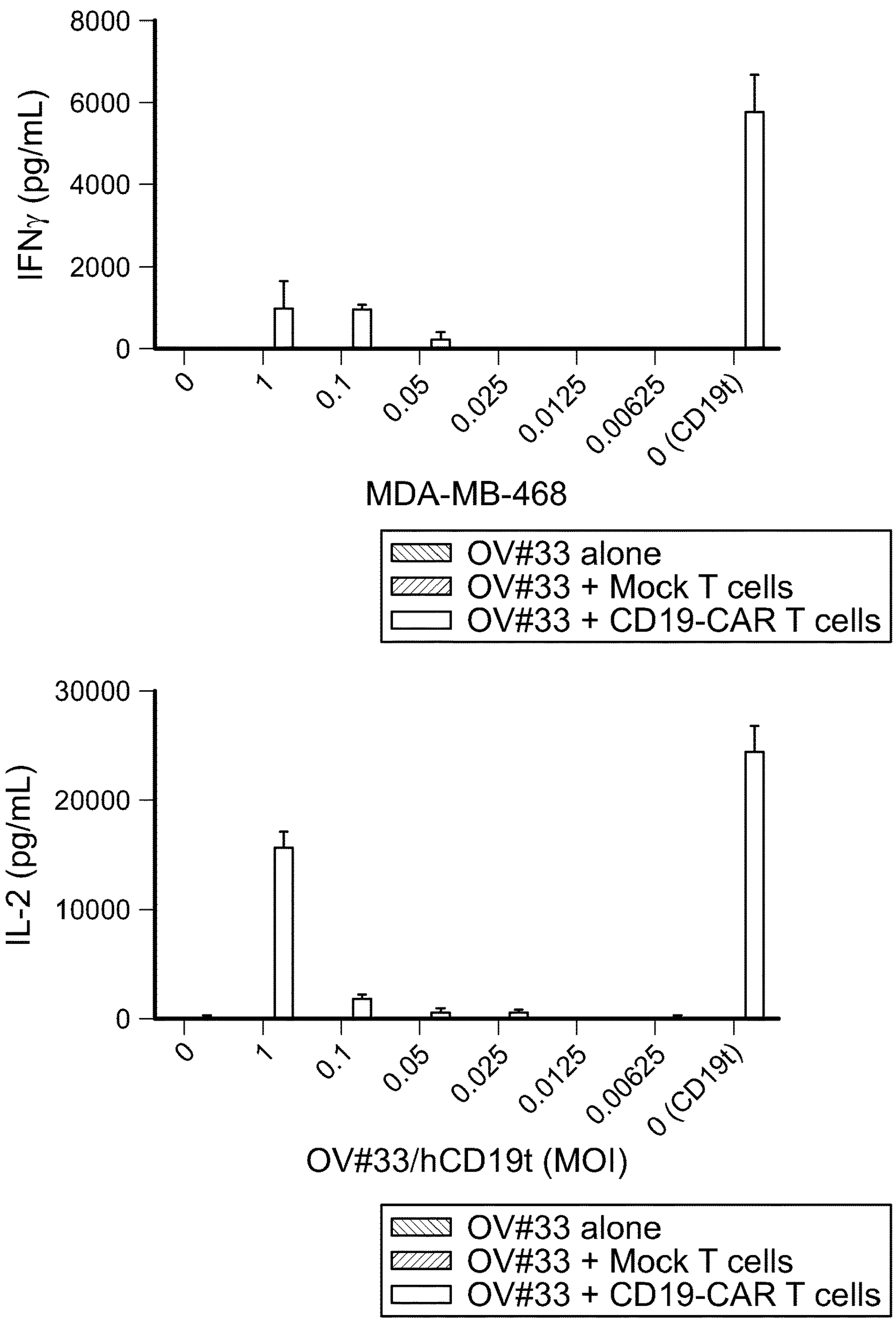
FIG. 10. Supernatant taken from a 48-hour long term kill assay with 33-CD19t virus. The T cell production of IL-2 (bottom) and IFN-γ (top) was detected by an enzyme linked immunosorbent assay (ELISA).

FIG. 10 depicts the results of a study measuring IL-2 (lower panel) and IFN-gamma (upper panel) levels in a long term killing assay. In this study, MDA-MB-468 cells were exposed to recombinant oncolytic virus 33-CD19t only; recombinant oncolytic virus 33-CD19t and mock transfected T cells; or recombinant oncolytic virus 33-CD19t and transfected T cells expressing the CD19 targeted CAR.

Figure 11:
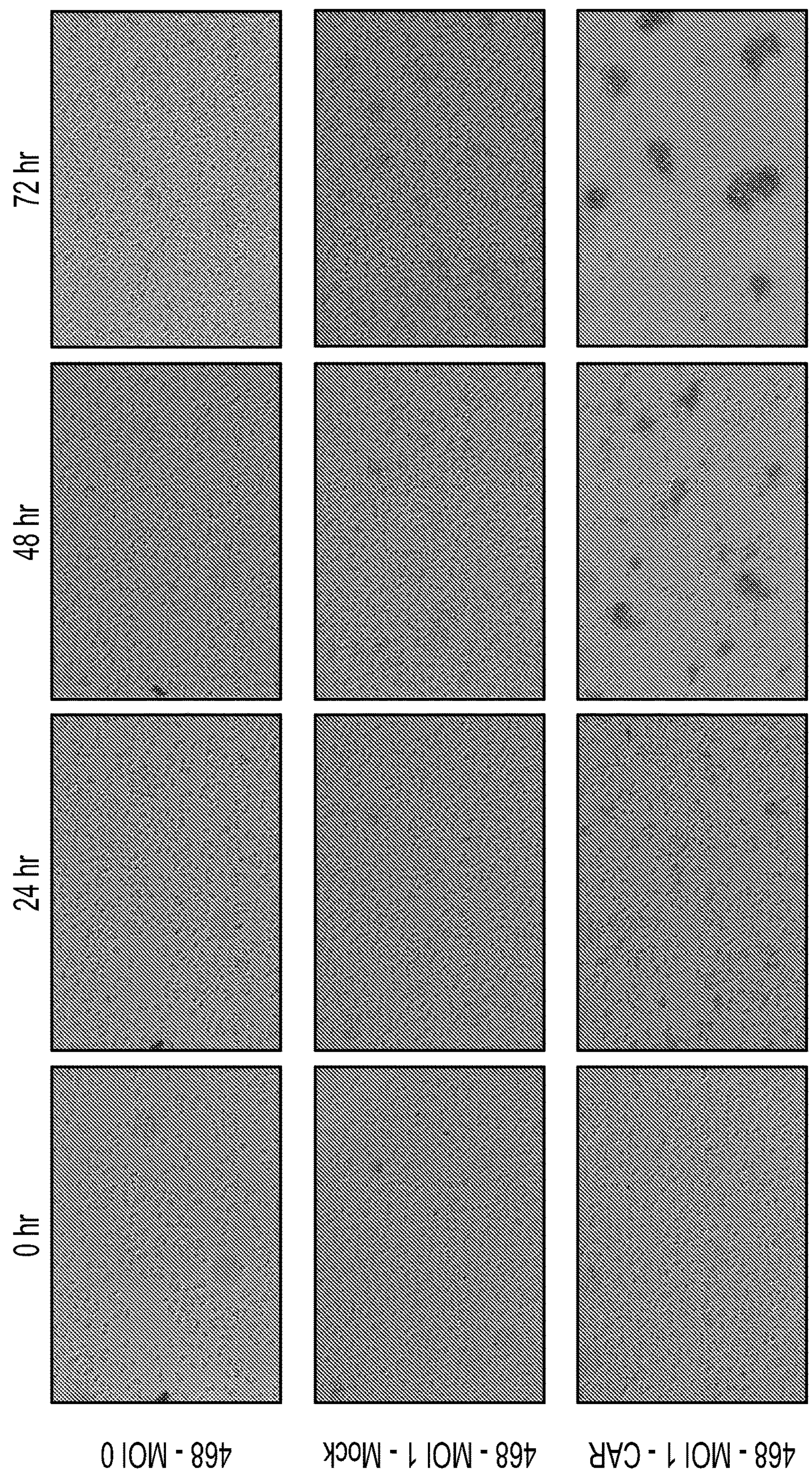
FIG. 11. Cell culture images of 24, 48 and 72-hour tumor killing assays (10×) comparing Mock to CAR T cell treatment after treatment with virus.

FIG. 11 is a series of images of cell cultures from a cell killing assay. In this study, MDA-MB-468 cells were exposed to recombinant oncolytic virus 33-CD19t at MOI=1 in the presence of mock transfected T cells or transfected T cells expressing the CD19 targeted CAR. The top series of images are of MDA-MB-468 cells cultured in the absence of either recombinant oncolytic virus 33-CD19t or transfected T cells expressing the CD19 targeted CAR.

Figure 12A:
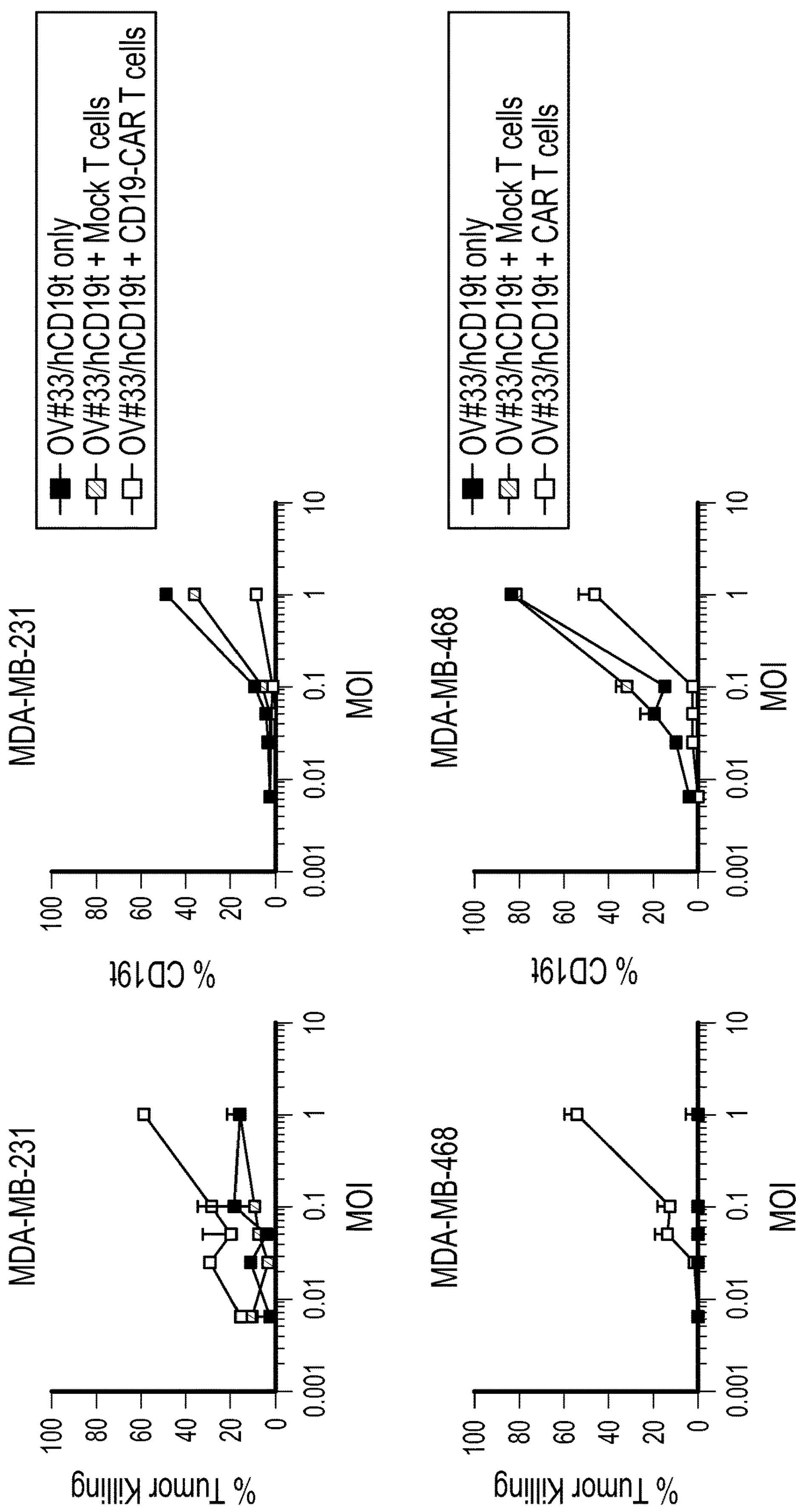
FIG. 12. Long term killing assays of MDA-MB-468 cells. Mock or CD19 CAR T cell and 33-CD19t virus were exposed to the cells and cultures were analyzed to determine CD19t expression and % tumor killing compared to a virus control (left) at (A) 24-hours, (B) 48-hours, and (C) 72-hours.
Figure 12B:
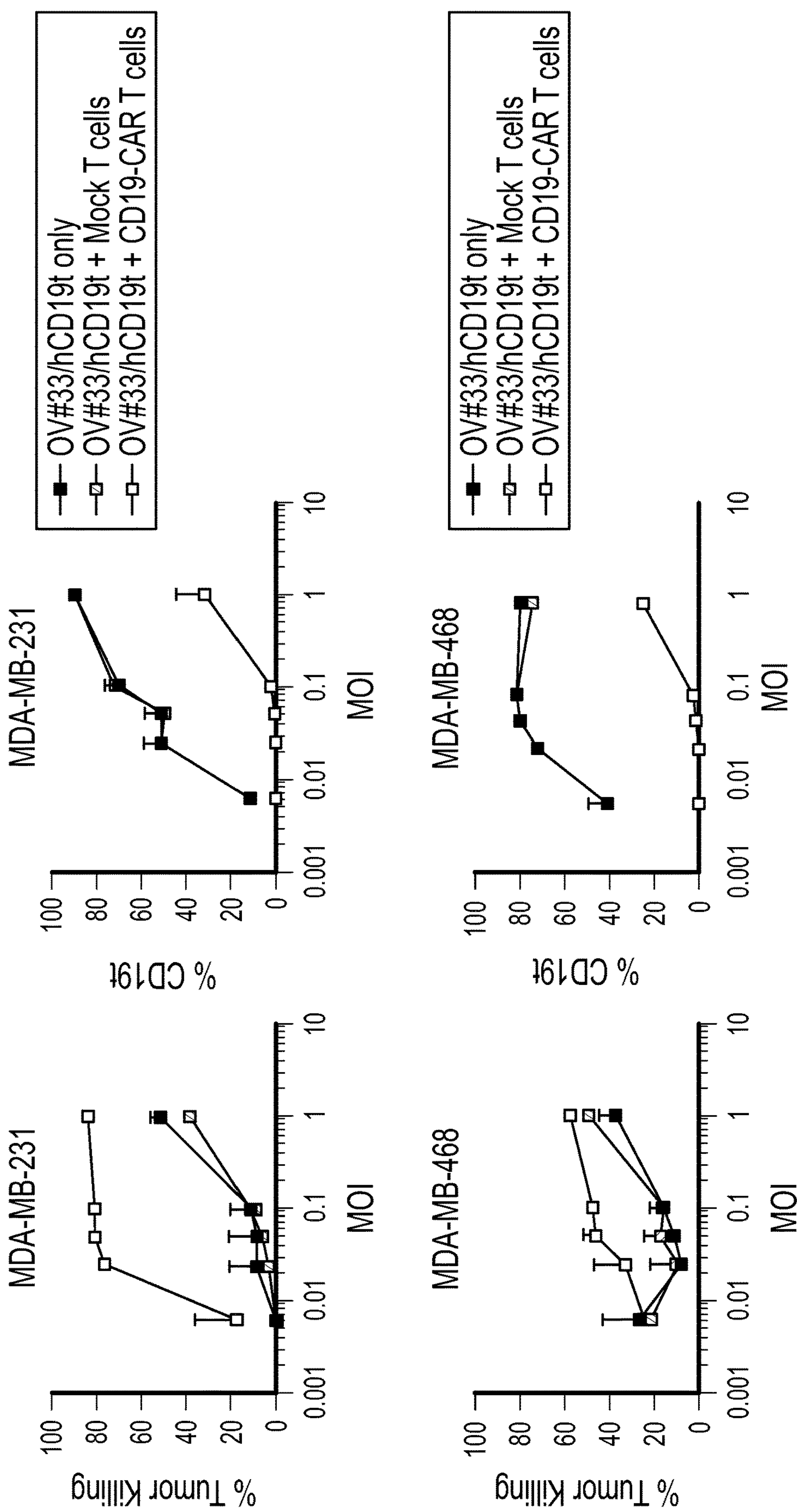
Figure 12C:
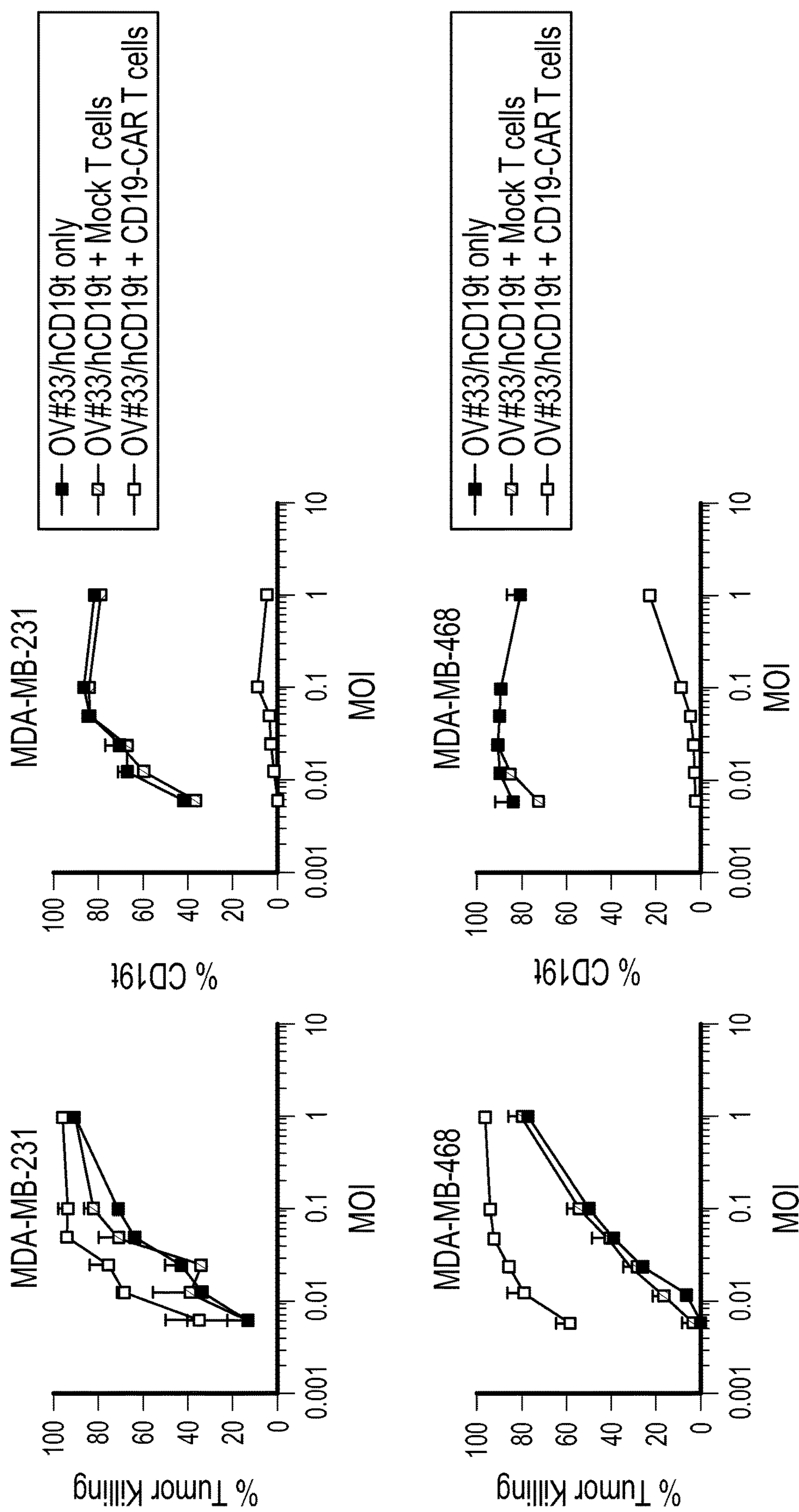
Figure 13A:
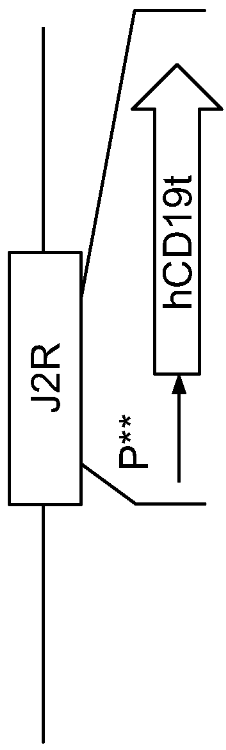
FIG. 13. An oncolytic virus can effectively deliver CD19t to solid tumors and activate CD19-CAR T cells in vitro. (A) Schematic of vaccinia oncolytic virus [CF33-(SE)hCD19t], showing incorporation of human truncated CD19 (CD19t) under the control of the synthetic early promoter (PSE) inserted into the J2R locus replacing the thymidine kinase gene. (B) Immunofluorescence microscopy of MDA-MB-468 cells infected for 24 h with OV19t at MOI 0.025 (left) and MOI 1 (middle), or cells transduced with lentivirus to stably express CD19t (right). Images are at 10× magnification, and insets are at 40× magnification. (C) FACS plots displaying the cell surface expression of CD19t and intracellular expression of vaccinia virus on MDA-MB-468 tumor cells determined by flow cytometry after 24 h of OV19t infection at increasing MOIs. (D) Quantification of CD19t (left), vaccinia (middle), and viability (right) of MDA-MB-468 tumor cells following 24, 48, and 72 h co-culture with indicated MOIs of OV19t. (E) Quantification of CD25 (left) and CD137 (right) expression on Mock (untransduced) or CD19-CAR T cells following a 24 hour co-culture with tumor cells at an effector:tumor (E:T) ratio of 1:2 with or without treatment with indicated MOI of OV19t.
Figure 13B:
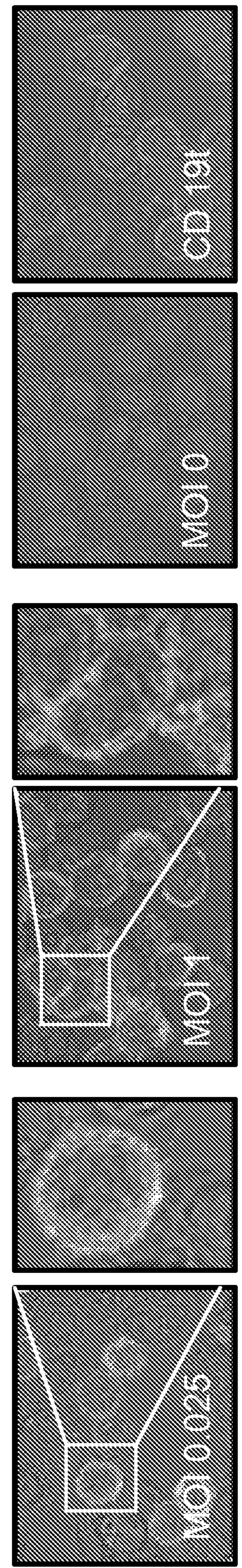
Figure 13C:
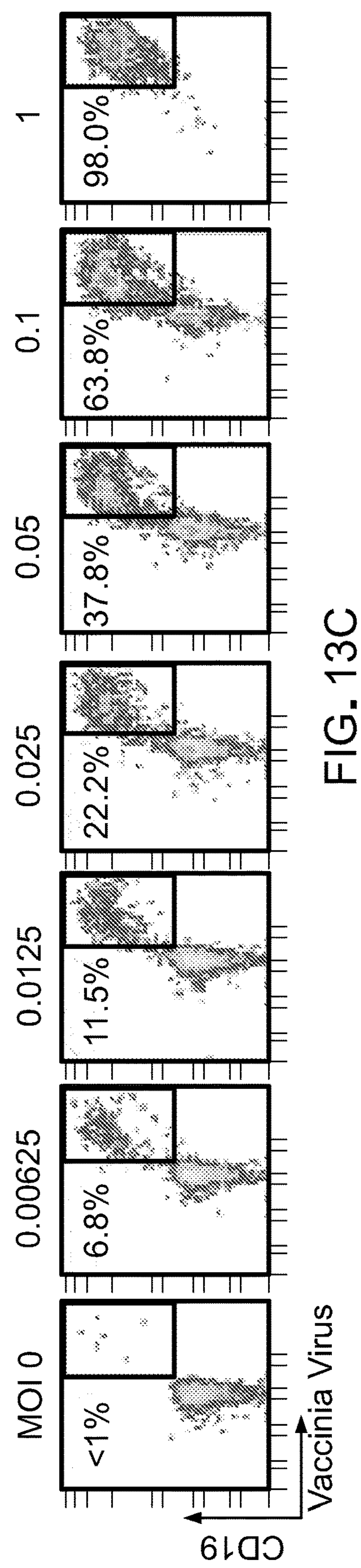
Figure 13D:
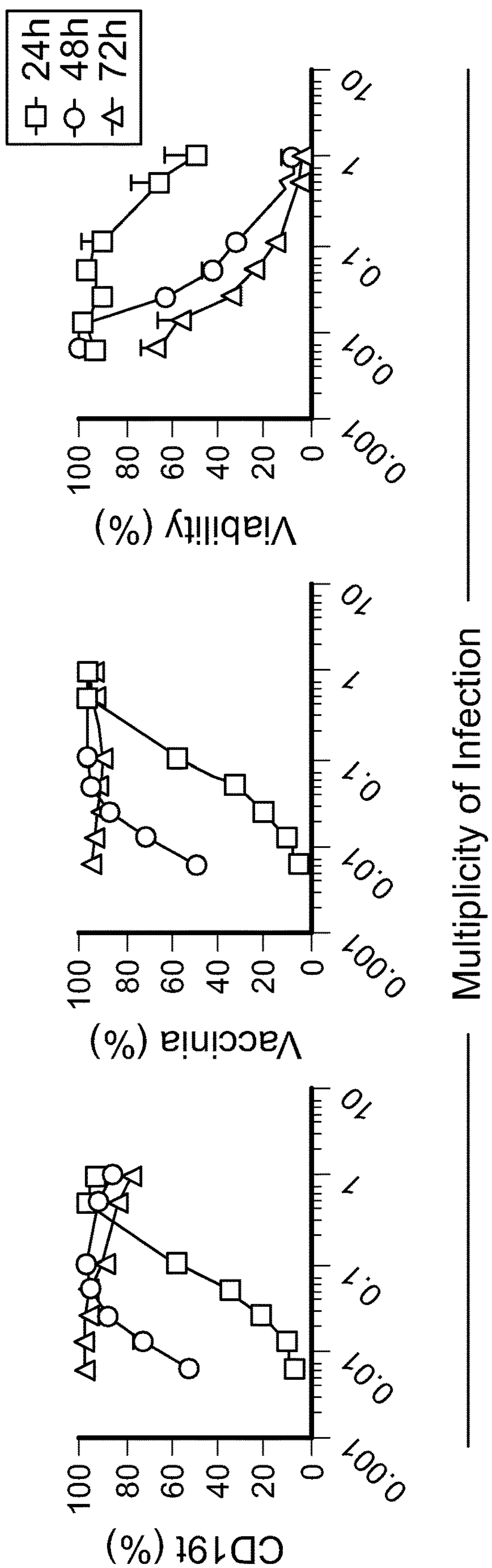
Figure 13E:
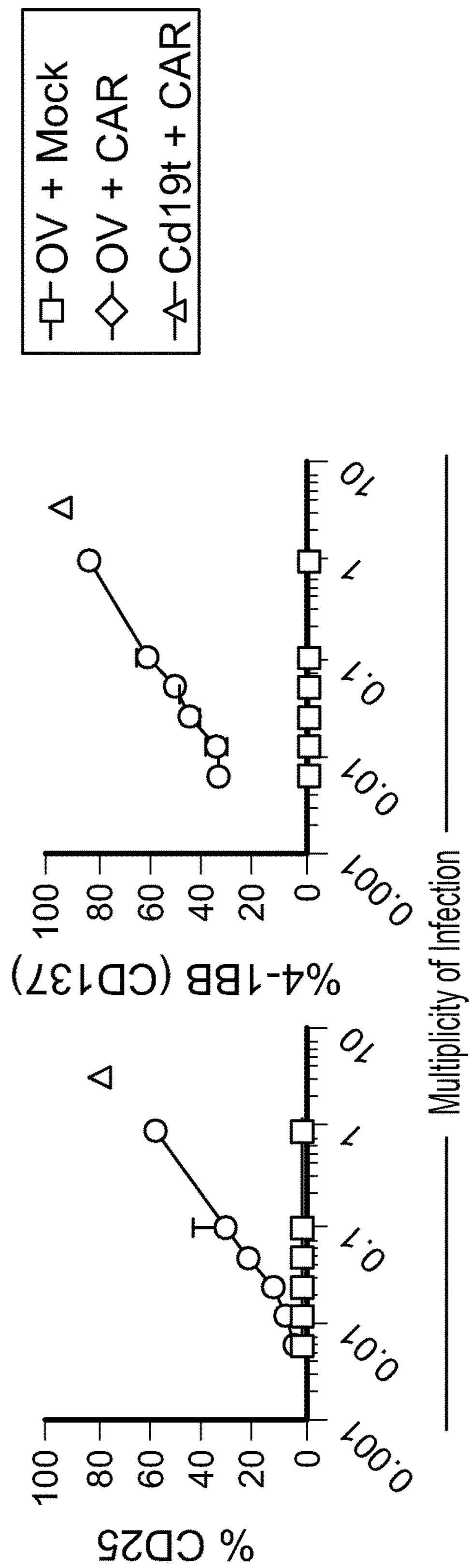
Figure 14A:
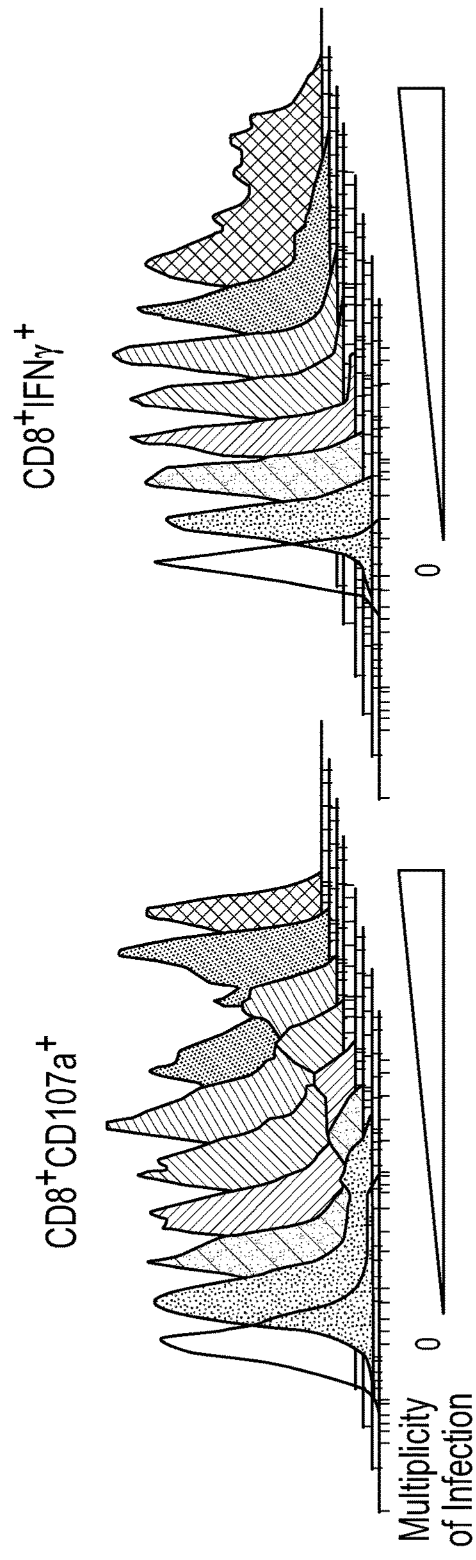
FIG. 14. OV19t oncolytic virus can force expression of CD19t in tumor cells, which re-direct activation and cytotoxicity of CD19-CAR T cells in vitro. (A) Representative flow cytometric analysis showing cell surface CD107a (left) and intracellular IFNγ expression (right) in $CD8^{+}CAR^{+}$ T cells following a 16 h co-culture with MDA-MB-468 tumor cells at a 1:1 E:T ratio with or without treatment with indicated MOI of OV19t. (B) IFNγ production measured by ELISA in supernatants collected from co-cultures with or without treatment with OV19t at indicated MOIs for 24, 48, and 72 h. (C) Tumor killing assay assessed by flow cytometry comparing Mock or CD19-CAR T cells following a 24, 48, or 72 h co-culture with MDA-MB-468 tumor cells treated with indicated MOIs of OV19t. (D) CD19t expression on tumor cells in killing assay described in c). (D) Virus titers in supernatant collected from co-cultures of T cells and tumors cells treated with indicated MOIs of OV19t.
Figure 14B:
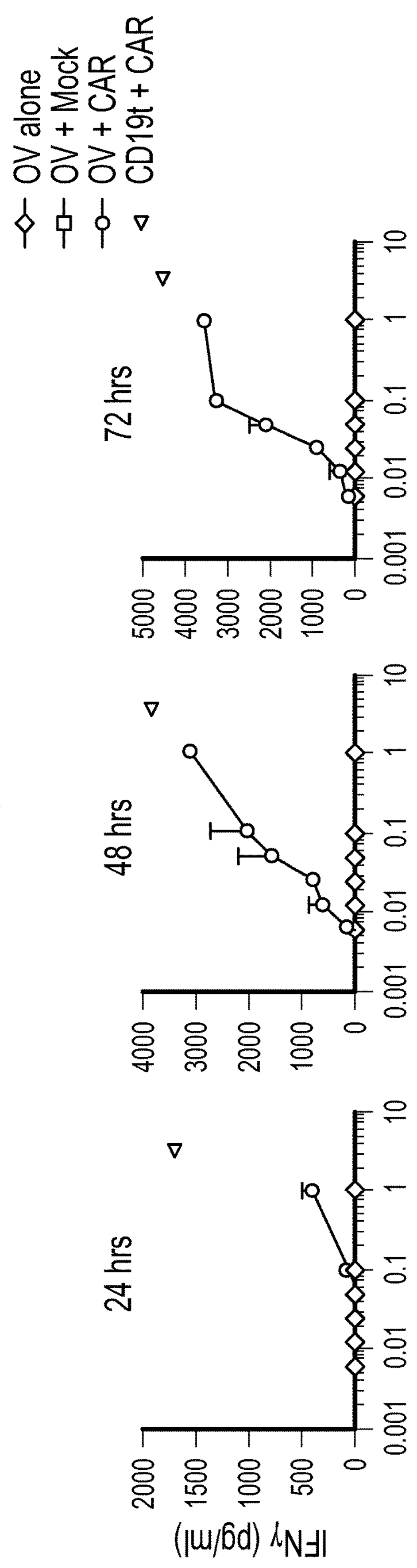
Figure 14C:
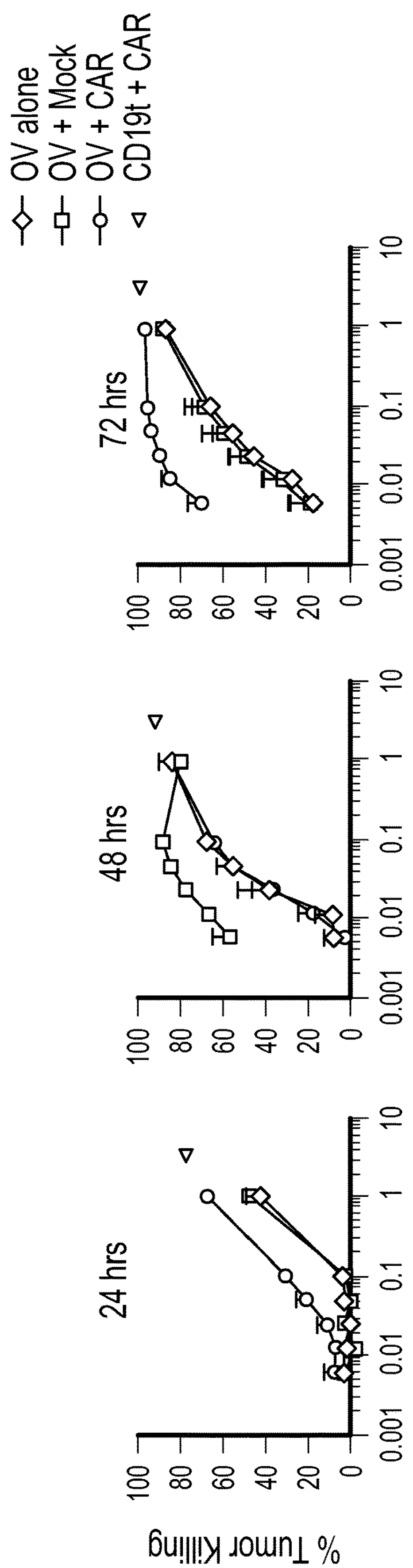
Figure 14D:
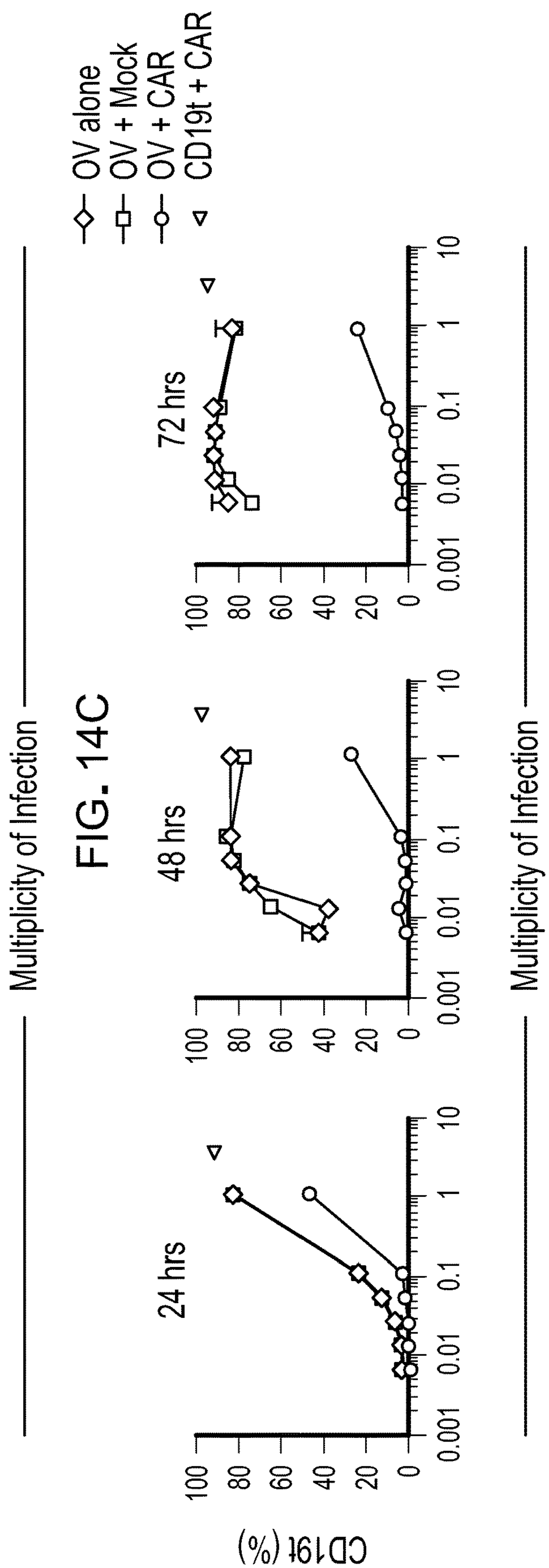
Figure 14E:
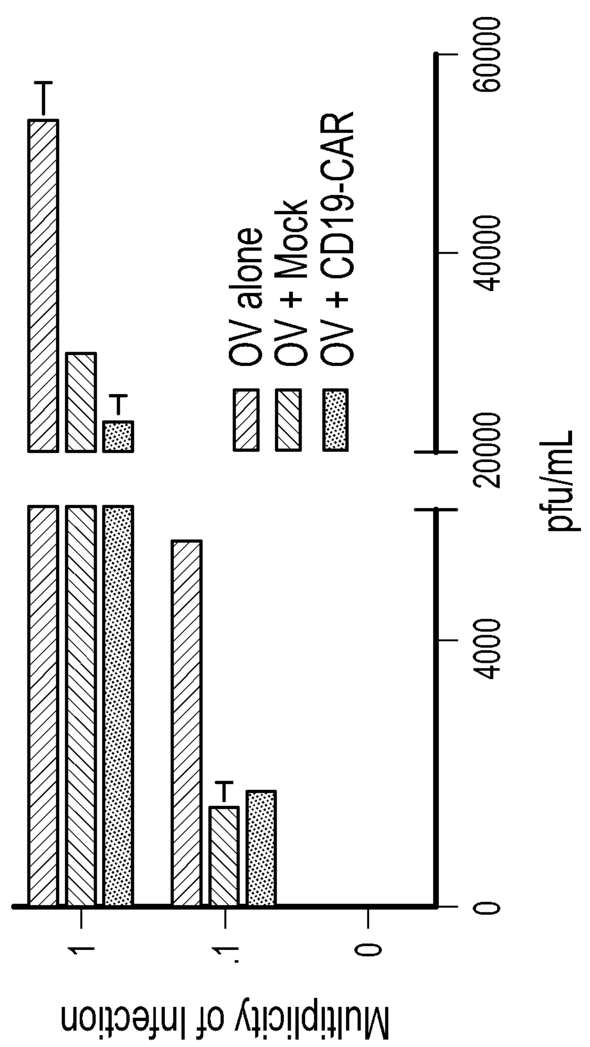
Figure 15A:
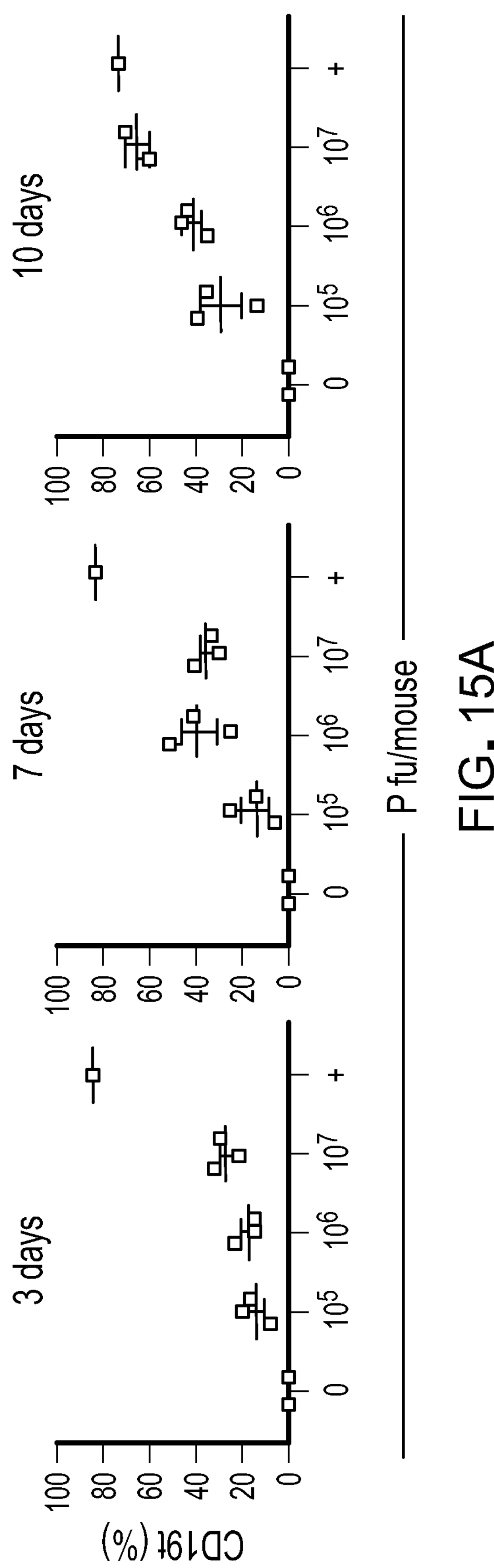
FIG. 15. Anti-tumor efficacy of combination therapy of OV19t and CD19-CAR T cells in a TNBC xenograft model. (A) Mice were engrafted with subcutaneous MDA-MB-468 tumors ($5\times10^{6}$ cells) and intratumorally treated with 0, $10^{5}$, $10^{6}$, or $10^{7}$ plaque-forming units (pfu) per mouse, which were harvested at day 3 (left), 7 (middle), or 10 (right) after treatment for quantification of CD19t expression via flow cytometry. (+) represents MDA-MB-468 tumors previously lentivirally transduced to stably express CD19t. (B) Tumor volume ($mm^{3}$) in NSG mice bearing subcutaneous MDA-MB-468 ($5\times10^{6}$ cells) tumors on day 0, and treated with OV19t ($10^{7}$ pfu) on day 36. On day 46, mice were treated with either Mock or CD19-CAR T cells ($5\times10^{6}$ cells). (C) Average tumor volumes on day 73 of in vivo experiment described in (B). (D) Schematic of combination therapy concept utilizing OV to introduce CAR targets to intractable solid tumors.
Figure 15B:
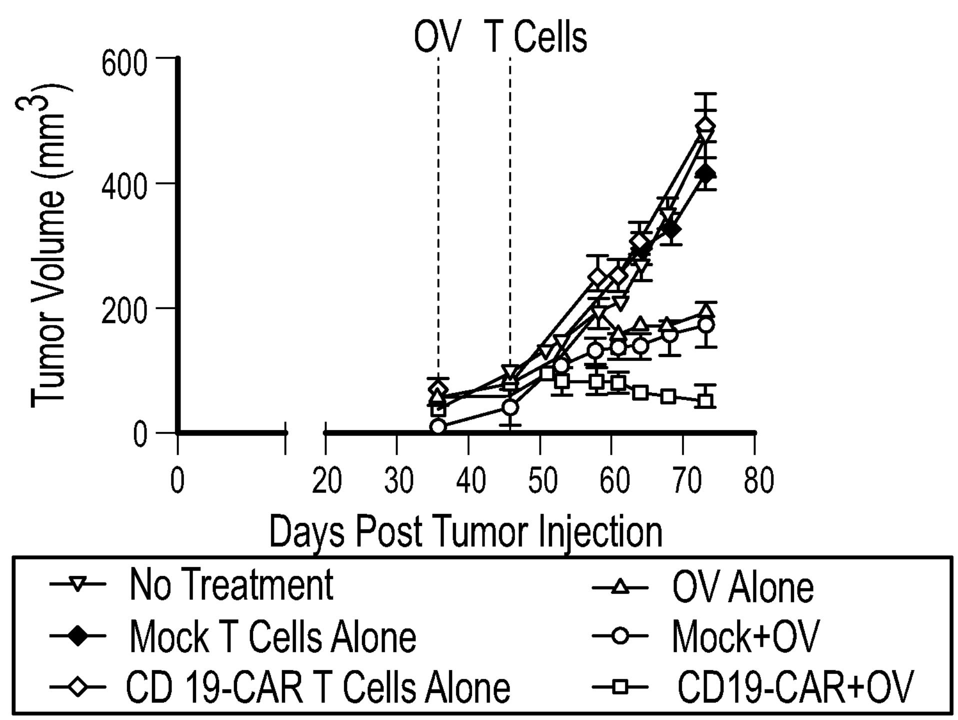
Figure 15C:
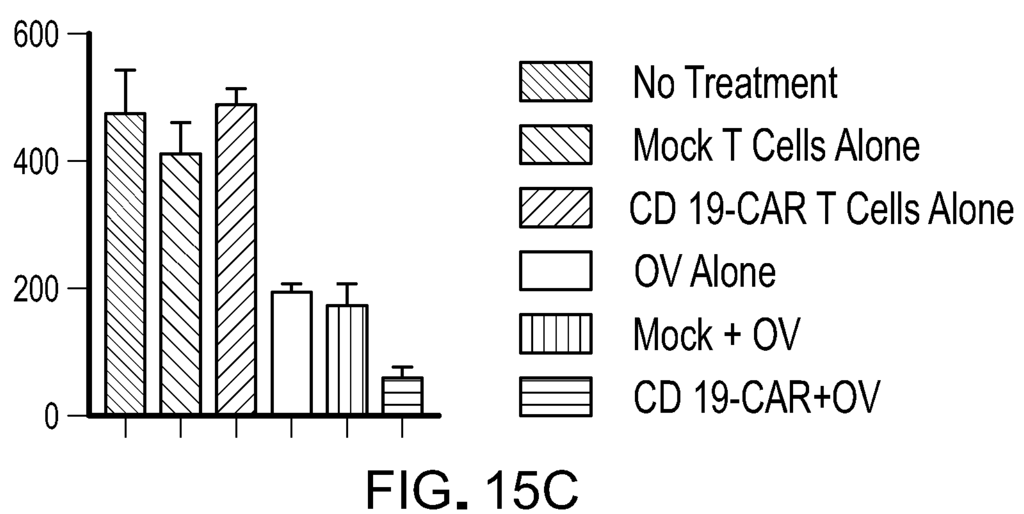
Figure 15E:
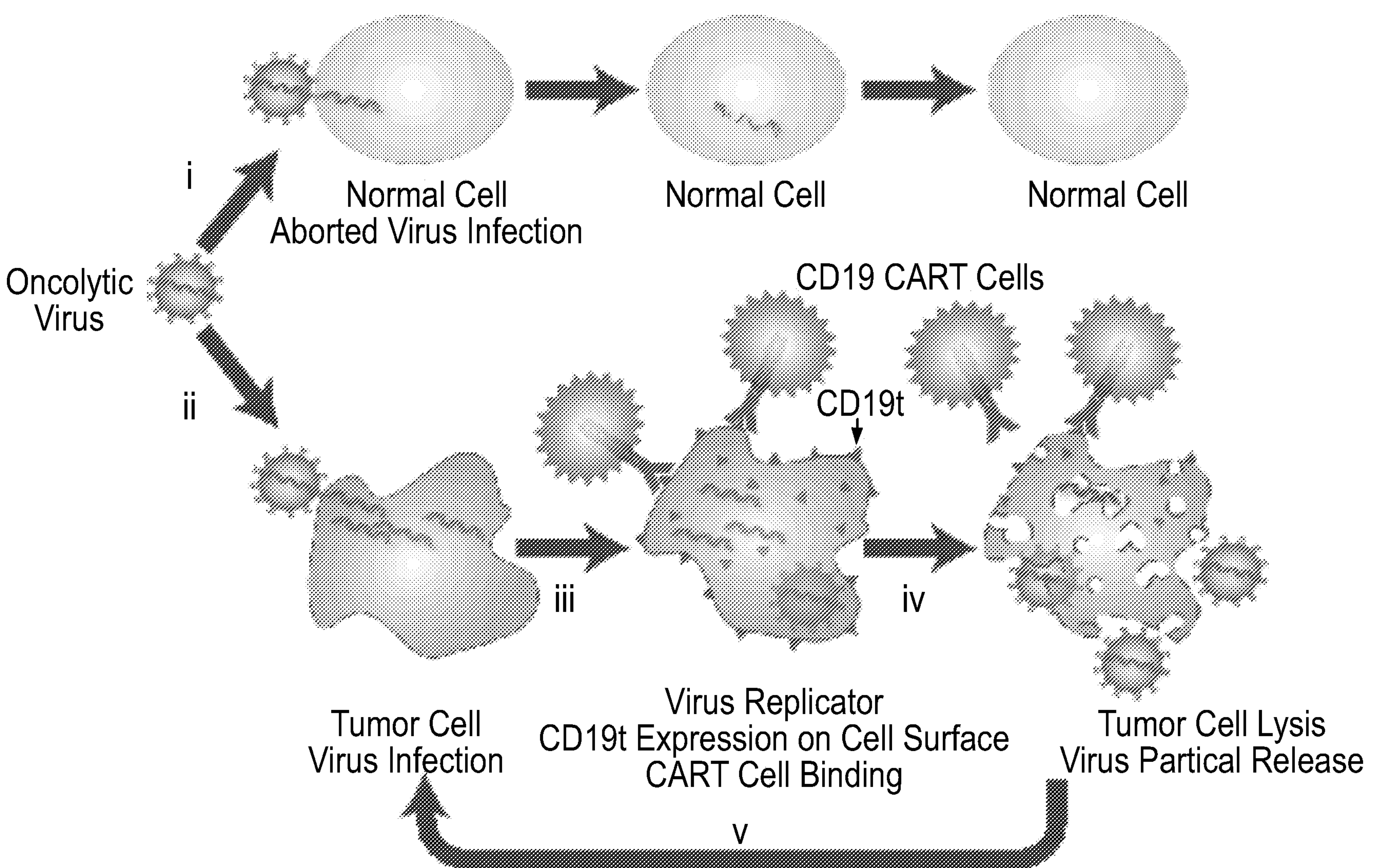

FIG. 12 depicts the results of a long term cell killing assay in which MDA-MB-468 cells or MMDA-MB-231 cells were cultured with recombinant oncolytic virus 33-CD19t only (at various MOI); recombinant oncolytic virus 33-CD19t (at various MOI) and mock transfected T cells; or recombinant oncolytic virus 33-CD19t (at various MOI) and transfected T cells expressing the CD19 targeted CAR. Tumor cell killing and CD19t expression were measured.

Taken together, the studies in this example demonstrate that: 1) in MDA-MB-48 cells exposed to recombinant oncolytic virus 33-CD19t, CD19t expression increases with higher MOI; 2) in MDA-MB-48 cells exposed to recombinant oncolytic virus 33-CD19t in the presence of CD19-CAR T cells, the T cells produce higher levels of IL-2 and IFN-gamma as the MOI is increased; and 3) CD19 CAR T cells show efficacy against in MDA-MB-48 cells exposed to recombinant oncolytic virus 33-CD19t.

Example 6. Recombinant Chimeric Poxvirus Expressing CD19t Together with a CD19 CAR are Effect in a TNBC Xenograft Model As shown in FIG. 13, an oncolytic virus can effectively deliver CD19t to solid tumors and activate CD19-CAR T cells in vitro. FIG. 13, panel A is a schematic of vaccinia oncolytic virus [CF33-(SE) hCD19t], showing incorporation of human truncated CD19 (CD19t) under the control of the synthetic early promoter (PSE) inserted into the J2R locus replacing the thymidine kinase gene. FIG. 13, panel B depicts munofluorescence microscopy of MDA-MB-468 cells infected for 24 h with OV19t at MOI 0.025 (left) and MOI 1 (middle), or cells transduced with lentivirus to stably express CD19t (right). Images are at 10× magnification, and insets are at 40× magnification. FIG. 13, panel C is a set of FACS plots displaying the cell surface expression of CD19t and intracellular expression of vaccinia virus on MDA-MB-468 tumor cells determined by flow cytometry after 24 h of OV19t infection at increasing MOIs. FIG. 13, panel D presents quantification of CD19t (left), vaccinia (middle), and viability (right) of MDA-MB-468 tumor cells following 24, 48, and 72 h co-culture with indicated MOIs of OV19t. FIG. 13, panel E show a quantification of CD25 (left) and CD137 (right) expression on Mock (untransduced) or CD19-CAR T cells following a 24 hour co-culture with tumor cells at an effector:tumor (E:T) ratio of 1:2 with or without treatment with indicated MOI of OV19t.

As shown in FIG. 14, OV19t oncolytic virus can force expression of CD19t in tumor cells, which re-direct activation and cytotoxicity of CD19-CAR T cells in vitro. FIG. 14, panel A is a representative flow cytometric analysis showing cell surface CD107a (left) and intracellular IFNγ expression (right) in $CD8^{+}CAR^{+}$ T cells following a 16 h co-culture with MDA-MB-468 tumor cells at a 1:1 E:T ratio with or without treatment with indicated MOI of OV19t. FIG. 14, panel B shows IFNγ production measured by ELISA in supernatants collected from co-cultures with or without treatment with OV19t at indicated MOIs for 24, 48, and 72 h. FIG. 14, panel C shows tumor killing assay assessed by flow cytometry comparing Mock or CD19-CAR T cells following a 24, 48, or 72 h co-culture with MDA-MB-468 tumor cells treated with indicated MOIs of OV19t. FIG. 14, panel D show CD19t expression on tumor cells in killing assay described in panel C. FIG. 14, panel D shows virus titers in supernatant collected from co-cultures of T cells and tumors cells treated with indicated MOIs of OV19t.

As shown in FIG. 15, combination therapy with OV19t and CD19-CAR T cells is effective in a TNBC xenograft model. FIG. 15, panel A shows ice were engrafted with subcutaneous MDA-MB-468 tumors ($5\times10^{6}$ cells) and intratumorally treated with 0, $10^{5}$, $10^{6}$, or $10^{7}$ plaque-forming units (pfu) per mouse, which were harvested at day 3 (left), 7 (middle), or 10 (right) after treatment for quantification of CD19t expression via flow cytometry. (+) represents MDA-MB-468 tumors previously lentivirally transduced to stably express CD19t. FIG. 15, panel B show stupor volume ($mm^{3}$) in NSG mice bearing subcutaneous MDA-MB-468 ($5\times10^{6}$ cells) tumors on day 0, and treated with OV19t ($10^{7}$ pfu) on day 36. On day 46, mice were treated with either Mock or CD19-CAR T cells ($5\times10^{6}$ cells). FIG. 15, panel C shows verage tumor volumes on day 73 of in vivo experiment described in panel B. FIG. 15, panel D is a schematic of combination therapy concept utilizing OV to introduce CAR targets to intractable solid tumors.

REFERENCES

1. Chen N G & Szalay A A (2011) Oncolytic virotherapy of cancer. *Cancer Management in Man: Chemotherapy, Biological Therapy, Hyperthermia and Supporting Measures*, Cancer Growth and Progression, ed Minev BR (Springer, New York), Vol 13, pp 295-316.

2. Chen N G & Szalay A A (2010) Oncolytic vaccinia virus: a theranostic agent for cancer. *Future Virol.* 5 (6): 763-784.
3. Andtbacka R H, et al. (2015) Talimogene Laherparepvec Improves Durable Response Rate in Patients With Advanced Melanoma. *J Clin Oncol* 33 (25): 2780-2788.
4. Anonymous (2015) First Oncolytic Viral Therapy for Melanoma. *Cancer discovery.*
5. Russell S J, Peng K W, & Bell J C (2012) Oncolytic virotherapy. *Nat Biotechnol* 30 (7): 658-670.
6. Thorne S H, et al. (2007) Rational strain selection and engineering creates a broad-spectrum, systemically effective oncolytic poxvirus, JX-963. *J Clin Invest* 117 (11): 3350-3358.
7. Yu W & Fang H (2007) Clinical trials with oncolytic adenovirus in China. *Curr Cancer Drug Targets* 7 (2): 141-148.
8. Evgin L, et al. (2010) Potent Oncolytic Activity of Raccoonpox Virus in the Absence of Natural Pathogenicity. *Mol Ther.*
9. Rintoul J L, et al. (2012) ORFV: a novel oncolytic and immune stimulating parapoxvirus therapeutic. *Mol Ther* 20 (6): 1148-1157.
10. Chan W M & McFadden G (2014) Oncolytic Poxviruses. *Annu Rev Virol* 1 (1): 119-141.

What is claimed is:

1. A recombinant oncolytic virus comprising a nucleotide sequence encoding a truncated human CD19 lacking a functional signaling domain and comprising the amino acid sequence: MPPPRLLFFLLFLTPMEVRPEE-PLVVKVEEGDNAVLQCLKGTSDGPTQQLTWSRE-SPLKP FLKLSLGLPGLGIHMR-PLAIWLFIFNVSQQMGGFYLCQPGPPSEKAWQPGWT VNVEGSG ELFRWNVSDLGGLGCGLKNRSSE GPSSPSGKLMSPKLYVWAKDRPEIWEGEPPCVPPRD SLNQSLSQDLTMAPGSTLWLSCGVPPDSVSRG-PLSWTHVHPKGPKSLLSLELKDDRPAR DMWVMETGLLLPRATAQDAGKYY-CHRGNLTMSFHLEITARPVLWHWLLRTGGWKVS AVTLAYLIFCLCSLVGILHLQRALVLRRKR (SEQ ID NO: 29), wherein the nucleotide sequence encoding the truncated CD19 is operably linked to a promoter and is inserted into the J2R locus of an oncolytic virus comprising nucleotide sequence that is at least 99% identical to SEQ ID NO:1, but lacks a sequence encoding thymidine kinase.

2. The recombinant oncolytic virus of claim 1 wherein the promotor is a viral early promoter.

3. The recombinant oncolytic of claim 1, wherein the promoter is a poxvirus early promoter.

4. A method for treating a patient suffering from cancer comprising:

administering to the patient the recombinant oncolytic virus of claim 1; and, simultaneously or subsequently, administering to the patient a T cell population expressing a chimeric antigen receptor (CAR) that is targeted human CD19.

5. The method of claim 4 wherein the T cell population comprises T cells transduced with a lentiviral vector encoding the CAR.

6. The method of claim 5 wherein the T cell population comprises T cells transfected with an RNA molecule encoding the CAR.

7. The method of claim 5 wherein the T cell population is administered 1-20 days after administration of the recombinant oncolytic virus.

8. The method of claim 5 wherein the T cell population is administered 5-100 days after administration of the recombinant oncolytic virus.

9. The method of claim 4 wherein the cancer is a solid tumor.

10. The method of claim 9 wherein the solid tumor is ovarian cancer or pancreatic cancer.

11. The recombinant oncolytic virus of claim 1, wherein the oncolytic virus comprises the nucleotide sequence of SEQ ID NO:1.

* * * * *